(12) United States Patent
Greenlee et al.

(10) Patent No.: US 8,722,727 B2
(45) Date of Patent: May 13, 2014

(54) ANTIFUNGAL AGENTS

(75) Inventors: Mark L. Greenlee, Plainfield, NJ (US); Robert Wilkening, Maplewood, NJ (US); James Apgar, Edison, NJ (US); Donald Sperbeck, East Hanover, NJ (US); Kenneth J. Wildonger, Bridgewater, NJ (US); Dongfang Meng, Westfield, NJ (US); Dann L. Parker, Jr., Cranford, NJ (US); Ahmed Mamai, Raleigh, NC (US)

(73) Assignee: Seynix, Inc., Research Triangle Park, NC (US)

( * ) Notice: Subject to any disclaimer, the term of this patent is extended or adjusted under 35 U.S.C. 154(b) by 336 days.

(21) Appl. No.: 13/058,227

(22) PCT Filed: Aug. 10, 2009

(86) PCT No.: PCT/US2009/004569
§ 371 (c)(1),
(2), (4) Date: May 26, 2011

(87) PCT Pub. No.: WO2010/019206
PCT Pub. Date: Feb. 18, 2010

(65) Prior Publication Data
US 2011/0224228 A1    Sep. 15, 2011

Related U.S. Application Data

(60) Provisional application No. 61/136,099, filed on Aug. 12, 2008.

(51) Int. Cl.
*A61K 31/35* (2006.01)
*C07D 311/78* (2006.01)

(52) U.S. Cl.
USPC .......................................... 514/453; 549/382

(58) Field of Classification Search
USPC .......................................... 549/382; 514/453
See application file for complete search history.

(56) References Cited

U.S. PATENT DOCUMENTS

| 5,756,472 | A  | 5/1998 | Liesch et al. |
| 7,230,023 | B2 | 6/2007 | Mori et al. |
| 2008/0009504 | A1 | 1/2008 | Balkovec et al. |

FOREIGN PATENT DOCUMENTS

WO    WO-2007/126900 A2    11/2007
WO    WO-2007/127012 A1    11/2007

OTHER PUBLICATIONS

Bundgaard (ed.), *Design of Prodrugs*, Elsevier (1985).
Davies et al., "Recent Advances in Catalytic Intramolecular C-H Aminations," 44(23) Angew. Chem. Int'l Ed. 3518-20 (2005).
Ellman et al., "N-tert-Butanesulfinyl Imines: Versatile Intermediates for the Asymmetric Synthesis of Amines," 35(11) Acct. Chem. Res. 984-95 2002.
Gennaro (ed.), *Remington: The Science and Practice of Pharmacy*, 20th edition (2000).
Gontcharov et al., "tert-Butylsulfonamide. A New Nitrogen Source for Catalytic Aminohydroxylation and Aziridination of Olefins," 1(5) Org. Lett. 783-86 (1999).
Harwood et al., "Synthesis of Homochiral α-Substituted Alanine Derivatives by Diastereocontrolled Alkylation of (5R)-5-Phenyl-3-methyl-3,4-dehydromorpholinones," 11 Synlett 1051-53 (1996).
Hu, "Nucleophilic ring opening of aziridines." 60 Tetrahedron 2701-43 2004.
Jeong et al., "Bromine-Catalyzed Aziridination of Olefins. A Rare Example of Atom-Transfer Redox Catalysis by a Main Group Element," 120(26-30) J. Am. Chem. Soc. 6844-45 (1998).
Kawabata et al., "Asymmetric cyclization via memory of chirality: a concise access to cyclic amino acids with a quaternary stereocenter," 125(43) J. Am. Chem. Soc. 13012-13 (2003).
Kuethe et al., "A Concise Synthesis of (S)-N-Ethoxycarbonyl-α-methylvaline," 72(19) J. Org. Chem. 7469-72 (2007).
Liang et al., "Intramolecular C-N Bond Formation Reactions Catalyzed by Ruthenium Porphyrins: Amidation of Sulfamate Esters and Aziridination of Unsaturated Sulfonamides," 69(11) J. Org. Chem. 3610-19 (2004).
McCoull et al., "Recent Synthetic Applications of Chiral Aziridines," Synthesis 1347-65 (2000).
Melendez et al., "Synthesis and reactivity of cyclic sulfamidites and sulfamidates," 59 Tetrahedron 2581-616 (2003).
Morton et al., "Direct synthesis of chiral aziridines from N-tert-butyl-sulfinylketimines," Chem. Commun. 1833-35 (2006).
Onishi et al., "Discovery of Novel Antifungal (1,3)-?-D-Glucan Synthase Inhibitors," 44(2) Antimicrob. Agents Chemother. 368-77 (2000).
Osborn et al., "The asymmetric synthesis of aziridines," 8(11) Tetrahedron: Asymmetry 1693-715 (1997).
Pelaez et al., "The Discovery of Enfumafungin, a Novel Antifungal Compound Produced by an Endophytic Hormonema Species—Biological Activity and Taxonomy of the Producing Organisms," 23(3) Syst. Appl. Microbiol. 333-43 (2000).
Ruge et al., "Current state of three-dimensional characterisation of antifungal targets and its use for molecular modelling in drug design," 26 Int'l J. Antimicrob. Agents 427-41 (2005).
Schwartz et al., "Isolation and Structural Determination of Enfumafungin, a Triterpene Glycoside Antifungal Agent That Is a Specific Inhibitor of Glucan Synthesis," 122(16-20) J. Am. Chem. Soc. 4882-86 (2000).

(Continued)

*Primary Examiner* — Barbara P Badio
(74) *Attorney, Agent, or Firm* — Covington & Burling LLP; Paul J. Berman; Melody Wu

(57) ABSTRACT

Novel derivatives of enfumafungin are disclosed herein, along with' their pharmaceutically acceptable salts, hydrates and prodrugs. Also disclosed are compositions comprising such compounds, methods of preparing such compounds and method of using such compounds as antifungal agents and/or inhibitors of (1,3)-β-D-glucan synthase. The disclosed compounds, their pharmaceutically acceptable salts, hydrates and prodrugs, as well as compositions comprising such compounds, salts, hydrates and prodrugs, are useful for treating and/or preventing fungal infections and associated diseases and conditions.

35 Claims, No Drawings

(56) References Cited

OTHER PUBLICATIONS

Schwartz, "Cell wall active antifungal agents," 11(11) Exp. Opin. Ther. Patents 1761-72 (2001).

Shafiee et al., "Enzymatic deglycosylation of enfumafungin, a triterpene glycoside natural product, and its chemically synthesized analogues," 16(1) J. Mol. Catalysis B: Enzymatic 27-32 (2001).

Sweeney, "Aziridines: epoxides' ugly cousins?" 31 Chem. Soc. Rev. 247-58 (2002).

Vicario et al., "An improved procedure for the preparation of chiral nonracemic N-tosyl-2-alkylaziridines and N,2-dialkylaziridines on multigram-scale," iv ARKIVOC 304-11 (2007).

Wang et al., "Progress of the Structural Modification on Antifungal Azoles," 38(1) Chin. J. Pharms. 49-57 (2007), English Abstract.

Watson et al., "Advances in Nitrogen Transfer Reactions Involving Aziridines," 39(3) Accounts Chem. Res. 194-206 (2006).

ANTIFUNGAL AGENTS

JOINT RESEARCH AGREEMENT

The claimed subject matter was made as a result of activities undertaken within the scope of a joint research agreement between Merck & Co., Inc. and Scynexis, Inc.

FIELD OF THE INVENTION

The claimed subject matter relates to novel compounds and pharmaceutically acceptable salts, hydrates and prodrugs thereof, compositions containing such compounds, synthesis of such compounds, and use of such compounds as antifungal agents and/or inhibitors of (1,3)-β-D-glucan synthesis. The compounds described herein are derivatives of enfumafungin. The novel compounds of this disclosure, their pharmaceutically acceptable salts, hydrates and prodrugs, and compositions comprising such compounds, salts, hydrates and/or prodrugs, are useful for treating and/or preventing antifungal infections and associated diseases and conditions.

BACKGROUND OF THE INVENTION

Fungal infection is a major healthcare problem, and the incidence of hospital-acquired fungal diseases continues to rise. Severe systemic fungal infection in hospitals (such as candidiasis, aspergillosis, histoplasmosis, blastomycosis and coccidioidomycosis) is commonly seen in neutropaenic patients following chemotherapy and in other oncology patients with immune suppression, in patients who are immune-compromised due to Acquired Immune Deficiency Syndrome (AIDS) caused by HIV infection, and in patients in intensive care. Systemic fungal infections cause ~25% of infection-related deaths in leukaemics. Infections due to *Candida* species are the fourth most important cause of nosocomial bloodstream infection. Serious fungal infections may cause 5-10% of deaths in patients undergoing lung, pancreas or liver transplantation. Treatment failures are still very common with all systemic mycoses. Secondary resistance also arises. Thus, there remains an increasing need for effective new therapy against mycotic infections.

Enfumafungin is a hemiacetal triterpene glycoside that is produced in fermentations of a *Hormonema* spp. associated with living leaves of *Juniperus communis* (U.S. Pat. No. 5,756,472; Pelaez et al., *Systematic and Applied Microbiology*, 23:333-343, 2000; Schwartz et al., *JACS*, 122:4882-4886, 2000; Schwartz, R. E., *Expert Opinion on Therapeutic Patents*, 11(11):1761-1772, 2001). Enfumafungin is one of the several triterpene glycosides that have in vitro antifungal activities. The mode of the antifungal action of enfumafungin and other antifungal triterpenoid glycosides was determined to be the inhibition of fungal cell wall glucan synthesis by their specific action on (1,3)-β-D-glucan synthase (Onishi et al., *Antimicrobial Agents and Chemotherapy*, 44:368-377, 2000; Pelaez et al., *Systematic and Applied Microbiology*, 23:333-343, 2000). 1,3-β-D-Glucan synthase remains an attractive target for antifungal drug action because it is present in many pathogenic fungi which affords broad antifungal spectrum and there is no mammalian counterpart and as such, compounds specifically inhibiting 1,3-β-D-Glucan synthase have little or no mechanism-based toxicity.

Various enfumafungin derivatives have been disclosed, e.g., in International Patent Publication Nos. WO 2007/126900 and WO 2007/127012.

SUMMARY OF THE INVENTION

The present invention relates to enfumafungin derivatives. These compounds or pharmaceutically acceptable salts are useful in the inhibition of (1,3)-β-D-glucan synthase and are useful in the prevention or treatment of mycotic infections caused by one or more of various pathogens including, but are not limited to, *Aspergillus, Cryptococcus, Candida, Mucor, Actinomyces, Histoplasma, Dermatophyte, Malassezia, Fusarium*, and *Pneumocystis carinii*. In particular, the present invention includes a compound of Formula I:

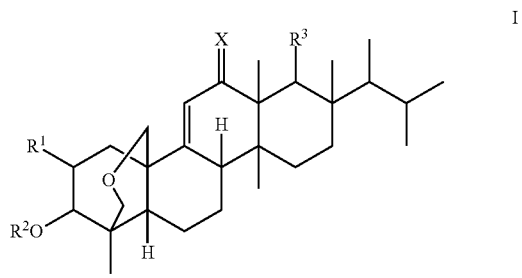

or a pharmaceutically acceptable salt thereof, wherein:
$R^1$ is a group of the following structure:

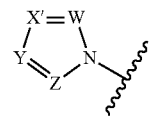

wherein W, X', Y, and Z are independently selected from N and $CR^e$ provided that only one of W, X', Y and Z is $CR^e$;
$R^e$ is independently selected from
a) H;
b) Halogen;
c) $NR^fR^g$;
d) $NHC(O)R^o$;
e) $NHC(O)NR^fR^g$;
f) $NHC(O)OR^o$;
g) $NO_2$;
h) $OR^o$;
i) $SR^o$;
j) $SO_2R^o$;
k) $SO_2N(R^o)_2$;
l) CN;
m) $C(O)R^o$;
n) $C(O)OR^o$;
o) $C(O)NR^fR^g$;
p) $C(=NR^o)N(R^o)_2$;
q) $C_1$-$C_6$-alkyl optionally substituted with 1 to 3 substituents independently selected from phenyl, pyridyl, $OR^o$, $N(R^o)_2$, $CO_2R^o$, $C(O)N(R^o)_2$ or halogen;
r) $C_2$-$C_6$-alkenyl optionally substituted with 1 to 3 substituents independently selected from phenyl, $OR^o$, $N(R^o)_2$, $CO_2R^o$, $C(O)N(R^o)_2$ or halogen;
s) $C_3$-$C_6$-cycloalkyl, optionally substituted with oxo, $OR^o$, $N(R^o)_2$, $CO_2R^o$ or $C(O)N(R^o)_2$;
t) heterocyclyl, wherein the heterocyclyl is a 4- to 6-membered saturated or unsaturated non-aromatic ring having 1, 2 or 3 heteroatoms selected from N, O or S, attached through a carbon or nitrogen on the ring, and optionally substituted on a ring carbon with 1 to 2 substituents independently selected from $N(R^o)_2$, imino, oxo, $OR^o$, $CO_2R^o$, $C(O)N(R^o)_2$ and $C_1$-$C_6$-alkyl unsubstituted or substituted with 1 to 3 substituents independently selected from $N(R^o)_2$, $OR^o$, $CO_2R^o$, $C(O)N(R^o)_2$ and halogen; the heterocyclyl may also be optionally substituted on a ring nitrogen atom that is not the point of attachment with $C(O)R^o$, $CO_2R^o$, $C(O)N(R^o)_2$, $SO_2R^o$ or $C_1$-$C_6$ alkyl unsubstituted or substituted with 1 to 3 substituents independently selected from) $N(R^o)_2$, $OR^o$, $CO_2R^o$, $C(O)N(R^o)_2$ and halogen; the heterocyclyl may also be optionally substituted on a sulfur atom with 1 or 2 oxo groups;

u) aryl, wherein aryl is phenyl or napthyl and aryl is unsubstituted or substituted with 1 or 2 substituents independently selected from halogen, $N(R^o)_2$, $OR^o$, $CO_2R^o$, CN, $C(O)N(R^o)_2$, $C(=NR^o)N(R^o)_2$, heterocyclyl as defined above, phenyl, pyridyl, and $C_1$-$C_6$-alkyl wherein said alkyl is optionally substituted with 1 to 3 substituents independently selected from $N(R^o)_2$, $OR^o$, or halogen;

v) heteroaryl, wherein heteroaryl is a 5- or 6-membered monocyclic aromatic ring or 9- or 10-membered bicyclic aromatic ring having 1, 2 or 3 heteroatoms selected from N, O or S, attached through a ring carbon or nitrogen, and optionally substituted on a ring carbon that is not the point of attachment, with 1 or 2 substituents independently selected from halogen, $CF_3$, $NR^fR^g$, $NHC(O)R^o$, $OR^o$, $CO_2R^o$, $CON(R^o)_2$, $C(=NR^o)N(R^o)_2$, CN, heterocyclyl as defined above, phenyl, pyridyl, and $C_1$-$C_6$ alkyl unsubstituted or substituted with 1 or 2 substituents independently selected from $N(R^o)_2$ and $OR^o$; the heteroaryl may also be optionally substituted on a ring nitrogen atom that is not the point of attachment with O or $C_1$-$C_6$ alkyl;

$R^f$ is H, $C_1$-$C_6$-alkyl, $C_3$-$C_6$-cycloalkyl or phenyl;

$R^g$ is H or $C_1$-$C_o$-alkyl optionally substituted with 1 to 3 substituents independently selected from phenyl, $OR^o$, $N(R^o)_2$ or halogen;

$R^f$ and $R^g$ are optionally taken together with the attached nitrogen atom to form a 3- to 7-membered ring having 0-1 additional heteroatoms independently selected from N, O and S wherein said ring may be optionally substituted on a ring nitrogen atom that is not the point of attachment with $C(O)R^o$, $CO_2R^o$, $C(O)N(R^o)_2$, $SO_2R^o$, or $C_1$-$C_6$ alkyl unsubstituted or substituted with 1 or 2 substituents independently selected from $N(R^o)_2$, $OR^o$, $CO_2R^o$, $C(O)N(R^o)_2$ or halogen; said ring may also be optionally substituted on a sulfur atom with 1 or 2 oxo groups;

$R^2$ is a group of the following structure:

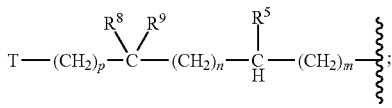

m is 0 or 1;
n is 0 or 1;
p is 0 or 1;
T is $NR^6R^7$ or $OR^{10}$;
$R^5$ is H or $C_1$-$C_6$-alkyl, unsubstituted or substituted with 1 or 2 substituents independently selected from $N(R^o)_2$ and $OR^o$;
$R^6$ is H, $C_1$-$C_6$-alkyl or $C_3$-$C_6$cycloalkyl;
$R^7$ is selected from the group consisting of:
a) H;
b) $C_1$-$C_6$-alkyl, unsubstituted or substituted with 1 or 2 substituents independently selected from $N(R^o)_2$, $OR^o$, $CO_2R^o$, $OC(O)R^o$, $NHC(O)R^o$, $C(O)N(R^o)_2$, phenyl, heteroaryl, and heterocyclyl, wherein heteroaryl and heterocyclyl are as defined above in the definition of $R^e$;
c) $C_3$-$C_6$-cycloalkyl;
d) $C(O)R^o$;
e) $C(O)OC_1$-$C_6$-alkyl;
f) $C(O)NHR^o$;
g) $C(=NH)R^o$;
h) $C(=NR^o)NHR^o$;

$R^6$ and $R^7$ are optionally taken together with the attached nitrogen atom to form a 4- to 7-membered saturated, unsaturated or aromatic ring having 0 or 1 additional heteroatoms independently selected from N, O and S, wherein said ring is optionally substituted on a ring carbon with 1 to 2 substituents independently selected from halogen, $CF_3$, $N(R^o)_2$, $OR^o$, $CO_2R^o$, $C(O)N(R^o)_2$, and $C_1$-$C_6$ alkyl unsubstituted or substituted with 1 or 2 substituents independently selected from $OR^o$ and $N(R^o)_2$; said ring may also be optionally substituted on a ring nitrogen atom that is not the point of attachment with $C(O)R^o$, $CO_2R^o$, $C(O)N(R^o)_2$, $SO_2R^o$ or $C_1$-$C_6$ alkyl unsubstituted or substituted with 1 to 3 substituents independently selected from $N(R^o)_2$, $OR^o$, $CO_2R^o$, $C(O)N(R^o)_2$ and halogen; said ring may also be optionally substituted on a sulfur atom with 1 or 2 oxo groups;

$R^6$ and $R^8$ are optionally taken together to form, with the intervening atoms, a 4- to 7-membered saturated ring having 0 or 1 additional heteroatoms independently selected from N, O and S wherein said ring is optionally substituted as defined above for $R^6$ and $R^7$ when joined together to form a ring;

$R^6$ and $R^5$ are optionally taken together to form, with the intervening atoms, a 4- to 7-membered saturated ring having 0 or 1 additional heteroatoms independently selected from N, O and S wherein said ring is optionally substituted as defined above for $R^6$ and $R^7$ when joined together to form a ring;

$R^8$ is selected from the group consisting of
a) hydrogen,
b) $C_1$-$C_6$-alkyl, unsubstituted or substituted with F, $OR^o$, $N(R^o)_2$ or $SO_2R^o$,
c) $C_3$-$C_6$-cycloalkyl,
d) $C_4$-$C_7$-cycloalkyl-alkyl,
e) aryl, wherein aryl is phenyl or naphthyl and said aryl is unsubstituted or substituted with 1 to 3 substituents selected $C_1$-$C_6$-alkyl, halogen, $OCF_3$, $CF_3$, $N(R^o)_2$ and $OR^o$, and
f) heteroaryl, wherein heteroaryl is as defined above in the definition of $R^e$;

$R^9$ is $C_1$-$C_6$-alkyl, unsubstituted or substituted with $OR^o$ or $SO_2R^o$;

$R^8$ and $R^9$ are optionally taken together to form a 3- to 7-membered saturated ring having 0 or 1 additional heteroatoms independently selected from N, O, and S, wherein said ring is optionally substituted as defined above for $R^6$ and $R^7$ when joined to form a ring;

$R^{10}$ is selected from the group consisting of
a) H,
b) $C_1$-$C_6$-alkyl, unsubstituted or substituted with 1 or 2 substituents selected from $N(R^o)_2$, $OR^o$, $CO_2R^o$, $OC(O)R^o$, $NHC(O)R^o$, $C(O)N(R^o)_2$, phenyl, heteroaryl, and heterocyclyl, wherein heteroaryl and heterocyclyl are as defined above in the definition of $R^e$,
c) $C_3$-$C_6$-cycloalkyl,
d) $C(O)R^o$,
e) $C(O)NHR^o$,
$R^3$ is $C(O)R^{14}$;
$R^{14}$ is OH, $OR^{15}$ or $N(R^o)_2$;
$R^{15}$ is $C_1$-$C_6$-alkyl, unsubstituted or substituted with 1 or 2 substituents independently selected from phenyl and $OC(O)R^o$, wherein said phenyl is optionally substituted with 1 to 3 $OR^o$ groups;
X is O or H, H;
each $R^o$ is independently H, $C_1$-$C_6$ alkyl, $C_3$-$C_6$ cycloalkyl or benzyl.

These compounds are potent antifungal agents useful against pathogens associated with human and agricultural fungal infections.

Additional aspects of the invention relate to compositions comprising the compounds of the invention, optionally in the presence of a second therapeutic agent. In addition, aspects of the invention relate to methods of preparing a compound of the invention, to methods of preparing compositions of the invention, to methods of treating or preventing fungal infection in patients using a compound of the invention, and to methods of controlling fungal infection in patients using a compound of the invention.

Other embodiments, aspects and features of the present invention are either further described in or will be apparent from the ensuing description, examples and appended claims.

DETAILED DESCRIPTION OF THE INVENTION

The present invention relates to compounds of Formula (I) and pharmaceutically acceptable salts thereof. Different embodiments further describing Formula (I) variables are described below.

In a first embodiment of the invention, $R^3$ is $C(O)R^{14}$, wherein $R^{14}$ is OH, and the other variables are as provided for in Formula (I) above.

In a first aspect of this embodiment, the compound is of formula (Ia) wherein all of the variables are as provided for in Formula (I) above:

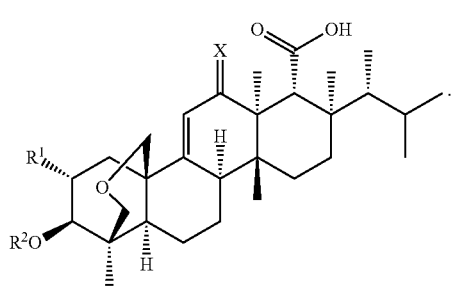

Ia

In a second embodiment of the invention, X is H, H, and the other variables are as provided for in Formula (I) above or in the first embodiment.

In a third embodiment of the invention, X is O, and the other variables are as provided for in Formula (I) above or in the first embodiment.

In a fourth embodiment of the invention, $R^2$ is a group of the following structure:

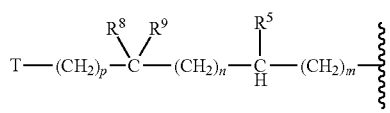

wherein T is $OR^{10}$ and the other variables are as provided for in Formula (I) above or in any of the first through third embodiments.

In a fifth embodiment of the invention, $R^2$ is a group of the following structure:

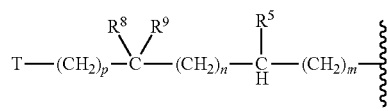

wherein T is $NR^6R^7$ and the other variables are as provided for in Formula (I) above or in any of the first through third embodiments.

In a first aspect of this embodiment, $R^2$ is a group of the following structure:

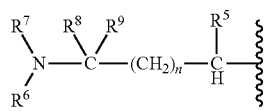

and the other variables are as provided for in Formula (I) above, or in any of the first through third embodiments.

In a second aspect of this embodiment, $R^2$ is a group of the following structure:

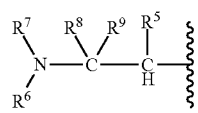

and the other variables are as provided for in Formula (I) above, or in any of the first through third embodiments.

In a further aspect, $R^5$ and $R^6$ may be joined together to form a ring providing $R^2$ of the following structure:

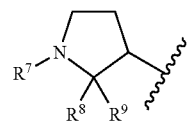

and the other variables are as provided for in Formula (I) above, or in any of the first through third embodiments.

In a third aspect of this embodiment, $R^2$ is a group of the following structure:

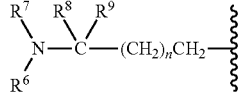

and the other variables are as provided for in Formula (I) above, or in any of the first through third embodiments.

In a fourth aspect of this embodiment, $R^2$ is a group of the following structure:

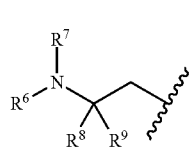

and the other variables are as provided for in Formula (I) above, or in an of the first through third embodiments.

In a further aspect, $R^6$ and $R^8$ may be joined together to form a ring providing $R^2$ of the following structure:

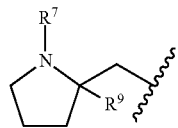

and the other variables are as provided for in Formula (I) above, or in any of the first through third embodiments.

In a fifth aspect of this embodiment, $R^2$ is a group of the following structure:

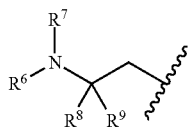

wherein
$R^6$ is H or $C_1$-$C_3$-alkyl;
$R^7$ is H or methyl;
$R^8$ is $C_1$-$C_5$-alkyl, $C_3$-$C_5$ cycloalkyl or $C_4$-$C_6$ cycloalkyl-alkyl;
$R^9$ is H or $C_1$-$C_3$-alkyl;
or $R^8$ and $R^9$ are optionally taken together to form a 5- to 6-membered saturated ring having 0-1 heteroatom selected from O or S; and the other variables are as provided for in Formula (I) above or in any of the first through third embodiments.

In a sixth aspect of this embodiment, $R^2$ is a group of the following structure:

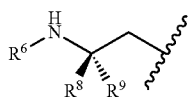

wherein
$R^6$ is H, methyl, ethyl or n-propyl;
$R^8$ is ethyl, i-propyl, t-butyl or 1-methylcyclopropyl;
$R^9$ is methyl or ethyl;
or $R^8$ and $R^9$ are optionally taken together to form a 6-membered saturated ring containing 0 or 1 oxygen atoms; and the other variables are as provided for in Formula (I) above or in any of the first through third embodiments.

In a seventh aspect of this embodiment, $R^2$ is selected from the group consisting of:

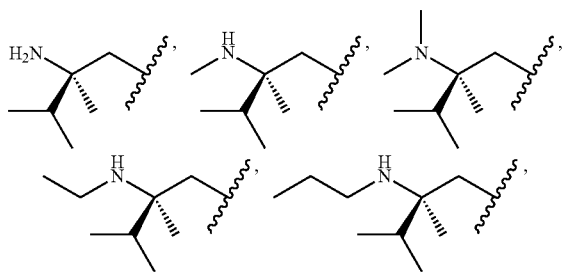

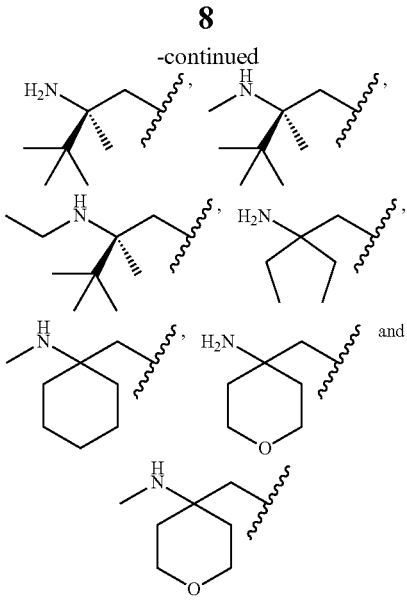

and the other variables are as provided for in Formula (I) above or in any of the first through third embodiments.

In a sixth embodiment of the invention, $R^1$ is a group of the following structure:

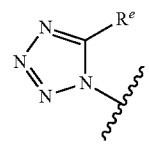

and the other variables are as provided for in Formula (I) above or in any of the first through fifth embodiments.

In a seventh embodiment of the invention, $R^1$ is a group of the following structure:

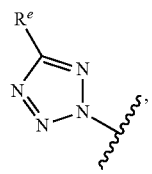

and the other variables are as provided for in Formula (I) above or in any of the first through fifth embodiments.

In a first aspect of this embodiment, $R^1$ is a group of the following structure:

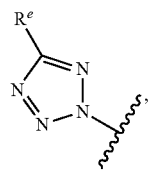

wherein $R^e$ is selected from the group consisting of:
a) H;
b) $NR^f R^g$;
c) $NHC(O)R^0$;

d) NHC(O)NR$^f$R$^g$;
e) NHC(O)OR$^0$;
f) OR$^0$;
g) C(O)R$^0$;
h) C(O)OR$^0$:
i) C(O)NR$^f$R$^g$;
j) C$_1$-C$_6$-alkyl optionally substituted with phenyl, pyridyl, OR$^0$, N(R$^0$)$_2$, CO$_2$R$^0$, C(O)N(R$^0$)$_2$, CF$_3$ or halogen;
k) C$_3$-C$_6$-cycloalkyl, optionally substituted with oxo, OR$^0$, N(R$^0$)$_2$, CO$_2$R$^0$ or C(O)N(R$^0$)$_2$; and
the other variables are as provided for in Formula (I) above or in any of the first through fifth embodiments.

In a second aspect of this embodiment, R$^1$ is a group of the following structure:

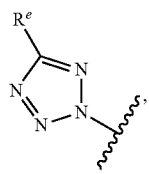

wherein R$^e$ is hydrogen or NR$^f$R$^g$, and R$^f$ and R$^g$ are as defined above and the other variables are as provided for in Formula (I) above or in any of the first through fifth embodiments.

In a third aspect of this embodiment, R$^1$ is selected from the following group:

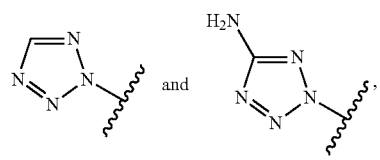 [SMILES: *n1ncnn1 ; *n1nnc(N)n1]

and the other variables are as provided for in Formula (I) above or in any of the first through fifth embodiments.

In one embodiment of the invention, a compound of Formula II, or a pharmaceutically acceptable salt thereof, is provided:

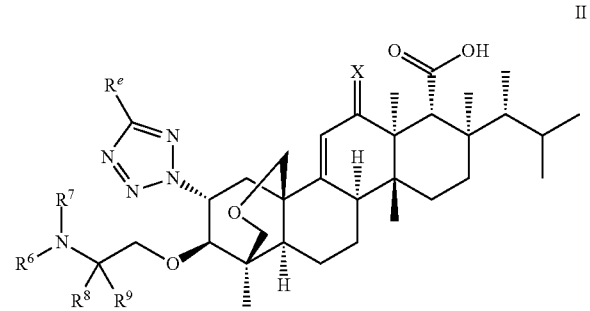

wherein:
X is O or H, H;
R$^e$ is hydrogen or NR$^f$R$^g$;
R$^f$ and R$^g$ are each independently hydrogen or methyl;
R$^6$ and R$^7$ are each independently hydrogen or C$_1$-C$_4$ alkyl;
R$^8$ is C$_1$-C$_4$ alkyl, C$_3$-C$_4$ cycloalkyl or C$_4$-C$_5$ cycloalkyl-alkyl;
R$^9$ is methyl or ethyl;

or R$^8$ and R$^9$ are optionally taken together to form a 5- to 6-membered saturated ring having 0-1 heteroatom selected from O or S.

In another embodiment of the invention, a compound of Formula IIa, or a pharmaceutically acceptable salt thereof, is provided:

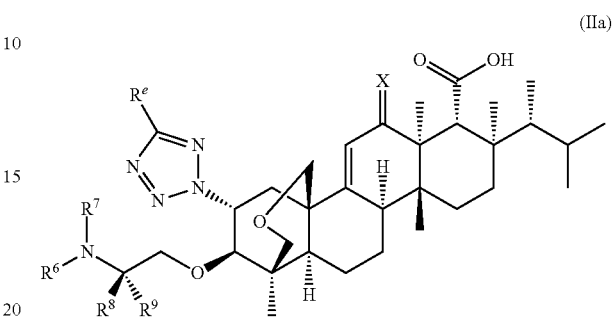

wherein the substituents are as provided for the general formula II.

In a first aspect of these embodiments (for formulas II and IIa), X is H, H, and the other substituents are as provided for the general formula II.

In a second aspect of these embodiments, R$^e$ is NH$_2$ or hydrogen and the other substituents are as provided in the first aspect or the general formula II.

In a third aspect of these embodiments, R$^e$ is NH$_2$ and the other substituents are as provided in the first aspect or the general formula II.

In a fourth aspect of these embodiments, R$^8$ is C$_1$-C$_4$ alkyl and R$^9$ is methyl; and the other substituents are as provided in the first to third aspects or the general formula II.

In a fifth aspect of these embodiments, R$^8$ is isopropyl or t-butyl, R$^9$ is methyl; and the other substituents are as provided in the first to third aspects or the general formula II.

In a sixth aspect of these embodiments, R$^6$ and R$^7$ are independently hydrogen or methyl and the other substituents are as provided in the first to fifth aspects or the general formula II.

In a seventh aspect of these embodiments, R$^6$ is hydrogen, methyl, ethyl or n-propyl, R$^7$ is hydrogen and the other substituents are as provided in the first to fifth aspects or the general formula II.

In another embodiment of the invention, the compound of the invention is selected from the exemplary species depicted in Examples 1 through 129 shown below (as the free base or a pharmaceutically acceptable salt thereof).

Other embodiments of the present invention include the following (where reference to a compound of formula (I) encompasses the various embodiments and aspects described above, as well as their pharmaceutically acceptable salts):

(a) A composition comprising a compound of Formula (I) and a carrier, adjuvant, or vehicle;

(b) A pharmaceutical composition comprising a compound of Formula (I) and a pharmaceutically acceptable carrier, adjuvant, or vehicle;

(c) The pharmaceutical composition of (b), further comprising a second therapeutic agent;

(d) The pharmaceutical composition of (c), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(e) The pharmaceutical composition of (d), wherein the second therapeutic agent is itraconazole, ketoconazole, miconazole, fluconazole, voriconazole, posaconazole, amphotericin B, flucytosine, anidulafungin, micafungin, or caspofungin;

(f) A pharmaceutical combination which is (1) a compound of Formula (I) and (2) a second therapeutic agent, wherein the compound of Formula (I) and the second therapeutic agent are each employed in an amount that renders the combination effective for treating or preventing fungal/bacterial infections;

(g) The combination of (f), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(h) The combination of (g), wherein the second therapeutic agent is itraconazole, ketoconazole, miconazole, fluconazole, voriconazole, posaconazole, amphotericin B, flucytosine, anidulafungin, micafungin, or caspofungin;

(i) A method of inhibiting (1,3)-β-D-glucan synthase in a subject in need thereof comprising administering to the subject an effective amount of a compound of Formula (I);

(j) A method of treating or preventing mycotic infections in a subject in need thereof comprising administering to the subject an effective amount of a compound of Formula (I);

(k) The method of (j), wherein the compound of Formula (I), is administered in combination, either sequentially or concurrently, with a second therapeutic agent effective against fungal/bacterial infections;

(l) The method of (k), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(m) The method of (1), wherein the second therapeutic agent is itraconazole, ketoconazole, miconazole, fluconazole, voriconazole, posaconazole, amphotericin B, flucytosine, anidulafungin, micafungin, or caspofungin;

(n) A method of inhibiting (1,3)-β-D-glucan synthase in a subject in need thereof comprising administering to the subject a pharmaceutical composition of (b), (c), (d), or (e) or the combination of (f), (g) or (h); and (o) A method of treating or preventing mycotic infections in a subject in need thereof comprising administering to the subject a pharmaceutical composition of (b), (c), (d), or (e) or the combination of (f), (g) or (h).

The present invention also includes a compound of the present invention (i) for use in, (ii) for use as a medicament for, or (iii) for use in the preparation of a medicament for: (a) inhibiting (1,3)-β-D-glucan synthase in a subject in need thereof, or (b) treating or preventing mycotic infections. In these uses, the compounds of the present invention can optionally be employed in combination, either sequentially or concurrently, with one or more therapeutic agents effective against fungal and/or bacterial infections.

In the embodiments of the compound as provided above, it is to be understood that each embodiment may be combined with one or more other embodiments, to the extent that such a combination provides a stable compound and is consistent with the description of the embodiments. It is further to be understood that the embodiments of compositions and methods provided as (a) through (o) above are understood to include all embodiments of the compounds, including such embodiments as result from combinations of embodiments of the compound.

In addition, it is understood that, in the description of embodiments of the compounds as set forth above, indicated substitutions are included only to the extent that the substitutents provide stable compounds consistent with the definition.

Additional embodiments of the invention include the pharmaceutical compositions, combinations and methods set forth in (a)-(o) above and the uses set forth in the preceding paragraph, wherein the compound of the present invention employed therein is a compound of one of the embodiments or aspects of the compounds described above. In all of these embodiments or aspects as well as those described hereinbelow, the compound may optionally be used in the form of a pharmaceutically acceptable salt or hydrate when appropriate.

The present compounds (including pharmaceutical acceptable salt and/or hydrate forms) have antimicrobial (e.g., antifungal) activities against yeasts and fungi, including one or more of the following: *Acremonium*, *Absidia* (e.g., *Absidia corymbifera*), *Alternaria*, *Aspergillus* (e.g., *Aspergillus clavatus*, *Aspergillus flavus*, *Aspergillus fumigatus*, *Aspergillus nidulans*, *Aspergillus niger*, *Aspergillus terreus*, and *Aspergillus versicolor*), *Bipolaris*, *Blastomyces* (e.g., *Blastomyces dermatitidis*), *Blastoschizomyces* (e.g., *Blastoschizomyces capitatus*), *Candida* (e.g., *Candida albicans*, *Candida glabrata* (*Torulopsis glabrata*), *Candida guilliermondii*, *Candida kefyr*, *Candida krusei*, *Candida lusitaniae*, *Candida parapsilosis*, *Candida pseudotropicalis*, *Candida stellatoidea*, *Candida tropicalis*, *Candida utilis*, *Candida lipolytica*, *Candida famata* and *Candida rugosa*), *Cladosporium* (e.g., *Cladosporium carrionii* and *Cladosporium trichloides*), *Coccidioides* (e.g., *Coccidioides immitis*), *Cryptococcus* (e.g., *Cryptococcus neoformans*), *Curvularia*, *Cunninghamella* (e.g., *Cunninghamella elegans*), *Dermatophyte*, *Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Histoplasma* (e.g., *Histoplasma capsulatum* var. *capsulatum*), *Malassezia* (e.g., *Malassezia furfur*), *Microsporum* (e.g., *Microsporum canis* and *Microsporum gypseum*), *Mucor*, *Paracoccidioides* (e.g., *Paracoccidioides brasiliensis*), *Penicillium* (e.g., *Penicillium marneffei*), *Phialophora*, *Pityrosporum ovale*, *Pneumocystis* (e.g., *Pneumocystis carinii*), *Pseudallescheria* (e.g., *Pseudallescheria boydii*), *Rhizopus* (e.g., *Rhizopus microsporus* var. *rhizopodiformis* and *Rhizopus oryzae*), *Saccharomyces* (e.g., *Saccharomyces cerevisiae*), *Scedosporium* (e.g., *Scedosporium apiosperum*), *Scopulariopsis*, *Sporothrix* (e.g., *Sporothrix schenckii*), *Trichoderma*, *Trichophyton* (e.g., *Trichophyton mentagrophytes* and *Trichophyton rubrum*), and *Trichosporon* (e.g., *Trichosporon asahii*, *Trichosporon beigelii* and *Trichosporon cutaneum*). The present compounds may also be used to treat infections caused by protozoa such as *Toxoplasma*, *Cryptosporidium*, *Leishmania*, *Tripanosoma*, *Giardia* and *Trichomonas*. The present compounds are believed to be not only useful against organisms causing systemic human pathogenic mycotic infections, but also useful against organisms causing superficial fungal infections such as *Trichoderma* sp. and other *Candida* spp. The compounds of the present invention are believed to be particularly effective against *Aspergilius flavus*, *Aspergillus*

*fumigatus, Candida albicans, Candida parapsilosis, Cryptococcus neoformans, Saccharomyces cerevisiae,* and *Trichophyton mentagrophytes.*

In view of their antifungal activity, compounds of Formula (I) are useful for the treatment and/or prevention of one or more of a variety of superficial, cutaneous, subcutaneous and systemic mycotic infections in skin, eye, hair, nail, oral mucosa, gastrointestinal tract, bronchus, lung, endocardium, brain, meninges, urinary organ, vaginal portion, oral cavity, ophthalmus, systemic, kidney, bronchus, heart, external auditory canal, bone, nasal cavity, paranasal cavity, spleen, liver, hypodermal tissue, lymph duct, gastrointestine, articulation, muscle, tendon, interstitial plasma cell in lung, blood, and so on.

Therefore, compounds of the present invention are useful for preventing and treating one or more of various infectious diseases, such as dermatophytosis (e.g., trichophytosis, ringworm or tinea infections), athletes foot, paronychia, pityriasis versicolor, erythrasma, intertrigo, fungal diaper rash, candida vulvitis, candida balanitis, otitis externa, candidiasis (cutaneous and mucocutaneous), chronic mucocandidiasis (e.g. thrush and vaginal candidiasis), cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and fungemia. The present compounds may also be used as prophylactic agents to prevent systemic and topical fungal infections. Use as prophylactic agents may, for example, be appropriate as part of a selective gut decontamination regimen in the prevention of infection in immuno-compromised patients (e.g. AIDS patients, patients receiving cancer therapy or transplant patients). Prevention of fungal overgrowth during antibiotic treatment may also be desirable in some disease syndromes or iatrogenic states.

Examples of azoles that may be used in combination with the present compounds include, but are not limited to, fluconazole, voriconazole, itraconazole, ketoconazole, miconazole, ravuconazole, detoconazole, clotrimazole, and posaconazole. Examples of polyenes that may be used in combination with the present compounds include, but are not limited to, amphotericin B, nystatin, liposamal and lipid forms thereof such as ABELCET, AMBISOME, and AMPHOCIL. Examples of purine or pyrimidine nucleotide inhibitors that may be used in combination with the present compounds include, but are not limited to, flucytosine or polyxins such as nikkomycines, in particular nikkomycine Z or nikkomycine X. Another class of therapeutic agents that may be used in combination with the present compounds includes chitin inhibitors. Examples of elongation factor inhibitors that may be used in combination with the present compounds include, but are not limited to, sordarin and analogs thereof. Examples of pneumocandin or echinocandin derivatives that may be used in combination with the present compounds include, but are not limited to, cilofungin, anidulafungin, micafungin, and caspofungin. Examples of mannan inhibitors that may be used in combination with the present compounds include but are not limited to predamycin. Examples of bactericidal/permeability-inducing (BPI) protein products that may be used in combination with the present compounds include but are not limited to XMP.97 and XMP.127. Examples of immunomodulators that may be used in combination with the present compounds include, but are not limited to, an interferon, (e.g., IL-1, IL-2, IL-3 and IL-8), defensines, tacrolimus and G-CSF (Granulocyte-colony stimulating factor).

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "cycloalkyl" refers to any cyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl.

The term "cycloalkyl-alkyl" (or equivalently "alkyl-cycloalkyl") as used herein, refers to a system that includes an alkyl portion as described above and also includes a cycloalkyl portion as described above. Attachment to a "cycloalkyl-alkyl" (or "alkyl-cycloalkyl") may be through either the cycloalkyl or the alkyl portion. The specified number of carbon atoms in "cycloalkyl-alkyl" systems refers to the total number of carbon atoms in both the alkyl and the cycloalkyl parts. Examples of $C_4$-$C_7$ cycloalkyl-alkyl include but are not limited to methylcyclopropyl, dimethylcyclopropyl, methylcyclobutyl, trimethylcyclobutyl, ethylcyclopentyl, methylcyclohexyl, cyclopropylmethyl, cyclopropylethyl, cyclobutylmethyl, cyclobutylpropyl, cyclopentylethyl and cyclohexylmethyl.

The term "alkenyl" refers to a straight or branched-chain acyclic unsaturated hydrocarbon having a number of carbon atoms in the specified range and containing at least one double bond. Thus, for example, "$C_2$-$C_3$ alkenyl" refers to vinyl, (1Z)-1-propenyl, (1E)-1-propenyl, 2-propenyl, or isopropenyl.

The term "halogen" (or "halo") refers to fluorine, chlorine, bromine and iodine (alternatively referred to as fluoro, chloro, bromo, and iodo).

The term "oxo" means =O and as used herein, the term "imino" means =$NR^0$, wherein $R^0$ is as previously defined.

As used herein, the term "or," as used herein, denotes alternatives that may, where appropriate, be combined.

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

Any of the various cycloalkyl and heterocyclic/heteroaryl rings and ring systems defined herein may be attached to the rest of the compound at any ring atom (i.e., any carbon atom or any heteroatom) provided that a stable compound results. Suitable 5- or 6-membered heteroaryl rings include, but are not limited to, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. Suitable 9- or 10-membered heteroaryl rings include, but are not limited to, quinolinyl, isoquinolinyl, indolyl, indazolyl, benzimidazolyl, benztriazoyl, imidazopyridinyl, triazolopyridinyl, and imidazopyrimidinyl. Suitable 4- to 6-membered heterocyclyls include, but are not limited to, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiadiazinanyl, tetrahydropyranyl, tetrahydrothiopyranyl, and dioxanyl.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). Reference to a compound also includes stable complexes of the compound such as a stable hydrate.

As a result of the selection of substituents and substituent patterns, certain of the compounds of the present invention can have asymmetric centers and can occur as mixtures of stereoisomers, or as individual diastereomers, or enantiomers. Unless otherwise indicated, all isomeric forms of these compounds, whether isolated or in mixtures, are within the scope of the present invention. Also included within the scope of the present invention are tautomeric forms of the present compounds as depicted.

When any variable occurs more than one time in any constituent or in Formula (I) or in any other formula depicting and describing compounds of the invention, its definition on each occurrence is independent of its definition at every other occurrence. Also, combinations of substituents and/or variables are permissible only if such combinations result in stable compounds.

The term "substituted" includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., an aryl, a cycloalkyl, a heteroaryl, or a heterocyclyl) provided such ring substitution is chemically allowed and results in a stable compound.

A bond terminated by a wavy line is used herein to signify the point of attachment of a substituent group or partial structure. This usage is illustrated by the following example:

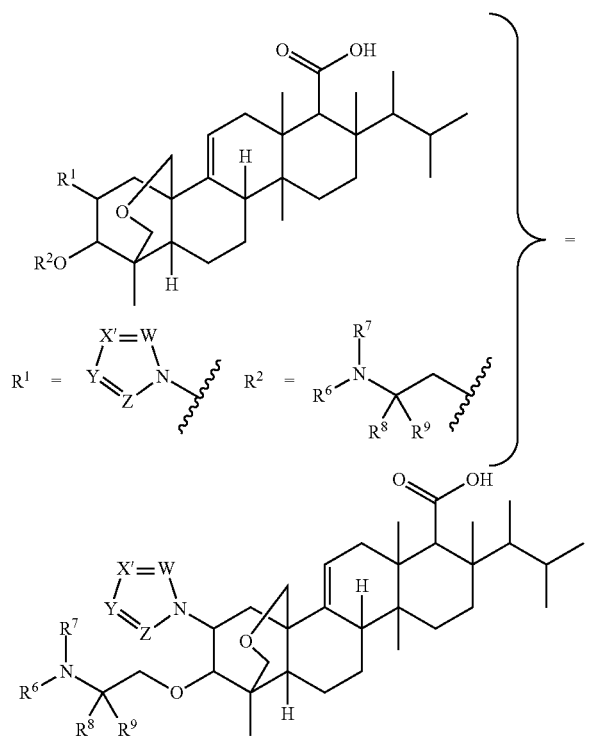

The compounds of this invention are also useful in the preparation and execution of screening assays for antifungal compounds. For example, the compounds of this invention are for isolating mutants, which are excellent screening tools for more powerful antifungal compounds.

All compounds of the present invention may be administered in the form of "pharmaceutically acceptable salts" or hydrates as appropriate. Other salts may, however, be useful in the preparation of the compounds according to the invention or of their pharmaceutically acceptable salts. For example, when the compounds of the present invention contain a basic amine group, they may be conveniently isolated as trifluoroacetic acid salts (e.g. following HPLC purification). Conversion of the trifluoroacetic acid salts to other salts, including pharmaceutically acceptable salts, may be accomplished by a number of standard methods known in the art. For example, an appropriate ion exchange resin may be employed to generate the desired salt. Alternatively, conversion of a trifluoroacetic acid salt to the parent free amine may be accomplished by standard methods known in the art (e.g. neutralization with an appropriate inorganic base such as $NaHCO_3$). Other desired amine salts may then be prepared in a conventional manner by reacting the free base with a suitable organic or inorganic acid. Representative pharmaceutically acceptable quaternary ammonium salts include the following: hydrochloride, sulfate, phosphate, carbonate, acetate, tartrate, citrate, malate, succinate, lactate, stearate, fumarate, hippurate, maleate, gluconate, ascorbate, adipate, gluceptate, glutamate, glucoronate, propionate, benzoate, mesylate, tosylate, oleate, lactobionate, laurylsulfate, besylate, caprylate, isetionate, gentisate, malonate, napsylate, edisylate, pamoate, xinafoate, napadisylate, hydrobromide, nitrate, oxalate, cinnamate, mandelate, undecylenate, and camsylate. Many of the compounds of the invention carry an acidic carboxylic acid moiety, in which case suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "administration" and variants thereof (e.g., "administering" a compound) in reference to a compound of the invention mean providing the compound or a prodrug of the compound to the subject in need of treatment. When a compound of the invention or a prodrug thereof is provided in combination with one or more other active agents (e.g., other antifungal/antibacterial agents useful for treating fungal/bacterial infections), "administration" and its variants are each understood to include concurrent and sequential provision of the compound or prodrug and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented or for reducing the likelihood of occurrence. The term also includes herein the amount of active compound sufficient to inhibit (1,3)-β-D-glucan synthase and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting (1,3)-β-D-glucan synthase or preventing or treating fungal infection, the compounds of the present invention, optionally in the form of a salt or a hydrate, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (e.g., nasal or buccal inhalation spray, aerosols from metered dose inhalator, and dry powder inhalator), by nebulizer, ocularly, topically, transdermally, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in Remington's Pharmaceutical Sciences, 20$^{th}$ edition, edited by A. R. Gennaro, Mack Publishing Co., 2000.

The compounds of this invention can be administered, e.g., orally or intravenously, in a dosage range of, for example, 0.001 to 1000 mg/kg of mammal (e.g., human) body weight per day in a single dose or in divided doses. An example of a dosage range is 0.01 to 500 mg/kg body weight per day orally or intravenously in a single dose or in divided doses. Another example of a dosage range is 0.1 to 100 mg/kg body weight per day orally or intravenously in single or divided doses. For oral administration, the compositions can be provided in the form of tablets or capsules containing, for example, 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention also includes processes for making compounds of Formula (I). The compounds of the present invention may be prepared according to the following reaction schemes and examples, or modifications thereof, from starting material enfumafungin. Enfumafungin is a natural product produced from a fungus strain of *Hormonema* sp. (deposited under the Budapest Treaty in the culture collection of the American Type Culture Collection and assigned accession number ATCC 74360) that was isolated from living leaves of an unidentified shrub collected in Navalquejigo, province of Madrid, Spain, as described in U.S. Pat. No. 5,756,472, the contents of which are hereby incorporated by reference in its entirety.

The following two structures illustrate the systematic name and numbering conventions employed for the compounds of the present invention.

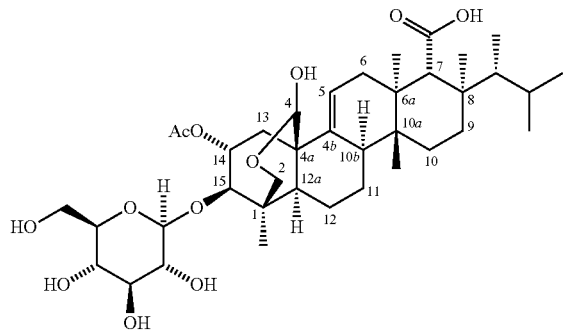

(1S,4aR,6aS,7R,8R,10aR,10bR,12aR,14R,15R)-14-(acetyloxy)-8-[(1R)-1,2-dimethylpropyl]-15-(β-D-glucopyranosyloxy)-1,6,6a,7,8,9,10,10a,10b,11,12,12a-dodecahydro-4-hydroxy-1,6a,8,10a-tetramethyl-4H-1,4a-propano-2H-phenanthro[1,2-c]pyran-7-carboxylic acid (common name: enfumafungin)

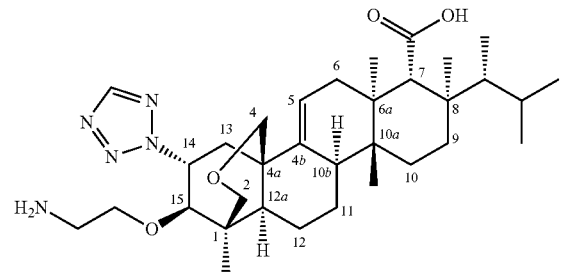

(1S,4aR,6aS,7R,8R,10aR,10bR,12aR,14R,15R)-15-(aminoethoxy)-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

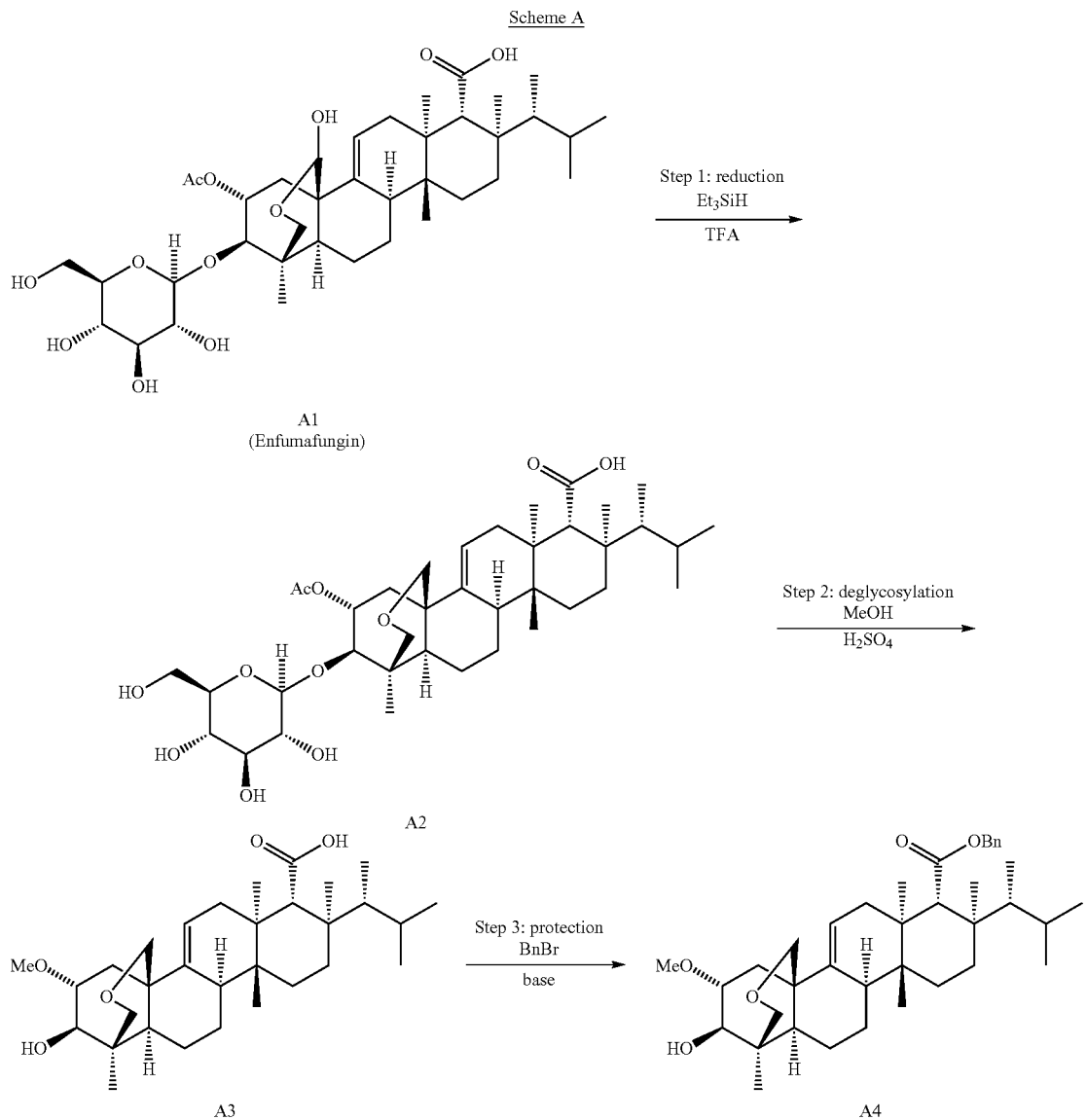

Scheme A illustrates a method for deglycosylation of the natural product enfumafungin and additional modification to prepare the molecule for further elaboration. In a first step, the lactol group of enfumafungin is reduced by treatment with a suitable reducing agent such as triethylsilane under acidic conditions (e.g. trifluoroacetic acid) to give compound A2. Removal of the glucose moiety may be accomplished by heating A2 in methanol in the presence of a strong acid such as sulfuric acid. Under these conditions, the acetoxy group at C14 is also replaced by methoxy to produce the methyl ether compound A3. Other methods for deglycosylation of A2 and related compounds are also known (International Patent Publication No. WO 2007/127012; and Shafiee et al., *J. Molecular Catalysis B: Enzymatic,* 2001(16), pp. 27-32). Next, selective protection of the carboxylic acid of A3 may by accomplished by treatment with benzyl bromide in the presence of a suitable base such as sodium bicarbonate or potassium carbonate to give A4. Other suitable protecting groups known in the art may also be employed.

Schemes B to E illustrate methods of introducing the $R^2$ substituent on the C15 hydroxy group. Additional methods are also described in International Patent Publication No. WO 2007/127012. In the Schemes the variables $R^5$, $R^6$, $R^7$, $R^8$ and $R^9$ are as previously defined or are precursor groups thereto. Additional variables are as defined in the individual schemes.

Scheme B
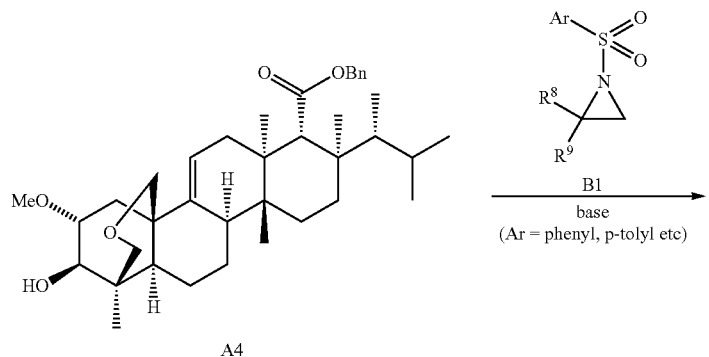
A4
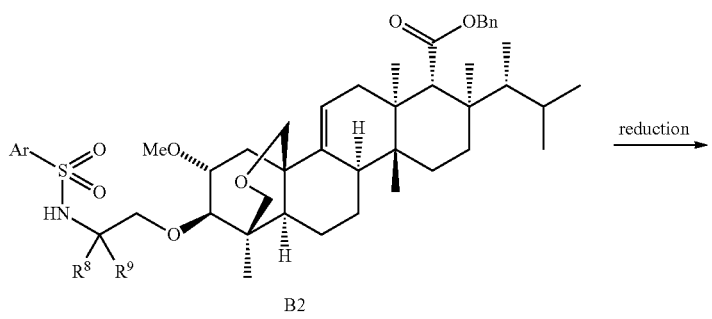
B2
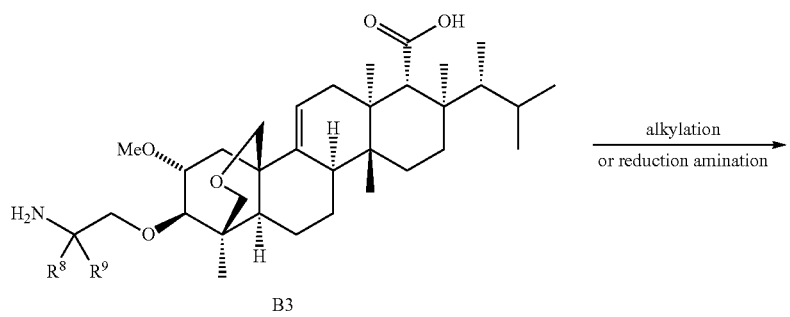
B3
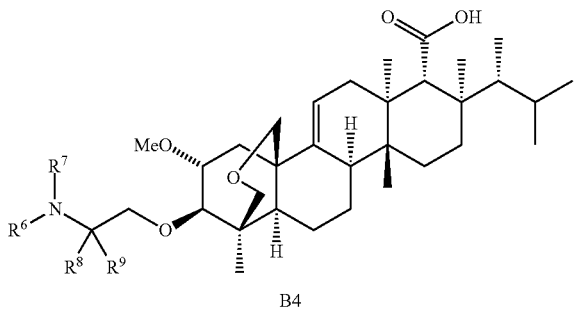
B4

As shown in Scheme B, reaction of A4 with an N-sulfonyl aziridine (B1) in the presence of a suitable base such as potassium hydride, sodium hydride or potassium tert-pentylate and optionally in the presence of an appropriate cation complexing agent such as 18-Crown-6 or 15-Crown-5, gives intermediate B2. Aziridines B1 are prepared by methods known in the art (see e.g. *Acc. Chem. Res.* 2006, 39, 194-206; *Tetrahedron* 2004, 60, 2701-2743; *J. Am. Chem. Soc.* 1998, 120, 6844; *Org. Lett.* 1999, 5, 783-786; *Chem. Soc. Rev.* 2002, 31, 247; *Synthesis* 2000, 1347; *ARKIVOC* 2007, 4, 304-311; *Tetrahedron: Asymmetry* 1997, 8, 1693; *Chem. Commun.* 2006, 1833-1835.) and as exemplified further below. Removal of the N-sulfonyl group of B2 is accomplished by dissolving metal reduction with sodium or lithium in liquid ammonia employing a suitable co-solvent such as dimethoxyethane or tetrahydrofuran. This step also conveniently deprotects the carboxylic acid when it is protected as a benzyl ester, giving intermediate B3. It will be appreciated by one skilled in the art that other protecting group strategies may also be employed. Further substitution of the amino group of B3 may be carried-out at this point by standard methods known in the art such as alkylation or reductive amination to give compound B4.

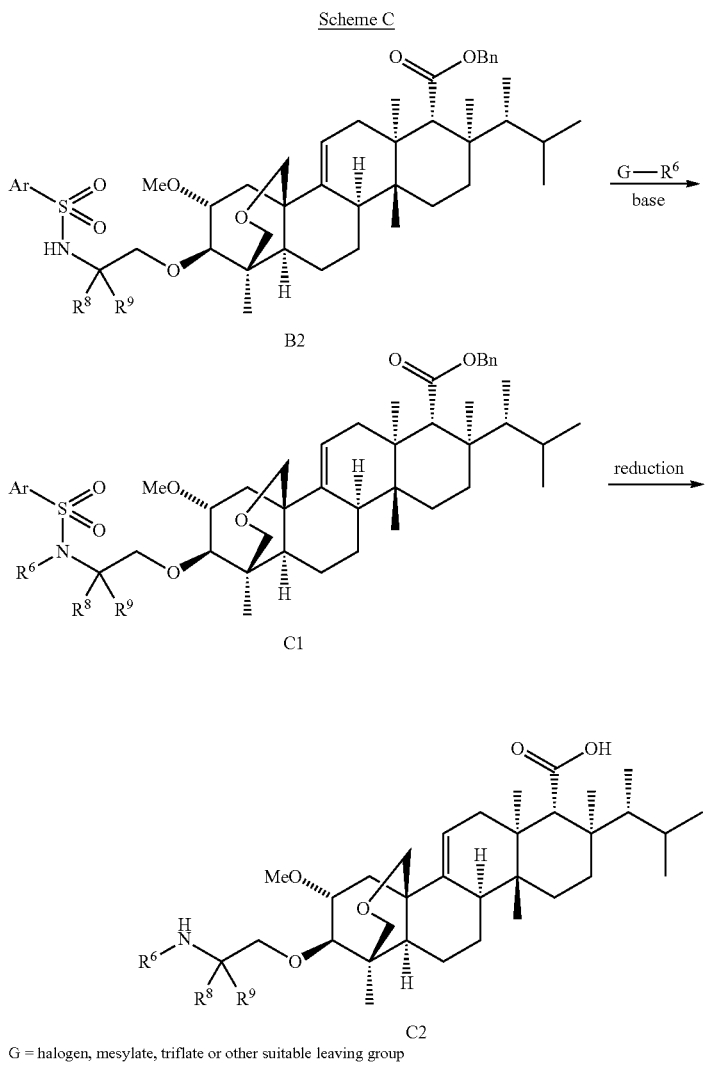

G = halogen, mesylate, triflate or other suitable leaving group

Scheme C illustrates an alternative method of substituting the amino group by alkylating the N-sulfonyl intermediate B2 with an appropriate alkylating agent such as methyl iodide, ethyl iodide or allyl bromide in the presence of a suitable base such as sodium hydride to give C1. Dissolving metal reduction as described previously for B2 then gives C2. The synthesis of Scheme C is particularly useful for introducing a single substitution on the aminoether nitrogen. In Scheme C introduction of an $R^6$ group is illustrated, but it will be apparent to one skilled in the art that the synthesis would work equally well for introduction of an $R^7$ group.

Scheme D

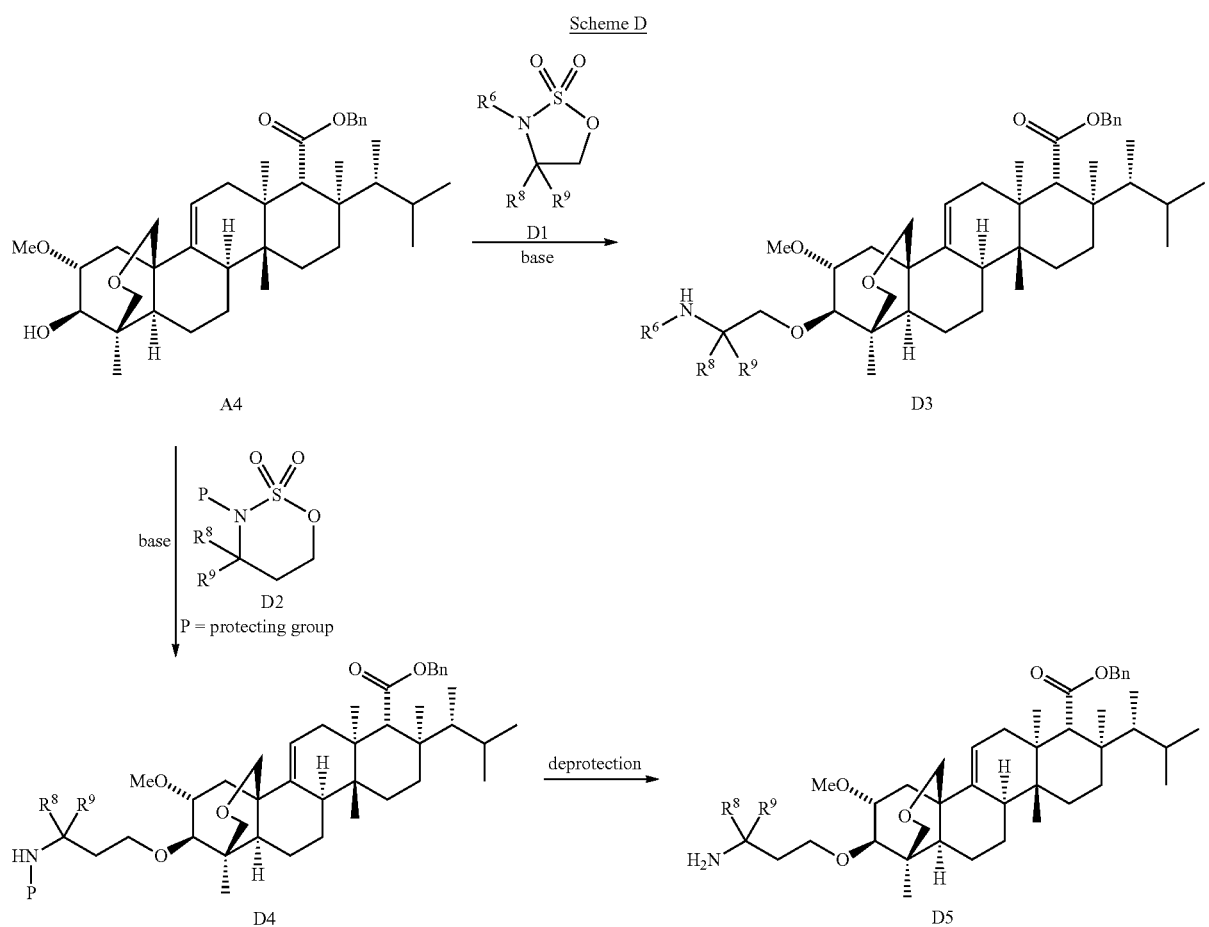

Scheme D describes additional methods for introducing the $R^2$ group. Reaction of A4 with the 5-membered cyclic sulfamidate reagent D1 gives intermediate D3. This reaction is carried-out under conditions analogous to those described in Scheme B for coupling with aziridine B1. An acidic aqueous work-up is carried-out which cleaves the initial N-sulfated product to give the amine D3. Similarly, reaction of A4 with the 6-membered cyclic sulfamidate reagent D2 gives D4 and after removal of the amine protecting group the aminopropyl ether intermediate D5 is obtained. Suitable protecting groups for D2 and D4 include t-butyloxycarbonyl (Boc) and benzyloxycarbonyl (Cbz). The cyclic sulfamidate reagents D1 and D2 are prepared by methods known in the art (e.g. Tetrahedron 2003, 59, 2581-2616; J. Org. Chem. 2004, 69, 3610-3619; Angew. Chem. Int. Ed. 2005, 44, 3518-3520) and as exemplified further below. While in Scheme D the synthesis of D3 with $R^6$ substitution on the nitrogen of the aminoether is illustrated, it will be apparent to one skilled in the art that the method would work equally well for the synthesis of a D3 compound with $R^7$ substitution on the nitrogen of the aminoether by employing the appropriately substituted D1 compound.

Scheme E

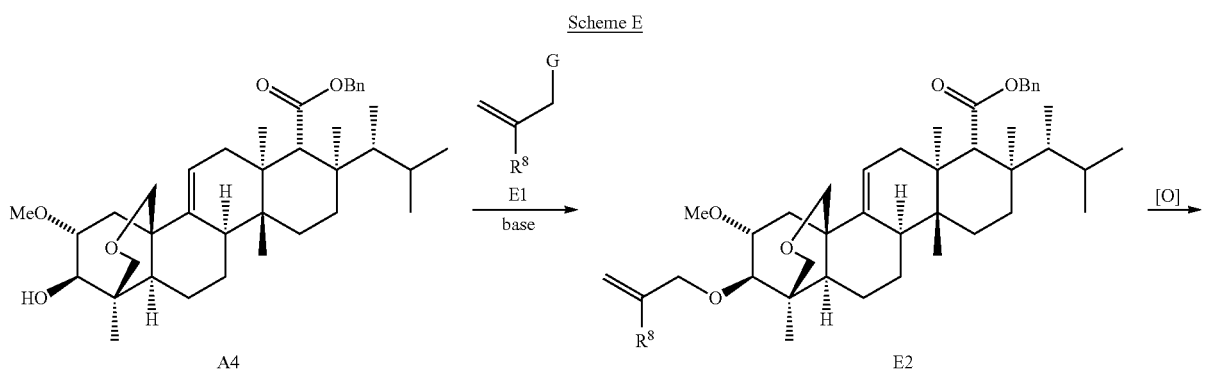

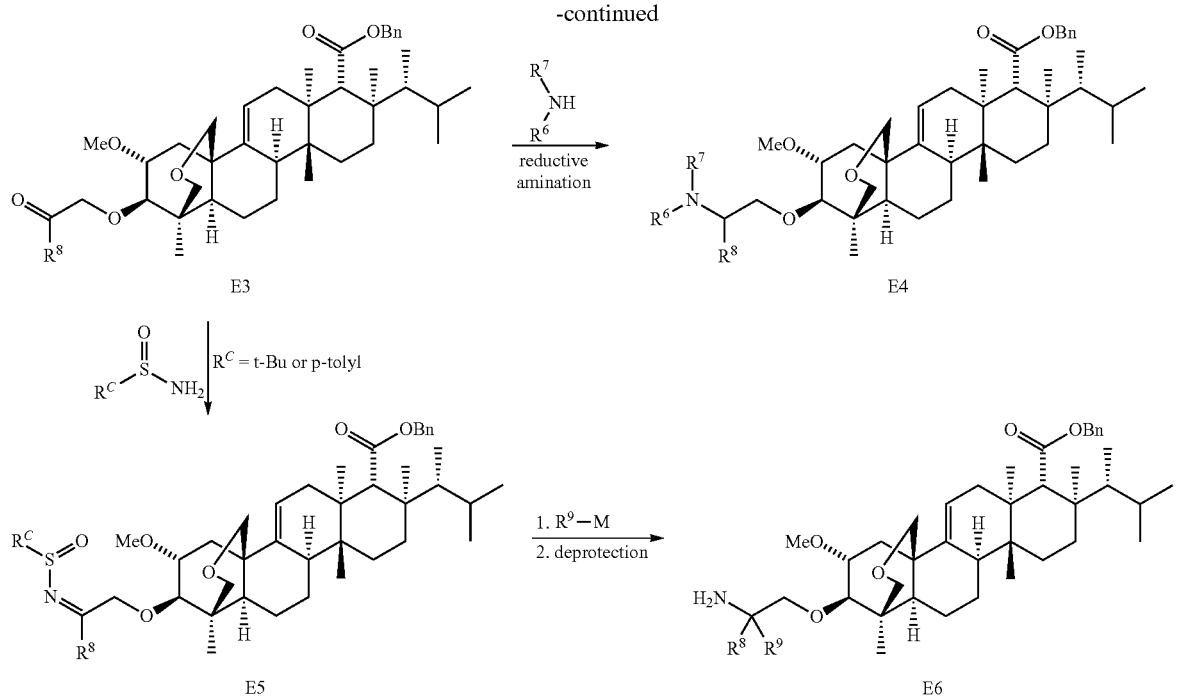

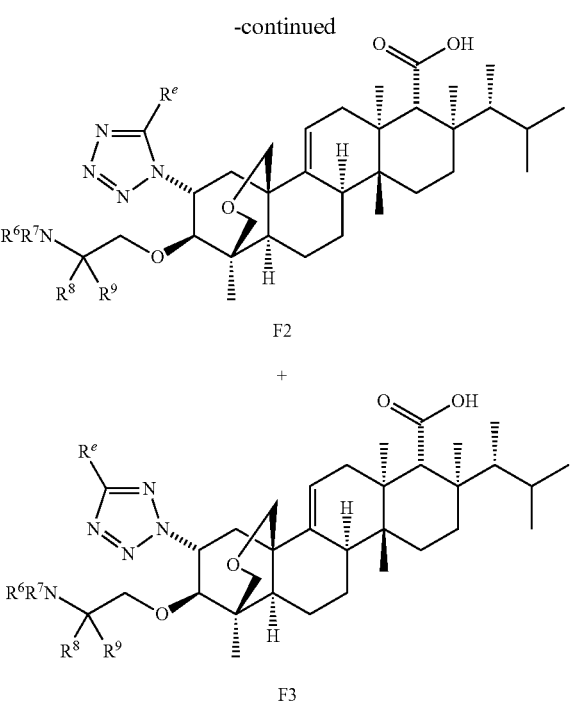

Scheme E illustrates additional methods for introduction of the $R^2$ substitution on the C15 hydroxy group. Alkylation of A4 with an allylic halide or other suitably activated allylic species (E1) gives the allylic ether E2. Suitable bases for this reaction are sodium hydride or potassium hydride and the like. Oxidative cleavage of the alkenyl group under standard conditions (e.g. $OsO_4/NaIO_4$) gives the corresponding ketone (or aldehyde) E3. Reductive amination of E3 by standard methods (e.g. $R^6R^7NH$, $NaBH_3CN$, AcOH, MeOH, THF) then gives the aminoether E4. Alternatively, E3 can be converted to the sulfinylimine E5 by reaction with an alkyl- or arylsulfinylamide in the presence of a dehydrating agent such as copper sulfate or titanium ethoxide. Reaction of E5 with an alkyllithium reagent (e.g. $R^9Li/Me_3Al$), alkyl Grignard reagent (e.g. $R^9MgBr$) or (for $R^9$=H) a metal hydride reducing agent (e.g. lithium triethylborohydride) followed by acid treatment (e.g. HCl/MeOH) to cleave the N-sulfinyl group gives E6. In one useful variation of this synthesis Scheme, use of an enantiomerically pure alkyl- or arylsulfinylamide reagent for this sequence allows for control of the stereochemistry of the substitution adjacent to the amine in E6 (see e.g. *Acc. Chem. Res.* 2002, 35, 984-995). In another useful variation of this Scheme, the roles of $R^8$ and $R^9$ as illustrated in Scheme E may be reversed. In another useful variation of Scheme E, it will be appreciated by one skilled in the art that at the stage of intermediate E3, an $R^5$ substituent may be introduced by alkylation at the position adjacent to the carbonyl group using conventional conditions and reagents [e.g. $R^5I$, $LiN(i-Pr)_2$].

Scheme F

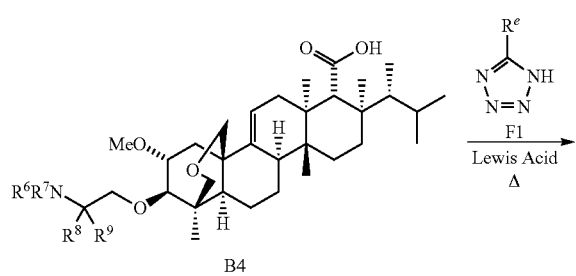

Scheme F illustrates the introduction of a tetrazole heterocycle at the C14 position. In the Scheme, the variables $R^e$, $R^6$, $R^7$, $R^8$ and $R^9$ are as previously defined or are precursor groups thereto. The displacement reaction between B4 and the tetrazole derivative F1 is promoted by a Lewis acid reagent. Suitable Lewis acid reagents include boron trifluoride diethyl etherate, copper trifluoromethansulfonate, zinc trifluoromethanesulfonate and the like. The reaction is conducted in a non-coordinating aprotic solvent such as 1,2-dichloroethane at a temperature of between about 20° C. and about 100° C. This displacement reaction generally occurs with retention of configuration at C14, possibly due to participation by the proximal bridging ether oxygen. Two regioisomeric products F2 and F3 may be formed in this reaction. When both isomers are formed, it is often possible and desirable to separate them chromatographically or by other means. The ratio of the two isomers may vary depending on the substituent group $R^e$, but often F3 is the predominant isomer. Depending on the desired $R^e$ substituent, the tetrazole derivatives F1 are generally readily available either from commercial sources or through preparation by known literature methods. In Scheme F, introduction of the tetrazole heterocycle is exemplified by starting with intermediate B4, but it is understood that the same method works equally well starting with many other intermediates including but not limited to B3, C2, D3, D5, E4, and E6. In addition, many of the intermediates and final compounds described in International Patent Publication No. WO 2007/127012 may also serve as starting materials for introduction of tetrazole groups as described in Scheme F.

The antifungal activity of the present compounds can be demonstrated by various assays known in the art, for example, by their glucan synthesis inhibitory activity ($IC_{50}$), minimum inhibitory concentration (MIC-100) or minimum prominent inhibition (MIC-50) against yeasts and minimum effective concentration (MEC) against filamentous moulds and dermatophytes in a broth microdilution assay, or in vivo anti-*Candida* activity in a mouse (TOKA). Compounds provided in the Examples were generally found to inhibit the growth of *Candida* spp. in the range of <0.03-32 µg/mL or to give an MEC against *Aspergillus fumigatus* in the range of <0.03-32 µg/mL.

Glucan Synthase Inhibition

The in vitro evaluation of glucan synthase inhibitory activity of compounds was measured in a polymerization assay in 96-well format. Each well contained 100 µL of $^3$H-UDPG at 0.5 mM (6000 to 8000 dpm/nmol), 50 mM HEPES pH 7.5 (Sigma), 10% w/v glycerol (Sigma), 1.5 mg/mL bovine serum albumin (Sigma A 9647. Lot 44H0190), 25 mM KF (Fisher), 1 mM EDTA (Gibco ULTRAPURE), 25 µM GTP-γ-S, enzyme sufficient to give 3 to 6 nmoles incorporation during the 60 min incubation at 22° C., and test compound added from wells in 3-fold serial dilutions in 100% DMSO (1 µL/well). The reaction was stopped by the addition of 100 µL of 20% trichloroacetic acid. Plates were chilled for a minimum of 10 min, and precipitated glucan collected by filtration on GF/C plates (Packard UNIFILTER®-96), washed with 5 cycles of water (about 1 mL/well each cycle) using a Packard FILTERMATE HARVESTER. 40 µL/well scintillation fluid (Packard ULTIMA GOLD TM-XR) was added and the sealed plates counted in a WALLAC BETA counter in top-counting mode at an efficiency of approximately 40%.

Stock solutions were stored at 10 mg/mL in DMSO at −20° C. For each new enzyme preparation, the initial titration performed started at 1 mg/mL, which was prepared by making a 10-fold dilution in DMSO (5 µL to 50 µL). 40 µL of this stock was placed in column 12 of a round-bottomed 96-well microtiter plate. 40 µL DMSO was added to columns 1 to 11 in the same row and ten 3-fold serial dilutions performed, by transferring 20 µL from column 12 to column 11 etc., with 4 mixings before each transfer. No test compound was transferred to from column 2 to column 1. Duplicate aliquots of 1 µL of all 12 dilutions were then transferred to the side walls of a 96-well Bioblock 1.1 mL plate (Fisher brand) to create two rows. Graphs of the primary data were created in PRISM software (the average of two determinations) using PRISM's curve fitting program (sigmoidal dose response non-linear regression). The amount of compound required to inhibit glucan synthase activity by 50% in this assay ($IC_{50}$-ng/mL) was calculated.

Routine analysis was performed with glucan synthase (GS) prepared from *Candida albicans* MY1055 by the following procedure: MY1055 was grown in 10 liters YPD medium (10 g yeast extract, 20 g tryptone, 20 g glucose per liter) with vigorous shaking at 30° C., to early stationary phase. Cells were harvested by centrifugation, the pellet was washed and frozen at −70° C. until breakage. Thawed pellets were shaken with an equal volume of breakage buffer (50 mM HEPES pH 7.4, 10% glycerol, 1 mM EDTA, 1 mM PMSF, 1 mM DTT) and 4 times their weight of 0.5 mm acid washed glass beads for 2 hours at 4° C. Extent of breakage was assessed visually at 40× magnification. After low speed centrifugation to remove cell debris, the supernatant was centrifuged at 100,000×g for 60 min. to separate membranes plus ribosomes from cytoplasmic components. Membranes were further washed two additional times with breakage buffer using the same centrifugation conditions and finally suspended in breakage buffer at 25 to 30 mg/mL protein (Biorad) for storage at −70° C. Extraction of GS activity from membranes was performed at a protein concentration of 5 mg/mL in extraction buffer (50 mM $NaPO_4$ pH 7.5, 0.1 M KCl, 0.1M Na citrate, 20% glycerol, 5 µM GTP-γ-S, 1 mM DTT, 1 mM PMSF, 3 µg/mL pepstatin) plus 0.25% W1 by gentle mixing at 4° C. for 60 min, followed by centrifugation at 100,000×g for 60 min. After centrifugation, clear supernatant was removed from a pellet consisting of a hard layer usually with small amounts of gelatinous unextracted membranes above it.

Trapping was initiated immediately by 5-fold dilution in trapping buffer (50 mM HEPES pH 7.5, 10 mM KF, 1 mM EDTA, 2 mg/mL BSA) plus 2.5 mM UDPG and 10 µM GTP-γ-S. After incubation at 25° C. for 60 to 90 minutes, glucan was harvested by low speed centrifugation (3,000×g, 10 min). The soft pellet was washed 3 times with wash buffer (50 mM HEPES, 20% glycerol, 1 mM EDTA) plus 2.5 mM UDPG and 5 µM GTP-γ-S, once without UDPG, and suspended in about 5 volumes of PE extraction buffer (50 mM HEPES, 30% glycerol, 1 mM EDTA, 20 µM GTP-γ-S, 0.4% CHAPS, 0.08% cholesterol hemisuccinate) using a DOUNCE homogenizer. The suspension was frozen overnight at −70° C., and then centrifuged at 100,000×g for 10 min. The post-centrifugation supernatant was frozen as aliquots at −70° C. for subsequent assays.

Susceptibility Testing

To each well of a 96-well plate 100 µL of appropriate test medium (example: RPMI-1640 containing 0.165 M MOPS+3 g/L glutamine w/o sodium bicarbonate or RPMI-1640 containing 0.165 M MOPS+3 g/L glutamine w/o sodium bicarbonate with 3.2% DMSO or 2× RPMI-1640 containing 0.33 M MOPS+6 g/L glutamine w/o sodium bicarbonate with 6.4% DMSO for the plates with final concentration of 50% serum) was added.

The test compound was dissolved at concentration of 10 mg/mL in DMSO and diluted 1:78 into appropriate test medium with no DMSO or 1.92% DMSO or 5.12% DMSO. Example: added 25 µL of 10 mg/ml compound stock solution to 1925 µL of RPMI-1640 containing 0.165 M MOPS+3 g/L glutamine w/o sodium bicarbonate with 1.92% DMSO. The test compound concentration achieved was 128 µg/ml and DMSO concentration of 3.2%. To the first well of each row of appropriate test medium plate 100 µL of the compound stock solutions (128 µg/mL) were added. Compounds were serially diluted two-fold across the plate to column 11 (column 12 was the growth control well) and the last 100 µL was discarded yielding compound concentrations of 64 to 0.06

μg/mL. For plates with dermatophytes the last 100 μL were placed in the first row of a second plate and serial diluted two-fold and yielding compound concentrations of 64-0.00004 μg/mL. Amphotericin B and caspofungin, the control compounds, were prepared as a stock solution of 10 mg/mL in DMSO and prepared in micro-titer plate as stated above for test compounds.

Yeasts

In the microbroth dilution assay for yeasts, microorganisms *Candida* spp., *Cryptococcus neoformans* (MY2062) and *Saccharomyces cerevisiae* (MY2255) were selected by streaking a yeast culture on SABOURAUD Dextrose Agar (SDA) incubating for 24-48 hours at 35-37° C., thereafter selecting 1 characteristic colony and transferring to a fresh plate and incubating under same conditions. From the regrowth, 3 to 5 colonies were selected and suspended in 5 mL of sterile normal saline (BBL) and adjusted to match the turbidity of a 0.5 McFarland standard using DADE/BEHRING turbidity meter (preferred OD of 0.06 to 0.12). This resulted in a concentration of approximately $1-5\times10^6$ CFU/mL. The inocula were further diluted 1:1000 into RPMI-1640 containing 0.165 M MOPS+3 g/L glutamine w/o sodium bicarbonate with 3.2% DMSO. Assay plates previously titrated with test compound in RPMI-1640 containing 0.165 M MOPS+3 g/L glutamine w/o sodium bicarbonate with 3.2% DMSO were then inoculated with 100 μL/well of this dilution of culture. This resulted in a final organism concentration of $5\times10^2$ to $2.5\times10^3$ CFU/mL and final compound concentrations of 32 to 0.03 μg/mL. In addition *C. albicans* (MY1055) was also tested with heat inactivated (1 hour at 55° C.) mouse serum which was filtered twice using 0.22 micron GP EXPRESS PLUS MILLIPORE filtration system. This standardized suspension was diluted 1:1000 into mouse serum. Assay plates previously titrated with drug in 2× RPMI-1640 containing 0.33 M MOPS+6 g/l glutamine w/o sodium bicarbonate with 6.4% DMSO were then inoculated with 100 μl/well of this dilution of culture. This resulted in a final organism concentration of $5\times10^2$ to $2.5\times10^3$ CFU/mL and final compound concentration of 32 to 0.03 μg/ml and 50% mouse serum. Plates were incubated at 35-37° C. and MICs were read at 24 hours for *Candida* and 48 hours for *Cryptococcus neoformans*.

Filamentous Fungi

In the microbroth dilution assay for filamentous fungi *Aspergillus fumigatus* (MF5668) and dermatophyte *Trichophyton mentagrophytes* (MF7004) these microorganisms were grown on Sabouraud Dextrose Agar (SDA) slants at 35-37° C. for *Aspergillus fumigatus* and at 30° C. for *Trichophyton mentagrophytes* for 7 days prior to use. Inocula for filamentous fungi were prepared by adding 5 mL of sterile normal saline to slant followed by gently scraping the surface of stock slants growth with a sterile DACRON swab suspending the spores (conidia) in saline. Each spore suspension was then transferred to another tube and adjusted to match the turbidity of a 0.5 McFarland standard using the DADE/BEHRING turbidity meter (preferred OD of 0.06-0.09) for *A. fumigatus* and (preferred OD of 0.13-0.17) for dermatophyte *T. mentagrophytes*. This resulted in a concentration of approximately $1-5\times10^6$ CFU/mL. A spore count was performed on each culture suspension with a hemocytometer to insure the correct inoculum. This standardized suspension for *A. fumigatus* was diluted 1:500 in RPMI-1640 containing 0.165 M MOPS+3 g/L glutamine w/o sodium bicarbonate with 3.2% DMSO. This standardized suspension for *T. mentagrophytes* was diluted 1:500 in RPMI-1640 containing 0.165 M MOPS+3 g/L glutamine w/o sodium bicarbonate. Assay plates previously titrated with test compound in either RPMI-1640 containing 0.165 M MOPS+3 g/L glutamine w/o sodium bicarbonate with 3.2% DMSO or RPMI-1640 containing 0.165 M MOPS+3 g/L glutamine w/o sodium bicarbonate were then inoculated with 100 μL/well of this dilution. In addition *A. fumigatus* (MF5668) was also tested with heat inactivated human serum which was filtered once using 0.22 micron GP EXPRESS PLUS MILLIPORE filtration system. This standardized suspension was diluted 1:500 in human serum. Assay plates previously titrated with test compound in 2× RPMI-1640 containing 0.33 molar MOPS+6 g/L glutamine w/o sodium bicarbonate were then inoculated with 100 μl/well of this dilution of culture. Plates were incubated at 35° C. and MICs were read at 48 hours for *Aspergillus fumigatus*, and plates incubated at 30° C. and MICs were read at 96 hours for Dermatophyte *T. mentagrophytes*.

In the above testing, viable cell counts were performed on 0.5 McFarland samples to verify the CFU/mL. Serial dilutions (1:10) with the 0.5 McFarland were made in saline. One-hundred μl of each dilution ($10^4$, $10^5$, $10^6$) was spread onto a SABOURAUD Dextrose Agar (SDA) plates which were then incubated for 24 to 48 or 96 (dermatophytes) hours at 35° C. or 30° C. After incubation colonies were counted and recorded. Growth and sterility controls for each organism were also carried out. Column 12 was the growth control and contains no test compound. Row H was not inoculated with organism or test compound and was used as sterility control for each plate.

The minimum inhibitory concentration (MIC-100) for all test compounds is determined to be the lowest concentration of compound at which there was no visible growth as compared to growth control without test compound. The minimum prominent inhibition (MIC-80) in growth is indicated as 80% inhibition in growth compared to growth control without test compound. For *Aspergillus* and dermatophyte *T. mentagrophytes* minimum effective concentration (MEC) was determined as narly morphology of hyphae both macroscopic and microscopic.

In Vivo Anti-*Candida* Activity

A disseminated *Candida* infection is induced in DBA/2 mice by the I.V. inoculation of 0.2 mL of a yeast cell suspension containing $3.0\times10^4$ CFU of *C. albicans* MY1055 into the lateral tail vein. Therapy is initiated within 15 to 30 minutes after challenge. Mice are treated with test compound, either (1) I.P., b.i.d. for a total of 2 days, or (2) P.O., b.i.d. for a total of 2 days. For each route of administration and diluent, an appropriate sham-treated control group is included.

Kidneys from euthanized mice (4-5/group) are removed four days after challenge using aseptic techniques, weighed and placed in sterile WHIRL PAK bags containing 5 mL sterile saline. Kidneys are homogenized in the bags, serially diluted in saline and aliquots are plated on SD agar plates. Plates are incubated at 35° C. and enumerated after 30 to 48 hours for *C. albicans* colony forming units (CFUs). Means from CFU/g of paired kidneys of treated groups are compared to the means from sham-treated controls. Percent sterilization is indicated by the number of mice with no detectable yeast, where the limit of detection (because of the dilution scheme) is 50 yeast cells per pair of kidneys. For data from individual mice where no detectable yeast are recovered from paired kidneys, 9.8 is entered into the MICROSOFT EXCEL spread sheets formula [$\log_{10}$(5×raw count)/paired kidney weight)] so that the counts would be one less than the limit of detection (49 cells per pair of kidneys).

Mean $\log_{10}$ yeast CFU/g of paired kidneys are compared to the sham treated controls using Student's t-test (two tailed, unpaired) on MICROSOFT EXCEL. Comparisons are deemed significant at the p=0.05 level. Mean percent reduction in CFU/g of paired kidneys for treated groups at 4 days following challenge relative to control are computed. A linear trend is typically evident when dose and CFU are both expressed in $\log_{10}$ scale. Inverse regression (2) is subsequently used to estimate $ED_{90}$ and $ED_{99}$ values, defined as the doses (mg/kg) that reduced the number of CFU per organ by 90 and 99%, respectively.

Compounds provided in the Examples generally have GS $IC_{50}$ values less than 500 ng/mL and MIC-100 values against one or more organisms of <0.03-32 µg/mL; however, some compounds may have an $IC_{50}$ in the range of from about 500 to more than 10,000 ng/mL. Compounds provided in the Examples generally display prominent inhibition of growth in vitro (MIC-50) in the range of <0.03-32 µg/mL and MECs of <0.03-32 µg/mL. As for activity in the disseminated *Candida* infection, useful compounds will lower the number of fungal CFU/g kidney by greater than 1 $\log_{10}$ unit compared to sham treated controls and compounds that lower the CFU/g by 2 $\log_{10}$ units are especially useful.

Example Numbers correspond to the examples described in the Examples section.

| EXAMPLE NUMBER | Candida Albicans GS $IC_{50}$ (ng/mL) |
|---|---|
| 1B | 6 |
| 2A | 53 |
| 4B | 43 |
| 6 | 3 |
| 8 | 9 |
| 9 | 37 |
| 11 | 57 |
| 13 | 2 |
| 15A | 45 |
| 20 | 3 |
| 22 | 4 |
| 23 | 5 |
| 25 | 27 |
| 27 | 4 |
| 30 | 2 |
| 32 | 8 |
| 36 | 6 |
| 38A | 57 |
| 39B | 11 |
| 41A | 119 |
| 43B | 57 |
| 46 | 14 |
| 49 | 18 |
| 51 | 2 |
| 52 | 2 |
| 55 | 8 |
| 57 | 6 |
| 61 | 8 |
| 69 | 20 |
| 71 | 9 |
| 77 | 14 |
| 80 | 4 |
| 83 | 11 |
| 88 | 18 |
| 93 | 6 |
| 97 | 9 |
| 101 | 8 |
| 104 | 69 |
| 109 | 31 |
| 112 | 6 |
| 114 | 12 |
| 120 | 44 |
| 122 | 11 |
| 127 | 22 |
| 129 | 5 |

The following examples serve only to illustrate the invention and its practice. The examples are not to be construed as limitations on the scope or spirit of the invention.

Abbreviations
Boc t-Butyloxycarbonyl
Cbz Benzyloxycarbonyl (also CBz)
$CDCl_3$ Deuterio-trichloromethane
$CH_3CN$ Acetonitrile
DCE Dichloroethane
DCM Dichloromethane
DMAC Dimethylacetamide
DMAP 4-Dimethylaminopyridine
DMF Dimethylformamide
DMSO Dimethyl sulfoxide
Et Ethyl
EtOAc or EA Ethyl acetate
$Et_3SiH$ Triethylsilane
$H_2$ Hydrogen or hydrogen atmosphere
$H_2O$ Water
HOAc Acetic acid
HPLC High pressure liquid chromatography
$H_2SO_4$ Sulfuric acid
HCl Hydrochloric acid
$K_2CO_3$ Potassium carbonate
LAH $LiAlH_4$
LDA Lithium diisopropylamide
MCPBA meta-Chloroperoxybenzoic acid
Me Methyl
MeOH Methanol
MOPS 3-(N-morpholino)propanesulfonic acid
NaCl Sodium chloride
$NaHCO_3$ Sodium bicarbonate
$NH_4Cl$ Ammonium chloride
$Na_2SO_4$ Sodium sulfate
NMO 4-methylmorpholine N-oxide
PMSF Phenylmethanesulphonylfluoride
PTAB Phenyltrimethylammonium tribromide
RT or r.t. Room temperature, approximately 25° C.
$SiO_2$ Silica
TEA Triethylamine
TFA Trifluoroacetic acid
THF Tetrahydofuran
TLC Thin layer chromatography
UDGP Uridine-diphosphate glucose

PREPARATION 1

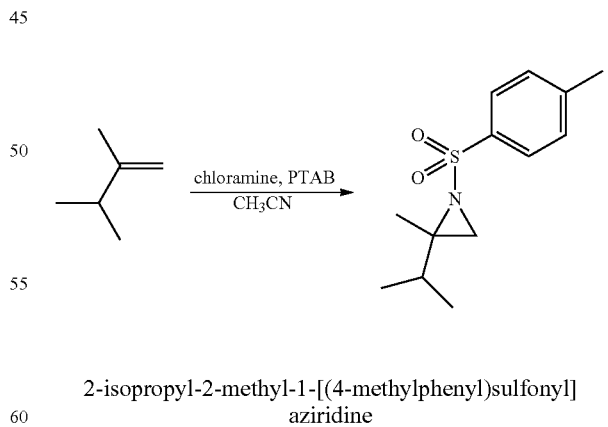

2-isopropyl-2-methyl-1-[(4-methylphenyl)sulfonyl] aziridine

To a solution of 2,3-dimethyl butene (300 ml, 2.42 mol) in 7.8 L of dry acetonitrile was added Chloramine-T (749.9 g, 1.1 eq) portionwise over 90 min. The temperature was maintained at approximately 20° C. To this reaction mixture was added phenyltrimethylammonium tribromide (91.4 g, 0.1 eq) in 10 g portions over 90 min. The temperature increased to 26° C. during the addition. The reaction mixture was stirred at room temperature for 2 days. The reaction mixture was concentrated down to approximately 15% of the initial volume and was them filtered, washing the solid with 1 L of acetonitrile. The organic liquid phase was concentrated and the residue dissolved in 2.5 L of EtOAc. The resulting solution was washed twice with water, dried over MgSO₄, and concentrated to give a solid. The crude was purified on a large plug of celite using gradient elution 5% to 25% EtOAc/heptanes to afford 317 g of 2-isopropyl-2-methyl-1-[(4-methylphenyl)sulfonyl]aziridine as a solid.

PREPARATION 2

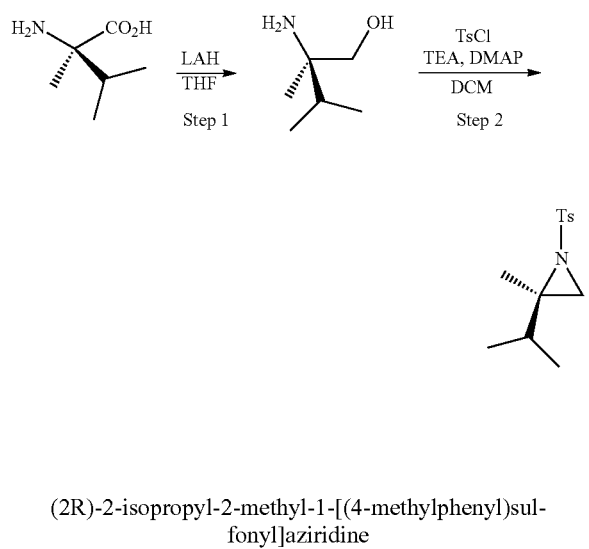

(2R)-2-isopropyl-2-methyl-1-[(4-methylphenyl)sulfonyl]aziridine

Step 1

(R)-α-methylvaline (8.05 g, 61.4 mmol) was added in small portions to a cold (0° C.) solution of LiAlH₄ in THF (1 M, 123 mL, 123 mmol), maintaining the reaction temperature below 15° C. The reaction was stirred at 0° C. for a few minutes then heated at reflux for 4 h. The reaction mixture was cooled to RT and quenched by addition of sodium sulfate decahydrate/Celite (1:1 by weight) until gas evolution ceased. The reaction mixture was filtered, washing with THF and methanol. The filtrate was concentrated under reduced pressure to provide 4.7 g of amino alcohol as a colorless oil.

Step 2

To a solution of the amino alcohol product from Step 1 (4.70 g, 40.1 mmol), Et₃N (22.36 mL, 160 mmol) and 4-dimethylaminopyridine (0.490 g, 4.01 mmol) in anhydrous CH₂Cl₂ (200 mL) at 0° C. was added p-toluenesulfonyl chloride (22.94 g, 120 mmol) in portions during 10 min. The reaction mixture was stirred at room temperature overnight. The volatiles were evaporated in vacuo by rotary evaporation and the residue was partitioned between CH₂Cl₂ and 1N HCl. The organic layer was washed with 1N HCl and dried over Na₂SO₄. The solvent was evaporated and the residue was chromatographed on silica gel using 1:1 CH₂Cl₂/hexane as eluant to remove excess TsCl and then 100% CH₂Cl₂ to elute the product. The title compound was obtained as an off-white solid (5.40 g).

¹NMR (400 MHz, CDCl₃) δ 0.94 (d, J=6.88 Hz, 3 H), 0.98 (d, J=6.88 Hz, 3 H), 1.49 (quint, J=6.88 Hz, 1 H), 1.59 (s, 3 H), 2.20 (s, 1 H), 2.43 (s, 3 H), 2.60 (s, 1 H), 7.31 (d, J=8.0 Hz, 2 H), 7.83 (d, J=8.0 Hz, 2 H).

PREPARATION 3

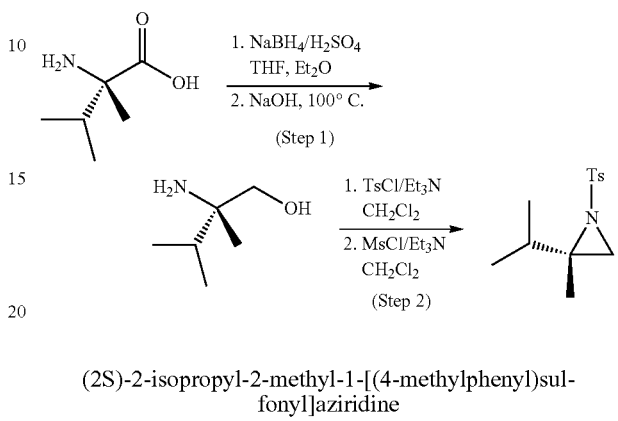

(2S)-2-isopropyl-2-methyl-1-[(4-methylphenyl)sulfonyl]aziridine

Step 1:

NaBH₄ (94.5 g, 2.498 mol) was charged into a 5 L three-necked flask containing 540 ml of dry THF. This solution was cooled with an ice bath. The (S)-α-methylvaline (75 g, 0.572 mol) was added to this solution. The mixture was stirred for 20 min under N₂ then a solution of H₂SO₄ (66.7 ml, 1.252 mol) in 160 ml of dry ether was added dropwise over a period of 3.5 h. The reaction mixture was stirred for one hour while in the ice bath then allowed to warm to RT overnight. TLC in CH₂Cl₂/MeOH (70/30) indicated the reaction was complete. The reaction was cooled with an ice bath and quenched by the slow addition of 250 ml of MeOH over 45 min. The mixture was then stirred at RT for 15 min then NaOH (5N, 700 ml) was added very slowly. The flask was equipped with a distillation head and heated to 100° C. with a heating mantle. The volatiles (bp<100° C.) were removed by distillation. The resulting mixture was heated to 100° C. (internal temp.) for 3 h then cooled to RT. Water (1 L) was added and the mixture was extracted with CH₂Cl₂ (6×500 ml). The combined organic layers were dried over Na₂SO₄, filtered and concentrated to afford the amino alcohol product as a yellow oil (64.2 g).

¹NMR (400 MHz, CDCl₃) δ ppm 0.87 (d, J=6.93 Hz, 3 H) 0.91 (d, J=6.93 Hz, 3 H) 0.95 (s, 3 H) 1.57-1.68 (m, 1 H) 3.30 (d, J=10.30 Hz, 1 H) 3.34 (d, J=10.30 Hz, 1 H).

Step 2

A solution of amino alcohol from above (32 g, 273.5 mmol) in dry CH₂Cl₂ (1.7 L) was cooled with an ice bath and Et₃N (198 ml, 1422 mmol) was added. A solution p-toluenesulfonyl chloride (62.5 g, 328.2 mmol) in CH₂Cl₂ (250 ml) was added dropwise over a period of 3 h. The ice bath was removed and the solution was stirred at RT overnight. The mixture was cooled in an ice bath and Et₃N (61.6 ml, 442 mmol) was added followed by the dropwise addition of methanesulfonyl chloride (40 ml, 516.8 mmol). The reaction mixture was stirred for 4 h while keeping the temperature below 12° C. Water (600 ml) was added to the mixture followed by brine (350 ml). The aqueous layer was extracted with CH₂Cl₂ (3×500 ml). The combined organic layers were dried over Na₂SO₄, filtered concentrated. The crude product was purified over a pad of silica gel (EtOAc/Heptanes: 5/95 then 10/90) to afford the title compound as a white solid (36 g).

¹H NMR (400 MHz, CDCl₃) δ ppm 0.94 (d, J=6.78 Hz, 3 H) 0.98 (d, J=6.78 Hz, 3 H) 1.44-1.53 (m, 1 H) 1.59 (s, 3 H) 2.20 (s, 1 H) 2.42 (s, 3 H) 2.60 (s, 1 H) 7.30 (d, J=7.90 Hz, 2 H) 7.83 (d, J=7.90 Hz, 2 H).

PREPARATION 4

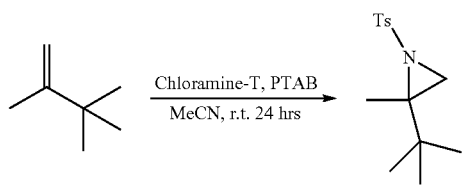

2-(1,1-dimethylethyl)-2-methyl-1-[(4-methylphenyl)sulfonyl]aziridine

Chloramine-T trihydrate (10.19 g, 36.2 mmol) was placed under high vacuum for 15 hours and the remaining material (8.3 g) was suspended in acetonitrile (121 mL) at room temperature under nitrogen. To this suspension was added 2,2,3-trimethylbut-1-ene (50.6 mL. 362 mmol) followed by phenyltrimethylammonium tribromide (13.6 g, 36.2 mmol) in two roughly equal portions. After twenty hours the reaction mixture was concentrated to half volume and then filtered through a sintered glass funnel. The filtrate was concentrated to half volume again which caused further precipitation. This suspension was filtered washing with acetonitrile and the filtrate concentrated. The resulting material was dissolved/suspended in dichloromethane, filtered and the resulting filtrate was concentrated to an orange oil. This oil was diluted with ethyl acetate and washed with water. The organic phase was dried with $MgSO_4$, filtered and concentrated. The crude material was purified by column chromatography using a Biotage 65i column eluting with (0-100% EtOAc/hexane) to give 2-(1,1-dimethylethyl)-2-methyl-1-[(4-methylphenyl)sulfonyl]aziridine as a colorless solid (5.2 g).

$^1$H NMR ($CDCl_3$, 500 MHz, ppm) δ 0.92 (s, 9H), 1.72 (s, 3H), 2.33 (s, 1H), 2.43 (s, 3H), 2.51 (s, 1H), 7.30 (d, J=8.1 Hz, 2H), 7.83 (d, J=8.1 Hz, 2H)

PREPARATION 5A

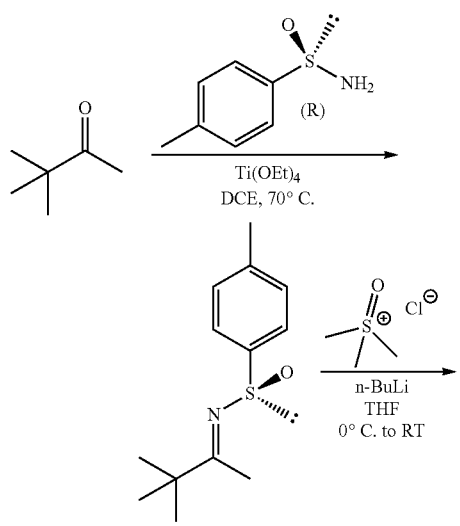

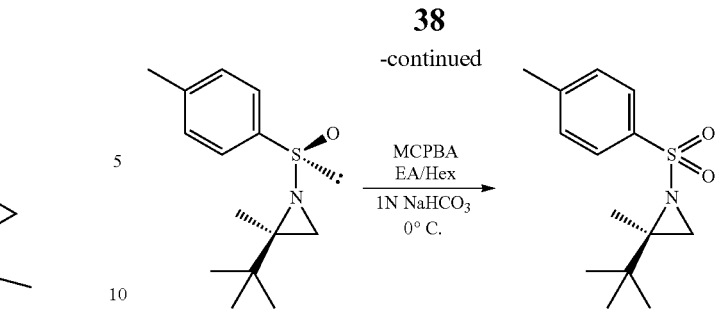

(2R)-2-(1,1-dimethylethyl)-2-methyl-1-[(4-methylphenyl)sulfonyl]aziridine

Step 1

To (R)-p-toluenesulfinamide (2.00 g, 12.89 mmol) in a 250 mL flask under argon were added dichloroethane (50 mL), t-butylmethylketone (8.1 mL, 64.4 mmol) and $Ti(OEt)_4$ (13.5 mL, 64.4 mmol). The stirred reaction solution was heated at 70° C. overnight. After 21 h, the yellow solution was cooled to RT and poured into a vigorously stirred suspension of 15 g of Celite in 100 mL of hexane, rinsing the flask with dichloromethane. To the stirred suspension was added 15 mL of $H_2O$ dropwise. After several minutes, the mixture became very thick. Stirring was continued for 5 min. The resulting thick slurry was filtered through a 350 mL coarse sintered filter funnel. The solid was washed twice with 50 mL of 10% dichloromethane/hexane by resuspending the solid by stirring with a spatula and then filtering. The two-phase filtrate was transferred to a separatory funnel and the organic layer was washed with water and brine and dried over $Na_2SO_4$. Filtration and concentration by rotary evaporation gave 3.07 g of a yellow oil. Chromatography on an ISCO CombiFlash system (40 g silica gel column, 10:90 to 50:50 EA/hex, 20 min gradient, 40 mL/min, detection at 254 nM) gave 2.49 g of a pale yellow oil which solidified upon storage at −20° C.

$^1$H NMR ($CD_2Cl_2$, 500 MHz, ppm) δ 1.16 (s, 9H), 2.33 (s, 3H), 2.43 (s, 3H), 7.35 (d, J=8.1 Hz), 7.63, (d, J=8.1 Hz).

Step 2

A mixture of the trimethylsulfoxonium chloride (2.37 g, 18.6 mmol) in THF (35 mL) was sonicated briefly to break-up lumps and then cooled to 0° C. and BuLi/hex (2.5M) was added dropwise. The stirred reaction mixture was heterogeneous. After 25 min., a solution of the ketimine product from Step 1 (1.45 g, 6.11 mmol) in THF (5+1 mL) was added dropwise to the stirred suspension during 15 min. The resulting white suspension stirred at 0° C. for 3 h and then allowed to warm to RT overnight. The reaction mixture was quenched with sat. $NH_4Cl$ and partitioned between sat. $NH_4Cl$ and ethyl acetate. The organic phase was washed with water and brine, dried over $Na_2SO_4$ and evaporated to give 1.539 g of a pale yellow oil.

$^1$H NMR ($CD_2Cl_2$, 500 MHz, ppm) δ 0.97 (s, 9H), 1.53 (s, 3H), 1.82 (s, 1H), 2.28 (s, 1H), 2.43 (s, 3H), 7.33 (d, J=8.1 Hz), 7.61, (d, J=8.1 Hz).

Step 3

The product from Step 2 (1.539 g, 6.2 mmol) was dissolved in EA (20 mL) and hexane (40 mL). After addition of 1M $NaHCO_3$ solution (30 mL) the two phase reaction mixture was vigorously stirred and cooled to 0° C. Commercial grade MCPBA (2.11 g, ~9 mmol) was added in several portions during 5 min. The reaction was monitored by TLC (30:70 EA/hex). At T=45 min, the reaction was quenched by addition of 5% $Na_2S_2O_3$ (30 mL) and the mixture was stirred for several minutes until a negative starch-iodide test was obtained. The reaction mixture was diluted with ethyl acetate and the organic phase was washed with sat. NaHCO$_3$, H$_2$O and brine. Drying over Na$_2$SO$_4$ and evaporation gave 1.56 g of the title compound as an off-white crystalline solid.

$^1$H NMR (CD$_2$Cl$_2$, 500 MHz, ppm) δ 0.94 (s, 9H), 1.71 (s, 3H), 2.37 (s, 1H), 2.46 (s, 3H), 2.51 (s, 1H), 7.36 (d, J=8.1 Hz), 7.82, (d, J=8.1 Hz).

PREPARATION 5B

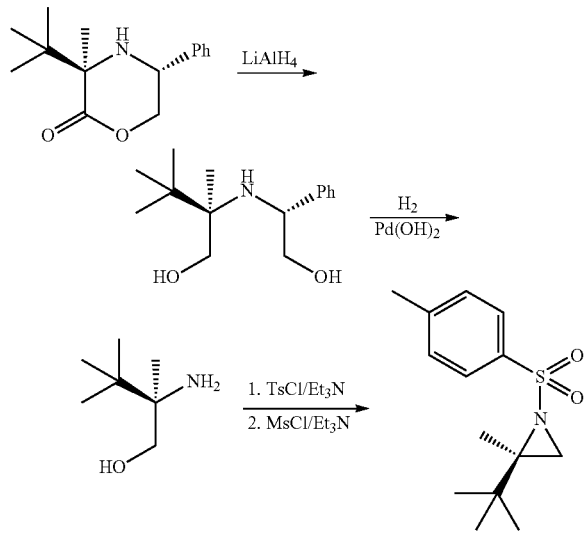

(2R)-2-(1,1-dimethylethyl)-2-methyl-1-[(4-methylphenyl)sulfonyl]aziridine

Step 1

To a solution of (3R,5R)-3-(1,1-dimethylethyl)-3-methyl-5-phenylmorpholin-2-one (Harwood, L. M. et al. *Synlett* 1996, 1051; 17.3 g, 70 mmol) in THF (1 L) at 0° C. was added LiAlH$_4$ (70 mL of a 2M solution in THF, 140 mmol) dropwise. The mixture was heated at 45° C. for 3 h. The reaction mixture was cooled to 0° C. and quenched carefully by sequential addition of 6 mL of water, 6 mL of 15% aqueous NaOH, and 18 mL of water. The slurry was stirred vigorously. The solid was removed by suction filtration, and the filter cake was thoroughly washed with ether and CH$_2$Cl$_2$. The filtrate was concentrated under reduced pressure to afford the product (17.0 g, 100%) as a viscous oil.

$^1$H NMR (400 MHz, CDCl$_3$) δ 0.96 (s, 3 H) 1.02 (s, 9 H) 3.09 (d, J=11.32 Hz, 1 H) 3.39-3.46 (m, 1 H) 3.46 (d, J=11.32 Hz, 1 H) 3.62 (dd, J=10.52, 4.71 Hz, 1 H) 4.02 (dd, J=9.22, 4.69 Hz, 1 H) 7.08-7.44 (m, 5 H).

Step 2:

To a solution of the product from Step 1 (17.0 g, 70 mmol) in MeOH was added HOAc (5 mL) and palladium hydroxide (5 g of 20 wt % on carbon). The flask was evacuated and filled with hydrogen several times. The suspension was stirred at room temperature under H$_2$ (balloon, 1 atm) for 3 h. The reaction mixture was filtered through a pad of Celite, the filter cake was washed with additional MeOH, and the filtrate was concentrated under reduced pressure. The residue was purified by flash chromatography, elution with 0-10% MeOH in CH$_2$Cl$_2$ with 1% HOAc followed by 100% MeOH with 1% HOAc, to provide 8.84 g of the product as an acetic acid salt.

Anhydrous K$_2$CO$_3$ (50 g) was added to a solution of the acetate salt (7.03 g, 38.0 mmol) in CH$_2$Cl$_2$ (500 mL). The resulting suspension was stirred under nitrogen overnight after which the inorganic salts were removed by suction filtration. The filtrate was concentrated under reduced pressure and the residue was dried azeotropically using PhCH$_3$ until a constant weight was obtained to give the amino alcohol product (4.98 g, 66% overall).

$^1$H NMR (400 MHz, CDCl$_3$) δ 0.93 (s, 9 H) 1.05 (s, 3 H) 3.34 (d, J=10.05 Hz, 1 H) 3.45 (d, J=10.05 Hz, 1 H).

Step 3:

A solution of the amino alcohol from Step 2 (4.98 g, 38.0 mmol) in CH$_2$Cl$_2$ (200 mL) at 0° C. was treated with Et$_3$N (26 mL, 190 mmol) followed by a solution of p-toluenesulfonyl chloride (8.7 g, 45.6 mmol) in CH$_2$Cl$_2$ (50 mL) over 40 min. The reaction mixture was stirred at room temperature for 4 d. The mixture was cooled to 0° C. after which Et$_3$N (8.50 mL, 60.8 mmol) and methanesulfonyl chloride (5.88 mL, 76.0 mmol) were added. The mixture was stirred at 0° C. for 4 h. The reaction mixture was poured into a 1:1 mixture of saturated aqueous NaCl and water and was extracted with CH$_2$Cl$_2$. The organic layer was washed with saturated aqueous NaCl, dried (Na$_2$SO$_4$) filtered, and concentrated under reduced pressure. The residue was purified by flash chromatography, elution with 0-50% EtOAc in heptane, to provide the title compound (5.88 g, 58%) as a white solid.

$^1$H NMR (400 MHz, CDCl$_3$) δ 0.93 (s, 9 H) 1.73 (s, 3 H) 2.34 (s, 1 H) 2.44 (s, 3 H) 2.52 (s, 1 H) 7.31 (d, J=7.96 Hz, 2 H) 7.84 (d, J=8.35 Hz, 2 H).

PREPARATION 6

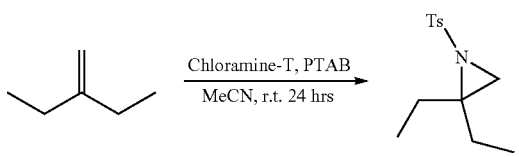

2,2-diethyl-1-[(4-methylphenyl)sulfonyl]-aziridine

Chloramine-T (10 g, 43.9 mmol) was suspended in acetonitrile (146 mL) at room temperature under nitrogen. To this suspension was added 2-ethylbut-1-ene (5.55 g, 65.9 mmol) followed by phenyltrimethylammonium tribromide (1.65 g, 4.39 mmol) in two roughly equal portions. After three days the reaction mixture was concentrated to half volume and then filtered through a sintered glass funnel. The filtrate was concentrated to half volume again which caused further precipitation. This mixture was filtered and the filtrate was partitioned between ethyl acetate and water. The organic phase was dried with MgSO$_4$, filtered and concentrated. The crude material was purified by column chromatography using a Biotage 65i column eluting with (0-100% EtOAc/hexane) to give 2,2-diethyl-1-[(4-methylphenyl)sulfonyl]-aziridine as a colorless solid (4.5 g).

$^1$H NMR (CDCl$_3$, 500 MHz, ppm) δ 1.00 (t, J=7.5 Hz, 6H), 1.75 (dddd, J=14.6 Hz, 7.5 Hz, 7.5 Hz, 7.5 Hz, 2H), 1.90

(dddd, J=14.6 Hz, 7.5 Hz, 7.5 Hz, 7.5 Hz, 2H), 2.41 (s, 2H), 2.43 (s, 3H), 7.38 (d, J=8.0 Hz, 2H), 7.78 (d, J=8.4 Hz, 2H).

PREPARATION 7

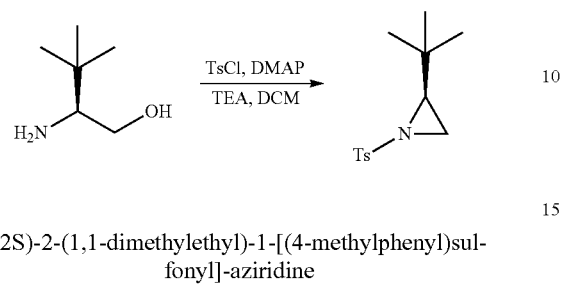

(2S)-2-(1,1-dimethylethyl)-1-[(4-methylphenyl)sulfonyl]-aziridine

To a solution of S-(+)-tert-leucinol (4.0 g, 34 mmol) in dichloromethane (170 mL) was added triethylamine (16.7 mL, 120 mmol), p-toluenesulfonyl chloride (26 g, 140 mmol, added in portions) and DMAP (420 mg, 3.4 mmol). The cooling bath was removed after 30 minutes and the reaction stirred at room temperature and additional reagents were added during the reaction: TsCl (at 16 hours 5.3 g, at 40 hours 3 g), triethylamine (at 24 hours, 3 mL) and DMAP (at 20 hours, 200 mg and at 40 hours 150 mg). After 40 hours at room temperature the reaction was heated to 40° C. After a total of 44 hours the reaction was cooled to room temperature and filtered. The filtrate was concentrated in vacuo then partitioned between ethyl acetate and water. The organic phase was washed with brine, dried over MgSO$_4$ then filtered and concentrated. Column chromatography (Biotage 65i column, 10-100% EtOAc/hexane) afforded (2S)-2-(1,1-dimethylethyl)-1-[(4-methylphenyl)sulfonyl]-aziridine as an oil (6.3 g) which solidified upon storage at −20° C.

$^1$H NMR (CDCl$_3$, 500 MHz, ppm) δ 0.79 (s, 9H), 2.17 (d, J=4.6 Hz, 1H), 2.44 (s, 3H), 2.52 (d, J=7.1 Hz, 1H), 2.55 (d, J=4.6 Hz, 1H) 7.33 (d, J=8.0 Hz, 2H), 7.83 (d, J=8.2 Hz, 2H).

PREPARATION 8

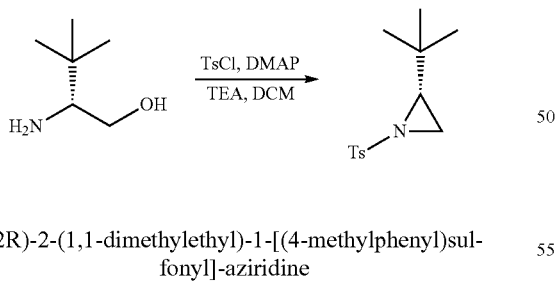

(2R)-2-(1,1-dimethylethyl)-1-[(4-methylphenyl)sulfonyl]-aziridine

A solution of R-(−)-tert-leucinol (4.0 g, 34 mmol) in dichloromethane (170 mL) was treated with triethylamine (19 mL, 140 mmol), p-toluenesulfonyl chloride (26 g, 140 mmol) and DMAP (834 mg, 6.83 mmol) and heated to 40° C. under nitrogen. After approximately 18 hours the reaction was cooled to room temperature and filtered. The filtrate was concentrated in vacuo then partitioned between ethyl acetate and water. The organic phase was washed with brine, dried over MgSO$_4$ then filtered and concentrated. Column chromatography (Biotage 65i column, 10-100% EtOAc/hexane) afforded (2R)-2-(1,1-dimethylethyl)-1-[(4-methylphenyl)sulfonyl]-aziridine as an oil (3.7 g) which solidified upon storage at −20° C.

$^1$H NMR (CDCl$_3$, 500 MHz, ppm) δ 0.78 (s, 9H), 2.17 (d, J=4.6 Hz, 1H), 2.44 (s, 3H), 2.52 (d, J=7.1 Hz, 1H), 2.55 (d, J=4.6 Hz, 1H) 7.33 (d, J=8.0 Hz, 2H), 7.83 (d, J=8.2 Hz, 2H).

PREPARATION 9

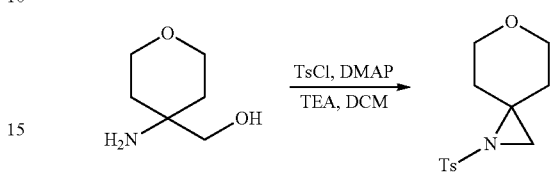

1-[(4-methylphenyl)sulfonyl]-6-oxa-1-azaspiro[-2.5]octane

A solution of 4-aminotetrahydro-2H-pyran-4-methanol (16 g, 122 mmol) in dichloromethane (700 mL) was treated with triethylamine (85 mL, 610 mmol), p-toluenesulfonyl chloride (69.8 g, 366 mmol) and DMAP (1490 mg, 12.2 mmol) under nitrogen. After approximately 18 hours at room temperature, the reaction was filtered through a pad of silica gel. The filtrate was concentrated in vacuo then purified by chromatography on silica gel (5-20% EtOAc/hexane) to afford intermediate the title compound (12.5 g) as a white solid.

$^1$H NMR (CDCl$_3$, 500 MHz, ppm) δ 1.92 (m, 2H), 2.08 (m, 2H), 2.47 (s, 3H), 2.52 (s, 2H), 3.76 (m, 2H), 3.99 (m, 2H), 7.35 (d, J=8.0 Hz, 2H), 7.86 (d, J=8.5 Hz, 2H)

PREPARATION 10

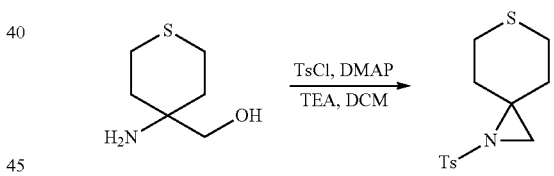

1-[(4-methylphenyl)sulfonyl]-6-thia-1-azaspiro[2.5]octane

Prepared analogously to the compound of Preparation 9, by starting with 4-aminotetrahydro-2H-thiopyran-4-methanol.

$^1$H NMR (CDCl$_3$, 500 MHz, ppm) δ 2.15 (m, 2H), 2.22 (m, 2H), 2.24 (s, 3H), 2.42 (s, 2H), 2.70 (m, 2H), 3.00 (m, 2H), 7.35 (d, J=8.0 Hz, 2H), 7.86 (d, J=8.3 Hz, 2H)

PREPARATION 11

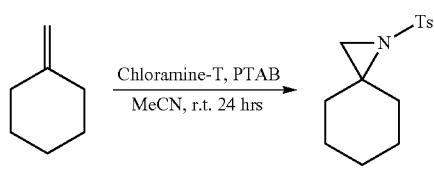

1-[(4-methylphenyl)sulfonyl]-1-azaspiro[2.5]octane

To a stirred suspension of dried Chloramine-T (5.10 g, 20.76 mmol) in CH₃CN (100 mL) under a nitrogen atmosphere methylenecyclohexane (9.98 g, 104 mmol) was added. Phenyltrimethylammonium tribromide (7.80 g, 20.76 mmol) was added in three portions over 10 min. The mixture was stirred at room temperature for 16 hours. The solvent was evaporated and the residue was partitioned between dichloromethane and water. The organic layer was dried over Na₂SO₄ and the solvent was evaporated. The residue was chromatographed on silica gel with an ISCO Combiflash using EtOAc/hexanes (5-30% gradient) to afford the title compound as a white solid (2.66 g).

¹H NMR (CDCl₃, 500 MHz, ppm) δ 1.4-1.5 (m,4H), 1.7-1.9 (m, 6H), 2.4 (s, 2H), 2.45 (s, 3H), 7.3 (d, 2H), 7.85 (d, 2H).

PREPARATION 12

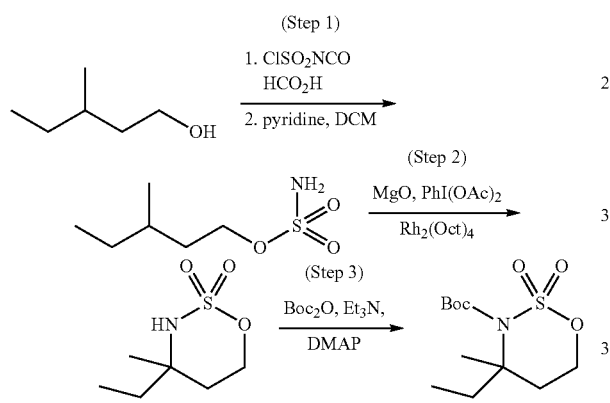

[cf. J. Du Bois et. al., JACS, 2001, 123, 6935]

1,1-dimethylethyl 4-ethyl-4-methyldihydro-1,2,3-oxathiazine-3(4H)-carboxylate 2,2-dioxide Step 1:
Formic acid (65 mL, 17.2 mmol) was added dropwise to neat chlorosulfonyl isocyanate (1.5 mL, 17.2 mmol) at 0° C. with rapid stirring. Vigorous gas evolution was observed during the addition process. The resulting viscous suspension was stirred for 5 min at 0° C. during which time the mixture solidified. Dichloromethane (9 mL) was added and the solution was stirred for 1 h at 0° C. then 8 h at 25° C. The reaction mixture was cooled to 0° C. and a solution of 3-methylpentan-1-ol (11.5 mmol) and pyridine (1.4 mL, 17.2 mmol) in 8 mL of dichloromethane was added dropwise. The contents were warmed to 25° C. and stirred for 3 h. The reaction mixture was treated with EtOAc (80 mL) and water (50 mL), and the aqueous layer was extracted with EtOAc (2×20 mL). The combined organic phase was washed with brine, dried over MgSO₄, filtered and then concentrated. The crude product was purified by multiple flash chromatographies (7% ethyl acetate/dichloromethane) to give 3-methylpentyl sulfamate.

Step 2:
To a solution of 3-methylpentyl sulfamate from Step 1 (1.25 mmol) in 8 mL of dichloromethane was added sequentially MgO (116 mg, 30 mmol), PhI(OAc)₂ (443 mg 1.4 mmol), and Rh₂(oct)₄ (20 mg, 0.025 mmol). The suspension was stirred vigorously and heated at 40° C. for 3 h. The reaction mixture was cooled to room temperature, diluted with 20 mL of dichloromethane, and filtered through a pad of Celite then concentrated. The crude product was purified by multiple flash chromatographies (5% ethyl acetate/dichloromethane) to give 4-ethyl-4-methyltetrahydro-1,2,3-oxathiazine 2,2-dioxide.

Step 3:
To a solution of 4-ethyl-4-methyltetrahydro-1,2,3-oxathiazine 2,2-dioxide from Step 2 (5 g) in 100 mL of dichloromethane was added sequentially Et₃N (7.5 mL), DMAP (1 g), and Boc anhydride (8 g). The mixture was stirred vigorously for 5 minutes, and filtered through a pad of silica then concentrated. The crude product was purified by multiple flash chromatographies (30% ethyl acetate/hexane) to give the title compound (3 g).

¹H NMR (CDCl₃, 500 MHz, ppm) δ 0.96 (t, J=7.5 Hz, 3H), 1.55 (s, 9H), 1.64 (s, 3H), 1.86 (m, 1H), 2.00 (m, 1H), 2.28 (m, 1H), 2.62 (m, 1H), 4.64 (m, 2H).

PREPARATION 13

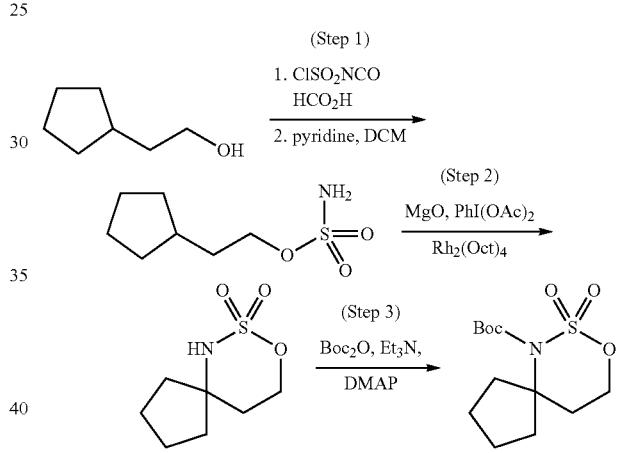

1,1-dimethylethyl 8-oxa-7-thia-6-azaspiro[4.5]decane-6-carboxylate 7,7-dioxide

In a manner analogous to that described for Preparation 11, the title compound was prepared starting with 2-cyclopentylethanol.

¹H NMR (CDCl₃, 500 MHz, ppm) δ 1.55 (s, 9H), 1.62 (m, 2H), 1.88-1.96 (m, 4H), 2.25 (t, J=6.4 Hz, 2H), 2.31 (m, 2H), 4.64 (t, J=6.4 Hz, 2H).

PREPARATION 14

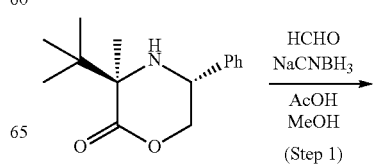

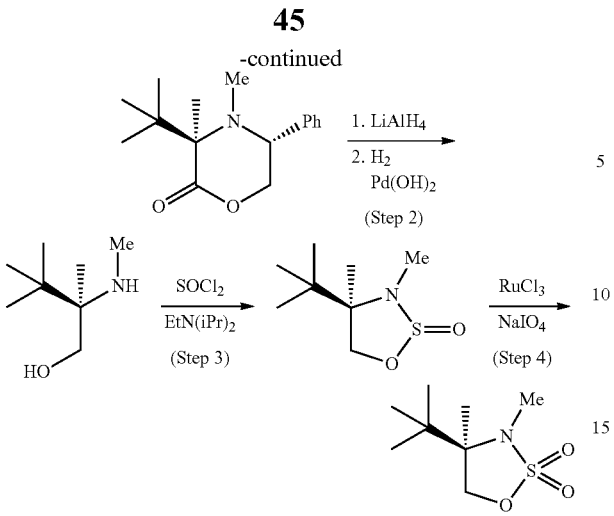

(4R)-4-(1,1-dimethylethyl)-3,4-dimethyl-1,2,3-oxathiazolidine 2,2-dioxide

Step 1:

To a solution of compound (3R,5R)-3-(1,1-dimethylethyl)-3-methyl-5-phenylmorpholin-2-one (100 mg, 0.40 mmol) in MeOH was added formaldehyde (1.40 mL, 37 wt % in water, 16.2 mmol), HOAc (0.14 mL, 2.4 mmol), and sodium cyanoborohydride (100 mg, 1.60 mmol). The reaction mixture was stirred at room temperature overnight, and the solvent was removed under reduced pressure. The residue was partitioned between EtOAc and saturated aqueous $NaHCO_3$, and the layers were separated. The organic layer was washed with saturated aqueous $NaHCO_3$, saturated aqueous NaCl, dried with $Na_2SO_4$, and concentrated under reduce pressure to provide the product (99.7 mg, 95%) as a viscous oil.

$^1$H NMR (400 MHz, $CDCl_3$) δ 1.08 (s, 9 H) 1.30 (s, 3 H) 2.28 (s, 3 H) 3.97 (d, J=2.54 Hz, 1 H) 4.45 (dd, J=10.91, 2.37 Hz, 1 H) 4.89 (dd, J=10.88, 3.66 Hz, 1 H) 7.13-7.41 (m, 5 H).

Step 2:

Employing procedures analogous to those described for Steps 1 and 2 of Preparation 5B, the desired amino alcohol was prepared from the product of Step 1.

$^1$H NMR (400 MHz, $CDCl_3$) δ 1.08 (s, 9 H) 1.17 (s, 3 H) 1.99 (s, 3 H) 2.63 (s, 3 H) 3.53 (d, J=12.35 Hz, 1 H) 3.84 (d, J=12.30 Hz, 1 H) 5.32 (br. s., 4 H)

Step 3:

To a solution of the amino alcohol product from Step 2 (59.4 mg, 0.29 mmol) in $CH_2Cl_2$ (3 mL) at 0° C. was added N,N-diisopropylethylamine (0.15 mL, 0.87 mmol) and thionyl chloride (21.0 µL, 0.29 mmol), and the resulting solution was stirred at 0° C. for 45 min. The reaction mixture was diluted with $CH_2Cl_2$ and washed with saturated aqueous NaCl, dried with $Na_2SO_4$, and concentrated under reduced pressure. The residue was purified by flash chromatography to provide two diastereoisomers (22.1 mg, 40%) as white solids.

ISOMER A: $^1$H NMR (400 MHz, $CDCl_3$) δ ppm 1.05 (s, 9 H) 1.24 (d, J=0.63 Hz, 3 H) 2.87 (s, 3 H) 4.12 (d, J=8.88 Hz, 1 H) 4.87 (dd, J=8.88, 0.68 Hz, 1 H);

ISOMER B: $^1$H NMR (400 MHz, $CDCl_3$) δ ppm 0.92 (s, 9 H) 1.38 (s, 3 H) 2.72 (s, 3 H) 4.42 (d, J=9.27 Hz, 1 H) 4.59 (d, J=9.23 Hz, 1 H)

Step 4:

A solution of the two diastereoisomers from Step 3 (15.2 mg, 0.08 mmol) in $CH_3CN$ (0.5 mL) was added to a solution of ruthenium trichloride (1 mg, 0.0008 mmol) and sodium periodate (19 mg, 0.09 mmol) in water (1 mL) and $CH_3CN$ (1 mL). The reaction mixture was stirred at room temperature for 1 h, diluted with EtOAc and washed with water. The aqueous layer was extracted with EtOAc. The combined organic layers were dried ($Na_2SO_4$), and concentrated under reduced pressure to provide the title compound (13.9 mg, 84%) directly as a white solid.

$^1$H NMR (400 MHz, $CDCl_3$) δ.00 (s, 9 H) 1.31 (s, 3 H) 2.81 (s, 3 H) 4.03 (d, J=9.32 Hz, 1 H) 4.55 (d, J=9.32 Hz, 1 H).

PREPARATION 15

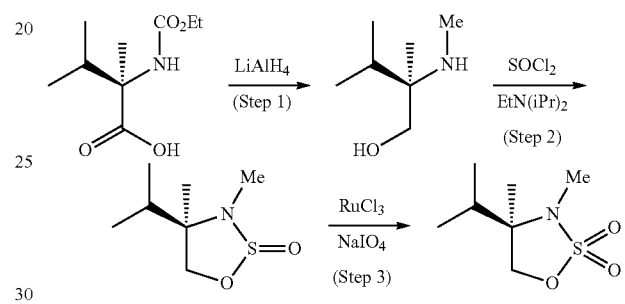

(4R)-3,4-dimethyl-4-(1-methylethyl)-1,2,3-oxathiazolidine 2,2-dioxide

Starting with (2R)-2-{[(ethyloxy)carbonyl]amino}-2,3-dimethylbutanoic acid (prepared as described in *J. Org. Chem.* 2007, 72, 7469-7472 but employing D-tartaric acid for the resolution step) and employing procedures analogous to those described for Preparation 5B Step 1 and Preparation 14 Steps 3 and 4, the title compound was prepared and isolated as a waxy solid.

$^1$H NMR (400 MHz, $CDCl_3$) δ: 4.38 (d, J=8.8 Hz, 1 H), 4.06 (d, J=8.8 Hz, 1 H), 2.65 (s, 3 H), 1.85 (m, 1 H), 1.32 (s, 3 H), 0.94 (d, J=6.9 Hz, 3 H), 0.89 (d, J=6.9 Hz, 3 H) ppm.

PREPARATION 16

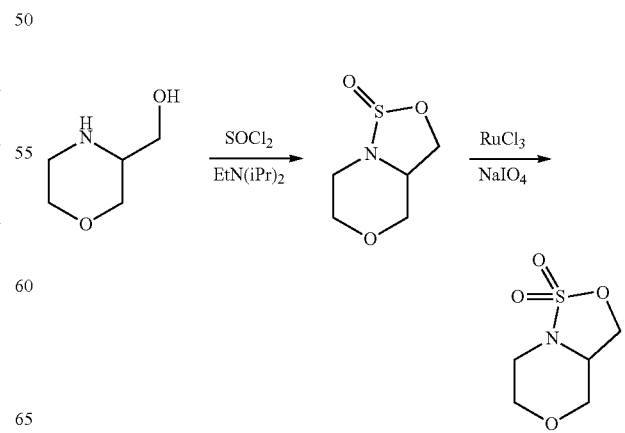

tetrahydro-3H-[1,2,3]oxathiazolo[4,3-c][1,4]ox-
azine-1,1-dioxide

Following procedures analogous to those described for Steps 3 and 4 of Preparation 14, 3-hydroxymethylmorpholine was converted to the title compound.

$^1$H NMR (400 MHz, CDCl$_3$) δ 3.17 (ddd, J=12.10, 8.86, 3.34 Hz, 1 H) 3.38 (dt, J=12.08, 3.60 Hz, 1 H) 3.62 (dd, J=11.57, 7.76 Hz, 1 H) 3.76 (ddd, J=11.87, 8.85, 3.15 Hz, 1 H) 3.80-3.93 (m, J=15.62, 12.17, 3.36, 3.36 Hz, 2 H) 4.03 (dd, J=11.59, 3.39 Hz, 1 H) 4.32 (d, J=9.08 Hz, 1 H) 4.59 (dd, J=8.00, 6.44 Hz, 1 H).

PREPARATION 17

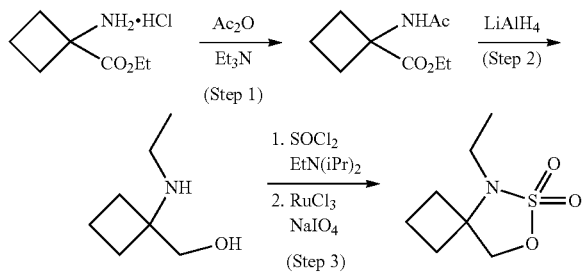

5-ethyl-7-oxa-6-thia-5-azaspiro[3.4]octane
6,6-dioxide

Step 1:

Et$_3$N (14.0 mL, 100 mmol) was added to a solution of 1-amino-cyclobutanecarboxylic acid ethyl ester hydrochloride (6.0 g, 33.4 mmol) in CH$_2$Cl$_2$ (40 mL) at 0° C. Acetic anhydride (3.8 mL, 40 mmol) was added, and the reaction mixture was stirred at 0° C. for 3 h. The reaction mixture was diluted with EtOAc (ca. 250 mL) and washed with water (ca. 100 mL). The aqueous layer was extracted with EtOAc. The combined organic layers were dried with Na$_2$SO$_4$, filtered and concentrated under reduced pressure to yield the product (7.0 g, 100%).

$^1$H NMR (400 MHz, CDCl$_3$) δ 1.30 (t, J=7.13 Hz, 3 H) 2.01 (s, 3 H) 2.02-2.13 (m, 2 H) 2.33-2.52 (m, 2 H) 2.52-2.74 (m, 2 H) 4.24 (q, J=7.13 Hz, 2 H) 6.15 (br s, 1 H).

Step 2:

A solution of the product compound from Step 1 (7.0 g, 33.4 mmol) in THF (60 mL) was added dropwise to a solution of LiAlH$_4$ (50 mL of a 2.0 M solution in THF, 100 mmol) in THF (40 mL) at room temperature. The reaction was heated at 50° C. overnight. The reaction mixture was cooled to 0° C. and quenched by careful sequential addition of water (3.8 mL), 15% aqueous NaOH (3.8 mL), and water (12 mL). The mixture was stirred vigorously overnight and the salts were removed by suction filtration. The filter cake was washed with THF (2×200 mL), and the filtrate was concentrated under reduced pressure to give the desired amino alcohol (4.3 g, 100%).

$^1$H NMR (400 MHz, CDCl$_3$) δ 1.10 (t, J=7.13 Hz, 3 H) 1.64-1.84 (m, 2 H) 1.84-1.97 (m, 4 H) 2.50 (q, J=7.14 Hz, 2 H) 3.51 (s, 2 H)

Step 3:

Following procedures analogous to those described for Steps 3 and 4 of Preparation 14, the amino alcohol product from Step 2 was converted to the title compound.

$^1$H NMR (400 MHz, CDCl$_3$) δ 1.38 (t, J=7.30 Hz, 3 H) 1.63-1.94 (m, 2 H) 2.09 (ddd, J=8.21, 5.50, 3.07 Hz, 2 H) 2.50 (dd, J=10.35, 3.03 Hz, 2 H) 3.26 (q, J=7.27 Hz, 2 H) 4.53 (s, 2 H)

PREPARATION 18

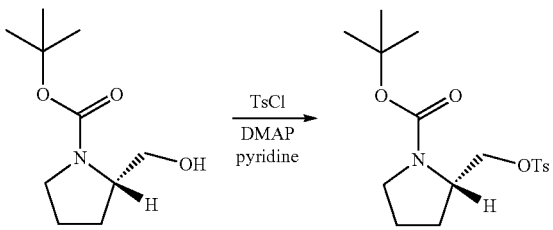 [SMILES: CC(C)(C)OC(=O)N1CCC[C@H]1CO ; "TsCl" ; Cc1ccc(S(=O)(=O)OC[C@@H]2CCCN2C(=O)OC(C)(C)C)cc1]

1,1-dimethylethyl(2R)-2-({[(4-methylphenyl)sulfo-
nyl]oxy}methyl)cyclopentanecarboxylate To a solution of N-Boc-L-prolinol (520 mg, 2.6 mmol) and pyridine (0.63 mL, 7.8 mmol) in CH$_2$Cl$_2$ (40 mL) was added in one portion p-toluenesulfonyl chloride (542 mg, 2.86 mmol) followed by DMAP (130 mg, 1.1 mmol). The reaction was stirred for 24 h at which time saturated aqueous NH$_4$Cl was added and the mixture was extracted with CH$_2$Cl$_2$. The combined organic extracts were dried (Na$_2$SO$_4$), and concentrated under reduced pressure. The residue was purified by flash chromatography, elution with 0-100% EtOAc in heptane, to afford the title compound (720 mg, 78%) as a clear oil.

$^1$H NMR (400 MHz, DMSO-d$_6$) δ 1.12-1.43 (rotameric d, 9 H) 1.54-1.83 (m, 3H) 1.90 (br s, 1 H) 2.42 (s, 3 H) 2.98-3.27 (m, 2 H) 3.83 (br s, 1 H) 3.90-4.21 (m, 2 H) 7.48 (d, J=8.10 Hz, 2 H) 7.77 (d, J=8.20 Hz, 2 H)

PREPARATION 19

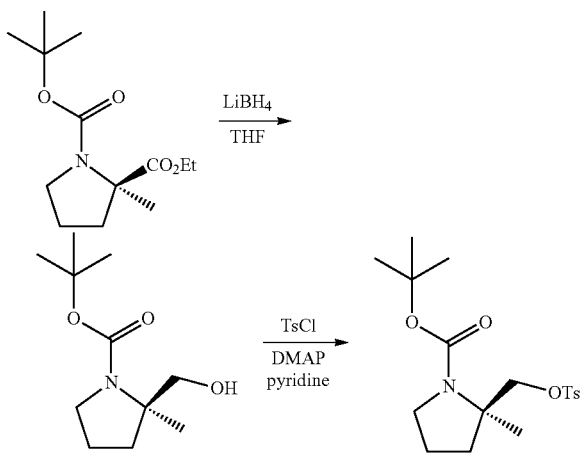

1,1-dimethylethyl(2R)-2-methyl-2-({[(4-methylphe-
nyl)sulfonyl]oxy}methyl)pyrrolidine-1-carboxylate Step 1:

To a solution of 1-(1,1-dimethylethyl)2-ethyl(2R)-2-methylpyrrolidine-1,2-dicarboxylate (Kawabata, T. et al, *JACS*

2003, 125, 13012; 2.33 g, 9.0 mmol) in THF (40 mL) maintained at 0° C. was added LiBH₄ (22.7 mL of a 2M solution in THF, 45 mmol) over 10 min. The reaction was stirred for 15 min at which time the ice bath was removed and stirring was continued for 48 h. The reaction was cooled to 0° C. and saturated aqueous NH₄Cl was added carefully. After gas evolution had ceased, the mixture was diluted with water and EtOAc and the layers were separated. The aqueous phase was extracted with EtOac. The combined organic extracts were washed with half-saturated aqueous NaCl, dried with Na₂SO₄, and concentrated under reduced pressure. The residue was purified by flash chromatography, elution with 0-100% EtOAc in heptane, to afford the product (1.88 g, 96.5%) as a clear oil.

¹H NMR (400 MHz, CDCl₃) δ 1.36 (s, 3 H) 1.46 (s, 9 H) 1.55-2.02 (m, 4 H) 3.21-3.76 (m, 4 H) 5.28 (d, J=9.42 Hz, 1 H)

Step 2:

Following a procedure analogous to that described for Preparation 18, the product from Step 1 was converted to the title compound.

¹H NMR (400 MHz, CDCl₃) δ 1.29 (d, J=9.81 Hz, 3 H) 1.38 (d, J=15.42 Hz, 9 H) 1.60-1.90 (m, 3 H) 2.01-2.24 (m, 1 H) 2.45 (d, J=2.83 Hz, 3 H) 3.29-3.54 (m, 2 H) 3.99-4.49 (m, 2 H) 7.34 (dd, J=12.67, 8.03 Hz, 2 H) 7.78 (t, J=7.32 Hz, 2 H).

INTERMEDIATE 1

Benzyl(1S,4aR,6aS,7R,8R,10aR,10bR,12aR,14R,15R)-8-[(1R)-1,2-dimethylpropyl]-15-hydroxy-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

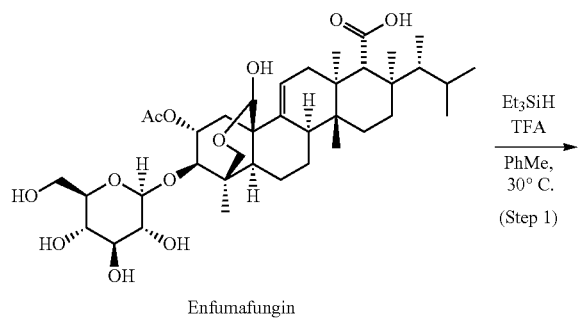

Enfumafungin

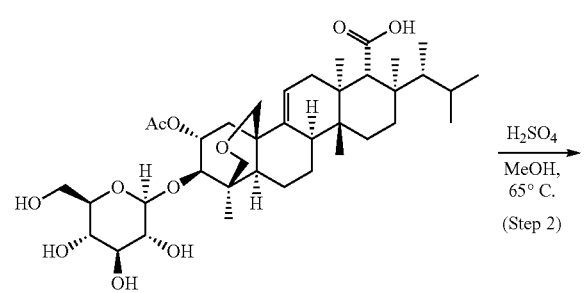

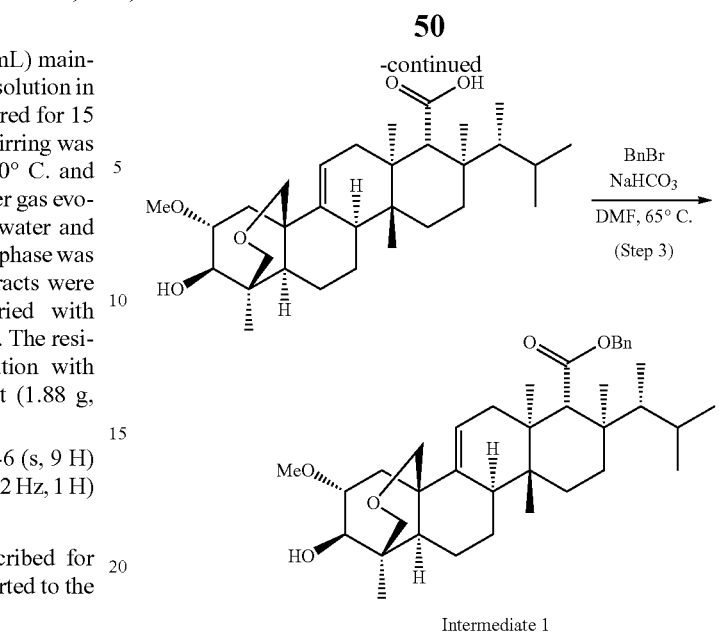

Intermediate 1

Step 1:

To a slurry of enfumafungin (90.0 g, 126.9 mmol) in 846 ml of toluene with mechanical stirring at room temperature was added Et₃SiH (202.2 ml, 1269.5 mmol) in one portion. Trifluoroacetic acid (202.4 ml, 2627.8 mmol) was then added dropwise at a rapid rate. Once the trifluoroacetic acid addition was complete, the resulting amber colored solution was allowed to stir at room temperature for 2.5 hours. The TFA/toluene solution was then concentrated to dryness. Fresh toluene (300-500 ml) was added and the mixture was once again concentrated to dryness. The toluene stripping procedure was repeated two additional times. The crude solid was then dried overnight on a high vacuum line to yield 120 g of a purple brown solid. This material was carried on to the next step without additional purification.

Step 2:

To a solution of the solid from above (120 g crude material, ~126.9 mmol) in MeOH (1.27 L) with mechanical stirring, H₂SO₄ (31.2 ml, 585.3 mmol) was added dropwise at a fast rate. Once the addition was complete, the resulting solution was warmed to 65° C. and was allowed to stir for 4.5 hours. During the course of the reaction a white solid precipitated. The reaction was cooled to room temperature and the white solid was isolated by filtration. The solid was then washed with MeOH (2×200 ml) and CH₃CN (2×200 ml). After drying, 47.91 g white solid was recovered.

Additional material was isolated from the initial filtrate and subsequent washings as follows. The total liquid volume was reduced to ⅓ by evaporation in vacuo. An excess of water was added and a purple white solid precipitated. The solid was filtered, washed with 3:7 MeOH:water (2×100 mL) and CH₃CN (2×100 mL) and dried to give an additional 7.30 g of product as a brownish white solid. The combined yield of product was 55.21 g (86.5%).

Step 3:

The product from Step 2 (55.21 g, 109.8 mmol), NaHCO₃ (147.5 g, 1756.8 mmol) and benzyl bromide (65.29 ml, 549.0 mmol) were combined in 550 ml DMF with mechanical stirring. The mixture was warmed to 65° C. and was allowed to stir for 4.5 hours. The DMF was removed in vacuo and the resulting crude material was dissolved in 1 L of 3:2 water/MeOH. The mixture was vigorously stirred for 2-3 hours. During this time a brownish white solid formed. The precipitate was filtered and washed with additional 3:2 water/MeOH (2×250 mL). The solid was then rinsed with heptane and was allowed to air aspirate to initial dryness. The white solid recovered was then transferred to a recrystallizing dish and placed in a vacuum oven at 30° C. for four hours to give 52.2 g of white solid.

Additional material was isolated from the water:MeOH and heptane filtrates as follows. The combined solutions were extracted with EtOAc. The combined EtOAc washings were dried over $Na_2SO_4$ and concentrated to dryness. The resulting material was purified by $SiO_2$ chromatography (3:7 EtOAc: DCM) to yield an additional 5.42 g of product as a white solid. The total combined yield of Intermediate 1 was 57.6 g (88.5%).

$^1$H NMR (400 MHz, $CDCl_3$, ppm) δ 0.71-0.74 (m, 6H), 0.78 (d, J=6.83 Hz, 3H), 0.80-0.83 (m, 6H), 1.15 (s, 3H), 1.16-1.21 (m, 1H), 1.23 (s, 3H), 1.24-1.29 (m, 2H), 1.32-1.53 (m, 4H), 1.56-1.62 (m, 1H), 1.70-1.81 (m, 3H), 1.87-1.95 (m, 1H), 1.99-2.04 (m, 1H), 2.07-2.16 (m, 1H), 2.30 (d, J=2.25 Hz, 1H), 2.40-2.47 (m, 1H), 2.88 (s, 1H), 3.18 (d, J=8.88 Hz, 1H), 3.31 (d, J=11.76 Hz, 1H), 3.40-3.42 (m, 2H), 3.43 (s, 3H), 3.77 (d, J=11.81 Hz, 1H), 4.09-4.19 (m, 1H), 4.98 (d, 1H), 5.12 (d, 1H), 5.39-5.43 (m, 1H), and 7.32-7.39 (m, 5H).

INTERMEDIATE 2

(1S,4aR,6aS,7R,8R,10aR,10bR,12aR,14R,15R)-15-(2-aminoethoxy)-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

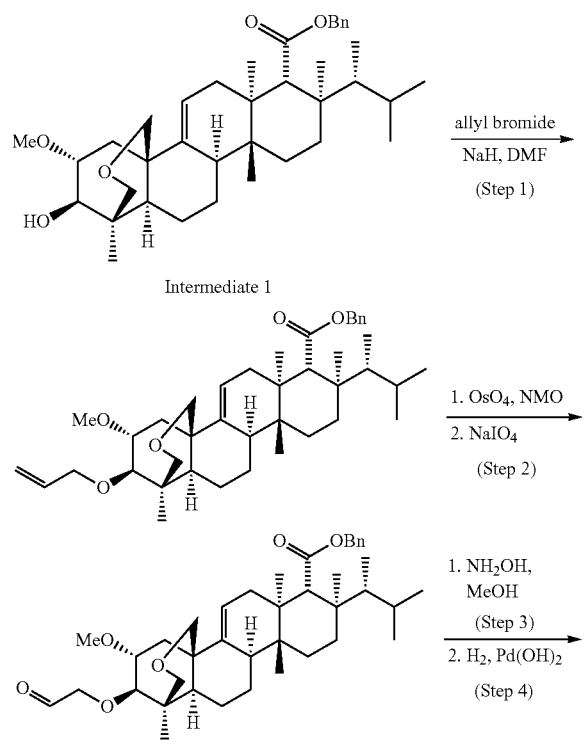

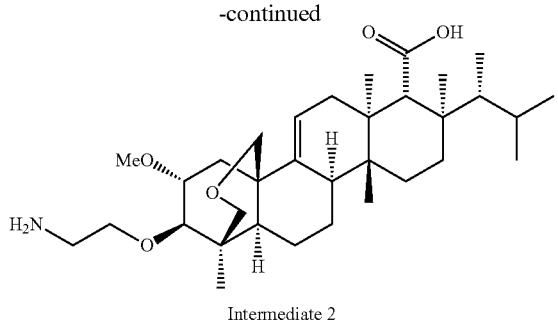

Intermediate 2

Step 1:

To a chilled solution of Intermediate 1 (611 mg; 1.025 mmol) in dimethylformamide (9 mL) was added sodium hydride (328 mg; 8.2 mmol) and allyl bromide (355 μL). The reaction was stirred at room temperature for 16 hours. The reaction was judged complete by TLC analysis. The reaction contents were concentrated and the residue was flash chromatographed (silica gel; 80:20 heptane: ethyl acetate) to yield 529 mg of purified material.

Step 2:

The material from above (529 mg) was dissolved in acetone (6.8 mL) and water (0.8 mL). Osmium tetroxide (4% solution; 531 μL; 0.08 mmol) and 4-methylmorpholine N-oxide ((196 mg) were added and the reaction stirred at room temperature for 16 hours. The reaction was judged complete by TLC analysis. Florisil (550 mg) and sodium bisulfite (550 mg) were added and the reaction solution was stirred for 1 hour at room temperature. The reaction contents were filtered over a pad of Celite and concentrated. The residue was dissolved in tetrahydrofuran (12 mL) and water (3 mL) and sodium periodate (490 mg) was added. The reaction solution was stirred for 2 hours at room temperature and judged complete by TLC analysis. Water (5 mL) was added and the aqueous phase was thrice washed with ethyl acetate. The organic phase was dried over magnesium sulfate and concentrated. The residue was flash chromatographed (silica gel; 70:30 heptane: ethyl acetate) to yield the aldehyde intermediate (550 mg).

Step 3:

A mixture of aldehyde intermediate prepared as described in Step 2 (1 g, 1.58 mmol), hydroxylamine hydrochloride (1.1 g, 15.8 mmol) and sodium bicarbonate (5.3 g, 63.2 mmol) was suspended in methanol (50 mL) and stirred at room temperature for 1 hour. Ethyl acetate (200 mL) and water (200 mL) were added, the ethyl acetate layer was washed with brine (1×50 mL), dried with magnesium sulfate, filtered and evaporated to give the product as a foam (1.1 g). Examination of the solid by $^1$H NMR showed an approximately 1:1 mixture of E- and Z-oxime stereoisomers.

Step 4:

A mixture of the oxime from Step 3 (1.1 g, 1.58 mmol), TFA (608 uL, 7.9 mmol) and 20% Pd(OH)$_2$/C in methanol (50 mL) was stirred under a balloon of hydrogen for 3 hours at room temperature. The suspension was filtered, evaporated and freeze-dried from a mixture of ethanol and benzene to give Intermediate 2 as a white solid.

$^1$H NMR $CD_3OD$ δ (PPM) 5.54 (dd, 1H, H5); 4.23 (m, 1H, H14); 3.87 (m, 1H); 3.68 (m); 3.62 (d, 1H); 3.40-3.43 (m); 3.39 (s, 3H, OMe); 3.32 (dd, 1H), 3.02-3.08 (m); 2.93 (d, 1H); 2.85 (s, 1H, H7), 2.54 (dd, 1H, H13); 2.19 (m, 1H); 2.08 (m, 1H); 1.96 (m, 1H); 1.70-1.84 (m); 1.46-1.64 (m); 1.22-1.28 (m); 1.21 (s, 3H, Me); 1.16 (s, 3H, Me); 0.90 (d, 3H, Me); 0.85 (s, 3H, Me); 0.78 (d, 3H, Me); 0.75 (d, 3H, Me) and 0.75 (s, 3H, Me).

LC/MS m/z (positive ion scan) M+1=546.98

INTERMEDIATE 3

(1S,4aR,6aS,7R,8R,10aR,10bR,12aR,14R,15R)-15-(2-amino-2-methylpropoxy)-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

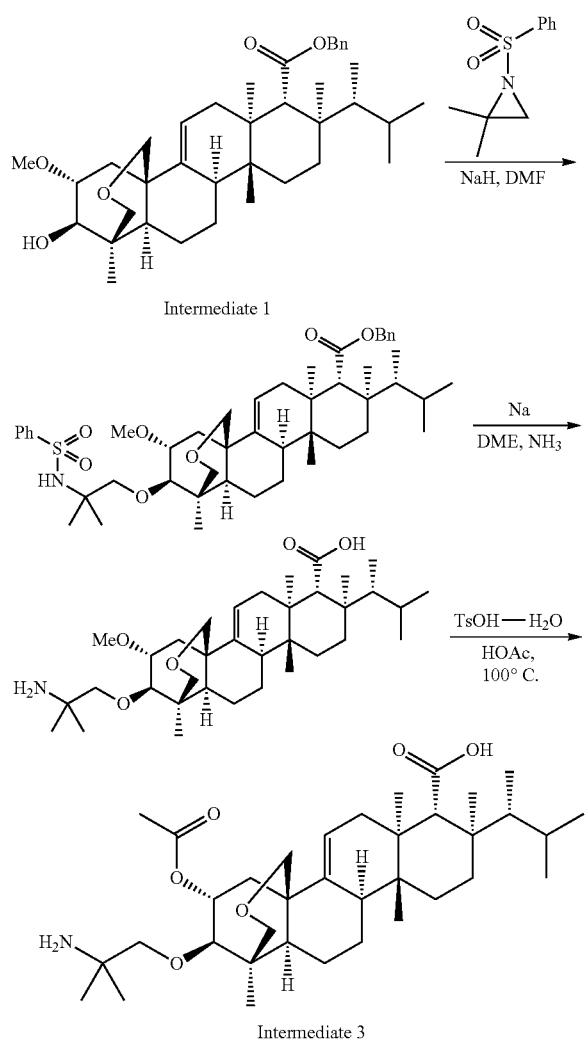

Step 1

To a solution of Intermediate 1 (1.5 g; 2.5 mmol) in dimethylformamide (30 mL) was added sodium hydride (1.0 g; 60% dispersion, 25.3 mmol) and 1-benzenesulfonyl-2,2-dimethyl-aziridine (2.67 g; 12.5 mmol). The reaction mixture was heated to 70° C. and stirred for 1 hour; the reaction was judged complete by TLC analysis. The reaction was cooled to room temperature and ethyl acetate (100 mL), methanol (10 mL) and water (50 mL) were added. The aqueous phase was twice washed with ethyl acetate. The organic phases were combined, dried over magnesium sulfate, and concentrated. The residue was flash chromatographed (silica gel; 90:10 heptane:ethyl acetate) to yield a white solid (1.75 g).

Step 2

A portion of the purified material from Step 1 (800 mg) was dissolved in dimethoxyethane (20 mL) and the solution was chilled to −70° C. Ammonia (20 g) was added to the reaction solution and sodium metal (enough to sustain a blue color) was added over the course of 1.5 hours. The reaction solution was stirred at −60° C. for 2 hours and then warmed to ammonia reflux for 30 minutes. The reaction was judged complete and methanol (15 mL) was slowly added. The reaction was then warmed to 0° C. and water (50 mL) was added. The aqueous phase was thrice washed with ethyl acetate (75 mL); the organic phases were combined, dried over magnesium sulfate, and concentrated to give the product as a white solid.

Step 3

To a stirred solution of the white solid from Step 2 in acetic acid (100 mL) was added p-TsOH—H$_2$O (0.93 g) and the reaction mixture was heated at 113° C. for 1.5 h. The reaction mixture was then allowed to cool to room temperature and the acetic acid was evaporated under reduced pressure. The residue was dissolved in EtOAc (200 mL) and washed with a saturated NaHCO$_3$ solution (100 mL) carefully. The aqueous phase was re-extracted with EtOAc (2×100 mL). The combined organic solutions were dried over anhydrous MgSO$_4$. After filtration and evaporation of the solvent Intermediate 3 was isolated as a white solid (0.87 g).

$^1$H NMR (CD$_3$OD, 600 MHz, ppm) δ 0.75 (s, 3H, Me), 0.77 (d, 3H, Me), 0.83 (s, 3H, Me), 0.85 (d, 3H, Me), 0.90 (d, 3H, Me), 1.16 (s, 3H, Me), 1.20 (s, 3H, Me), 1.30 (s, 3H, Me), 1.31 (s, 3H, Me), 1.22-1.44 (m), 1.45-1.52 (m), 1.53-1.69 (m), 1.72-1.87 (m), 1.92-1.97 (m), 2.04 (s, 3H, Me), 2.06-2.11 (m), 2.15-2.22 (m), 2.42 (dd, 1H, H1), 2.84 (s, 1H, H18), 3.22 (d, 1H), 3.38 (d, 1H), 3.43 (dd, 1H), 3.47 (d, 1H), 3.57 (d, 1H), 3.63 (d, 1H), 3.79 (d, 1H), 5.46 (dd, 1H, H11), 5.77-5.82 (m, 1H, H2).

Mass Spectrum: (ESI) m/z=603.02 (M+H).

INTERMEDIATES 4 & 5

Benzyl(1S,4aR,6aS,7R,8R,10aR,10bR,12aR,14R,15R)-15-[[(2R)-2,3-dimethyl-2-[[(4-methylphenyl)sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate (Intermediate 4) and Benzyl(1S,4aR,6aS,7R,8R,10aR,10bR,12aR,14R,15R)-15-[[(2S)-2,3-dimethyl-2-[[(4-methylphenyl)sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate (Intermediate 5)

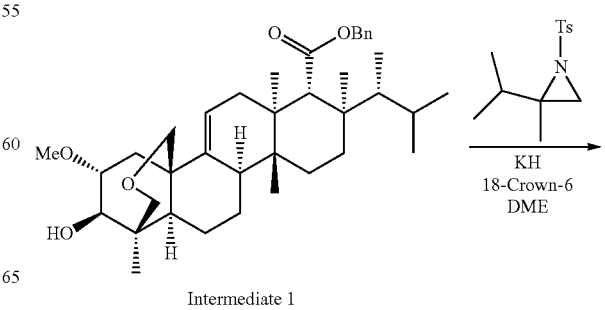

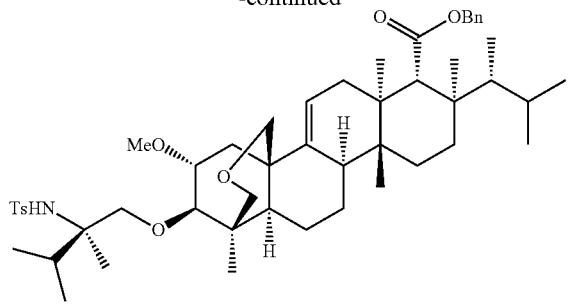

Intermediate 4

+

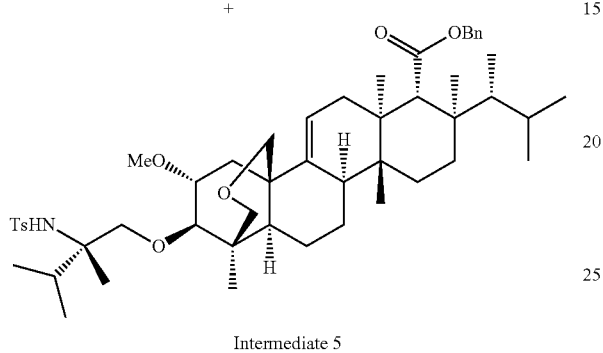

Intermediate 5

To a stirred solution of Intermediate 1 dissolved in anhydrous dimethoxyethane (400 mL) was added 18-crown-6 (33.7 g, 127.5 mmol) and 2-isopropyl-2-methyl-1-[(4-methylphenyl)sulfonyl]aziridine (21.4 g, 84.6 mmol, 1.66 equiv). The mixture was stirred under nitrogen for 10 min until all solids were dissolved. Potassium hydride (30% in oil, 17.0 g, 127.5 mmol, 2.5 equiv) was added portionwise (ca. 1 g portions) over a period of about 30 minutes. After the completion of the addition, the resulting suspension was stirred at room temperature for about 3 h. The reaction was carefully quenched by the dropwise addition of methanol (40 mL). The reaction mixture was then diluted with water (300 mL) and extracted with EtOAc (300 mL). The organic solution was washed with water (2×200 mL) and dried over anhydrous MgSO$_4$. The drying agent was removed by filtration and the organic solvent was removed under reduced pressure to afford the desired compound (67.4 g) as a mixture of diastereomers. Separation of the diastereomers was accomplished by chromatography on silica gel (0-15% EtOAc/heptanes) to give the faster eluting isomer, Intermediate 4, and the slower eluting isomer, Intermediate 5.

INTERMEDIATE 4

$^1$H NMR CDCl$_3$ δ (PPM) 7.81 (d, 1H, ArH); 7.38 (m, ArH); 7.34 (m, ArH); 7.26 (m, ArH); 6.65 (s, NH); 5.44 (m, 1H, H5); 5.12 (d, 2H, CH$_2$Ar); 4.99 (d, 2H, CH$_2$Ar); 4.23 (m, 1H, H14); 3.69 (d, 1H); 3.65 (d, 1H); 3.47 (s, 3H, OMe); 3.38 (m); 3.26 (d, 1H); 3.21 (d, 1H); 2.89 (s, 1H, H7); 2.83 (d, 1H); 2.49 (dd, 1H, H13); 2.42 (s, ArMe); 2.12 (m, 1H); 2.02-2.08 (m); 1.90-1.94 (m); 1.66-1.78 (m); 1.44-1.51 (m); 1.35-1.39 (m); 1.14-1.30 (m); 1.25 (s, 3H, Me); 1.18 (s, 3H, Me); 0.95 (d, 3H, Me); 0.93 (s, 3H, Me); 0.88 (d, 3H, Me); 0.82 (d, 3H, Me); 0.78 (d, 3H, Me); 0.73 (d, 3H, Me); 0.72 (s, 3H, Me) and 0.67 (s, 3H, Me).

INTERMEDIATE 5

$^1$H NMR CDCl$_3$ δ (PPM) 7.77 (d, 1H, ArH); 7.37 (m, ArH); 7.33 (m, ArH); 7.27 (s, ArH); 7.26 (d, ArH); 5.41 (m, 1H, H5); 5.19 (s, NH); 5.11 (d, 2H, CH$_2$Ar); 4.98 (d, 2H, CH$_2$Ar); 4.22 (m, 1H, H14); 3.72 (d, 1H); 3.68 (d, 1H); 3.50 (d, 1H); 3.39 m); 3.37 (s, 3H, OMe); 3.30 (d, 1H); 2.89 (s, 1H, H7), 2.82 (d, 1H); 2.42-2.45 (m); 2.41 (s, ArMe); 2.11 (m, 1H); 2.00-2.04 (m); 1.89-1.94 (m); 1.70-1.79 (m); 1.44-1.58 (m); 1.35-1.39 (m); 1.14-1.27 (m); 1.23 (s, 3H, Me); 1.15 (s, 3H, Me); 1.00 (s, 3H, Me); 0.88 (d, 3H, Me); 0.86 (d, 3H, Me); 0.82 (s, 3H, Me); 0.81 (d, 3H, Me); 0.78 (d, 3H, Me); 0.73 (d, 3H, Me) and 0.72 (s, 3H, Me).

INTERMEDIATE 4

Alternate Synthesis

Benzyl(1S,4aR,6aS,7R,8R,10aR,10bR,12aR,14R,15R)-15-[[(2R)-2,3-dimethyl-2-[[(4-methylphenyl)sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

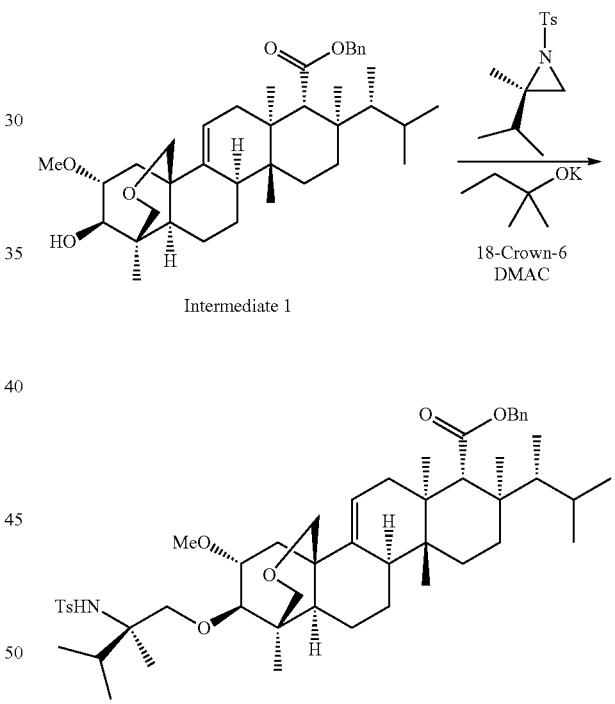

To a solution of Intermediate 1 (8.0 g, 13.49 mmol) in DMAC (50 mL) under a nitrogen atmosphere was added (2R)-2-isopropyl-2-methyl-1-[(4-methylphenyl)sulfonyl]aziridine (6.15 g, 24.29 mmol) and 18-crown-6 (3.57 g, 13.49 mmol). A solution of potassium tert pentoxide in toluene (~1.7 M, 9.53 mL, 16.19 mmol) was added in one portion. The mixture was stirred at room temperature for 16 hours and partitioned between EtOAc and 1 N HCl. The organic layer was washed with brine and dried over Na$_2$SO$_4$. The solvent was evaporated and the residue was chromatographed with an ISCO Combiflash using 15-30% EtOAc/hexanes as gradient to afford Intermediate 4 as a pale yellow solid (7.50 g)

INTERMEDIATE 5

Alternate Synthesis

Benzyl(1S,4aR,6aS,7R,8R,10aR,10bR,12aR,14R,15R)-15-[[(2S)-2,3-dimethyl-2-[[(4-methylphenyl)sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

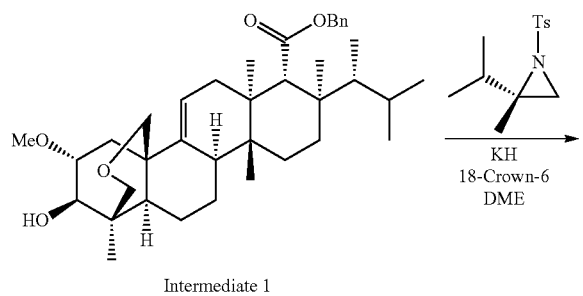

Intermediate 1

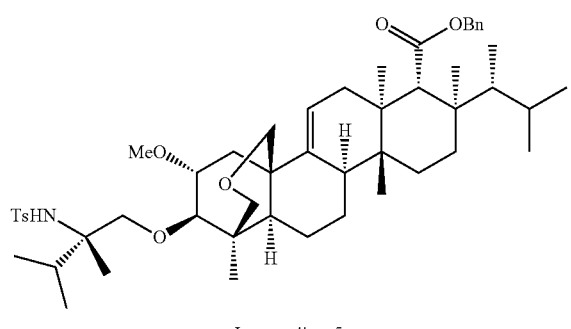

Intermediate 5

To a stirred solution of Intermediate 1 (60 g, 101 mmol) in anhydrous dimethoxyethane (800 mL) was added 18-crown-6 (67.4 g, 255 mmol) and (2S)-2-isopropyl-2-methyl-1-[(4-methylphenyl)sulfonyl]aziridine (42.8 g, 169.2 mmol). The mixture was stirred under nitrogen for 30 min until all solids were dissolved. Potassium hydride (30% in oil, 34.0 g, 255 mmol) was added portionwise (ca. 5 g portions) over a period of about 1 hour. The reaction temperature increased from 18° C. to 27° C. After the completion of the addition the resulting suspension was stirred at room temperature for about 3 h. The reaction was carefully quenched by the dropwise addition of methanol (80 mL). Following an initial period of bubbling, the rate of addition of methanol addition can be increased and a clear solution was obtained. The reaction mixture was then diluted with water (600 mL) and extracted with EtOAc (900 mL). The organic solution was diluted with $CH_2Cl_2$ (1 L) and dried over anhydrous $MgSO_4$. The drying agent was removed by filtration and the organic solvent was removed under reduced pressure to afford the crude compound (143.4 g). This material was purified on silica gel using ethyl acetate/heptanes to give the desired compound (75.4 g).

INTERMEDIATE 6

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

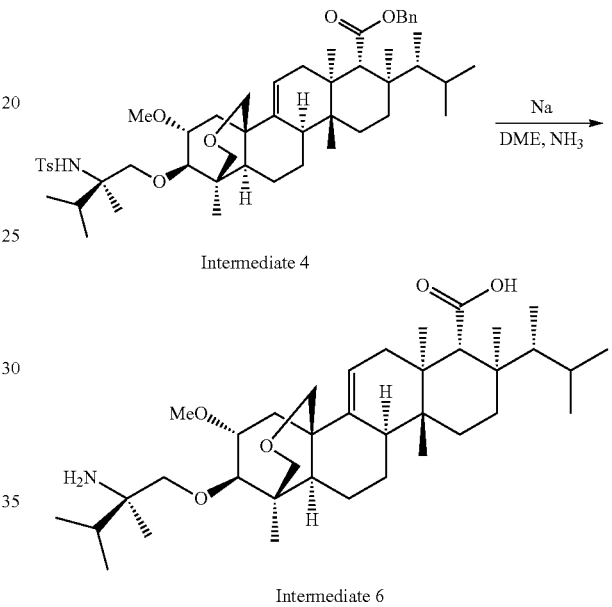

A 500 mL round bottom flask was cooled in a dry ice acetone bath and approximately 100 mL of ammonia was distilled into the flask. The flask was removed from the bath and allowed to warm to reflux. Sodium (5.7 g) was added to give a deep blue solution. DME (15 mL) was added followed by the dropwise addition of Intermediate 4 (5 grams) in DME (20 mL) over 6 minutes. The deep blue color persisted over the addition and the next 1.5 hours. At 1.5 hours, LC/MS analysis of an aliquot showed complete conversion to the product. Workup was as follows: The dropwise addition of methanol (130 mL) (with a stream of nitrogen blown over the surface) produced a heavy white suspension. The nitrogen stream was continued an additional 30 minutes. Ethyl acetate (800 mL) and water (400 mL) were added and the aqueous layer was re-extracted with more ethyl acetate (200 mL). The combined ethyl acetate was dried with magnesium sulfate, filtered and evaporated to give Intermediate 6 as a white solid (3.18 grams). No purification was necessary.

$^1$H NMR $CD_3OD$ δ (PPM) 5.52 (dd, 1H, H5); 4.23 (m, 1H, H14); 3.70 (m); 3.38 (s, 3H, OMe); 3.28-3.34 (m); 2.71 (s, 1H, H7), 2.54 (dd, 1H, H13), 2.29 (m); 1.98-2.08 (m); 1.54-1.84 (m); 1.44-1.50 (m); 1.34-1.41 (m); 1.27 (s, 3H, Me); 1.19 (s, 3H, Me); 1.15-1.24 (m); 1.10 (s, 3H, Me); 0.99 (d, 3H, Me); 0.96 (d, 3H, Me); 0.89 (d, 3H, Me); 0.83 (d, 3H, Me); 0.79 (s, 3H, Me); 0.77 (d, 3H, Me) and 0.76 (s, 3H, Me).

LC/MS m/z (positive ion scan) M+1=602.62.

INTERMEDIATE 7

(1S,4aR,6aS,7R,8R,10aR,10bR,12aR,14R,15R)-15-[[(2S)-2-amino-2,3-dimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

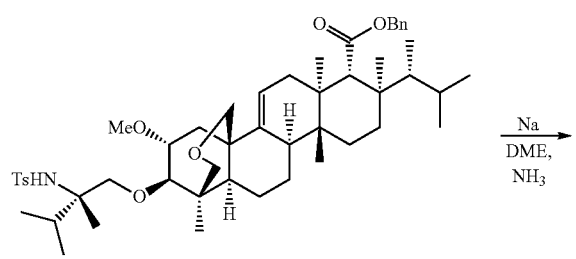

Intermediate 5

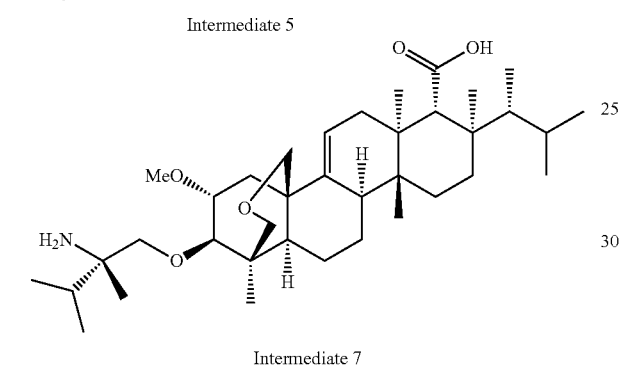

Intermediate 7

A solution of Intermediate 5 (18.21 g, 21.60 mmol) in dimethoxyethane (300 mL) was added over about 20 minutes to liquid ammonia (approx. 400 mL) kept at −35 to −50° C. (bath temp). Sodium metal (4.0 g, in 0.2 g portions that were quickly washed with heptane prior to addition) was added to the ammonia solution over a period of 30 minutes ensuring that the reaction temperature was maintained at about −35° C. (bath temp). The deep blue reaction mixture was allowed to stir for 3 h. Analysis by TLC (50% EtOAc in Heptanes and 10% MeOH in DCM) indicated an incomplete reaction so additional sodium metal (1.0 g, divided into 0.5 g portions) was added over the course of about 10 minutes as described above. The reaction was stirred for an additional 2 h, whereupon the reaction was judged to be complete by TLC and LC-MS analysis. The reaction was quenched by the careful addition of isopropanol (10 mL, added dropwise over about 15 minutes), followed by 1:1 isopropanol-MeOH (80 mL over 30 minutes), and MeOH (40 mL over 30 minutes). The reaction mixture was stirred for 1 h and water (15 mL) was then added over 15 minutes. The ammonia was allowed to evaporate (several hours or overnight) and then water (300 mL) was added to the reaction. The mixture was extracted with EtOAc (3×350 mL). The organic solution was dried over anhydrous MgSO$_4$. Removal of the drying agent and evaporation of the solvent gave a white solid (7.96 g). The aqueous solution was treated with brine (400 mL) and re-extracted with dichloromethane (3×300 mL). The combined dichloromethane extracts were dried (MgSO$_4$), filtered and evaporated to afford additional white solid (4.53 g). The combined yield of Intermediate 7 was 12.49 g, which was used directly in the next step.

$^1$H NMR CD$_3$OD δ (PPM) 5.52 (dd, 1H, H5); 4.21 (m, 1H, H14); 3.83 (d, 1H)); 3.69 (d, 1H); 3.51 (d, 1H); 3.40 (s, 3H, OMe); 3.32 (d, 1H); 2.99 (d, 1H); 2.73 (s, 1H, H7); 2.53 (dd, 1H, H13), 2.30 (m); 1.98-2.078 (m); 1.94 (m); 1.66-1.84 (m); 1.54-1.61 (m); 1.44-1.49 (m); 1.40 (m); 1.33-1.37 (m); 1.26 (s, 3H, Me); 1.16-1.28 (m); 1.21 (s, 3H, Me); 1.10 (s, 3H, Me); 0.97 (d, 3H, Me); 0.96 (d, 3H, Me); 0.89 (d, 3H, Me); 0.84 (d, 3H, Me); 0.79 (s, 3H, Me); 0.76 (d, 3H, Me) and 0.75 (s, 3H, Me).

LC/MS m/z (positive ion scan) M+1=602.62

INTERMEDIATE 8

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

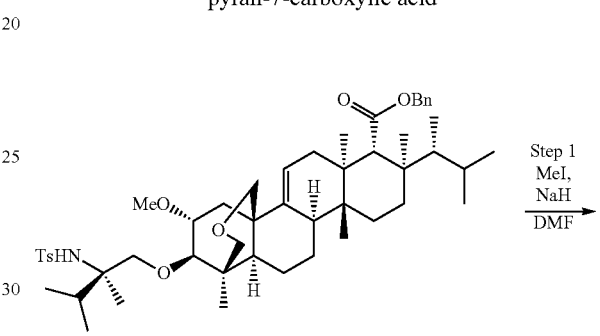

Intermediate 4

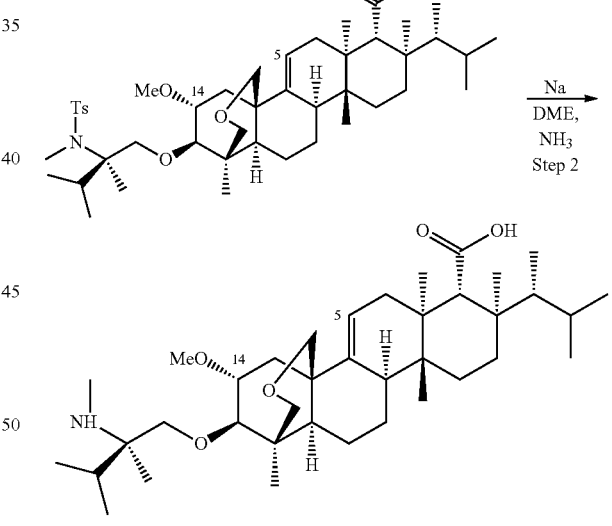

Intermediate 8

Step 1

Sodium hydride, a 60% dispersion in mineral oil (52 mg, 1.3 mmol), was added to a suspension of Intermediate 4 (1.1 g, 1.3 mmol) and methyl iodide (0.81 mL, 13 mmol) in anhydrous dimethylformamide (2.6 mL). The suspension was heated in a 50° C. oil bath for 1.5 hours, whereupon additional sodium hydride (47 mg, 1.2 mmol) was added. After an additional 1.5 hours, the mixture was cooled to room temperature, ethyl acetate (50 mL), water (50 mL) and 2 N hydrochloric acid (7 mL) were added and the organic layer was washed with water (4×50 mL), brine (1×20 mL), dried with magnesium sulfate, filtered and evaporated to give a product as a foam (1.1 grams).

Selected $^1$H NMR (CDCl$_3$, 600 MHz, ppm) 2.42 (s, 3H, PhMe), 3.06 (s, 3H, NMe); 3.28 (s, 3H, OMe); 4.14 (m, 1H, H14); 5.00 and 5.14 (2d, 2H, CH$_2$Ph), 5.22 (dd, 1H, H5), 7.25 (d, 2H, ArH), 7.75 (d, 2H, ArH).

Step 2

A solution of the product from Step 1 (1.1 g, 1.28 mmol) in anhydrous dimethoxyethane (6 mL) was added dropwise over 5 minutes to refluxing ammonia (ca. 20 mL) containing dimethoxyethane (4 mL) and sodium (1.68 g, 73.4 mmol). Additional ammonia (ca. 10 mL) was added and the deep blue colored mixture was stirred an additional 80 minutes. Dropwise addition of methanol (30 mL) produced a heavy white suspension over which a stream of nitrogen was passed for approximately 20 minutes. Ethyl acetate (200 mL) and water (100 mL) were added, the aqueous layer was re-extracted with more ethyl acetate (1×50 mL) and the combined ethyl acetate layers were dried with magnesium sulfate, filtered and evaporated to give Intermediate 8 as a foam (0.8 g).

Selected $^1$H NMR (CDCl$_3$, 600 MHz, ppm) 2.64 (s, 3H, NMe); 3.32 (s, 3H, OMe); 4.22 (m, 1H, H14), 5.57 (dd, 1H, H5).

LC/MS m/z (positive ion scan) M+1=616.60.

INTERMEDIATE 9

(1S,4aR,6aS,7R,8R,10aR,10bR,12aR,14R,15R)-15-[[(2S)-2,3-dimethyl-2-(methylamino)butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

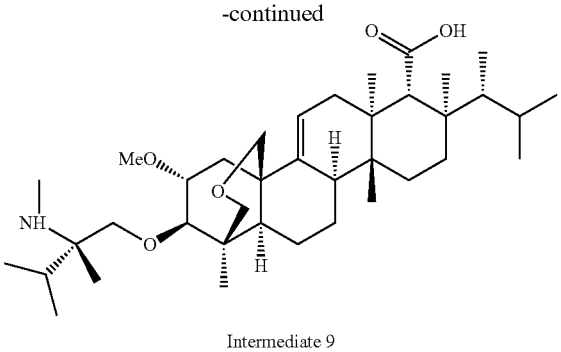

Intermediate 9

By a procedure analogous to that described for the synthesis of Intermediate 8, Intermediate 9 was synthesized starting with Intermediate 5.

$^1$H NMR CD$_3$OD δ (PPM) 5.54 (dd, 1H, H5); 4.24 (m, 1H, H14); 3.96 (d, 1H); 3.71 (d, 1H); 3.61 (m); 3.42 (s, 3H, OMe); 3.35 (m); 3.29 (m); 2.97 (d, 1H); 2.85 (s, 1H, H7), 2.66 (s, 3H, NMe); 2.57 (dd, 1H, H13), 2.19 (m); 2.14 (m); 2.06-2.11 (m); 1.94-1.98 (m); 1.70-1.96 (m); 1.58-1.65 (m); 1.46-1.52 (m); 1.38-1.42 (m); 1.22-1.30 (m); 1.22 (s, 3H, Me); 1.21 (s, 3H, Me); 1.17 (s, 3H, Me); 1.10 (d, 3H, Me); 0.99 (d, 3H, Me); 0.90 (d, 3H, Me); 0.85 (d, 3H, Me); 0.79 (s, 3H, Me); 0.77 (d, 3H, Me) and 0.76 (s, 3H, Me).

LC/MS m/z (positive ion scan) M+1=616.60.

INTERMEDIATE 10

(1S,4aR,6aS,7R,8R,10aR,10bR,12aR,14R,15R)-15-[[(2R)-2-(dimethylamino)-2,3-dimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

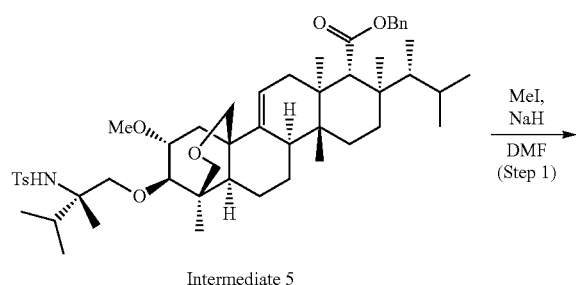

Intermediate 5

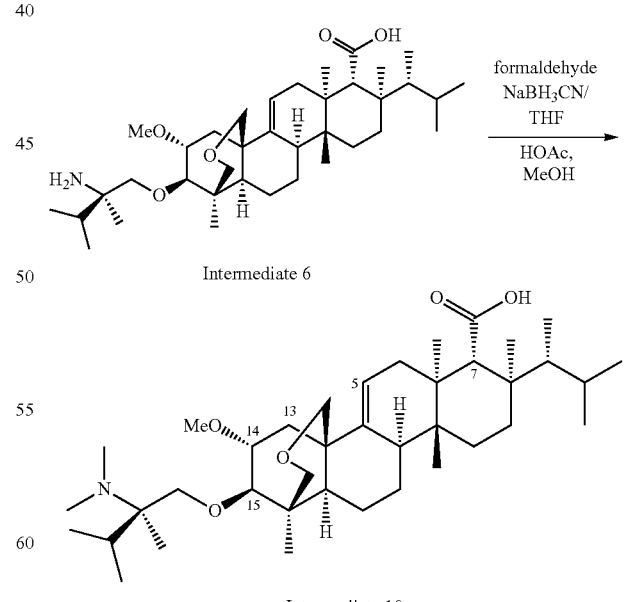

Intermediate 10

Acetic acid (0.25 ml, 4.37 mmol), formaldehyde 37% in water (0.66 ml, 8.86 mmol), and sodium cyanoborohydride 1.0 M in THF (8.8 ml, 8.80 mmol) were added to a stirred solution of Intermediate 6 (1.31 g, 2.18 mmol) in methanol (22.0 ml). The reaction mixture was a colorless solution. After about 16.5 hours, LCMS showed complete consumption of Intermediate 6. The reaction mixture was partitioned between ethyl acetate (200 ml) and water (200 ml). The aqueous layer was extracted with ethyl acetate (1×100 ml). The organic layers were combined, dried over magnesium sulfate, and filtered. The solvent was evaporated under reduced pressure. The residue was lyophilized from ethanol and benzene to give Intermediate 10 (1.29 g) as a white solid.

$^1$H NMR (CD$_3$OD, 500 MHz, ppm) δ 0.78 (s, 3H, Me), 0.79 (d, 3H, Me), 0.85 (s, 3H, Me), 0.88 (d, 3H, Me), 0.92 (d, 3H, Me), 1.10 (d, 3H, Me), 1.15 (d, 3H, Me), 1.18 (s, 3H, Me), 1.19 (s, 3H, Me), 1.23 (s, 3H, Me), 1.21-1.36 (m), 1.40-1.45 (m), 1.48-1.55 (m), 1.58-1.68 (m), 1.72-1.88 (m), 1.95-2.02 (m), 2.08-2.13 (m), 2.18-2.25 (m), 2.41-2.48 (m), 2.60 (dd, 1H, H13), 2.87 (s, 1H, H7), 2.98 (d, 1H), 2.99 (s, 6H, 2Me), 3.39 (d, 1H), 3.44 (s, 2H), 3.63 (d, 1H), 3.78 (d, 1H), 4.04 (d, 1H), 4.25-4.31 (m, 1H, H14), 5.57 (dd, 1H, H5).

Mass Spectrum: (ESI) m/z=630.62 (M+H).

INTERMEDIATE 11

(1S,4aR,6aS,7R,8R,10aR,10bR,12aR,14R,15R)-15-[[(2S)-2-(dimethylamino)-2,3-dimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

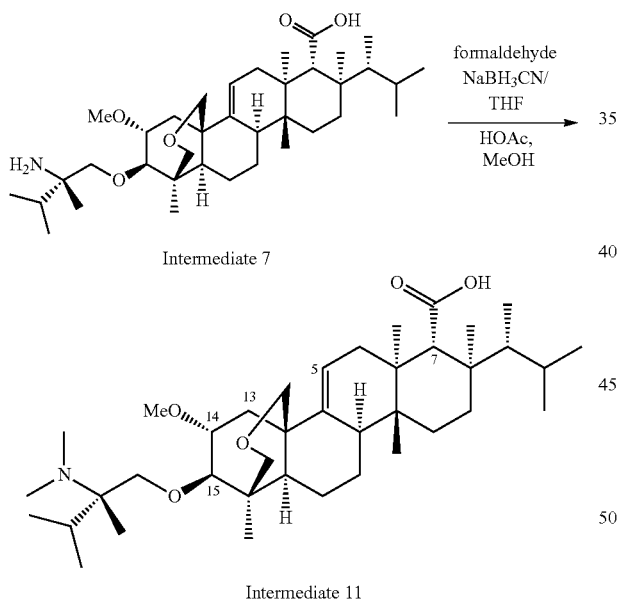

Intermediate 11 was prepared in a manner analogous to that described for Intermediate 10, but starting with Intermediate 7.

$^1$H NMR (CD$_3$OD, 600 MHz, ppm) δ 0.75 (s, 3H, Me), 0.76 (d, 3H, Me), 0.80 (s, 3H, Me), 0.84 (d, 3H, Me), 0.90 (d, 3H, Me), 1.05 (d, 3H, Me), 1.06 (d, 3H, Me), 1.18 (s, 3H, Me), 1.20 (s, 3H, Me), 1.22 (s, 3H, Me), 1.21-1.40 (m), 1.45-1.51 (m), 1.54-1.65 (m), 1.69-1.85 (m), 1.96-2.01 (m), 2.05-2.10 (m), 2.20-2.30 (m), 2.57 (dd, 1H, H13), 2.79 (s, 1H, H7), 2.84 (s, 6H, 2Me), 2.92 (d, 1H), 3.35 (d, 1H), 3.41 (s, 1H), 3.65 (d, 1H), 3.66 (d, 1H), 4.10 (d, 1H), 4.19-4.25 (m, 1H, H14), 5.53 (dd, 1H, H5).

Mass Spectrum: (ESI) m/z=630.62 (M+H).

INTERMEDIATE 12 & 13

Benzyl(1S,4aR,6aS,7R,8R,10aR,10bR,12aR,14R,15R)-8-[(1R)-1,2-dimethylpropyl]-14-methoxy-15-[[(2R)-2,3,3-trimethyl-2-[[(4-methylphenyl)sulfonyl]amino]butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate (Intermediate 12) and Benzyl(1S,4aR,6aS,7R,8R,10aR,10bR,12aR,14R,15R)-8-[(1R)-1,2-dimethylpropyl]-14-methoxy-15-[[(2S)-2,3,3-trimethyl-2-[[(4-methylphenyl)sulfonyl]amino]butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate (Intermediate 13)

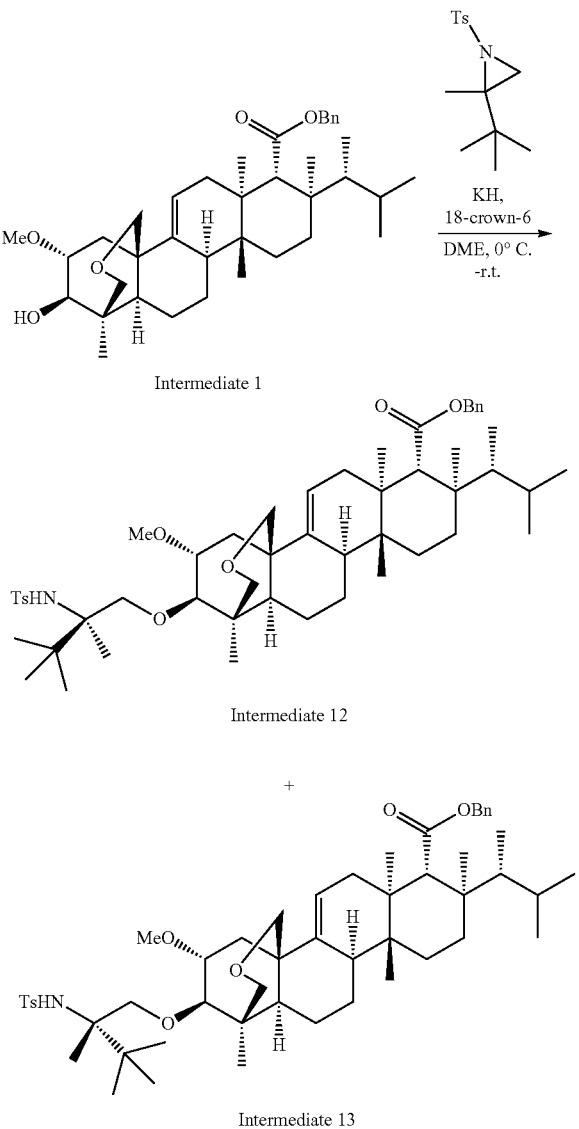

Intermediate 1 (5.00 g, 8.43 mmol), 18-crown-6 (11.15 g, 42.2 mmol), and 2-(1,1-dimethylethyl)-2-methyl-1-[(4-methylphenyl)sulfonyl]aziridine (4.51 g, 8.67 mmol) were dissolved in toluene and concentrated then placed under high vacuum for 1 hour. The resulting mixture was dissolved in dimethoxyethane (84 mL) placed under nitrogen atmosphere and cooled to 0° C. Potassium hydride (30% dispersion in mineral oil, 3.38 g, 25 mmol) was added and the reaction evacuated and charged with nitrogen (repeat evac./charge three times). The reaction was allowed to slowly warm to room temperature and after two hours additional 2-(1,1-dimethylethyl)-2-methyl-1-[(4-methylphenyl)sulfonyl]aziridine (0.43 g, 0,83 mmol) was added. After an additional hour the reaction was quenched by the addition of methanol followed by 1 N aq. HCl. The reaction mixture was partitioned between ethyl acetate and water and the aqueous extracted with ethyl acetate as necessary. The combined organic phase was dried over $MgSO_4$, filtered then concentrated. The crude product was purified by multiple flash chromatographies on Biotage 65i columns (0-100% ethyl acetate/hexane) which resolved the two diastereomeric products; the faster eluting Intermediate 12 (1.3 g) and the slower eluting Intermediate 13 (3.0 g).

INTERMEDIATE 12

$^1$H NMR (CDCl$_3$, 500 MHz, ppm) δ 0.63 (s, 3H), 0.71 (s, 3H) 0.72 (d, 3H, partially obscured), 0.78 (d, J=5.8 Hz, 3H), 0.81 (d, J=5.7 Hz, 3H), 0.96 (s, 3H), 1.02 (s, 9H), 1.14-1.3 (m), 1.2 (s, 3H), 1.25 (s, 3H), 1.32-1.8 (m), 1.92 (m, 1H), 2.04 (m, 1H), 2.12 (m, 1H), 2.41 (s, 3H), 2.52 (m, 1H), 2.72 (d, J=9.0 Hz, 1H), 2.88 (s, 1H), 2.98 (d, J=10.9 Hz, 1H), 3.25 (d, J=11.2 Hz, 1H), 3.35-3.4 (m, 2H), 3.49 (s, 3H), 3.63 (d, J=11.9 Hz, 1H), 3.85 (d, J=10.8 Hz, 1H), 4.25 (m, 1H), 4.98 (d, J=12.4 Hz, 1H), 5.12 (d, J=12.4 Hz, 1H), 5.44 (m, 1H), 6.89 (s, 1H), 7.25 (d, 2H, partially obscured), 7.32-7.4 (m, 5H), 7.84 (d, J=8.3 Hz, 2H).

INTERMEDIATE 13

$^1$H NMR (CDCl$_3$, 500 MHz, ppm) δ 0.71 (s, 3H), 0.72 (d, 3H, partially obscured), 0.77 (d, J=6.7 Hz, 3H), 0.81 (d, J=6.6 Hz, 3H), 0.83 (s, 3H), 0.97 (s, 9H), 1.02 (s, 3H), 1.12-1.28 (m), 1.14 (s, 3H), 1.24 (s, 3H), 1.34-1.6 (m), 1.68-1.8 (m), 1.92 (m, 1H), 2.02 (m, 1H), 2.11 (m, 1H), 2.40 (s, 3H), 2.45 (m, 1H, partially obscured), 2.77 (d, J=8.2 Hz, 1H), 2.87 (s, 1H), 2.96 (d, J=9.6 Hz, 1H), 3.29 (d, J=11.7 Hz, 1H), 3.34-3.41 (3d, 3H), 3.35 (s, 3H), 3.6 (d, J=11.6 Hz, 1H), 4.25 (m, 1H), 4.98 (d, J=12.3 Hz, 1H), 5.08 (s, 1H), 5.10 (d, J=12.4 Hz, 1H), 5.41 (m, 1H), 7.25 (d, 2H, partially obscured), 7.3-7.4 (m, 5H), 7.78 (d, J=5.8 Hz, 2H).

INTERMEDIATE 12

Alternative Synthesis

Benzyl(1S,4aR,6aS,7R,8R,10aR,10bR,12aR,14R,15R)-8-[(1R)-1,2-dimethylpropyl]-14-methoxy-15-[[(2R)-2,3,3-trimethyl-2-[[(4-methylphenyl)sulfonyl]amino]butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

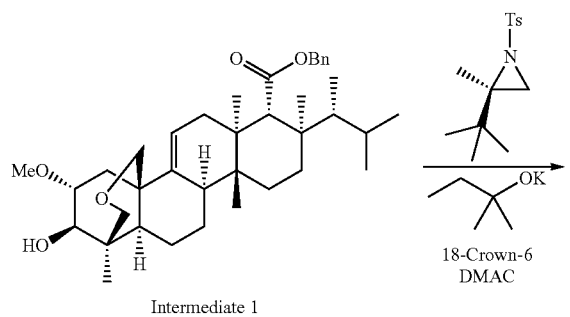

Intermediate 1

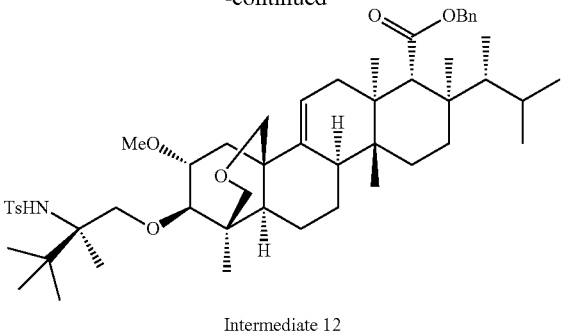

Intermediate 12

A solution of Intermediate 1 (21.26 g, 35.9 mmol), 18-crown-6 (11.37 g, 43.0 mmol), and (2R)-2-(1,1-dimethylethyl)-2-methyl-1-[(4-methylphenyl)sulfonyl]aziridine (9.59 g, 35.9 mmol), in toluene (25 mL) was evaporated under vacuum to azeotropically dry the reagents. The resulting oil was dissolved in N,N-dimethylacetamide (200 mL) and the solution was cooled under nitrogen in an ice bath. To the ice cold stirred solution was added over a 2 minute period a solution of potassium 2-methyl-2-butoxide in toluene (1.7M, 25.3 mL, 43.0 mmol). The reaction was slowly allowed to warm to room temperature and monitored by TLC. After the reaction was judged complete, the reaction was quenched with 2N hydrochloric acid (22 mL), diluted with dichloromethane (500 mL), and the mixture was washed with water (3×300 mL). The organic phase was dried over magnesium sulfate, filtered, and evaporated to an oil which was flash chromatographed (silica gel, 5-60% ethyl acetate:hexane) to give Intermediate 12 as a white solid (24.04 g).

INTERMEDIATE 14

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

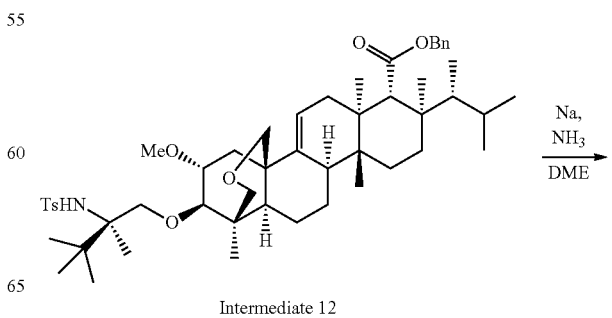

Intermediate 12

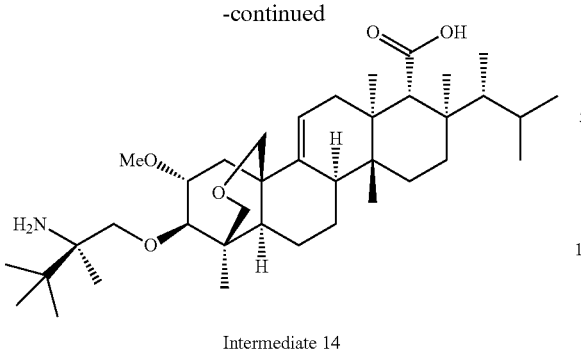

Intermediate 14

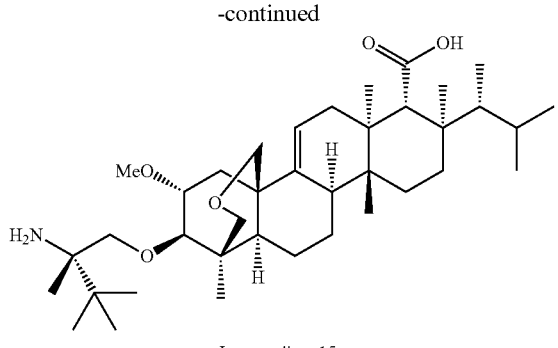

Intermediate 15

Ammonia (approx. 150 mL) was condensed into a 3-neck flask equipped with a cold-finger condenser and sodium (approx. 5 g, 220 mmol) was added to give a deep blue solution. To this solution was added a solution of Intermediate 12 (13.3 g, 15.5 mmol) in dimethoxymethane (130 mL) and the reaction was refluxed at −33° C. for 1.5 hours. The reaction was quenched by the careful addition of methanol followed by water until the reaction was a white slurry. The solvents were evaporated by a stream of nitrogen overnight. After approximately 18 hours methanol (approx 50 mL) was added and the resulting white slurry/partial solution was stirred for about 10 minutes to ensure that all solids were in suspension (as opposed to fixed to the flask wall). This mixture was partitioned between ethyl acetate and water and the aqueous extracted twice with ethyl acetate. The combined organic phase was dried over MgSO$_4$, filtered then concentrated to give Intermediate 14 (9.8 g) as an off-white solid.

$^1$H NMR (CD$_3$OD, 500 MHz, ppm) δ 0.77 (s, 3H), 0.78 (d, J=7.4 Hz, 3H), 0.81 (s, 3H), 0.85 (d, J=6.9 Hz, 3H), 0.89 (d, J=6.8 Hz, 3H), 1.05 (s, 9H), 1.19 (s, 3H), 1.20 (s, 3H), 1.32 (s, 3H), 1.18-1.36 (m), 1.4 (m, 1H), 1.48 (m, 1H), 1.56-1.86 (m), 2.05 (m, 1H), 2.23 (m, 1H), 2.55 (dd, J=13.3 Hz, 6.7 Hz, 1H), 2.71 (s, 1H), 3.25 (m, 1H), 3.30 (m, 1H, partially obscured), 3.4 (AB, 2H, partially obscured), 3.4 (s, 3H), 3.67 (d, J=11.9 Hz, 1H), 3.74 (d, J=11.3 Hz, 1H), 3.92 (d, J=11.2 Hz, 1H), 4.24 (m, 1H), 5.54 (m, 1H).

m/z=616.34 (M+H).

INTERMEDIATE 15

(1S,4aR,6aS,7R,8R,10aR,10bR,12aR,14R,15R)-15-[[(2S)-2-amino-2,3,3-trimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

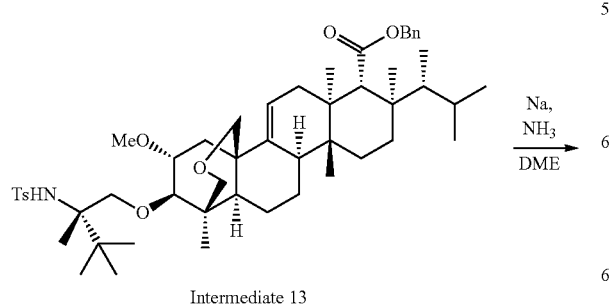

Intermediate 13

Intermediate 15 was prepared in a manner analogous to that described for intermediate 14, but starting with Intermediate 13.

$^1$H NMR (CD$_3$OD, 500 MHz, ppm) δ 0.75 (d, 3H, partially obscured), 0.76 (s, 3H), 0.81 (s, 3H), 0.84 (d, J=6.4 Hz, 3H), 0.89 (d, J=6.4 Hz, 3H), 1.00 (s, 3H), 1.03 (s, 9H), 1.14-1.3 (m), 1.28 (s, 3H), 1.34-1.5 (m), 1.55-1.84 (m), 2.02 (m, 1H), 2.29 (m, 1H), 2.55 (dd, J=13.3 Hz, 6.9 Hz, 1H), 2.75 (s, 1H), 3.17 (d, J=8.7 Hz, 1H), 3.3 (m, obscured), 3.4 (m, obscured), 3.42 (s, 3H), 3.68 (d, J=11.9 Hz, 1H), 3.74 (d, J=11.2 Hz, 1H), 3.89 (d, J=11.2 Hz, 1H), 4.28 (m, 1H), 5.54 (m, 1H).

INTERMEDIATE 16

(1S,4aR,6aS,7R,8R,10aR,10bR,12aR,14R,15R)-8-[(1R)-1,2-dimethylpropyl]-14-methoxy-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

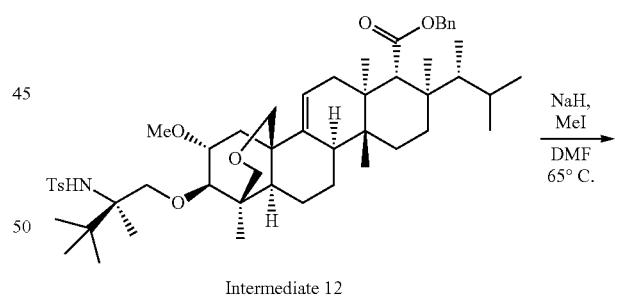

Intermediate 12

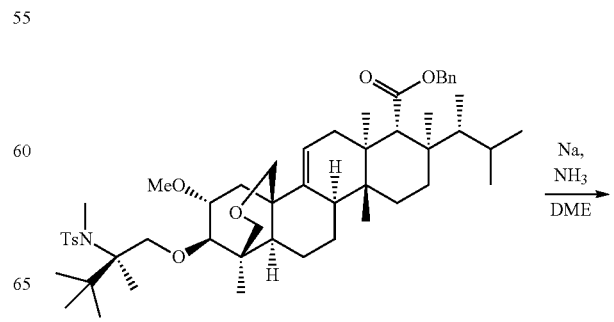

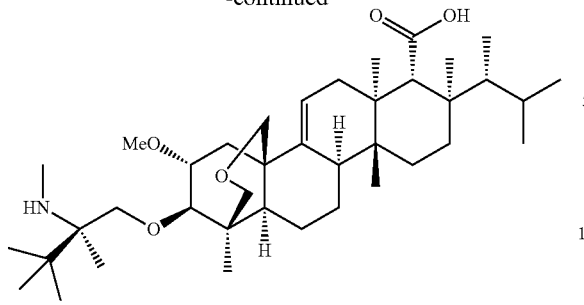

Intermediate 16

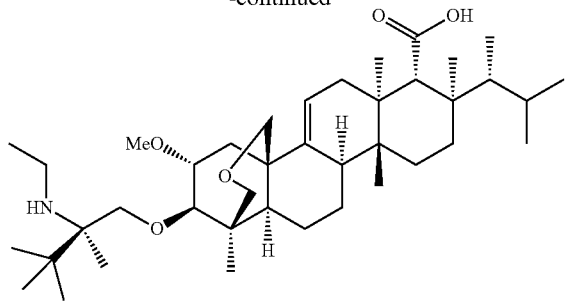

Intermediate 17

Sodium hydride (60% dispersion in mineral oil, 930 mg, 23 mmol) was washed with hexane and the hexane decanted. This procedure was repeated and the remaining hexane removed in vacuo. This pre-washed sodium hydride was suspended in DMF (10 mL) and a solution of Intermediate 12 (2.0 g, 2.3 mmol) in DMF (13 mL) was added. Methyl iodide (1.45 mL, 23 mmol) was added and the reaction mixture heat at 65° C. under nitrogen for 90 minutes. After cooling to room temperature the reaction was partitioned between ethyl acetate and saturated aqueous bicarbonate. The organic phase was washed with brine, dried with MgSO$_4$ filtered and concentrated in vacuo. Column chromatography (Biotage 40+M column, 5-100% EA/Hex) yielded the product (1.95 g)

The product from Step 1 was subjected to sodium/ammonia reduction by a procedure analogous to that described for the preparation of Intermediate 14. The product thus obtained was lyophilized from MeOH/benzene to give Intermediate 16 (1.4 g) as an off-white solid.

$^1$H NMR (CD$_3$OD, 500 MHz, ppm) δ 0.76 (s, 3H), 0.77 (d, 3H, partially obscured), 0.82 (s, 3H), 0.84 (d, J=6.8 Hz, 3H), 0.91 (d, J=6.7 Hz, 3H), 1.06 (s, 3H), 1.07 (s, 9H), 1.16-1.3 (m), 1.15 (s, 3H), 1.22 (s, 3H), 1.3-1.5 (m), 1.6 (m), 1.64-1.84 (m), 1.96-2.1 (m, 2H), 2.31 (m, 1H), 2.57 (m, 1H, partially obscured), 2.57 (s, 3H), 2.74 (s, 1H), 2.93 (d, J=8.5 Hz, 1H), 3.35 (m, 1H, partially obscured), 3.36 (s, 3H), 3.41 (br s, 2H), 3.62 (d, J=11.6 Hz, 1H), 3.8 (AB, 2H), 4.23 (m, 1H), 5.53 (m, 1H).

m/z=630.59 (M+H).

INTERMEDIATE 17

(1S,4aR,6aS,7R,8R,10aR,10bR,12aR,14R,15R)-8-[(1R)-1,2-dimethylpropyl]-15-[[(2R)-2-(ethylamino)-2,3,3-trimethylbutyl]oxy]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid A solution of Intermediate 14 (140 mg, 0.23 mmol) in MeOH was treated with acetic acid (0.013 mL, 0.23 mmol) and acetaldehyde (0.32 mL, 5.7 mmol) at 0° C. After 20 minutes sodium cyanoborohydride (1 M in THF, 0.57 mL, 0.57 mmol) was added and the reaction allowed to slowly warm to room temperature. After 24 hours the reaction was partitioned between ethyl acetate and water and the aqueous phase extracted with ethyl acetate multiple times. The combined organic phase was dried with MgSO$_4$, filtered and concentrated to give Intermediate 17 (165 mg).

$^1$H NMR (CD$_3$OD, 500 MHz, ppm) δ 0.76 (s, 3H), 0.78 (d, J=6.6 Hz, 3H), 0.82 (s, 3H), 0.86 (d, J=6.6 Hz, 3H), 0.91 (d, J=6.8 Hz, 3H), 1.15 (s, 9H), 1.18 (s, 3H), 1.19 (s, 3H), 1.22 (s, 3H), 1.22-1.64 (m), 1.40 (t, J=7.3 Hz, 3H), 1.7-1.86 (m), 1.97 (m, 1H), 2.09 (m: 1H), 2.20 (m, 1H), 2.61 (dd, J=13.2 Hz, 6.6 Hz, 1H), 2.86 (s, 1H), 3.01 (d, J=8.7 Hz, 1H), 3.12 (m, 1H), 3.36 (m, partially obscured), 3.37 (s, 3H), 3.43 (br s, 2H), 3.61 (d, J=11.2 Hz, 1H), 3.81 (d, J=11.6 Hz, 1H), 3.99 (d, J=12.3 Hz, 1H), 4.29 (m, 1H), 5.56 (m, 1H).

m/z=644.27 (M +H).

INTERMEDIATE 18

Benzyl(1S,4aR,6aS,7R,8R,10aR,10bR,12aR,14R,15R)-8-[(1R)-1,2-dimethylpropyl]-15-[2-ethyl-2-[[(4-methylphenyl)sulfonyl]amino]butoxy]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

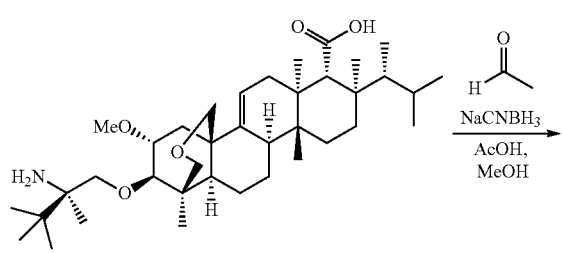

Intermediate 14

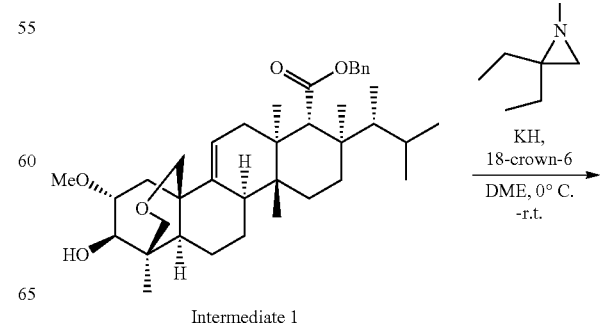

Intermediate 1

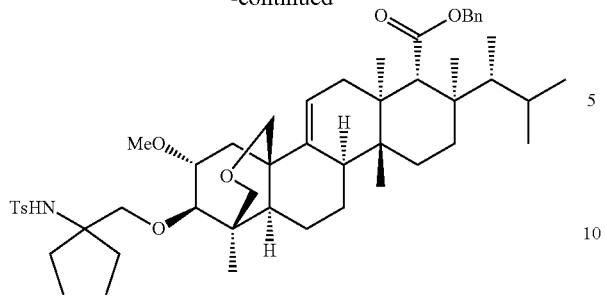

Intermediate 18

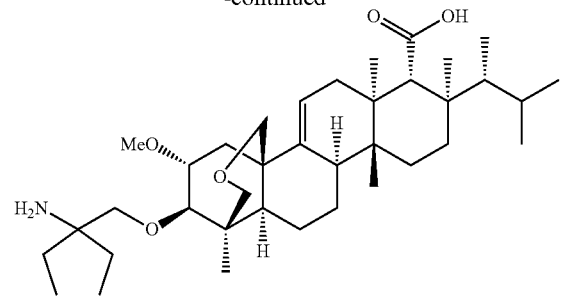

Intermediate 19

Intermediate 1 (5.00 g, 8.43 mmol), 18-crown-6 (11.15 g, 42.2 mmol), and 2,2-diethyl-1-[(4-methylphenyl)sulfonyl]-aziridine (4.27 g, 16.87 mmol) were dissolved in toluene and concentrated then placed under high vacuum for 1 hour. The resulting mixture was dissolved in dimethoxyethane (84 mL) placed under nitrogen atmosphere and cooled to 0° C. Potassium hydride (30% dispersion in mineral oil, 3.38 g, 25 mmol) was added and the reaction evacuated and charged with nitrogen (repeat three times). The reaction was allowed to slowly warm to room temperature over one hour. The reaction was quenched by the addition of water followed by 1 N aq. HCl. The reaction mixture was partitioned between ethyl acetate and water and the aqueous extracted with ethyl acetate. The combined organic phase was dried over MgSO$_4$, filtered then concentrated. The crude product was purified by flash chromatography on a Biotage 65i column (0-100% ethyl acetate/hexane) to give Intermediate 18 (6.9 g) as a colorless foam.

$^1$H NMR (CDCl$_3$, 500 MHz, ppm) δ 0.70-0.78 (m, 18H), 0.80 (d, J=6.6 Hz, 3H), 1.14-1.28 (m), 1.15 (s, 3H), 1.23 (s, 3H), 1.32-1.78 (m), 1.87-2.04 (m, 2H), 2.11 (m, 1H), 2.40 (s, 3H), 2.46 (dd, J=13.5 Hz, 6.8 Hz, 1H), 2.83 (d, J=8.5 Hz, 1H), 2.87 (s, 1H), 3.27 (d, J=11.4 Hz, 1H) 3.35-3.4 (m, 2H), 3.42 (s, 3H), 3.50 (d, J=9.9 Hz, 1H), 3.61 (d, J=9.6 Hz, 1H), 3.64 (d, J=11.7 Hz, 1H), 4.24 (m, 1H), 4.97 (d, J=12.4 Hz, 1H), 5.11 (d, J=12.4 Hz, 1H), 5.42 (m, 1H), 5.78 (s, 1H), 7.25 (d, 2H, partially obscured), 7.3-7.4 (m, 5H), 7.76 (d, J=8.5 Hz, 2H).

Ammonia (approx. 30 mL) was condensed into a 3-neck flask equipped with a cold-finger condenser and sodium (approx. 500 mg, 22 mmol) was added to give a deep blue solution. To this solution was added a solution of Intermediate 18 (2.0 g, 2.4 mmol) in dimethoxymethane (20 mL) and the reaction was refluxed at −33° C. for 1.5 hours. The reaction was quenched by the careful addition of methanol followed by water until the reaction was a white slurry. The solvents were evaporated by a stream of nitrogen overnight. At this point methanol (approx 10mL) was added and the resulting white slurry/partial solution was stirred for about 10 minutes to ensure that all solids were in suspension (as opposed to fixed to the flask wall). This mixture was partitioned between ethyl acetate and water and the aqueous extracted twice with ethyl acetate. The combined organic phase was dried over MgSO$_4$, filtered then concentrated then lyophilized from benzene to give Intermediate 19 as a colorless solid.

$^1$H NMR (CD$_3$OD, 500 MHz, ppm) δ 0.76 (s, 3H), 0.77 (d, J=3H, partially obscured), 0.80 (s, 3H), 0.84 (d, J=6.6 Hz, 1H), 0.90 (d, J=6.9 Hz, 3H), 0.91 (t, J=7.5 Hz, 3H), 0.93 (t, J=7.5 Hz, 3H), 1.17-1.84 (m), 1.21 (s, 3H), 1.27 (s, 3H), 1.98-2.08 (m), 2.31 (m, 1H), 2.54 (dd, J=13.3 Hz, 6.9 Hz, 1H), 2.72 (s, 1H), 3.03 (d, J=8.6 Hz, 1H), 3.34 (d, 1H, partially obscured), 3.39 (s, 3H), 3.40 (br s, 2H), 3.56 (d, J=10.3 Hz, 1H), 3.67 (d, J=11.7 Hz, 1H), 3.73 (d, H=10.2 Hz, 1H), 4.22 (m, 1H), 5.52 (m, 1H).

m/z=602.64 (M +H).

INTERMEDIATE 19

(1S,4aR,6aS,7R,8R,10aR,10bR,12aR,14R,15R)-15-(2-amino-2-ethylbutoxy)-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

INTERMEDIATE 20

(1S,4aR,6aS,7R,8R,10aR,10bR,12aR,14R,15R)-8-[(1R)-1,2-dimethylpropyl]-15-[2-ethyl-2-(methylamino)butoxy]-14-methoxy-1,6,6a,7,8,9,10,10a, 10b,11,12,12a-dodecahydro-1,6a,8,10a-tetramethyl-4H-1,4a-propano-2H-phenanthro[1,2-c]pyran-7-carboxylic acid

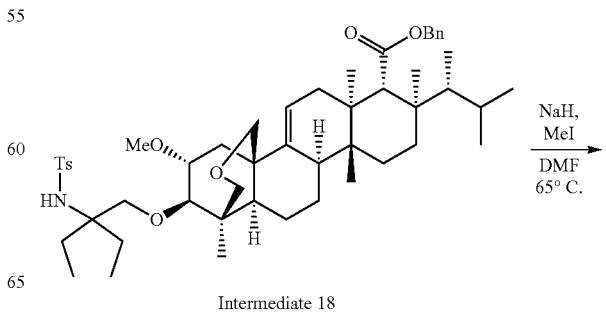

Intermediate 18

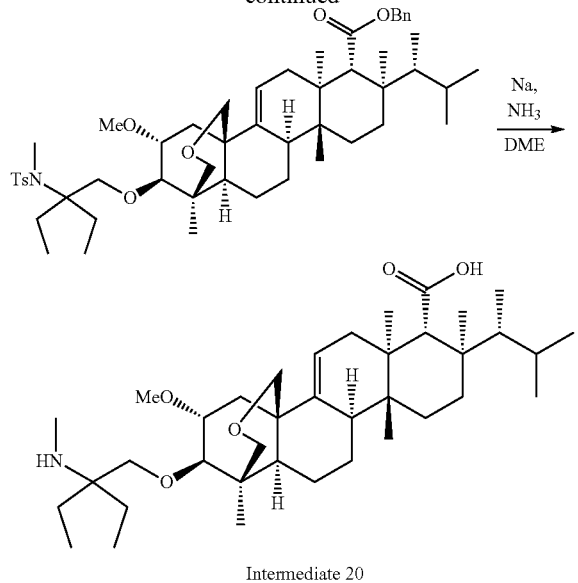

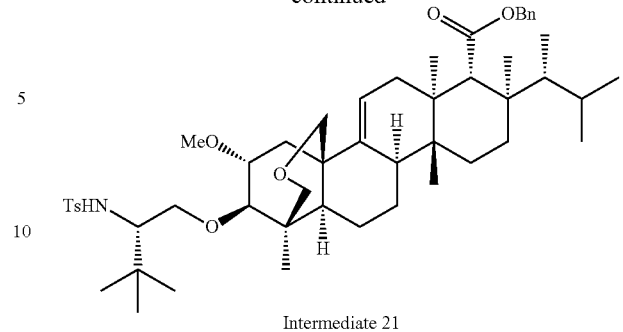

Intermediate 20

Starting with Intermediate 18, Intermediate 20 was prepared as an off-white solid in a manner analogous to that described for the preparation of Intermediate 16.

$^1$H NMR (CD$_3$OD, 500 MHz, ppm) δ 0.76 (s, 3H), 0.77 (d, 3H, partially obscured), 0.80 (s, 3H), 0.84 (d, J=6.7 Hz, 3H), 0.90 (d, J=7.0 Hz, 3H), 0.93 (t, J=7.6 Hz, 3H), 0.93 (t, J=7.6 Hz, 3H), 1.18-1.85 (m), 1.22 (s, 3H), 1.26 (s, 3H), 1.99-2.1 (m, 2H), 2.31 (m, 1H), 2.52 (s, 3H), 2.56 (dd, J=13.4 Hz, 6.9 Hz, 1H), 2.73 (s, 1H), 2.98 (d, J=8.5 Hz, 1H), 3.33 (d, J=11.9 Hz, 1H), 3.37 (s, 3H), 3.41 (br s, 2H), 3.54 (d, J=10.7 Hz, 1H), 3.68 (d, J=11.7 Hz, 1H), 3.82 (d, J=10.7 Hz, 1H), 4.22 (m, 1H), 5.53 (m, 1H).

m/z=616.55 (M+H).

INTERMEDIATE 21

Benzyl(1S,4aR,6aS,7R,8R,10aR,10bR,12aR,14R, 15R)-15-[[(2S)-3,3-dimethyl-2-[[(4-methylphenyl) sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate Intermediate 21

Intermediate 1 (7.5 g, 13 mmol), 18-crown-6 (16.7 g, 63.3 mmol), and (2S)-2-(1,1-dimethylethyl)-1-[(4-methylphenyl) sulfonyl]-aziridine (5.27 g, 20.8 mmol) were dissolved in toluene and concentrated then placed under high vacuum for 1 hour. The resulting mixture was dissolved in dimethoxy-ethane (63 mL) placed under nitrogen atmosphere and cooled to 0° C. Potassium hydride (30% dispersion in mineral oil, 3.7 g, 28 mmol) was added and then the reaction evacuated and charged with nitrogen (repeat three times). After 1 hour the reaction was quenched by the addition of methanol followed by 1 N aq. HCl. The reaction mixture was partitioned between ethyl acetate and water and the aqueous extracted with ethyl acetate. The combined organic phase was dried over MgSO$_4$, filtered then concentrated. Chromatography on Biotage 65i column (10-100% ethyl acetate/hexane) gave Intermediate 21 (7.4 g) as a colorless solid.

(CDCl$_3$, 500 MHz, ppm) δ 0.61 (s, 3H), 0.70 (s, 3H), 0.71 (d, J=7.3 Hz, 3H), 0.77 (d, J=6.8 Hz, 3H), 0.80 (d, J=8.0 Hz, 3H), 0.92 (s, 9H), 1.12 (s, 3H), 1.12-1.28 (m), 1.21 (s, 3H), 1.3-1.48 (m), 1.5-1.6 (m, 1H, partially obscured), 1.64-1.77 (m, 3H), 1.9 (m, 1H), 1.98 (m, 1H), 2.10 (m, 1H), 2.4 (m, 1H, partially obscured), 2.41 (s, 3H), 2.55 (d, J=8.5 Hz, 1H), 2.86 (s, 1H), 3.02 (m, 1H), 3.18 (dd, J=9.7 Hz, 4.0 Hz, 1H), 3.22 (d, J=12.5 Hz, 1H), 3.31 (s, 3H), 3.34 (AB, 2H, partially obscured), 3.50 (d, J=11.7 Hz, 1H), 4.01 (dd, J=9.9 Hz, 2.6 Hz, 1H), 4.08 (m, 1H), 4.96 (d, J=9.4 Hz, 1H), 4.97 (d, J=12.3 Hz, 1H), 5.09 (d, J=12.3 Hz, 1H), 5.38 (m, 1H), 7.25 (d, 2H, partially obscured), 7.3-7.38 (m, 5H), 7.73 (d, J=8.2 Hz, 2H).

INTERMEDIATE 22

(1S,4aR,6aS,7R,8R,10aR,10bR,12aR,14R,15R)-15-[[(2S)-2-amino-3,3-dimethylbutyl]oxy]-8-[(1R)-1,2-dimethylpropyl]-14-methoxy-1,6,6a,7,8,9,10,10a, 10b,11,12,12a-dodecahydro-1,6a,8,10a-tetramethyl-4H-1,4a-propano-2H-phenanthro[1,2-c]pyran-7-carboxylic acid

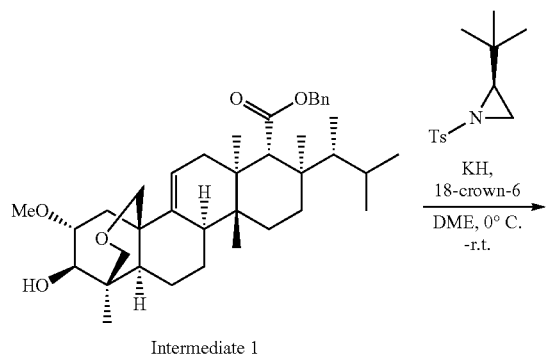

Intermediate 1

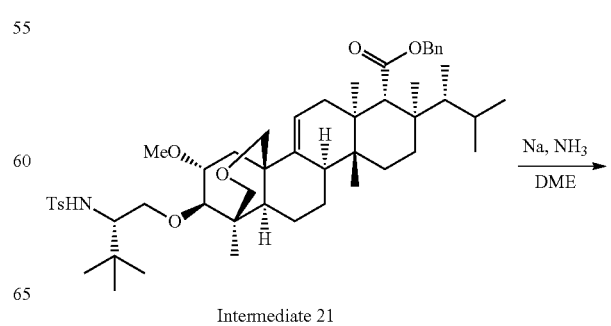

Intermediate 21

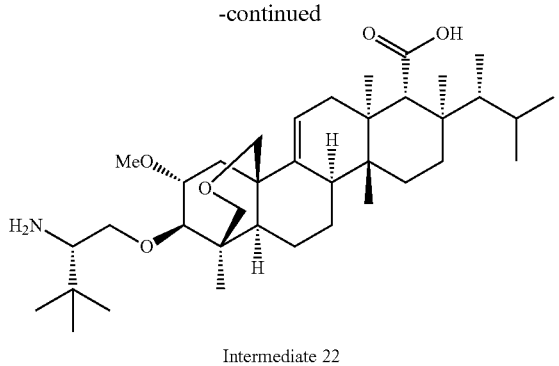

Intermediate 22

In a manner analogous to that described for Intermediate 14, Intermediate 22 was prepared starting with Intermediate 21.

$^1$H NMR (CD$_3$OD, 500 MHz, ppm) δ 0.75 (d, 3H, partially obscured), 0.76 (s, 3H), 0.81 (s, 3H), 0.84 (d, J=6.9 Hz, 3H), 0.88 (d, J=6.8 Hz, 3H), 1.02 (s, 9H), 1.18-1.24 (m) 1.19 (s, 3H), 1.30 (s, 3H), 1.36-1.85 (m), 2.0-2.06 (m), 2.29 (m, 1H), 2.54 (dd, J=13.1 Hz, 6.7 Hz, 1H), 2.78 (s, 1H), 2.94 (m, 1H), 3.25 (d, J=8.9 Hz, 1H), 3.34 (d, 1H, partially obscured), 3.4 (br s, 2H), 3.42 (s, 3H), 3.64 (d, J=11.7 Hz, 1H), 3.74 (m, 1H), 4.05 (m, 1H), 4.26 (m, 1H), 5.54 (m, 1H).

m/z=602.41 (M+H).

INTERMEDIATE 23

Benzyl(1S,4aR,6aS,7R,8R,10aR,10bR,12aR,14R, 15R)-15-[[(2R)-3,3-dimethyl-2-[[(4-methylphenyl) sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

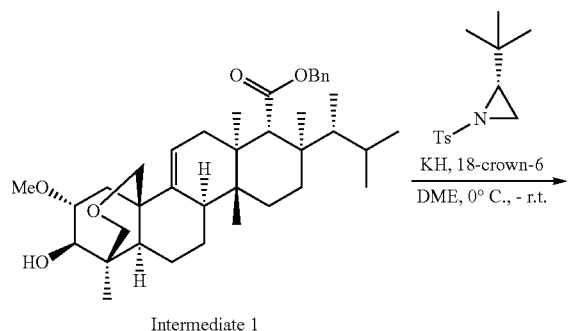

Intermediate 23

Intermediate 1 (4.5 g, 7.6 mmol), 18-crown-6 (10 g, 38 mmol), and (2R)-2-(1,1-dimethylethyl)-1-[(4-methylphenyl) sulfonyl]-aziridine (3.7 g, 15 mmol) were dissolved in toluene and concentrated then placed under high vacuum for 1 hour. The resulting mixture was dissolved in dimethoxyethane (38 mL) placed under nitrogen atmosphere and cooled to 0° C. Potassium hydride (30% dispersion in mineral oil, 2.7 g, 20 mmol) was added and the reaction evacuated and charged with nitrogen (repeat three times). After 1 hour the reaction was quenched by the addition of methanol followed by 1 N aq. HCl. The reaction mixture was partitioned between ethyl acetate and water and the aqueous extracted with ethyl acetate as necessary. The combined organic phase was dried over MgSO$_4$, filtered then concentrated. Chromatography on Biotage 65i column (0-100% ethyl acetate/hexane) gave Intermediate 23 (6.1 g) as a colorless foam.

$^1$H NMR (CDCl$_3$, 500 MHz, ppm) δ 0.49 (s, 3H), 0.71 (s, 3H), 0.73 (d, J=7.3 Hz, 3H), 0.78 (d, J=7.7 Hz, 3H), 0.79 (s, 3H), 0.81 (d, J=7.7 Hz, 3H), 0.95 (s, 9H), 1.1-1.3 (m), 1.22 (s, 3H), 1.25 (s, 3H), 1.34-1.77 (m), 1.82 (m, 1H), 2.02 (m, 1H), 2.11 (m, 1H), 2.29 (d, J=8.9 Hz, 1H), 2.44 (m, 1H, partially obscured), 2.43 (s, 3H), 2.84 (m, 2H), 2.88 (s, 1H), 3.18 (d, J=11.6 Hz, 1H), 3.33 (AB, 2H), 3.47 (s, 3H), 3.56 (d, J=11.6 Hz, 1H), 3.98 (d, J=9.8 Hz, 1H), 4.13 (m, 1H), 4.99 (d, J=12.1 Hz, 1H), 5.12 (d, J=12.1 Hz, 1H), 5.42 (m, 1H), 7.25 (d, 2H, partially obscured), 7.3-7.4 (m, 5H), 7.80 (d, J=8.0 Hz, 2H).

INTERMEDIATE 24

(1S,4aR,6aS,7R,8R,10aR,10bR,12aR,14R,15R)-15-[[(2R)-2-amino-3,3-dimethylbutyl]oxy]-8-[(1R)-1,2-dimethylpropyl]-14-methoxy-1,6,6a,7,8,9,10,10a, 10b,11,12,12a-dodecahydro-1,6a,8,10a-tetramethyl-4H-1,4a-propano-2H-phenanthro[1,2-c]pyran-7-carboxylic acid

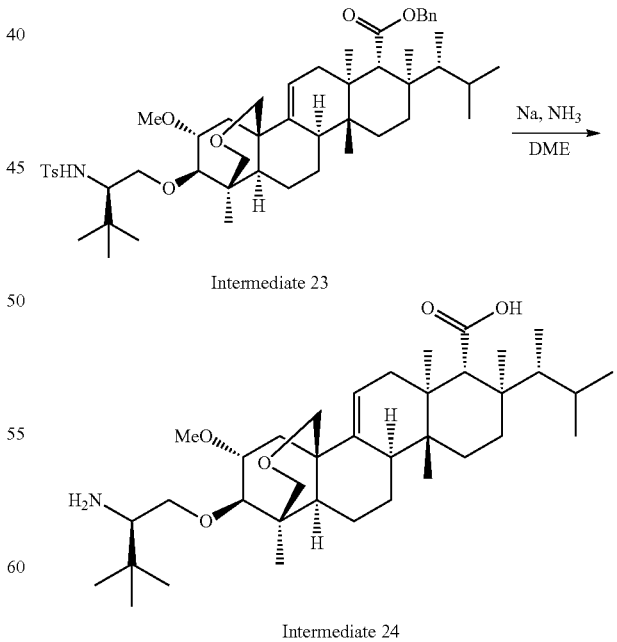

Intermediate 24

In a manner analogous to that described for Intermediate 14, Intermediate 24 was prepared starting with Intermediate 23.

¹H NMR (CDCl₃, 500 MHz, ppm) δ 0.76 (s, 3H) 0.77 (d, J=6.3 Hz, 3H), 0.81 (s, 3H), 0.86 (d, J=6.7 Hz, 3H), 0.91 (d, J=6.9 Hz, 3H), 1.05 (s, 9H), 1.18 (s, 3H), 1.2-1.32 (m) 1.22 (s, 3H), 1.38-1.66 (m), 1.69-1.87 (m), 1.98 (m, 1H), 2.09 (m, 1H), 2.21 (m, 1H), 2.56 (dd, J=13.2 Hz, 6.8 Hz, 1H), 2.84 (s, 1H), 2.86 (d, J=11.0 Hz, 1H), 3.18 (dd, J=8.2 Hz, 3.7 Hz, 1H), 3.34 (d, J=12.2 Hz, 1H), 3.41 (s, 3H), 3.42 (AB, 2H, partially obscured), 3.69 (d, J=12.3 Hz, 1H), 3.83 (m, 1H), 3.92 (m, 1H), 4.24 (m, 1H), 5.55 (m, 1H).

m/z=602.45 (M+H).

INTERMEDIATE 25

(1S,4aR,6aS,7R,8R,10aR,10bR,12aR,14R,15R)-15-[[(2R)-3,3-dimethyl-2-(methylamino)butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

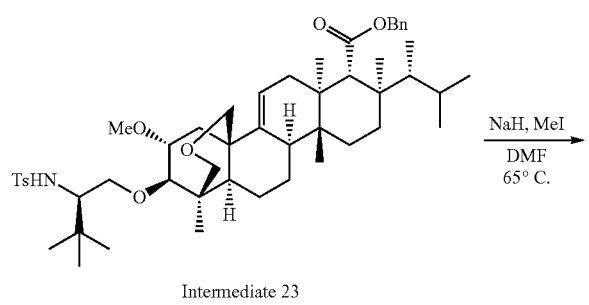

Intermediate 23

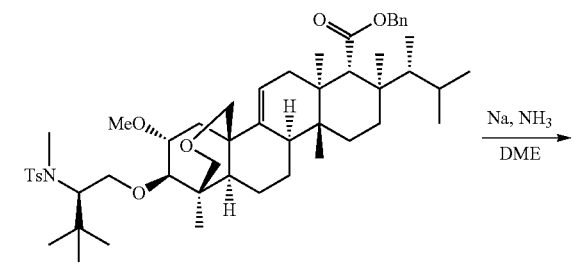

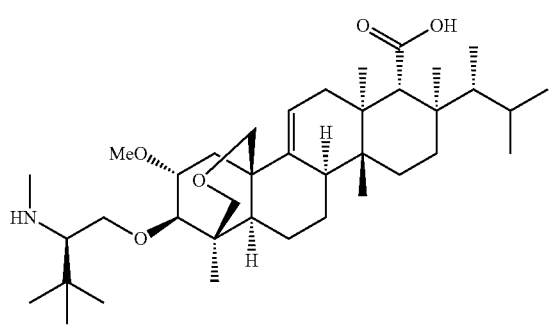

Intermediate 25

By a procedure analogous to that described for the preparation of Intermediate 16, Intermediate 25 was prepared starting with Intermediate 23.

m/z=616.54 (M+H)

INTERMEDIATE 26

Benzyl(1S,4aR,6aS,7R,8R,10aR,10bR,12aR,14R, 15R)-8-[(1R)-1,2-dimethylpropyl]-14-methoxy-15-[[tetrahydro-4-[[(4-methylphenyl)sulfonyl]amino]-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

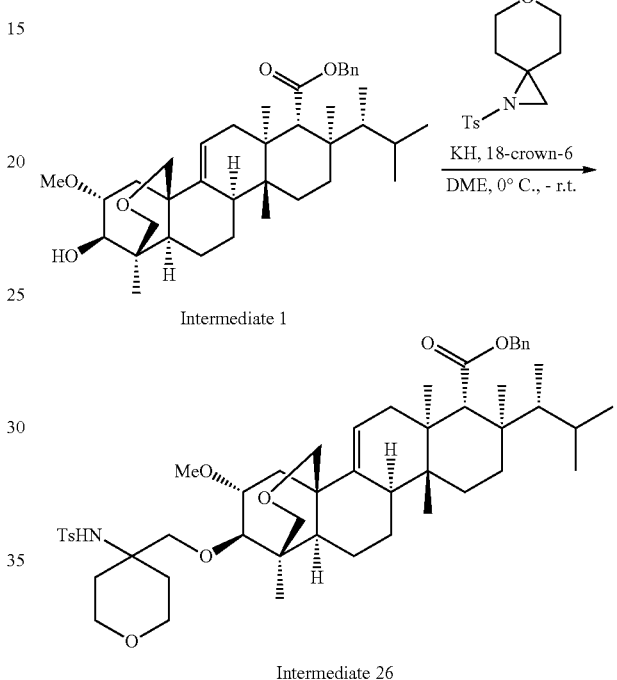

Intermediate 26

Intermediate 1 (0.38 g, 0.641 mmol), 18-crown-6 (0.508 g, 1.92 mmol), and 1-[(4-methylphenyl)sulfonyl]-6-oxa-1-azaspiro[2.5]octane (0.257 g, 0.961 mmol) were dissolved in toluene and concentrated then placed under high vacuum for 1 hour. The resulting mixture was dissolved in dimethoxyethane (10 mL) placed under nitrogen atmosphere and cooled to 0° C. Potassium hydride (30% dispersion in mineral oil, 0.171 g, 1.28 mmol) was added and the reaction evacuated and charged with nitrogen (repeat three times). After an additional hour the reaction mixture was treated with aqueous ammonium chloride carefully, and the mixture was extracted with dichloromethane (2×20 mL). The combined organic phase was dried over MgSO₄, filtered then concentrated. The crude product was purified by flash chromatography (10-50% ethyl acetate/hexane) to yield Intermediate 26 (0.5 g) as a white foam.

¹H NMR (CDCl₃, 500 MHz, ppm) δ 0.74 (s, 3H), 0.75 (s, 3H) 0.80 (d, J=6.9 Hz, 3H), 0.84 (d, J=6.7 Hz, 3H), 1.14-1.3 (m), 1.19 (s, 3H), 1.26 (s, 3H), 1.32-1.8 (m), 1.84-1.98 (m), 2-2.18 (m), 2.45 (s, 3H), 2.47 (m, 1H), 2.89 (d, J=9.4 Hz, 1H), 2.90 (s, 1H), 3.29 (d, J=9.3 Hz, 1H), 3.35-3.45 (m, 5H=C2 MeO+2H?), 3.54 (m, 2H), 3.57 (m, 2H), 3.64-3.72 (m, 2H), 3.79 (d, J=10.1 Hz, 1H), 4.20 (m, 1H), 5.0 (d, J=12.1 Hz, 1H), 5.14 (d, J=12.1 Hz, 1H), 5.44 (m, 1H), 5.85 (s, 1H), 7.30 (d, J=9.2 Hz, 2H), 7.32-7.4 (m, 5H), 7.81 (d, J=8.2 Hz, 2H).

INTERMEDIATE 27

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

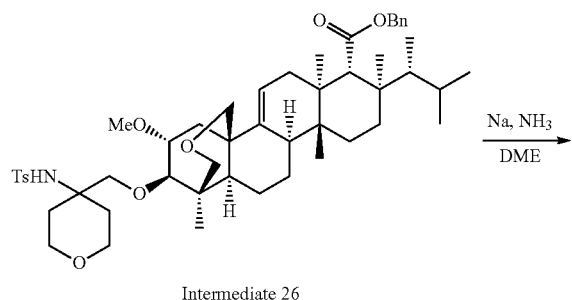

Intermediate 26

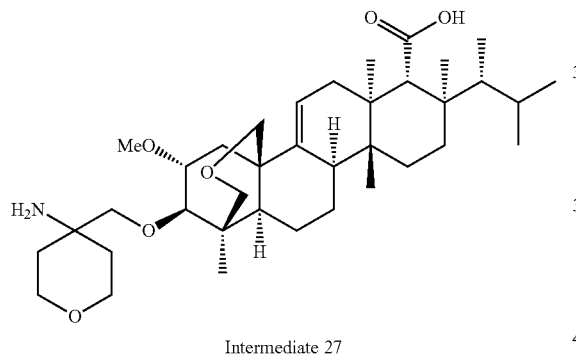

Intermediate 27

Ammonia (approx. 5 mL) was condensed into a 3-neck flask in a dry ice-acetone bath equipped with a cold-finger condenser and sodium (approx. 0.211 g, 9.11 mmol) was added to give a deep blue solution. To this solution was added a solution of Intermediate 26 (0.28 g, 0.326 mmol) in dimethoxymethane (8 mL) and the reaction was refluxed at −33° C. for 1.5 hours.

The reaction was quenched by the careful addition of methanol followed by water until the reaction was a white slurry. The solvents were evaporated by a stream of nitrogen overnight. After approximately 18 hours methanol (approx 5 mL) was added and the resulting white slurry/partial solution was stirred for about 10 minutes to ensure that all solids were in suspension (as opposed to fixed to the flask wall). This mixture was partitioned between ethyl acetate and water and the aqueous extracted twice with ethyl acetate. The combined organic phase was dried over $MgSO_4$, filtered then concentrated to give Intermediate 27 (0.16 g) as an off-white solid.

$^1$H NMR ($CD_3OD$, 500 MHz, ppm) δ 0.77 (s, 3H), 0.78 (d, J=7.3 Hz, 3H), 0.81 (s, 3H), 0.86 (d, J=6.6 Hz, 3H), 0.91 (d, J=6.8 Hz, 3H), 1.21 (s, 3H), 1.26 (s, 3H), 1.18-1.42 (m), 1.46-1.88 (m). 1.98 (m, 1H), 2.02 (m, 1H), 2.06 (m, 1H), 2.08 (m, 1H), 2.26 (m, 1H), 2.55 (dd, J=13.5 Hz, 6.9 Hz, 1H), 2.78 (s, 1H), 3.03 (d, J=8.7 Hz, 1H), 3.3-3.36 (m, 3H), 3.42 (s, 3H), 3.6-3.84 (m, 3H), 3.90 (d, J=10.3 Hz, 1H), 4.22 (m, 1H), 5.54 (m, 1H)

INTERMEDIATE 28

(1S,4aR,6aS,7R,8R,10aR,10bR,12aR,14R,15R)-8-[(1R)-1,2-dimethylpropyl]-14-methoxy-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

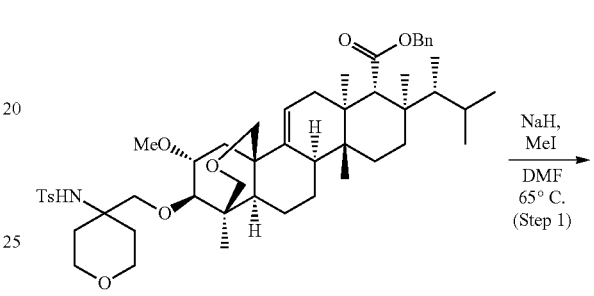

Intermediate 26

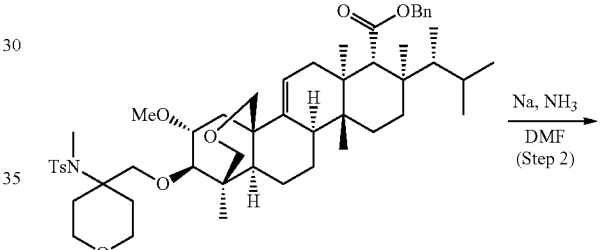

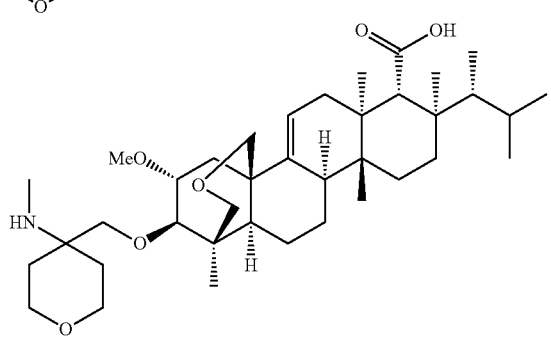

Intermediate 28

Step 1

Sodium hydride (60% dispersion in mineral oil, 84 mg, 2.1 mmol) was washed with hexane and the hexane decanted. This procedure was repeated and the remaining hexane removed in vacuo. This pre-washed sodium hydride was suspended in DMF (1 mL) and a solution of Intermediate 26 (0.18 g, 0.21 mmol) in DMF (1 mL) was added. Methyl iodide (0.131 mL, 2.1 mmol) was added and the reaction mixture heat at 60° C. under nitrogen for 60 minutes. After cooling to room temperature the reaction was partitioned between ethyl acetate and saturated aqueous bicarbonate. The organic phase was washed with brine, dried with $MgSO_4$ filtered and concentrated in vacuo to give the product (0.18 g, 98%)

Step 2

The product was subjected to the sodium/ammonia reduction by analogy to the preparation of intermediate 27 then lyophilized from MeOH/Benzene to give intermediate 28 (0.16 g) as an off-white foam.

$^1$H NMR (CD$_3$OD, 500 MHz, ppm) δ 0.78 (s, 3H), 0.79 (d, 3H, partially obscured), 0.80 (s, 3H), 0.86 (d, J=6.6 Hz, 3H), 0.91 (d, J=6.6 Hz, 3H), 1.21 (s, 3H), 1.18-1.42 (m), 1.50 (m, 1H), 1.56-1.96 (m), 1.98 (m, 1H), 2.02 (m, 1H), 2.08 (m, 1H), 2.10 (m, 1H), 2.26 (m, 1H), 2.55 (s, 3H), 2.57 (m, 1H, partially obscured), 2.80 (s, 1H), 2.99 (d, J=8.7 Hz, 1H), 3.31 (s, 3H), 3.43 (s, 3H), 3.58 (m, 2H), 3.68 (d, J=11.7 Hz, 1H), 3.82 (d, J=10.5 Hz, 1H), 3.84-3.9(m, 2H), 4.02 (d, J=10.7 Hz, 1H), 4.23 (m, 1H), 5.55 (m, 1H).

INTERMEDIATE 29

(1S,4aR,6aS,7R,8R,10aR,10bR,12aR,14R,15R)-8-[(1R)-1,2-dimethylpropyl]-15-[[4-(ethylamino)tetrahydro-2H-pyran-4-yl]methoxy]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

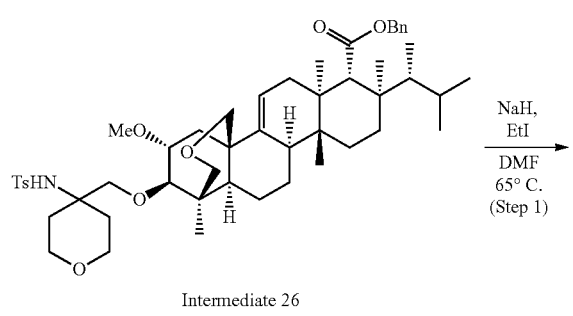

Intermediate 26

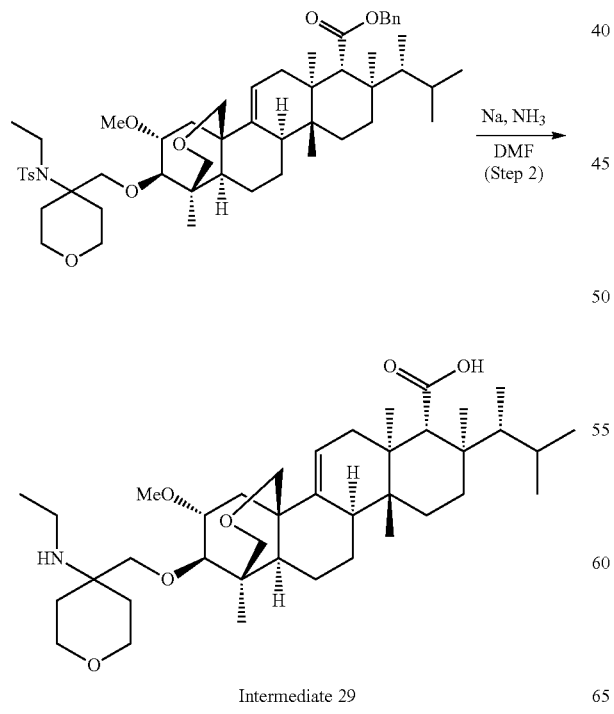

Intermediate 29

Step 1

Sodium hydride (60% dispersion in mineral oil, 84 mg, 2.1 mmol) was washed with hexane and the hexane decanted. This procedure was repeated and the remaining hexane removed in vacuo. This pre-washed sodium hydride was suspended in DMF (1 mL) and a solution of intermediate 26 (0.18 g, 0.21 mmol) in DMF (1 mL) was added. Ethyl iodide (0.169 mL, 2.1 mmol) was added and the reaction mixture heated at 60° C. under nitrogen for 60 minutes. After cooling to room temperature the reaction was partitioned between ethyl acetate and saturated aqueous bicarbonate. The organic phase was washed with brine, dried with MgSO$_4$ filtered and concentrated in vacuo to give the product (0.18 g).

Step 2

The product was subjected to sodium/ammonia reduction by analogy to the preparation of Intermediate 27 then lyophilized from MeOH/Benzene to give Intermediate 29 (0.16 g) as an off-white foam.

$^1$H NMR (CD$_3$OD, 500 MHz, ppm) δ 0.77 (s, 3H), 0.79 (d, 3H, partially obscured), 0.80 (s, 3H), 0.86 (d, J=6.7 Hz, 3H), 0.88 (d, J=5.3 Hz, 3H), 1.21 (s, 3H), 1.18-1.42 (m), 1.50 (m, 1H), 1.56-1.88 (m), 1.92 (m, 1H), 1.95 (m, 1H), 1.99 (m, 1H), 2.03 (m, 1H), 2.08 (m, 1H), 2.11 (m, 1H), 2.28 (m, 1H), 2.58 (m, 1H), 2.80 (s, 1H), 2.71(m, 1H), 2.99 (d, J=8.7 Hz, 1H), 3.02 (m, 1f1), 3.36 (s, 3H), 3.43 (s, 2H), 3.56 (m, 2H), 3.68 (d, J=11.7 Hz, 1H), 3.84-3.92(m, 3H), 4.04 (d, J=10.8 Hz, 1H), 4.22 (m, 1H), 5.55 (m, 1H).

INTERMEDIATE 30

(1S,4aR,6aS,7R,8R,10aR,10bR,12aR,14R,15R)-15-[(1-aminocyclohexyl)methoxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

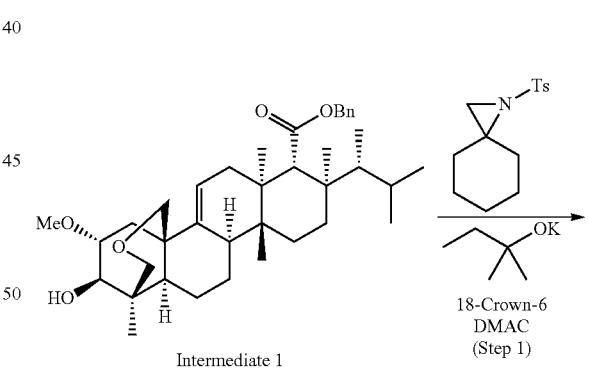

Intermediate 1

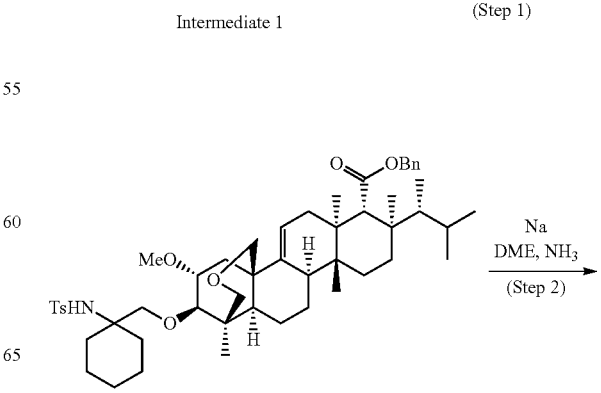

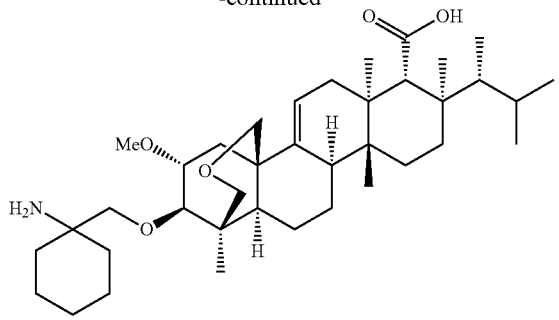

Intermediate 30

Step 1:

To a stirred solution of Intermediate 1 (5.0 g, 8.43 mmol), 1-[(4-methylphenyl)sulfonyl]-1-azaspiro[2.5]octane (4.03 g, 15.18 mmol) and 18-crown-6 (2.23 g, 8.43 mmol) in DMAC (16 mL) under a nitrogen atmosphere was added a solution of potassium tert-pentylate in toluene (~1.7 M, 5.95 mL, 10.12 mmol). The mixture was stirred at room temperature for 16 hours and partitioned between EtOAc and 1 N HCl. The organic layer was dried over $Na_2SO_4$. The solvent was evaporated and the residue was chromatographed on silica gel with an ISCO Combiflash using EtOAc/hexanes 15-30% to afford a pale yellow solid (5.62 g).

MS ESI m/z=881(M+Na).

Step 2:

Sodium metal (248 mg, 10.8 mmol) was added to a solution of liquid ammonia (20 mL) at −33° C. The mixture was diluted with dry DME (20 mL). A solution of the product compound from Step 1 (928 mg, 1.08 mmol) in DME (2 mL) was added dropwise over 5 min. The mixture was stirred at reflux for 2 hours and the reaction was quenched with careful addition of excess MeOH. The ammonia was allowed to evaporate and the mixture was partitioned between EtOAc and water. The organic layer was dried over $Na_2SO_4$ and the solvent was evaporated to give the title compound as a white solid (550 mg).

MS (ESI) m/z=614 (M+H).

INTERMEDIATE 31

(1S,4aR,6aS,7R,8R,10aR,10bR,12aR,14R,15R)-8-[(1R)-1,2-dimethylpropyl]-14-methoxy-15-[[1-(methylamino)cyclohexyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

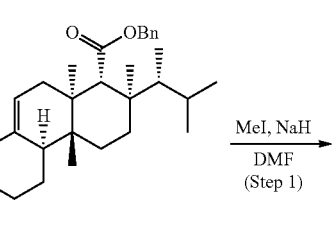

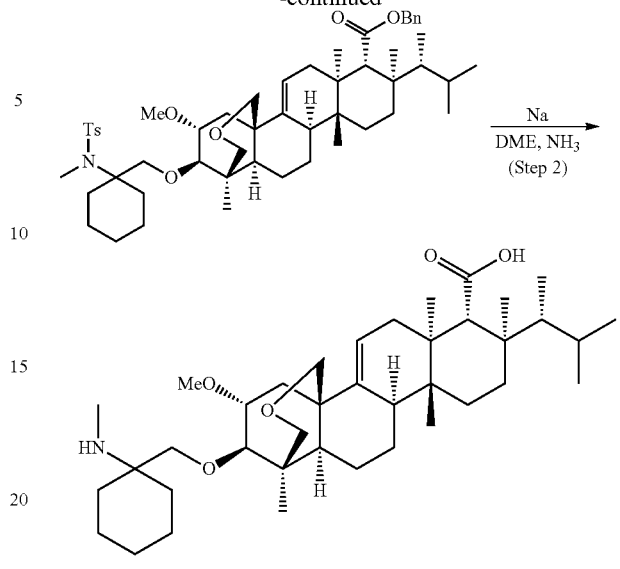

Intermediate 31

Step 1:

To a solution of the product compound of Step 1 in the synthesis of Intermediate 30 (155 mg, 0.181 mmol) in DMF (3 mL) under a nitrogen atmosphere was added a suspension of 30% NaH (14 mg, 0.361 mmol). The mixture was stirred at room temperature for 5 minutes and iodomethane (64 mg, 0.451 mmol) was added. The mixture was stirred for 16 hours and partitioned between EtOAc and 1 N HCl. The organic layer was dried over $Na_2SO_4$ and the solvent was evaporated to give an amber oil (158 mg).

Step 2:

Sodium metal (40 mg, 1.81 mmol) was added to a solution of liquid ammonia (10 mL) at −33° C. The mixture was diluted with dry DME (5 mL). A solution of product compound from Step 1 (158 mg, 0.181 mmol) in DME (2 mL) was added dropwise over 5 min. The mixture was stirred at reflux for 2 hours and the reaction was quenched by careful addition of excess MeOH. The ammonia was allowed to evaporate and the mixture was partitioned between EtOAc and water. The organic layer was dried over $Na_2SO_4$ and the solvent was evaporated to give the title compound as a white solid (100 mg).

MS (ESI) m/z=628 (M+H).

EXAMPLES

Unless otherwise indicated, compounds described in the following examples which contain a basic amine group were isolated as trifluoroacetic acid salts. Thus, where applicable, reference to a reaction "to give the title compound" or "to provide the title compound", "to give" a particular Example Number, "title compound was prepared", and similar language, refers the title compound as a TFA salt. Conversion to the parent free amines may be accomplished by standard methods known in the art (e.g. neutralization with an appropriate inorganic base such as $NaHCO_3$). Other desired amine salts may be prepared in a conventional manner by reacting the free base with a suitable organic or inorganic acid. Alternatively, a desired amine salt may be prepared directly from the trifluoroacetic acid salt by employing an appropriate ion exchange resin.

Example 1

(1S,4aR,6aS,7R,8R,10aR,10bR,12aR,14R,15R)-15-(2-amino-2-methylpropoxy)-8-[(1R)-1,2-dimethylpropyl]-14-(1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 1A) and (1S,4aR,6aS,7R,8R,10aR,10bR,12aR,14R,15R)-15-(2-amino-2-methylpropoxy)-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 1B)

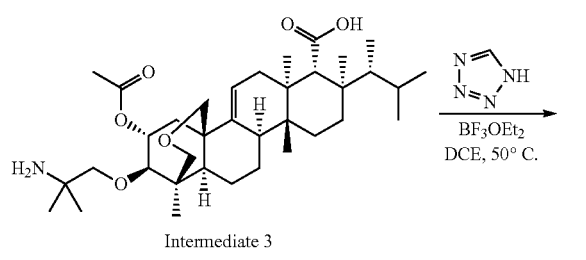

Intermediate 3

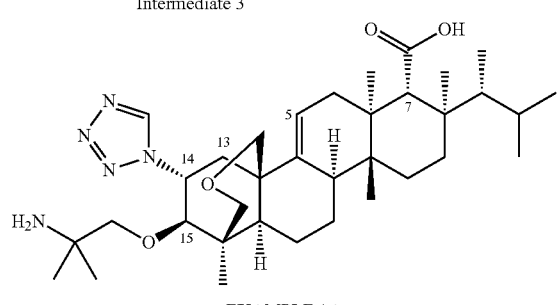

EXAMPLE 1A

+

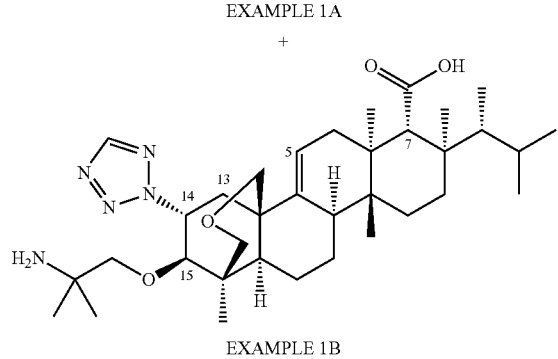

EXAMPLE 1B 1H-tetrazole (24.5 mg, 0.350 mmol) and BF$_3$O(CH$_2$CH$_3$)$_2$ (88 µl, 0.701 mmol) were added to a stirred solution of Intermediate 3 (50.3 mg, 0.070 mmol) in 1,2-dichloroethane (1.0 ml). The reaction mixture was heated to 50° C. After 2 hours, $^1$H NMR showed complete conversion to a mixture of the two tetrazole regioisomers. The reaction mixture was cooled to room temperature, the solvent was evaporated under reduced pressure, and the residue was placed under high vacuum. The residue was dissolved in methanol and purified using a single HPLC run on a 20×150 mm YMC Prep C18 ODS-A 10 µM column by eluting with acetonitrile/water+0.1% TFA. The HPLC fractions of the faster eluting regioisomer were combined, the solvent was evaporated under reduced pressure, and the residue was lyophilized from ethanol and benzene to give Example 1A as a white solid (8.2 mg). The HPLC fractions of the slower eluting regioisomer were combined, the solvent was evaporated under reduced pressure, and the residue was lyophilized from ethanol and benzene to give Example 1B as a white solid (12.2 mg). The regiochemisty of the tetrazole in Example 1A was assigned on the basis of an NOE from H14 to the tetrazole proton. Example 1B did not show an NOE from H14 to the tetrazole proton.

Example 1A $^1$H NMR (CD$_3$OD, 600 MHz, ppm) δ 0.76 (s, 3H, Me), 0.77 (d, 3H, Me), 0.85 (d, 3H, Me), 0.88 (s, 3H, Me), 0.89 (d, 3H, Me), 0.98 (s, 3H, Me), 1.12 (s, 3H, Me), 1.16 (s, 3H, Me), 1.20 (s, 3H, Me), 1.22-1.36 (m), 1.40-1.45 (m), 1.48-1.65 (m), 1.81-2.04 (m), 2.13-2.22 (m), 2.50 (d, 1H), 2.53 (dd, 1H, H13), 2.84 (s, 1H, H7), 3.47 (d, 1H), 3.50 (d, 1H), 3.54 (dd, 1H), 3.62 (d, 1H), 3.81 (d, 1H), 3.91 (d, 1H), 5.50 (dd, 1H, H5), 5.86-5.92 (m, 1H, H14), 9.33 (s, 1H, tetrazole).

Mass Spectrum: (ESI) m/z=613.02 (M+H).

Example 1B $^1$H NMR (CD$_3$OD, 600 MHz, ppm) δ 0.77 (s, 3H, Me), 0.77 (d, 3H, Me), 0.85 (d, 3H, Me), 0.89 (s, 3H, Me), 0.90 (d, 3H, Me), 0.93 (s, 3H, Me), 1.01 (s, 3H, Me), 1.15 (s, 3H, Me), 1.20 (s, 3H, Me), 1.22-1.37 (m), 1.40-1.45 (m), 1.48-1.65 (m), 1.81-1.96 (m), 1.98-2.04 (m), 2.13-2.22 (m), 2.46 (d, 1H), 2.52 (dd, 1H, H13), 2.84 (s, 1H, H7), 3.43 (d, 1H), 3.51 (d, 1H), 3.56 (dd, 1H), 3.64 (d, 1H), 3.87 (d, 1H), 3.94 (d, 1H), 5.50 (dd, 1H, H5), 6.15-6.21 (m, 1H, H14), 8.76 (s, 1H, tetrazole).

Mass Spectrum: (ESI) m/z=613.02 (M+H).

Example 2

(1S,4aR,6aS,7R,8R,10aR,10bR,12aR,14R,15R)-15-(2-amino-2,3-dimethylbutoxy)-8-[(1R)-1,2-dimethylpropyl]-14-(1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 2A) and (1S,4aR,6aS,7R,8R,10aR,10bR,12aR,14R,15R)-15-(2-amino-2,3-dimethylbutoxy)-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 2B)

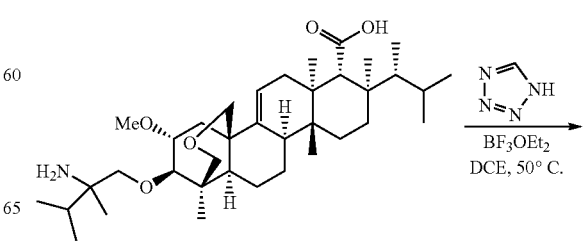

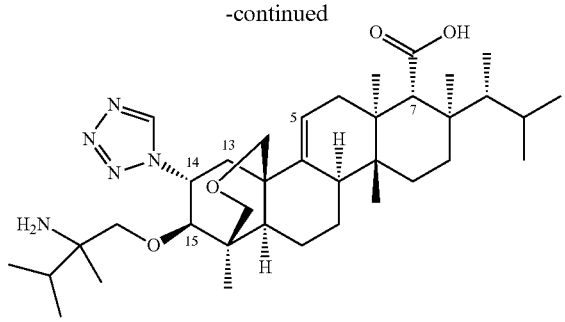

EXAMPLE 2A

+

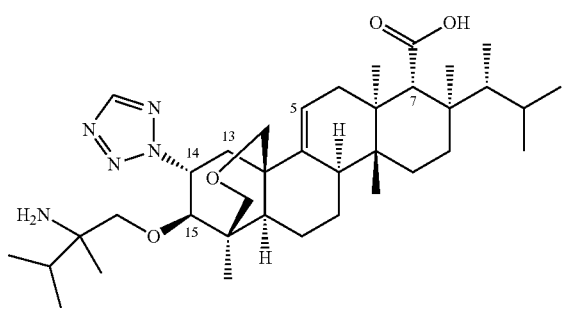

EXAMPLE 2B 1H-tetrazole (15.6 mg, 0.223 mmol) and BF$_3$O(CH$_2$CH$_3$)$_2$ (55 µl, 0.438 mmol) were added to a stirred solution of (1S,4aR,6aS,7R,8R,10aR,10bR,12aR,14R,15R)-15-(2-amino-2,3-dimethylbutoxy)-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (26.3 mg, 0.044 mmol; prepared as described for Intermediate 6, but as a ~1:1 mixture of diastereomers) in 1,2-dichloroethane (0.5 ml). The reaction mixture was heated to 50° C. After 3 hours, $^1$H NMR and LCMS showed complete conversion of starting material to a mixture of the two tetrazole regioisomers at C14. The reaction mixture was cooled to room temperature, the solvent was evaporated under reduced pressure, and the residue was placed under high vacuum. The residue was dissolved in methanol and separated using a single HPLC run on a 20×150 mm YMC Prep C18 ODS-A 10 µm column by eluting with acetonitrile/water+0.1% TFA. The HPLC fractions of the faster eluting regioisomer were combined, the solvent was evaporated under reduced pressure, and the residue was lyophilized from ethanol and benzene to give EXAMPLE 2A as a white solid (3.2 mg). The HPLC fractions of the slower eluting regioisomer were combined, the solvent was evaporated under reduced pressure, and the residue was lyophilized from ethanol and benzene to give EXAMPLE 2B as a white solid (7.1 mg).

Example 2A $^1$H NMR (CD$_3$OD, 600 MHz, ppm) δ 0.52 (d), 0.76 (s), 0.77 (d), 0.79 (d), 0.83 (s), 0.83 (d), 0.86 (d), 0.90 (d), 0.90 (s), 0.90 (s), 1.02 (s), 1.15 (s), 1.16 (s), 1.20 (s), 1.22-1.36 (m), 1.40-1.45 (m), 1.48-1.65 (m), 1.70-2.00 (m), 2.13-2.22 (m), 2.51 (dd), 2.54 (dd, H13), 2.61 (d), 2.79 (d), 2.84 (s, H7), 3.44 (d), 3.51 (d), 3.53 (d), 3.55 (dd), 3.62 (d), 3.62 (d), 3.88 (d), 3.92 (d), 3.92 (d), 3.95 (d), 5.49 (dd, H5), 5.50 (dd, H5), 5.86-5.93 (m, H14), 9.32 (s, tetrazole), 9.34 (s, tetrazole).

Mass Spectrum: (ESI) m/z=640.96 (M+H).

Example 2B $^1$H NMR (CD$_3$OD, 600 MHz, ppm) δ 0.52 (d), 0.76 (s), 0.76 (d), 0.79 (d), 0.79 (s), 0.83 (d), 0.85 (d), 0.89 (d), 0.91 (s), 0.91 (s), 1.00 (s), 1.14 (s), 1.14 (s), 1.20 (s), 1.22-1.37 (m), 1.40-1.45 (m), 1.48-1.56 (m), 1.59-1.65 (m), 1.72-1.81 (m), 1.82-2.01 (m), 2.12-2.22 (m), 2.50 (dd, H13), 2.52 (dd, H13), 2.55 (d), 2.68 (d), 2.84 (s, H7), 3.35 (d), 3.49 (d), 3.51 (d), 3.56 (d), 3.56 (d), 3.64 (d), 3.64 (d), 3.93 (d), 3.97 (d), 5.47-5.51 (m, H5), 6.14-6.22 (m, H14), 8.77 (s, tetrazole), 8.78 (s, tetrazole).

Mass Spectrum: (ESI) m/z=640.97 (M+H).

Example 3

(1S,4aR,6aS,7R,8R,10aR,10bR,12aR,14R,15R)-15-[[(2R)-2-(dimethylamino)-2,3-dimethylbutyl]oxy]-8-[(1R)-1,2-dimethylpropyl]-14-(1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 3A) and (1S,4aR,6aS,7R,8R,10aR,10bR,12aR,14R,15R)-15-[[(2R)-2-(dimethylamino)-2,3-dimethylbutyl]oxy]-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 3B)

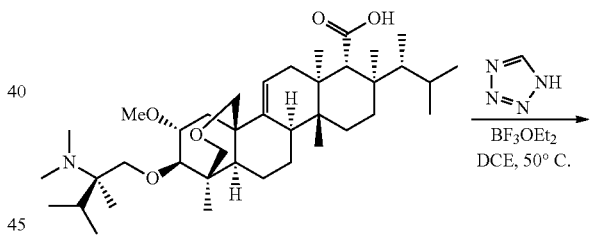

Intermediate 10

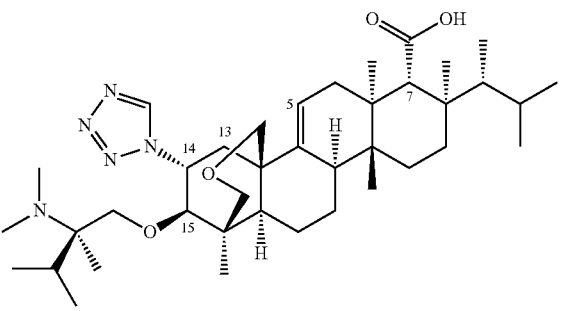

EXAMPLE 3A

+

89

-continued

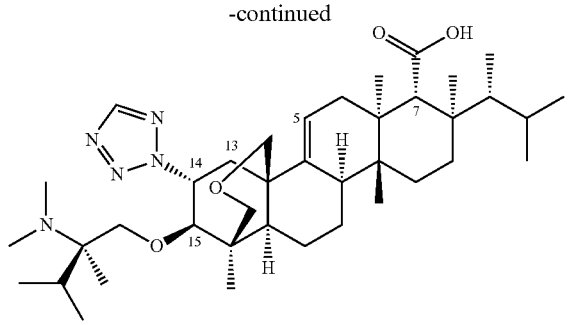

EXAMPLE 3B 1H-tetrazole (53.0 mg, 0.757 mmol) and $BF_3O(CH_2CH_3)_2$ (190 µl, 1.499 mmol) were added to a stirred solution of Intermediate 10 (95.3 mg, 0.151 mmol) in 1,2-dichloroethane (1.5 ml). The reaction mixture was a yellow solution that was heated to 50° C. After 1.5 hours, LCMS and $^1H$ NMR showed complete conversion of Intermediate 10 to a mixture of the two tetrazole regioisomers at C14. The reaction mixture was cooled to room temperature, the solvent was evaporated under reduced pressure, and the residue was placed under high vacuum. The residue was dissolved in methanol and separated using 3HPLC runs (~32 mg/run) on a 20×150 mm YMC Prep C18 ODS-A 10 µm column by eluting with acetonitrile/water+0.1% TFA. The HPLC fractions of the faster eluting regioisomer were combined, the solvent was evaporated under reduced pressure, and the residue was lyophilized from ethanol and benzene to give EXAMPLE 3A as a white solid (34.9 mg). The HPLC fractions of the slower eluting regioisomer were combined, the solvent was evaporated under reduced pressure, and the residue was lyophilized from ethanol and benzene to give EXAMPLE 3B as a white solid (24.2 mg).

Example 3A $^1$H NMR (CD$_3$OD, 600 MHz, ppm) δ 0.76 (s, 3H, Me), 0.77 (d, J=5.3 Hz, 3H, Me), 0.83 (s, 3H, Me), 0.85 (d, J=6.7 Hz, 3H, Me), 0.89 (d, J=6.9 Hz, 3H, Me), 0.90 (d, J=6.4 Hz, 3H), Me, 0.91 (d, J=6.8 Hz, 3H, Me), 0.94 (s, 3H, Me), 1.15 (s, 3H, Me), 1.20 (s, 3H, Me), 1.22-1.37 (m, 3H), 1.40-1.45 (m, 1H), 1.48-1.66 (m, 3H), 1.82-1.99 (m, 6H), 2.12-2.27 (m, 3H), 2.55 (dd, J=13.3, 6.3 Hz, 1H, H13), 2.69 (s, 3H, Me), 2.75 (s, 3H, Me), 2.83 (s, 1H, H7), 2.90 (d, J=12.1 Hz, 1H), 3.55 (d, 1H), 3.55 (dd, 1H), 3.63 (d, J=11.7 Hz, 1H), 3.73 (d, J=12.1 Hz, 1H), 3.77 (d, J=12.0 Hz, 1H), 3.96 (d, J=9.8 Hz, 1H), 5.49 (dd, 1H, H5), 5.91-5.96 (m, 1H, H14), 9.44 (s, 1H, tetrazole).

Mass Spectrum: (ESI) m/z=668.67 (M+H).

Example 3B $^1$H NMR (CD$_3$OD, 600 MHz, ppm) δ 0.76 (s, 3H, Me), 0.76 (d, J=6.7 Hz, 3H, Me), 0.83 (s, 3H, Me), 0.85 (d, J=6.7 Hz, 3H, Me), 0.89 (d, J=6.9 Hz, 3H, Me), 0.92 (d, J=6.9 Hz, 3H, Me), 0.94 (d, J=5.4 Hz, 3H, Me), 0.94 (s, 3H, Me), 1.13 (s, 3H, Me), 1.20 (s, 3H, Me), 1.22-1.37 (m, 3H), 1.40-1.45 (m, 1H), 1.48-1.65 (m, 3H), 1.82-1.99 (m, 6H), 2.11-2.22 (m, 2H), 2.28-2.35 (m, 1H), 2.52 (dd, J=13.5, 6.5 Hz, 1H, H13), 2.66 (s, 3H, Me), 2.75 (s, 3H, Me), 2.71 (d, J=12.1 Hz, 1H), 2.83 (s, 1H, H7), 3.56 (d, J=13.0 Hz, 2H), 3.63 (d, J=12.2 Hz, 1H), 3.65 (d, J=12.8 Hz, 1H), 3.80 (d, J=12.2 Hz, 1H), 3.99 (d, J=9.9 Hz, 1H), 5.48 (dd, 1H, H5), 6.16-6.22 (m, 1H, H14), 8.83 (s,1H, tetrazole).

Mass Spectrum: (ESI) m/z=668.66 (M+H).

90

Example 4

(1S,4aR,6aS,7R,8R,10aR,10bR,12aR,14R,15R)-15-[2-(dimethylamino)-2,3-dimethylbutoxy]-8-[(1R)-1,2-dimethylpropyl]-14-(1H-tetrazol-1-yl)-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (Example 4A) and (1S,4aR,6aS,7R,8R,10aR,10bR,12aR,14R,15R)-15-[2-(dimethylamino)-2,3-dimethylbutoxy]-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (Example 4B)

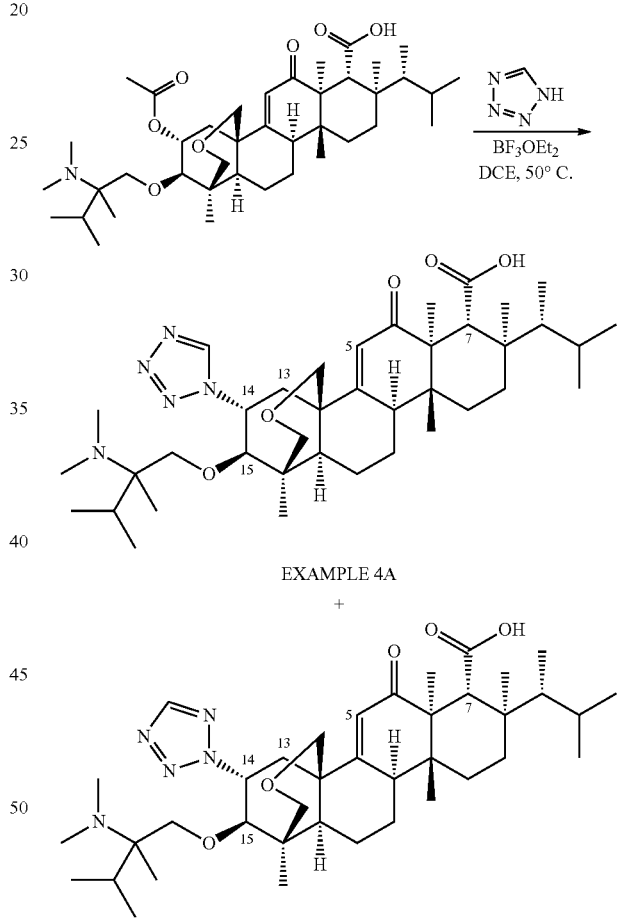

EXAMPLE 4A

+

EXAMPLE 4B 1H-tetrazole (31.8 mg, 0.454 mmol) and $BF_3O(CH_2CH_3)_2$ (104 µl, 0.828 mmol) were added to a stirred solution of (1S,4aR,6aS,7R,8R,10aR,10bR,12aR,14R,15R)-14-(acetyloxy)-15-[2-(dimethylamino)-2,3-dimethylbutoxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (the compound of Example 130 in WO2007127012, incorporated by reference herein in its entirety; 30.0 mg, 0.041 mmol) in 1,2-dichloroethane (0.5 ml). The reaction mixture was a yellow solution that was heated to 50° C. After 2 hours, LCMS and ¹H NMR showed complete conversion of SM to a mixture of the two tetrazole regioisomers at C14. The reaction mixture was cooled to room temperature, the solvent was evaporated under reduced pressure, and the residue was placed under high vacuum. The residue was dissolved in methanol and separated using a single HPLC run on a 20×150 mm YMC Prep C18 ODS-A 10 μm column by eluting with acetonitrile/water+0.1% TFA. The HPLC fractions of the faster eluting regioisomer were combined, the solvent was evaporated under reduced pressure, and the residue was lyophilized from ethanol and benzene to give EXAMPLE 4A as a white solid (8.6 mg). The HPLC fractions of the slower eluting regioisomer were combined, the solvent was evaporated under reduced pressure, and the residue was lyophilized from ethanol and benzene to give EXAMPLE 4B as a white solid (3.6 mg).

Example 4A

¹H NMR (CD₃OD, 600 MHz, ppm) δ 0.69 (d), 0.77 (d), 0.81 (s), 0.84 (s), 0.87 (d), 0.90 (d), 0.92 (d), 0.95 (d), 0.97 (d), 1.09 (s), 1.19 (s), 1.29-1.34 (m), 1.38-1.48 (m), 1.53-1.57 (m), 1.66-1.73 (m), 1.69 (s), 1.70 (s), 1.75-1.82 (m), 1.90-2.05 (m), 2.19-2.27 (m), 2.60 (dd, H13), 2.70 (s, Me), 2.75 (s, Me), 2.75 (s, Me), 2.76 (s, Me), 2.93 (d), 3.05 (d), 3.09 (s, H7), 3.58 (d), 3.58 (d), 3.63 (d), 3.63 (d), 3.69 (d), 3.70 (d) 3.70 (d), 3.76 (d), 3.82 (d), 3.87 (d), 4.01 (d), 4.02 (d), 5.77 (d, H5), 5.94-6.01 (m, H14), 9.44 (s, tetrazole), 9.44 (s, tetrazole).

Mass Spectrum: (ESI) m/z=682.97 (M+H).

Example 4B

¹H NMR (CD₃OD, 600 MHz, ppm) δ 0.72 (d), 0.77 (d), 0.81 (s), 0.84 (s), 0.87 (d), 0.93 (d), 0.95 (d), 0.95 (d), 0.96 (s), 0.98 (s), 1.09 (s), 1.21 (s), 1.27-1.33 (m), 1.38-1.57 (m), 1.66-1.82 (m), 1.68 (s), 1.69 (s), 1.90-2.10 (m), 1.18-2.24 (m), 2.30-2.36 (m), 2.59 (dd, H13), 2.67 (s, Me), 2.71 (d), 2.74 (s, Me), 2.77 (s, Me), 2.78 (s, Me), 2.84 (d), 3.09 (s, H7), 3.56 (d), 3.58 (d), 3.63 (d), 3.64 (d), 3.73 (d), 3.84 (d), 3.90 (d), 4.00 (d), 4.02 (d), 5.77 (d, H5), 6.21-6.27 (m, H14), 8.84 (s, tetrazole), 8.84 (s, tetrazole).

Mass Spectrum: (ESI) m/z=682.97 (M+H).

Example 5

(1S,4aR,6aS,7R,8R,10aR,10bR,12aR,14R,15R)-15-(2-amino-2,3-dimethylbutoxy)-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid

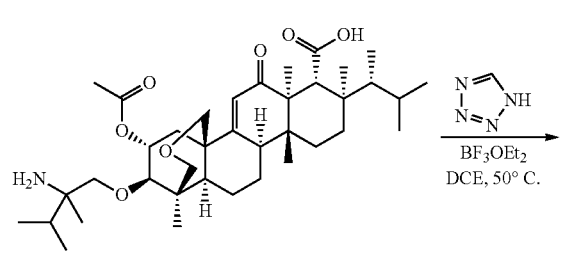

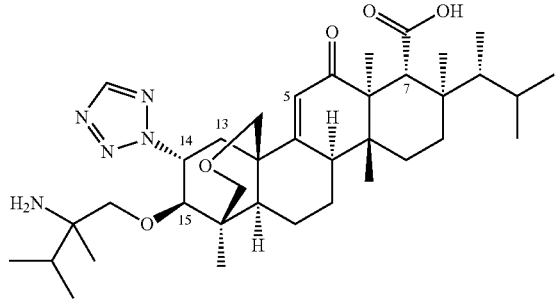

In a manner analogous to that described in Example 4, but starting with (1S,4aR,6aS,7R,8R,10aR,10bR,12aR,14R,15R)-14-(acetyloxy)-15-(2-amino-2,3-dimethylbutoxy)-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (the compound of Example 129 in WO2007127012), the title compound was prepared and isolated as a white solid. The corresponding 1H-tetrazol-1-yl isomer was not isolated.

¹H NMR (CD₃OD, 600 MHz, ppm) δ 0.64 (d), 0.77 (d), 0.80 (d), 0.81 (s), 0.82 (s), 0.84 (d), 0.87 (d), 0.94 (s), 0.95 (d), 1.02 (s), 1.09 (s), 1.26-1.34 (m), 1.37-1.49 (m), 1.52-1.57 (m), 1.66-1.82 (m), 1.68 (s), 1.69 (s), 1.93-2.11 (m), 2.18-2.25 (m), 2.55 (d), 2.57 (dd, 1H), 2.60 (dd, H13), 2.68 (d), 2.70-2.75 (m), 3.09 (s, H7), 3.36 (d), 3.50 (d), 3.54 (d), 3.63 (d), 3.63 (d), 3.71 (d), 3.72 (d), 3.95 (d), 3.96 (d), 3.99 (d), 4.01 (d), 5.77 (d, H11), 5.78 (d, H5), 6.20-6.27 (m, H14), 8.78 (s, tetrazole), 8.79 (s, tetrazole).

Mass Spectrum: (ESI) m/z=654.43 (M+H).

Example 6

(1S,4aR,6aS,7R,8R,10aR,10bR,12aR,14R,15R)-15-(2-amino-2-methylpropoxy)-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

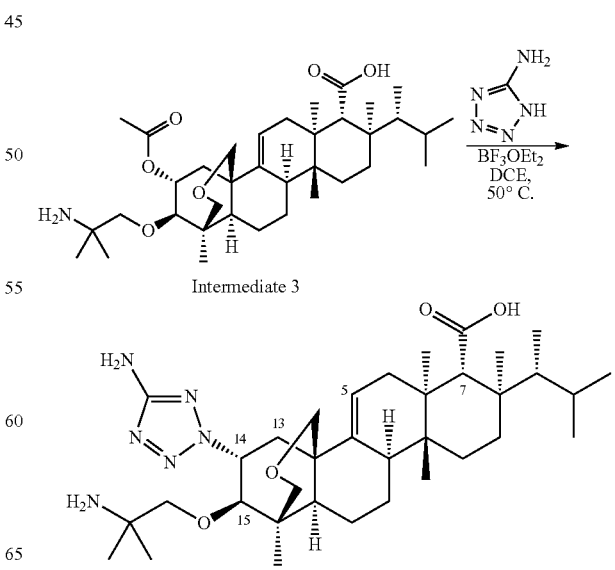

Intermediate 3

5-aminotetrazole (27.8 mg, 0.327 mmol) and $BF_3O(CH_2CH_3)2$ (80 μl, 0.637 mmol) were added to a stirred solution of Intermediate 3 (45.4 mg, 0.063 mmol) in 1,2-dichloroethane (0.7 ml). The reaction mixture was heated to 50° C. After 1.5 hours, LCMS and $^1$H NMR showed complete consumption of Intermediate 3. The reaction mixture was cooled to room temperature, the solvent was evaporated under reduced pressure, and the residue was placed under high vacuum. The residue was dissolved in methanol and purified using a single HPLC run on a 20×150 mm YMC Prep C18 ODS-A 10 μM column by eluting with acetonitrile/water+0.1% TFA. The product HPLC fractions were combined, the solvent was evaporated under reduced pressure, and the residue was lyophilized from ethanol and benzene to give the title compound as a white solid (18.9 mg).

$^1$H NMR (CD$_3$OD, 600 MHz, ppm) δ 0.76 (s, 3H, Me), 0.77 (d, 3H, Me), 0.85 (d, 3H, Me), 0.86 (s, 3H, Me), 0.99 (d, 3H, Me), 1.03 (s, 3H, Me), 1.15 (s, 3H, Me), 1.15 (s, 3H, Me), 1.20 (s, 3H, Me), 1.22-1.36 (m), 1.39-1.44 (m), 1.48-1.65 (m), 1.77-2.00 (m), 2.10-2.22 (m), 2.45 (dd, 1H, H13), 2.64 (d, 1H), 2.84 (s, 1H, H7), 3.45 (d, 1H), 3.48 (d, 1H), 3.53 (dd, 1H), 3.60 (d, 1H), 3.73 (d,1H), 3.90 (d,1H), 5.49 (dd, 1H, H5), 5.81-5.87 (m, 1H, H14).

Mass Spectrum: (ESI) m/z=627.35 (M+H).

Example 7

(1S,4aR,6aS,7R,8R,10aR,10bR,12aR,14R,15R)-15-[[(2R)-2-amino-2,3-dimethylbutyl]oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

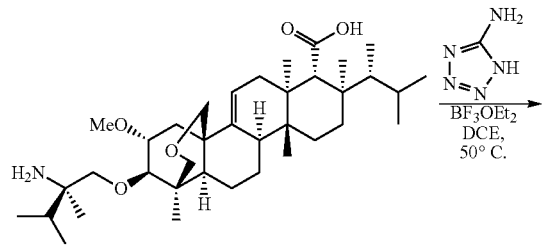

Intermediate 6

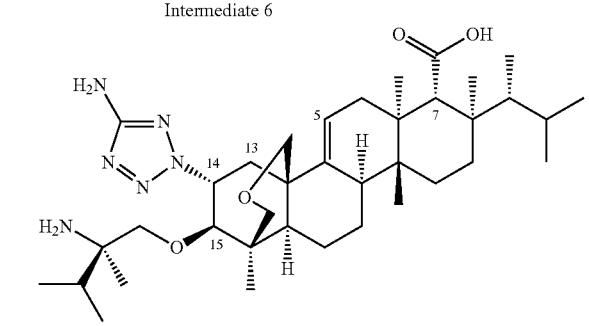

5-aminotetrazole (51.3 mg, 0.603 mmol) and $BF_3O(CH_2CH_3)_2$ (150 μl, 1.184 mmol) were added to a stirred solution of Intermediate 6 (71.5 mg, 0.119 mmol) in 1,2-dichloroethane (1.2 ml). The reaction mixture was a light yellow suspension that was heated to 50° C. After 2 hours, LCMS and $^1$H NMR showed complete consumption of Intermediate 6. The reaction mixture was cooled to room temperature, the solvent was evaporated under reduced pressure, and the residue was placed under high vacuum. The residue was dissolved in methanol and purified using 2HPLC runs (~35 mg/run) on a 20×150 mm YMC Prep C18 ODS-A 10 μm column by eluting with acetonitrile/water+0.1% TFA. The product HPLC fractions were combined, the solvent was evaporated under reduced pressure, and the residue was lyophilized from ethanol and benzene to give the title compound as a white solid (55.9 mg).

$^1$H NMR (CD$_3$OD, 600 MHz, ppm) δ 0.76 (s, 3H, Me), 0.77 (d, J=6.4 Hz, 3H, Me), 0.83 (d, J=6.9 Hz, 3H, Me), 0.85 (d, J=6.8 Hz, 3H, Me), 0.88 (s, 3H, Me), 0.88 (d, J=6.9 Hz, 3H, Me), 0.90 (d, J=6.9 Hz, 3H, Me), 0.91 (s, 3H, Me), 1.15 (s, 3H, Me), 1.21 (s, 3H, Me), 1.23-1.35 (m, 3H), 1.39-1.45 (m, 1H), 1.47-1.66 (m, 3H), 1.78-1.99 (m, 7H), 2.10-2.16 (m, 1H), 2.15-2.22 (m, 1H), 2.46 (dd, J=13.5, 6.5 Hz, 1H, H13), 2.73 (d, J=9.9 Hz, 1H), 2.84 (s, 1H, H7), 3.48 (d, J=11.1 Hz, 1H), 3.49 (d, J=9.8 Hz, 1H), 3.53 (dd, J=11.7, 1.9 Hz, 1H), 3.61 (d, J=11.6 Hz, 1H), 3.77 (d, J=9.8 Hz, 1H), 3.93 (d, J=12 Hz, 1H), 5.50 (dd, J=3.6, 1.8 Hz, 1H, H5), 5.83-5.87 (m, 1H, H 14).

Mass Spectrum: (ESI) m/z=655.60 (M+H).

Example 8

(1S,4aR,6aS,7R,8R,10aR,10bR,12aR,14R,15R)-14-(5-amino-2H-tetrazol-2-yl)-15-[[(2R)-2-(dimethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

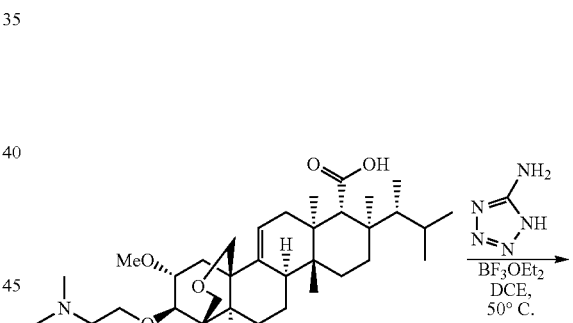

Intermediate 10

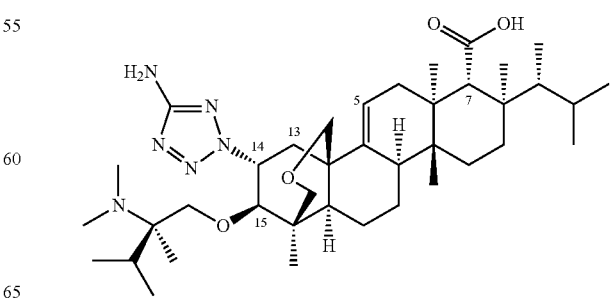

5-aminotetrazole (239.4 mg, 2.81 mmol) was added to a stirred solution of Intermediate 10 (354.2 mg, 0.562 mmol) in 1,2-dichloroethane (5.6 ml). BF$_3$O(CH$_2$CH$_3$)$_2$ (0.71 ml, 5.60 mmol) was added dropwise resulting in vigorous bubbling that quickly dissipated. The reaction mixture was a tan suspension that was heated to 50° C. After 1.75 hours, LCMS and $^1$H NMR showed complete consumption of Intermediate 10. The reaction mixture was cooled to room temperature, the solvent was evaporated under reduced pressure, and the residue was placed under high vacuum. The residue was dissolved in methanol (5 ml) and purified using 8 HPLC runs (~44 mg/run) on a 19×150 mm Sunfire Prep C18 OBD 10 μM column by eluting with acetonitrile/water+0.1% TFA. The product HPLC fractions were combined, the solvent was evaporated under reduced pressure, and the residue was lyophilized from ethanol and benzene to give 227.1 mg of the title compound as a white solid (trifluoroacetic acid salt).

$^1$H NMR (CD$_3$OD, 600 MHz, ppm) δ 0.76 (s, 3H, Me), 0.77 (d, J=7.5 Hz, 3H, Me), 0.85 (d, J=6.6 Hz, 3H, Me), 0.89 (d, J=6.8 Hz, 3H, Me), 0.92 (s, 3H, Me), 0.93 (s, 3H, Me), 0.96 (d, J=6.8 Hz, 3H, Me), 0.97 (d, J=6.9 Hz, 3H, Me), 1.14 (s, 3H, Me), 1.20 (s, 3H, Me), 1.22-1.35 (m, 3H), 1.39-1.44 (m, 1H), 1.47-1.65 (m, 3H), 1.80-1.96 (m, 6H), 20.9-2.15 (m, 1H), 2.15-2.22 (m, 1H), 2.31-2.38 (m, 1H), 2.45 (dd, J=13.5, 6.4 Hz, 1H, H13), 2.71 (s, 3H, Me), 2.79 (s, 3H, Me), 2.84 (s, 1H, H7), 2.95 (d, J=12.1 Hz, 1H), 3.52 (d, J=12.0 Hz, 1H), 3.53 (dd, J=11.7, 2.2 Hz, 1H), 3.62 (d, J=11.7 Hz, 1H), 3.65 (d, J=12.0 Hz, 1H), 3.76 (d, J=12.1 Hz, 1H), 3.84 (d, J=9.9 Hz, 1H), 5.49 (dd, J=3.9, 2.0 Hz, 1H, H5), 5.82-5.87 (m, 1H, H14).

Mass Spectrum: (ESI) m/z=683.65 (M+H).

Conversion of Example 8 to Hydrochloride Salt (Method A)

A portion of Example 8 TFA salt from above (73 mg) was dissolved in ethyl acetate (10 mL) and the solution was washed with saturated aqueous NaHCO$_3$ (3 mL) followed by brine (3 mL). The separated organic layer was dried over Na$_2$SO$_4$ and then evaporated to near dryness in vacuo. The residue was lyophilized from benzene/methanol to give the free base as a white solid (53.6 mg). A portion of the solid (30.1 mg, 0.044 mmol) was suspended in acetonitrile (1 mL)/water (1 mL) and 0.1N aqueous HCl solution (0.44 mL) was added giving a clear solution. The solution was diluted with additional water (2 mL) and frozen and lyophilized to give the hydrochloride salt as a white solid (31.5 mg).

Conversion of Example 8 to Hydrochloride Salt (Method B)

Example 8 TFA salt (1.335 g, 1.675 mmol), prepared according to the method described above, was dissolved in methanol (2 mL) and the solution was diluted with 2 mL of 1:1 MeCN/H$_2$O. The solution was loaded onto a column of Dowex® 1X8 chloride form ion exchange resin (50 g, ~1.8 meq/g) and the column was eluted with 1:1 MeCN/H$_2$O (~2 column volumes). The eluant was concentrated in vacuo to remove most of the acetonitrile and then frozen and lyophilized to give 1.035 g of the hydrochloride salt as a white solid.

Example 9

(1S,4aR,6aS,7R,8R,10aR,10bR,12aR,14R,15R)-15-[[(2R)-2-amino-2,3-dimethylbutyl]oxy]-14-(5-amino-1H-tetrazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

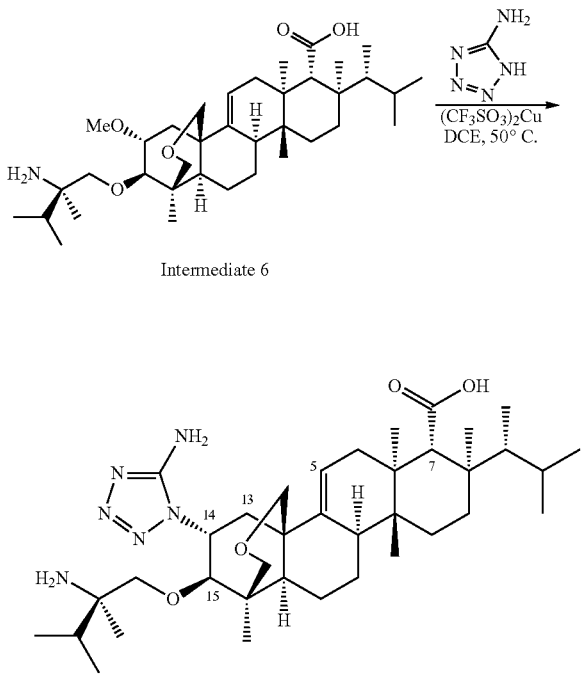

A suspension of Intermediate 6 (13 mg, 0.022 mmol), 5-aminotetrazole (12 mg, 0.141 mmol) and copper trifluoromethanesulfonate (7.81 mmol) in dichloroethane (0.5 mL) was stirred for 26 hours at 50° C. The suspension was cooled to room temperature, filtered, evaporated and the residue was dissolved in methanol (0.5 mL) and purified by reverse phase HPLC using a 19×150 mm Sunfire Preparative C18 OBD column. Fractions containing the product were evaporated and freeze-dried from a mixture of ethanol and benzene to give the title compound as a solid (1.0 mg).

$^1$H NMR CD$_3$OD δ (PPM) 5.50 (dd, 1H, H5); 5.32 (m, 1H, H14); 3.94 (d, 1H); 3.89 (d, 1H); 3.65 (d, 1H); 3.54 (dd, 1H), 3.50 (d, 1H); 2.92 (d, 1H); 2.84 (s, 1H, H7); 2.44 (dd, 1H, H13), 2.18 (m, 1H); 2.12-2.16 (m); 1.79-1.96 (m); 1.77 (m); 1.46-1.65 (m, 3H); 1.40-1.44 (m, 1H); 1.22-1.34 (m, 3H); 1.20 (s, 3H, Me); 1.16 (s, 3H, Me); 0.94 (s, 3H, Me); 0.89 (d, 3H, Me); 0.88 (s, 3H, Me); 0.85 (d, 3H, Me); 0.84 (d, 3H, Me); 0.82 (d, 3H, Me); 0.77 (d, 3H, Me) and 0.76 (s, 3H, Me).

LC/MS m/z (positive ion scan) M+1=655.43.

Example 10

(1S,4aR,6aS,7R,8R,10aR,10bR,12aR,14R,15R)-14-(5-amino-2H-tetrazol-2-yl)-15-[[(2R)-2,3-dimethyl-2-(1-piperidinyl)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

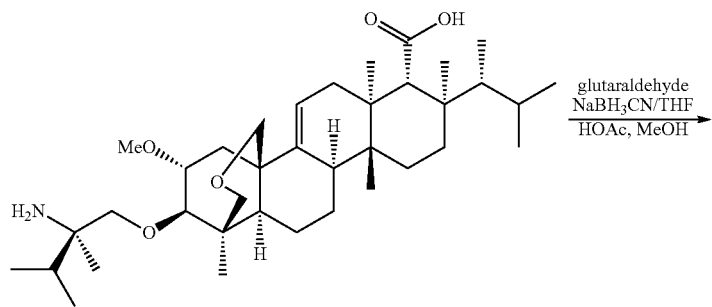

Intermediate 6

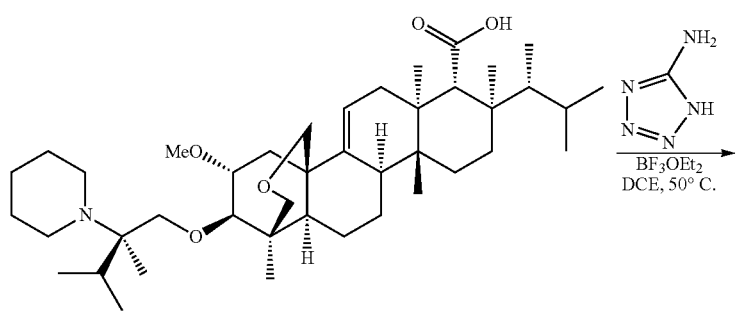

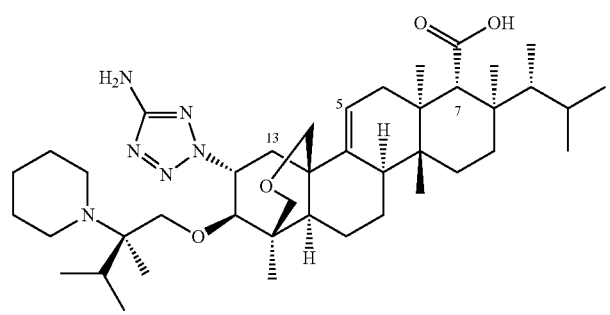

Acetic acid (17.5 µl, 0.306 mmol), glutaraldehyde 50% in water (110 µl, 0.604 mmol), and sodium cyanoborohydride 1.0 M in THF (0.61 ml, 0.610 mmol) were added to a stirred solution of Intermediate 6 (92.4 mg, 0.154 mmol) in methanol (3.0 ml). The reaction mixture was a colorless solution that was stirred at room temperature overnight. LCMS showed complete consumption of Intermediate 6. The reaction mixture was partitioned between ethyl acetate (50 ml) and water (50 ml). The aqueous layer was extracted with ethyl acetate (1×50 ml). The organic layers were combined, dried over magnesium sulfate, and filtered. The solvent was evaporated under reduced pressure to give the title compound as a colorless residue (94.6 mg).

$^1$H NMR (CD$_3$OD, 600 MHz, ppm) δ 0.78 (s, 3H, Me), 0.79 (d, 3H, Me), 0.83 (s, 3H, Me, 0.86 (d, 3H, Me), 0.93 (d, 3H, Me), 1.03 (d, 3H, Me), 1.07 (d, 3H, Me), 1.12 (s, 3H, Me), 1.22 (s, 3H, Me), 1.26 (s, 3H, Me), 1.20-1.95 (m), 1.99-2.12 (m), 2.25-2.33 (m), 2.49-2.56 (m), 2.60 (dd, 1H, H13), 2.79 (s, 1H, H7), 2.91 (d, 1H), 3.33-3.42 (m), 3.56 (d, 1H), 3.57 (d, 1H), 3.59 (d, 1H), 3.62 (d, 1H), 3.64 (d, 1H), 4.13 (d, 1H), 4.23-4.29 (m, 1H, H2), 4.48 (t), 4.51 (t), 5.56 (dd, 1H, H5).

Mass Spectrum: (ESI) m/z=670.67 (M+H).

Example 11

(1S,4aR,6aS,7R,8R,10aR,10bR,12aR,14R,15R)-14-(5-amino-2H-tetrazol-2-yl)-15-[[(2S)-2,3-dimethyl-2-(1-piperidinyl)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

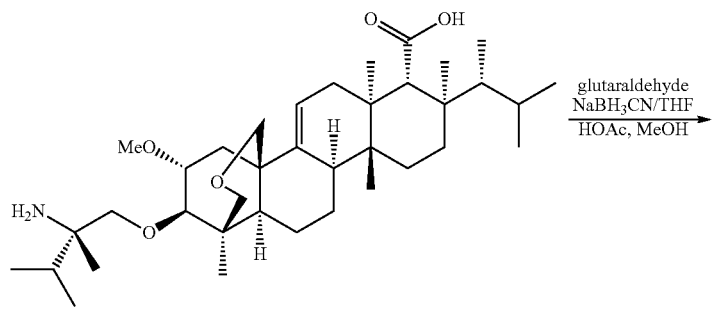

Intermediate 7

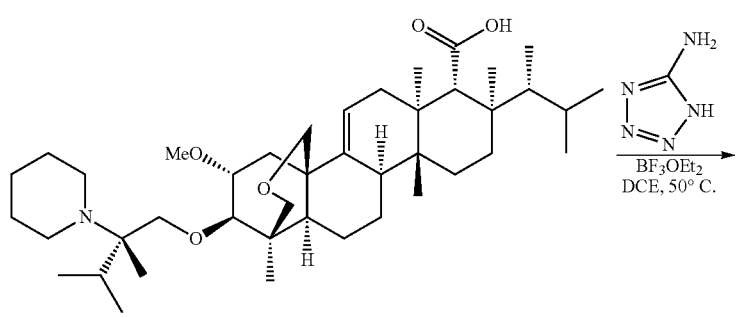

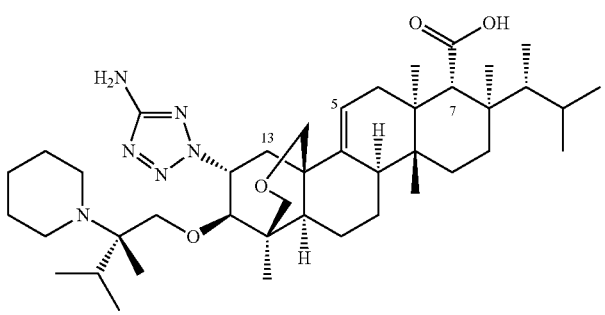

In a manner analogous to that described in Example 10, the title compound (1S,4aR,6aS,7R,8R,10aR,10bR,12aR,14R,15R)-14-(5-amino-2H-tetrazol-2-yl)-15-[[(2S)-2,3-dimethyl-2-(1-piperidinyl)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid was prepared starting with Intermediate 7.

$^1$H NMR (CD$_3$OD, 600 MHz, ppm) δ 0.76 (s, 3H, Me), 0.77 (d, 3H, Me), 0.81 (d, 3H, Me), 0.85 (d, 3H, Me), 0.89 (d, 3H, Me), 0.90 (s, 3H, Me), 0.93 (d, 3H, Me), 1.01-1.04 (m) 1.14 (s, 3H, Me), 1.20 (s, 3H, Me), 1.26 (s, 3H, Me), 1.22-2.22 (m), 2.45 (dd, 1H, H13), 2.81-2.86 (m), 2.84 (s, 1H, H7), 2.99-3.04 (m), 3.18 (d, 1H), 3.39-3.48 (m), 3.53 (d, 1H), 3.53 (d, 1H), 3.61 (d, 1H), 3.64 (d, 1H), 3.80 (d, 1H), 3.84 (d, 1H), 5.49 (dd, 1H, H5), 5.79-5.84 (m, 1H, H14).

Mass Spectrum: (ESI) m/z=723.69 (M+H).

Example 12

(1S,4aR,6aS,7R,8R,10aR,10bR,12aR,14R,15R)-14-(5-amino-2H-tetrazol-2-yl)-8-[(1R)-1,2-dimethylpropyl]-15-[[(2R)-2-[(2-hydroxyethyl)amino]-2,3-dimethylbutyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

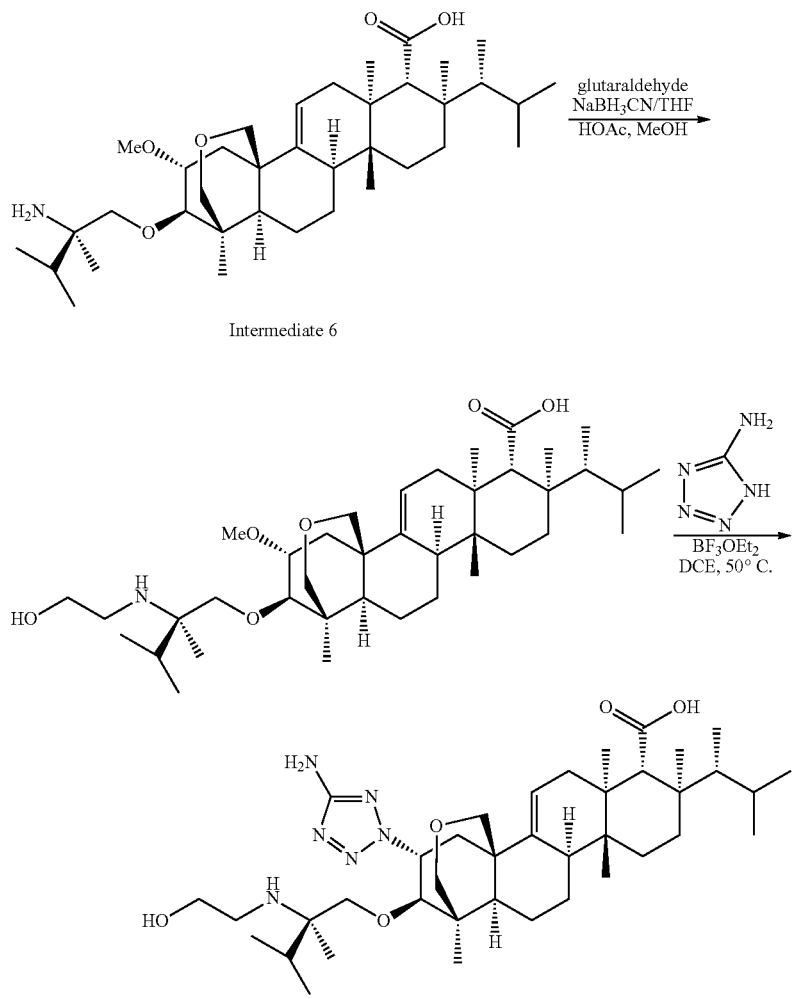

Intermediate 6

Step 1:

A mixture of Intermediate 6 (56 mg, 0.082 mmol), glycolaldehyde dimer (30 mg, 0.25 mmol), 1M sodium cyanoborohydride in THF (0.3 mL, 0.3 mmol) and acetic acid (25 µL, 0.44 mmol) was dissolved in methanol (0.44 mL) and stirred at room temperature for 4 hours. The mixture was added to ethyl acetate (30 mL) and water (20 mL). The aqueous layer was re-extracted (2×20 mL) and the combined ethyl acetate layers were dried with magnesium sulfate, filtered and evaporated to give the product as a solid (50 mg).

LC/MS m/z (positive ion scan) M+1=646.61.

Step 2:

A mixture of the product from Step 1 (50 mg, 0.077 mmol), 5-aminotetrazole (50 mg, 0.59 mmol) and borontrifluoride etherate (0.1 mL, 0.70 mmol) in dichloroethane (1.0 mL) was placed in a 50° C. oil bath for 1 hour. The mixture was evaporated to a foam and purified by reverse phase HPLC using a 19×150 mm Sunfire Preparative C18 OBD column. Fractions containing the product were evaporated and freeze-dried from a mixture of ethanol and benzene to give the title compound as a solid (15.1 mg).

$^1$H NMR CD$_3$OD δ (PPM) 5.87 (m, 1H, H14); 5.49 (dd, 1H, H5); 3.93 (d, 1H); 3.86 (d, 1H); 3.76 (dd, 2H, CH$_2$); 3.66 (d, 1H); 3.61 (d, 1H); 3.53 (dd, 1H), 3.48 (d, 1H); 2.97 (dd, 2H, CH$_2$); 2.89 (d, 1H); 2.84 (s, 1H, H7), 2.46 (dd, 1H, H13), 2.18 (m, 1H); 2.10-2.14 (m); 2.04 (m, 1H); 1.79-1.96 (m); 1.46-1.65 (m); 1.42 (m, 1H); 1.22-1.32 (m, 3H); 1.20 (s, 3H, Me); 1.14 (s, 3H, Me); 0.92 (d, 3H, Me); 0.89 (s, 3H, Me); 0.88 (d, 3H, Me); 0.86 (s, 3H, Me); 0.85 (d, 3H, Me); 0.81 (d, 3H, Me); 0.77 (d, 3H, Me) and 0.76 (s, 3H, Me).

LC/MS m/z (positive ion scan) M+1=699.69.

Example 13

(1S,4aR,6aS,7R,8R,10aR,10bR,12aR,14R,15R)-14-(5-amino-2H-tetrazol-2-yl)-8-[(1R)-1,2-dimethylpropyl]-15-[[(2R)-2-[(3-hydroxypropyl)amino]-2,3-dimethylbutyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

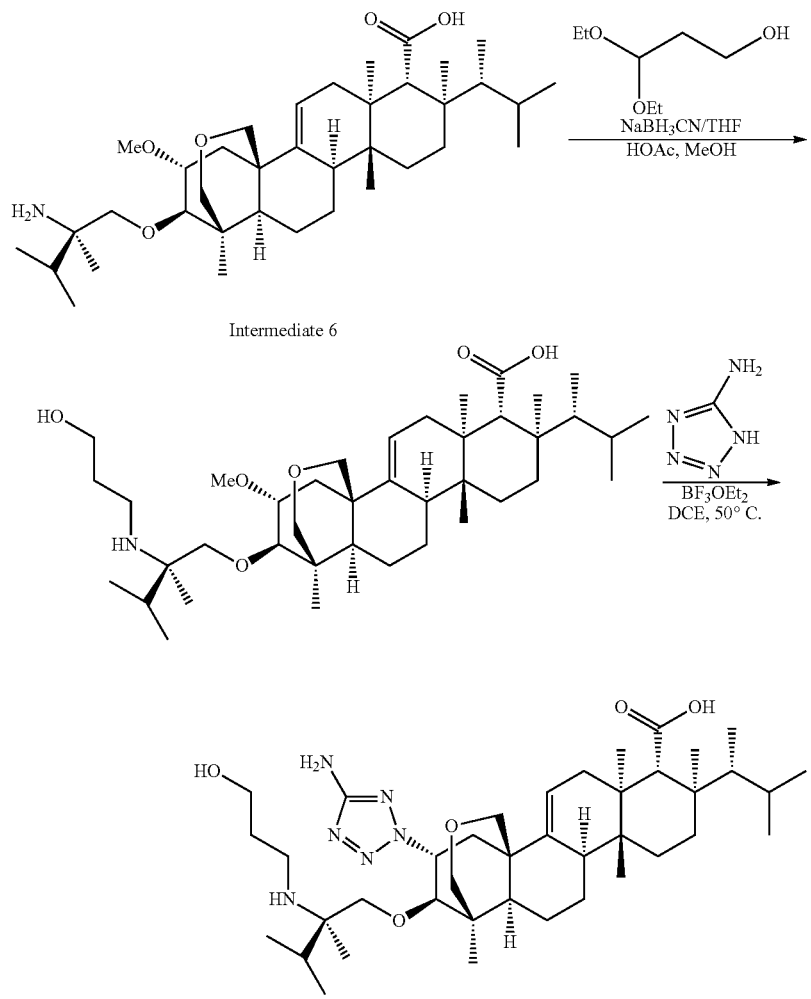

Intermediate 6

Step 1:

A mixture of Intermediate 6 (59 mg, 0.073 mmol), 3,3-diethoxy-1-propanol (115 μL, 0.73 mmol), 1M sodium cyanoborohydride in THF (0.37 mL, 0.37 mmol) and acetic acid (42 μL, 0.73 mmol) was dissolved in methanol (0.73 mL) and stirred at room temperature for 5 hours. The mixture was heated in a 50° C. oil bath for 48 hours. Toluenesulfonic acid hydrate (25 mg) was added during this time, as well as more 1M sodium cyanoborohydride (150 μL) and 3,3-diethoxy-1-propanol (115 μL). The mixture was cooled to room temperature and added to ethyl acetate (30 mL) and water (20 mL). The aqueous layer was re-extracted (1×20 mL) and the combined ethyl acetate layers were dried with magnesium sulfate, filtered and evaporated to a solid. The solid was purified by reverse phase HPLC using a 19×150 mm Sunfire Preparative C18 OBD column. Fractions containing the product were evaporated and freeze-dried from a mixture of ethanol and benzene to give the product as a solid (33.5 mg).

LC/MS m/z (positive ion scan) M+1=660.55.

Step 2:

Following a procedure analogous to that described in Step 2 of Example 12, the title compound was prepared starting with the product from Step 1 above.

$^1$H NMR CD$_3$OD δ (PPM) 5.86 (m, 1H, H14); 5.49 (dd, 1H, H5); 3.88 (d, 1H); 3.86 (d, 1H); 3.76 (m); 3.61 (d, 1H); 3.60 (d, 1H); 3.53 (dd, 1H); 3.49 (d, 1H); 3.01 (m, 2H); 2.95 (m, 2H); 2.84 (s, 1H, H7); 2.80 (d, 1H); 2.46 (dd, 1H, H13); 2.18 (m, 1H); 2.10-2.14 (m); 2.06 (m, 1H); 1.80-1.96 (m); 1.46-1.65 (m); 1.42 (m, 1H); 1.22-1.32 (m, 3H); 1.20 (s, 3H, Me); 1.15 (s, 3H, Me); 0.90 (s, 3H, Me); 0.89 (d); 0.85 (d, 3H, Me); 0.77 (d, 3H, Me) and 0.76 (s, 3H, Me).

LC/MS m/z (positive ion scan) M+1=713.64.

Example 14

(1S,4aR,6aS,7R,8R,10aR,10bR,12aR,14R,15R)-15-
[[(2R)-2-[(2-amino-2-oxoethyl)amino]-2,3-dimethyl-
butyl]oxy]-14-(5-amino-2H-tetrazol-2-yl)-8-[(1R)-1,
2-dimethylpropyl]-1,6,6a,7,8,9,10,10a,10b,11,12,
12a-dodecahydro-1,6a,8,10a-tetramethyl-4H-1,4a-
propano-2H-phenanthro[1,2-c]pyran-7-carboxylic
acid

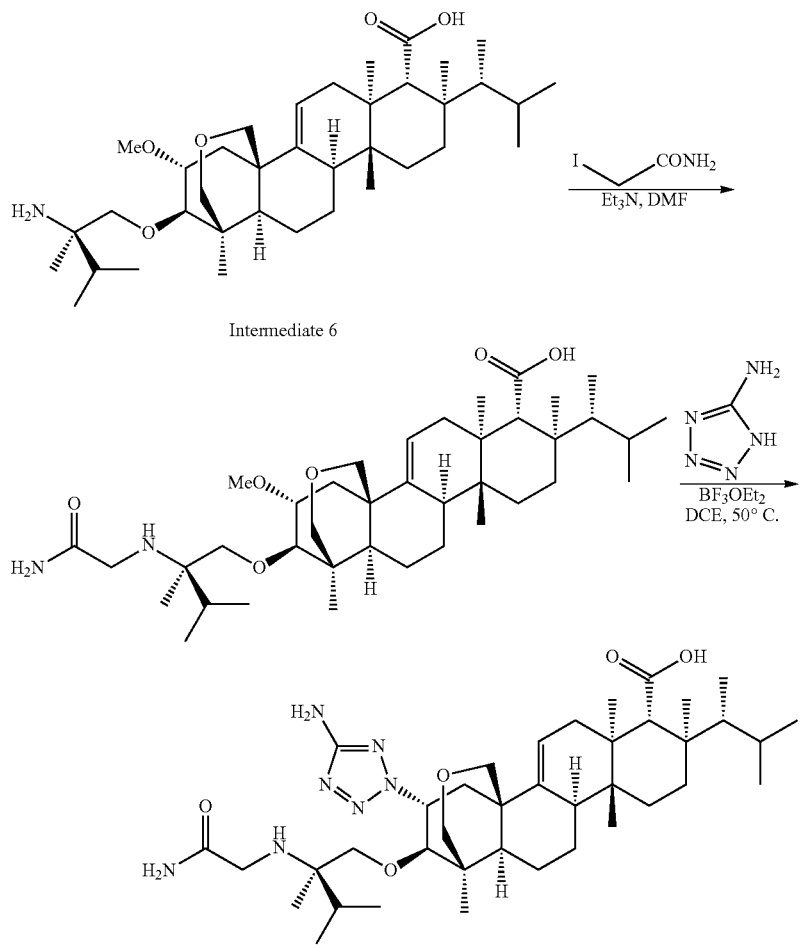

Step 1:

Intermediate 6 (30 mg, 0.044 mmol), iodoacetamide (24 mg, 0.132 mmol) and triethylamine (31 µL, 0.22 mmol) were dissolved in anhydrous dimethylformamide (0.4 mL) and stirred at room temperature for 3 hours. The mixture was then placed in a 50° C. oil bath for 2 hours, whereupon additional iodoacetamide (24 mg, 0.13 mmol) and triethylamine (50 µL, 0.36 mmol) were added. After an additional 1 hour at 50° C., the mixture was cooled to room temperature and purified by reverse phase HPLC using a 19×150 mm Sunfire Preparative C18 OBD column. The fractions containing the product were combined and evaporated to a solid (13.4 mg).

LC/MS m/z (positive ion scan) M+1=659.50.

Step 2:

A solution of the product from Step 1 (13.4 mg, 0.02 mmol), 5-aminotetrazole (14 mg, 0.165 mmol) and boron trifluoride etherate (50 µL, 0.388 mmol) in dichloroethane (0.5 mL) was heated for 2 hours in a 50° C. oil bath. The mixture was cooled to room temperature, evaporated and purified by reverse phase HPLC using a 19×150 mm Sunfire Preparative C18 OBD column. The fractions were combined, evaporated and freeze-dried from benzene to give the title compound as a solid (2.7 mg).

$^1$H NMR CD$_3$OD δ (PPM) 5.85 (m, 1H, H14); 5.49 (dd, 1H, H5); 3.90 (d, 1H); 3.82 (d, 1H); 3.68 (m, CH$_2$CONH$_2$); 3.65 (d, 1H); 3.61 (d, 1H); 3.52 (dd, 1H), 3.47 (d, 1H); 2.83 (s, 1H, H7), 2.76 (d, 1H); 2.46 (dd, 1H, H13); 2.18 (m, 1H); 2.12 (m, 1H); 1.78-2.02 (m); 1.62 (ddd, 1H); 1.50-1.58 (m); 1.40-1.44 (m); 1.22-1.34 (m); 1.20 (s, 3H, Me); 1.14 (s, 3H, Me); 0.92 (d, 3H, Me); 0.89 (s, 3H, Me); 0.89 (d, 3H, Me); 0.86 (s, 3H, Me); 0.85 (d, 3H, Me); 0.83 (d, 3H, Me); 0.77 (d, 3H, Me) and 0.76 (s, 3H, Me).

LC/MS m/z (positive ion scan) M+1=712.48.

Example 15

(1S,4aR,6aS,7R,8R,10aR,10bR,12aR,14R,15R)-14-(5-amino-2H-tetrazol-2-yl)-15-[[(2S)-2-(dimethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (Example 15A) and (1S,4aR,6aS,7R,8R,10aR,10bR,12aR,14R,15R)-14-(5-amino-2H-tetrazol-2-yl)-15-[[(2R)-2-(dimethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (Example 15B)

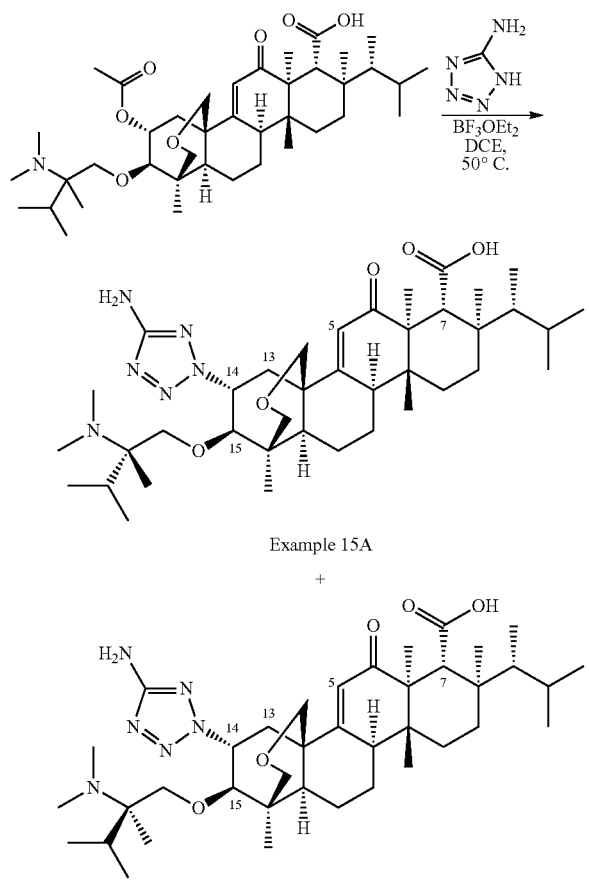

Example 15A
+
Example 15B 5-aminotetrazole (21.2 mg, 0.249 mmol) and BF$_3$O(CH$_2$CH$_3$)$_2$ (60 µl, 0.478 mmol) were added to a stirred solution of (1S,4aR,6aS,7R,8R,10aR,10bR,12aR,14R,15R)-14-(acetyloxy)-15-[2-(dimethylamino)-2,3-dimethylbutoxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (the compound of Example 130 in WO2007127012; 34.5 mg, 0.047 mmol) in 1,2-dichloroethane (0.5 ml). The reaction mixture was a yellow suspension that was heated to 50° C. After 22 hours, LCMS and $^1$H NMR showed complete consumption of the starting material. The reaction mixture was cooled to room temperature, the solvent was evaporated under reduced pressure, and the residue was placed under high vacuum. The residue was dissolved in methanol and separated using a single HPLC run on a 20×150 mm YMC Prep C18 ODS-A 10 µm column by eluting with acetonitrile/water+0.1% TFA. The HPLC fractions of the faster eluting diastereomer were combined, the solvent was evaporated under reduced pressure, and the residue was lyophilized from ethanol and benzene to give EXAMPLE 15A as a white solid (6.4 mg). The HPLC fractions of the slower eluting diastereomer were combined, the solvent was evaporated under reduced pressure, and the residue was lyophilized from ethanol and benzene to give EXAMPLE 15B as a white solid (5.0 mg).

Example 15A $^1$H NMR (CD$_3$OD, 600 MHz, ppm) δ 0.77 (d), 0.80 (s, 3H, Me), 0.81 (d, 3H, Me), 0.87 (d, 3H, Me), 0.91 (d, 3H, Me), 0.93 (s, 3H, Me), 0.95 (d, 3H, Me), 1.09 (s, 3H, Me), 1.23 (s, 3H, Me), 1.29-1.49 (m), 1.52-1.57 (m), 1.66-1.73 (m), 1.69 (s, 3H, Me), 1.75-1.81 (m), 1.91-2.07 (m), 2.18-2.25 (m), 2.52 (dd, 1H, H13), 2.68-2.74 (m), 2.79 (s, 3H, Me), 2.82 (s, 3H, Me), 3.06 (d, 1H), 3.09 (s, 1H, H7), 3.54 (d, 1H), 3.59 (d, 1H), 3.61 (dd, 1H), 3.69 (d, 1H), 3.86 (d, 1H), 5.78 (d, 1H, H5), 5.85-5.91 (m,1H, H14).

Mass Spectrum: (ESI) m/z=697.40 (M+H).

Example 15B $^1$H NMR (CD$_3$OD, 600 MHz, ppm) δ 0.77 (d, 3H, Me), 0.80 (s, 3H, Me), 0.87 (d, 3H, Me), 0.94 (s, 3H, Me), 0.95 (d, 3H, Me), 0.95 (s, 3H, Me), 0.96 (d, 3H, Me), 0.97 (d, 3H, Me), 1.09 (s, 3H, Me), 1.28-1.57 (m), 1.66-1.73 (m), 1.69 (s, 3H, Me), 1.75-1.81 (m), 1.91-2.03 (m), 2.19-2.25 (m), 2.32-2.38 (m), 2.52 (dd, 1H, H13), 2.71 (s, 3H, Me), 2.81 (s, 3H, Me), 2.95 (d, 1H), 3.09 (s, 1H, H7), 3.54 (d, 1H), 3.60 (dd, 1H), 3.67 (d, 1H), 3.69 (d, 1H), 3.80 (d, 1H), 3.87 (d, 1H), 5.78 (d, 1H, H5), 5.87-5.93 (m, 1H, H14).

Mass Spectrum: (ESI) m/z=697.44 (M+H).

Example 16

(1S,4aR,6aS,7R,8R,10aR,10bR,12aR,14R,15R)-15-(2-amino-2,3-dimethylbutoxy)-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid

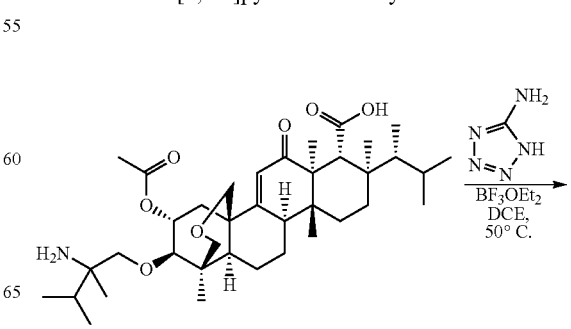

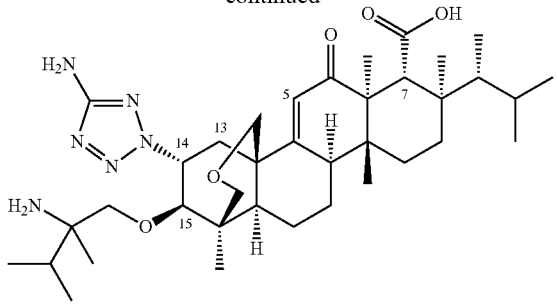

In a manner analogous to that described in Example 15, but starting with (1S,4aR,6aS,7R,8R,10aR,10bR,12aR,14R,15R)-14-(acetyloxy)-15-(2-amino-2,3-dimethylbutoxy)-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (the compound of Example 129 in WO2007127012), the title compound was prepared and isolated as a white solid. The product was a ~1:1 mixture of diastereomers.

$^1$H NMR (CD$_3$OD, 600 MHz, ppm) δ 0.65 (d), 0.77 (d), 0.81 (s), 0.84 (d), 0.87 (s), 0.88 (s), 0.88 (d), 0.92 (d), 0.92 (s), 0.95 (d), 1.06 (s), 1.09 (s), 1.26-1.34 (m), 1.37-1.49 (m), 1.52-1.57 (m), 1.66-1.73 (m), 1.69 (s), 1.70 (s), 1.89-2.07 (m), 2.19-2.26 (m), 2.50 (dd, H13), 2.53 (dd, H13), 2.69-2.75 (m), 2.73 (d), 2.90 (d), 3.09 (s, H7), 3.38 (d), 3.51 (d), 3.51 (d), 3.60 (d), 3.60 (d), 3.68 (d), 3.68 (d), 3.81 (d), 3.82 (d), 3.95 (d), 3.98 (d), 5.78 (d, H5), 5.79 (d, H5), 5.86-5.93 (m, H14).

Mass Spectrum: (ESI) m/z=669.39 (M+H).

Example 17

(1S,4aR,6aS,7R,8R,10aR,10bR,12aR,14R,15R)-14-(5-amino-2H-tetrazol-2-yl)-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

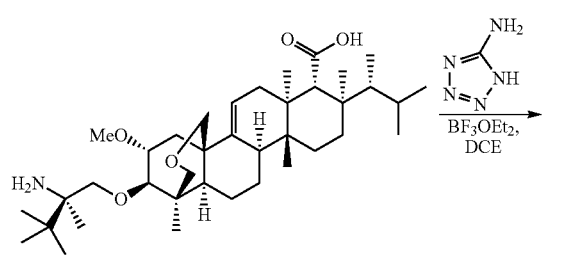

Intermediate 14

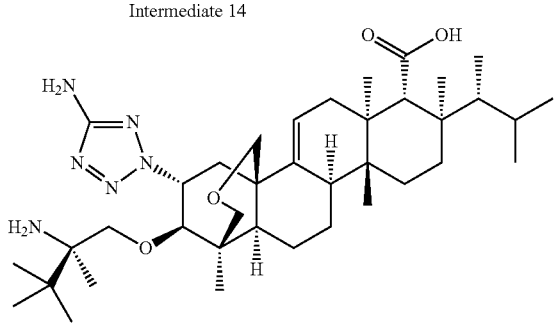

Intermediate 14 (120 mg, 0.20 mmol) and 5-aminotetrazole (83 mg, 0.98 mmol) were combined then diluted with dichloroethane (6.5 mL), then treated with BF$_3$OEt$_2$ (0.25 mL, 2 mmol) and this mixture was heated to 50° C. under nitrogen. After 1.5 hours the reaction was cooled to room temperature and filtered through a sintered glass funnel. The filtrate was concentrated and dissolved in methanol then purified by preparative LCMS (30×100 mm Waters Sunfire column, 5 μm, Electrospray positive detection, 0-100% MeCN/water with 0.05% TFA over 12 minutes, using Masslynx software). The product fractions were combined and partially concentrated by rotovap then frozen and lyophilized to give the title compound (32 mg) as a white amorphous solid.

$^1$H NMR (CD$_3$OD, 500 MHz, ppm) δ 0.77 (s, 3H), 0.78 (d, 3H, partially obscured), 0.86 (d, J=6.6 Hz, 3H), 0.88 (s, 9H), 0.90 (d, J=6.9 Hz, 3H), 0.91 (s, 3H), 0.93 (s, 3H), 1.16 (s, 3H), 1.21 (s, 3H), 1.2-1.36 (m), 1.4-1.66 (m), 1.78-1.98 (m), 2.1-2.24 (m), 2.47 (dd, J=13.5 Hz, 6.4 Hz, 1H), 2.79 (d, J=9.6 Hz, 1f1), 2.85 (s, 1H), 3.49 (d, J=11.6 Hz, 1H), 3.54 (d, J=11.6 Hz, 1H), 3.62 (d, J=11.6 Hz, 1H), 3.68 (d, J=9.8 Hz, 1H), 3.81 (d, J=10.1 Hz, 1H), 3.96 (d, J=12.1 Hz, 1H), 5.50 (m, 1H), 5.87 (m, 1H).

m/z=669.33 (M+H).

Example 18

(1S,4aR,6aS,7R,8R,10aR,10bR,12aR,14R,15R)-14-(5-amino-2H-tetrazol-2-yl)-15-[[(2S)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

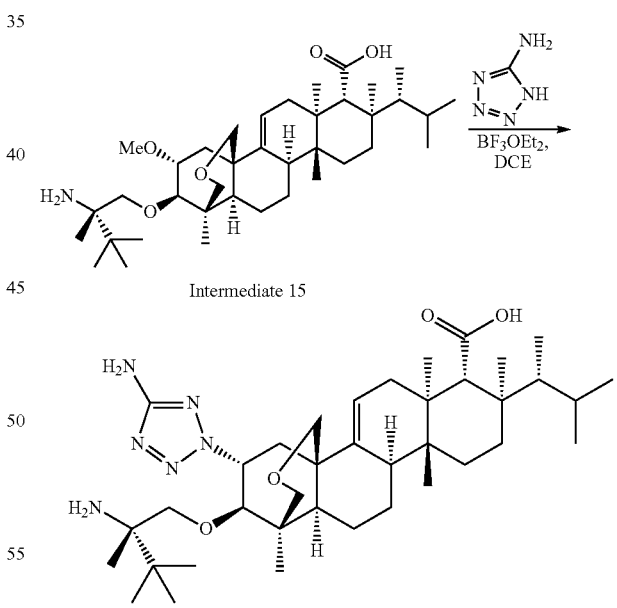

Intermediate 15

Intermediate 15 (60 mg, 0.10 mmol) and 5-aminotetrazole (41 mg, 0.49 mmol) were combined then diluted with dichloroethane (0.98 mL) then treated with BF$_3$OEt$_2$ (0.13 mL, 1 mmol) and this mixture was heated to 50° C. under nitrogen. After 1.5 hours the reaction was cooled to room temperature and filtered through a sintered glass funnel. The filtrate was concentrated and dissolved in methanol then purified by preparative LCMS (30×100 mm Waters Sunfire column, 5 μm, Electrospray positive detection, 0-100% MeCN/water with 0.05% TFA over 12 minutes, using Masslynx software). The product fractions were combined and partially concentrated by rotovap then frozen and lyophilized to give the title compound (18 mg) as a white amorphous solid.

$^1$H NMR (CD$_3$OD, 500 MHz, ppm) δ 0.77 (s, 3H), 0.78 (d, 3H, partially obscured), 0.86 (d, J=6.6 Hz, 3H), 0.88 (s, 9H), 0.90 (d, J=6.6 Hz, 3H), 1.16 (s, 3H), 1.21 (s, 3H), 1.24 (s, 3H), 1.2-1.64 (m), 1.78-2.0 (m), 2.02-2.22 (m), 2.47 (dd, J=13.5 Hz, 6.4 Hz, 1H), 2.70 (d, J=9.8 Hz, 1H), 2.85 (s, 1H), 3.28 (d, J=10.1 Hz, 1H), 3.49 (d, J=11.9 Hz, 1H), 3.54 (dd, J=11.8 Hz, 1.7 Hz, 1H), 3.62 (d, J=11.7 Hz, 1H), 3.68 (d, J=9.8 Hz, 1H), 3.91 (d, J=11.9 Hz, 1H), 5.50 (m, 1H), 5.85 (m, 1H).

m/z=669.46 (M+H).

Example 19

(1S,4aR,6aS,7R,8R,10aR,10bR,12aR,14R,15R)-14-(5-amino-2H-tetrazol-2-yl)-8-[(1R)-1,2-dimethylpropyl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

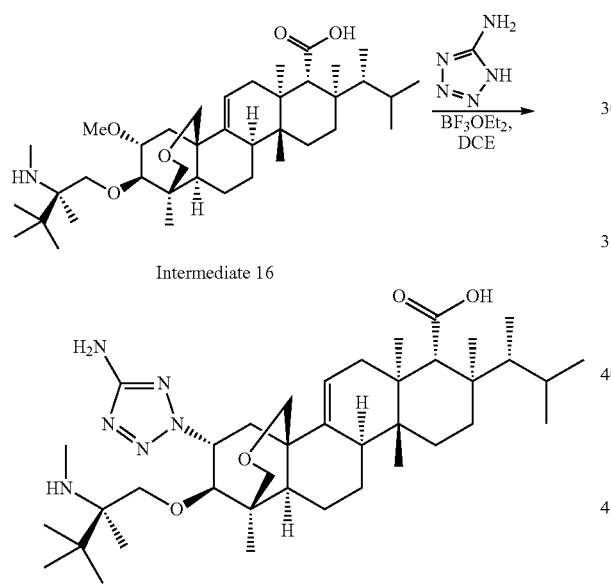

Intermediate 16 (63 mg, 0.10 mmol) and 5-aminotetrazole (43 mg, 0.5 mmol) were combined then diluted with dichloroethane (1 mL) then treated with BF$_3$OEt$_2$ (0.13 mL, 1 mmol) and this mixture was heated to 50° C. under nitrogen. After 1.5 hours the reaction was cooled to room temperature and filtered through a sintered glass funnel. The filtrate was concentrated and dissolved in methanol then purified by preparative LCMS (30×100 mm Waters Sunfire column, 5 μm, Electrospray positive detection, 0-100% MeCN/water with 0.05% TFA over 12 minutes, using Masslynx software). The product fractions were combined and partially concentrated by rotovap then frozen and lyophilized to give the title compound (27 mg) as a white amorphous solid.

$^1$H NMR (CD$_3$OD, 500 MHz, ppm) δ 0.77 (s, 3H), 0.78 (d, 3H, partially obscured), 0.86 (d, J=6.6 Hz, 3H), 0.90 (d, J=6.9 Hz, 3H), 0.92 (s, 3H), 0.93 (s, 3H), 0.94 (s, 9H), 1.15 (s, 3H), 1.21 (s, 3H), 1.22-1.67 (m), 1.8-1.98 (m), 2.13 (m, 1H), 2.19 (m, 1H), 2.46 (d, J=13.4 Hz, 6.5 Hz, 1H), 2.6 (s, 3H), 2.84 (s, 1H), 3.02 (d, J=11.2 Hz, 1H), 3.52 (d, J=12.2 Hz, 1H), 3.53 (dd, J=11.6 Hz, 2.0 Hz, 1H), 3.62 (d, J=11.6 Hz, 1H), 3.78 (d, J=12.1 Hz, 1H), 3.84 (d, J=11.0 Hz, 1H), 3.88 (d, J=10.1 Hz, 1H), 5.49 (m, 1H), 5.85 (m, 1H).

m/z=683.28 (M+H).

Example 20

(1S,4aR,6aS,7R,8R,10aR,10bR,12aR,14R,15R)-14-(5-amino-2H-tetrazol-2-yl)-8-[(1R)-1,2-dimethylpropyl]-15-[[(2R)-2-(ethylamino)-2,3,3-trimethylbutyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

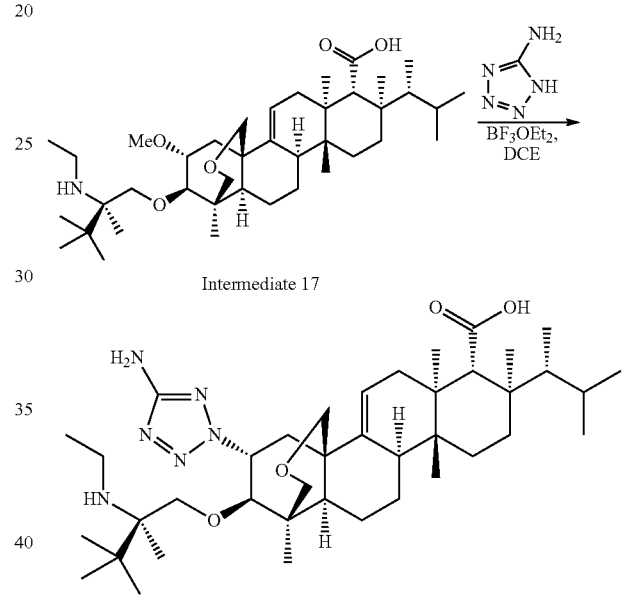

A solution of Intermediate 17 (165 mg, 0.23 mmol) in dichloroethane (2.3 mL) was treated with 5-aminotetrazole (96 mg, 1.1 mmol) then BF$_3$OEt$_2$ (0.29 mL, 2.3 mmol) and this mixture was heated to 50° C. under nitrogen. After 1.5 hours the reaction was cooled to room temperature and filtered through a sintered glass funnel. The filtrate was concentrated and dissolved in methanol then purified by preparative LCMS (30×100 mm Waters Sunfire column, 5 μm, Electrospray positive detection, 0-100% MeCN/water with 0.05% TFA over 12 minutes, using Masslynx software). The product fractions were combined and partially concentrated by rotovap then frozen and lyophilized to give the title compound (54 mg) as a white amorphous solid.

$^1$H NMR (CD$_3$OD, 500 MHz, ppm) δ 0.77 (s, 3H), 0.78 (d, 3H, partially obscured), 0.86 (d, J=6.7 Hz, 3H), 0.90 (d, J=6.9 Hz, 3H), 0.92 (s, 3H), 0.95 (s, 12H), 1.15 (s, 3H), 1.21 (s, 3H), 1.25 (m, 2H), 1.31 (t, J=7.5 Hz, 1H), 1.39-1.67 (m), 1.79-1.88 (m), 2.13 (m, 1H), 2.19 (m, 1H), 2.46 (dd, J=13.5 Hz, 6.6 Hz, 1H), 2.84 (s, 1H), 3.01 (d, J=11.2 Hz, 1H), 3.08 (q, J=7.2 Hz, 2H), 3.53 (d, J=12.1 Hz, 1H), 3.54 (dd, J=11.6 Hz, 1.9 Hz, 1H), 3.62 (d, J=11.6 Hz, 1H), 3.78 (d, J=11.9 Hz, 1H), 3.86-3.92 (m, 2H), 5.50 (m, 1H), 5.85 (m, 1H).

m/z=697.3 (M+H).

Example 21

(1S,4aR,6aS,7R,8R,10aR,10bR,12aR,14R,15R)-14-(5-amino-2H-tetrazol-2-yl)-15-[[(2S)-2-(dimethylamino)-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

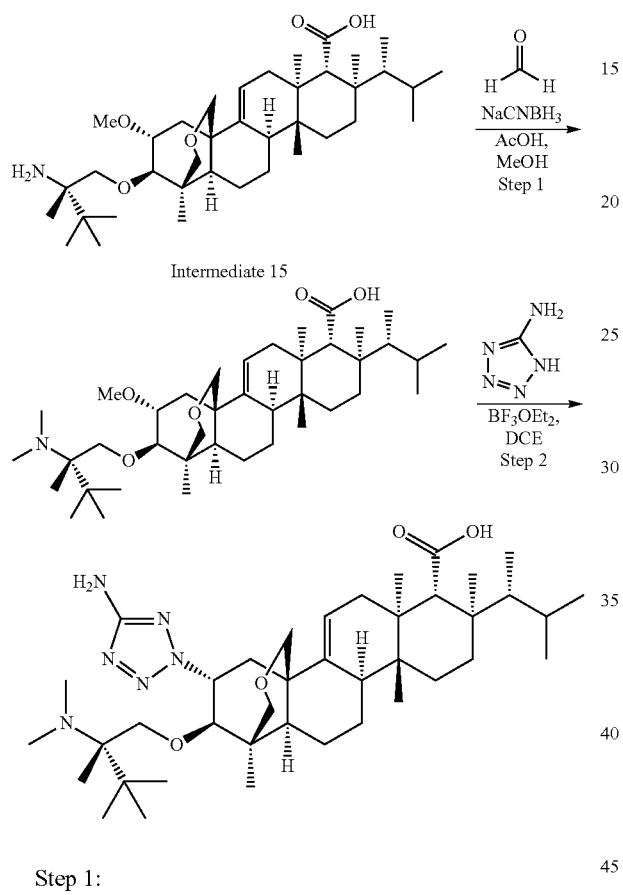

Step 1:

A solution of Intermediate 15 (70 mg, 0.11 mmol) in MeOH was treated with acetic acid (0.006 mL, 0.11 mmol), formaldehyde (37% aq., 0.21 mL, 2.8 mmol) and sodium cyanoborohydride (1 M in THF, 0.28 mL, 0.28 mmol) at room temperature under nitrogen. After 1 hour the reaction was concentrated in vacuo then partitioned between ethyl acetate and 5% aqueous sodium bicarbonate and the aqueous phase extracted with ethyl acetate multiple times. The combined organic phase was dried with $MgSO_4$, filtered and concentrated to give crude intermediate product (75 mg).

Step 2:

The product from Step 1 (75 mg, 0.11 mmol) in dichloroethane (1.1 mL) was treated with 5-aminotetrazole (46 mg, 0.54 mmol) then $BF_3OEt_2$ (0.14 mL, 1.1 mmol) and this mixture was heated to 50° C. under nitrogen. After 1.5 hours the reaction was cooled to room temperature and filtered through a sintered glass funnel. The filtrate was concentrated and dissolved in methanol then purified by preparative LCMS (30×100 mm Waters Sunfire column, 5 μm, Electrospray positive detection, 0-100% MeCN/water with 0.05% TFA over 12 minutes, using Masslynx software). The product fractions were combined and partially concentrated by rotovap then frozen and lyophilized to give the title compound (5 mg) as a white amorphous solid.

$^1$H NMR (CD$_3$OD, 500 MHz, ppm) δ 0.77 (s, 3H), 0.78 (d, 3H, partially obscured), 0.86 (d, J=6.6 Hz, 3H), 0.89 (d, J=6.9 Hz, 3H), 0.91 (s, 3H), 1.00 (s, 9H), 1.16 (s, 3H), 1.21 (s, 3H), 1.22-1.66 (m), 1.46 (s, 3H), 1.8-2.0 (m), 2.14 (m, 1H), 2.19 (m, 1H), 2.49 (dd, J=13.5 Hz, 6.7 Hz, 1H), 2.81 (s, 3H), 2.82 (s, 3H), 2.85 (s, 1H), 3.09 (d, J=11.4 Hz, 1H), 3.39 (d, J=11.4 Hz, 1H), 3.54 (m, 2H), 3.63 (d, J=11.6 Hz, 1H), 3.85 (m, 2H), 5.51 (m, 1H), 5.88 (m, 1H).

m/z=697.54 (M+H).

Example 22

(1S,4aR,6aS,7R;8R,10aR,10bR,12aR,14R,15R)-15-[[(2R)-2-amino-3,3-dimethylbutyl]oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

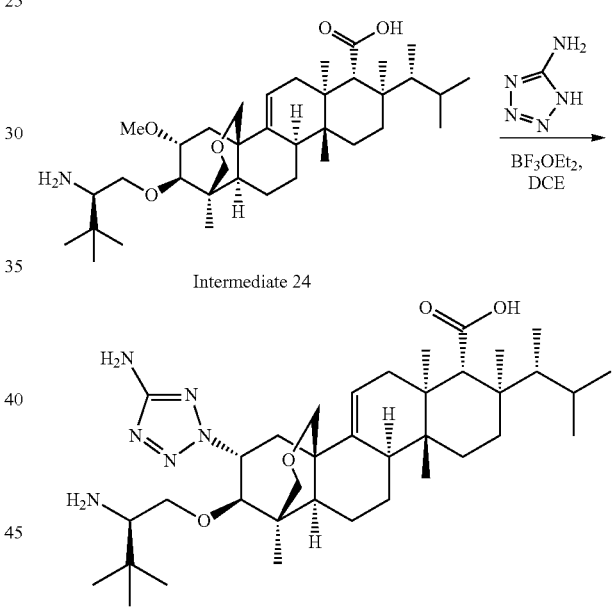

A solution of Intermediate 24 (95 mg, 0.16 mmol) in dichloroethane (1.6 mL) was treated with 5-aminotetrazole (67 mg, 0.79 mmol) then $BF_3OEt_2$ (0.20 mL, 1.6 mmol) and this mixture was heated to 50° C. under nitrogen. After 1.5 hours the reaction was cooled to room temperature and filtered through a sintered glass funnel. The filtrate was concentrated and dissolved in methanol then purified by preparative LCMS (30×100 mm Waters Sunfire column, 5 μm, Electrospray positive detection, 0-100% MeCN/water with 0.05% TFA over 12 minutes, using Masslynx software). The product fractions were combined and partially concentrated by rotovap then frozen and lyophilized to give the title compound (42 mg) as a white amorphous solid.

$^1$H NMR (CD$_3$OD, 500 MHz, ppm) δ 0.77 (s, 3H), 0.78 (d, 3H, partially obscured), 0.85 (d, 3H, partially obscured), 0.87 (s, 9H), 0.87 (s, 3H), 0.90 (d, J=6.8 Hz, 3H), 1.17 (s, 3H), 1.22 (s, 3H), 1.15-1.68 (m), 1.78-1.98 (m), 2.05 (m, 1H), 2.12-2.23 (m, 2H), 2.39 (dd, J=10.1 Hz, 3.4 Hz, 1H), 2.47 (dd, J=13.5

Hz, 6.4 Hz, 1H), 2.85 (s, 1H), 2.98 (dd, J=10.7 Hz, 3.4 Hz, 1H), 3.48 (d, J=11.9 Hz, 1H), 3.55 (m, 1H), 3.60 (m, 2H), 3.67 (d, J=9.9 Hz, 1H), 3.91 (d, J=11.9 Hz, 1H), 5.5 (m, 1H), 5.83 (m, 1H).

m/z=655.53 (M+H).

Example 23

(1S,4aR,6aS,7R,8R,10aR,10bR,12aR,14R,15R)-15-(2-amino-2-ethylbutoxy)-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

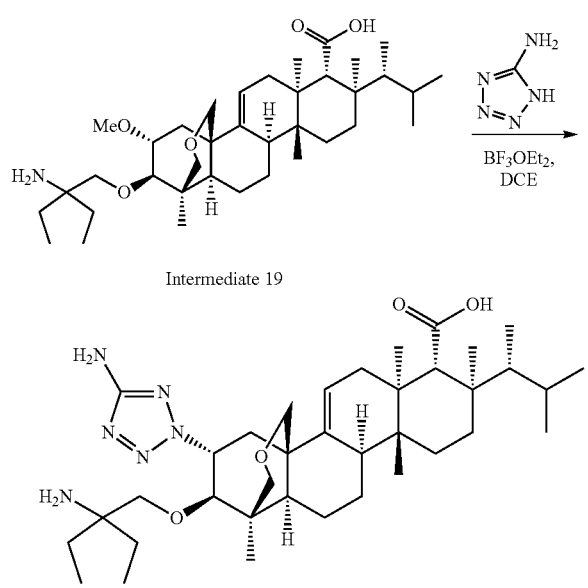

A solution of Intermediate 19 (120 mg, 0.2 mmol) in dichloroethane (2.0 mL) was treated with 5-aminotetrazole (85 mg, 1.0 mmol) then BF$_3$OEt$_2$ (0.25 mL, 2.0 mmol) and this mixture was heated to 50° C. under nitrogen. After 1.5 hours the reaction was cooled to room temperature and filtered through a sintered glass funnel. The filtrate was concentrated and dissolved in methanol then purified by preparative LCMS (30×100 mm Waters Sunfire column, 5 μm, Electrospray positive detection, 0-100% MeCN/water with 0.05% TFA over 12 minutes, using Masslynx software). The product fractions were combined and partially concentrated by rotovap then frozen and lyophilized to give the title compound (85 mg) as a white amorphous solid.

$^1$H NMR (CD$_3$OD, 500 MHz, ppm) δ 0.73 (t, J=7.7 Hz, 3H), 0.77 (s, 3H), 0.78 (d, 3H, partially obscured), 0.82 (t, J=7.7 Hz, 3H), 0.86 (d, J=6.8 Hz, 3H), 0.88 (s, 3H), 0.90 (d, J=6.9 Hz, 3H), 1.16 (s, 3H), 1.21 (s, 3H), 1.22-1.66 (m), 1.78-2.0 (m), 2.14 (m, 1H), 2.19 (m, 1H), 2.45 (dd, J=13.6 Hz, 6.6 Hz, 1H), 2.75 (d, J=9.8 Hz), 2.85 (s, 1H), 3.44 (d, J=9.8 Hz, 1H), 3.48 (d, J=11.9 Hz, 1H), 3.53 (dd, J=11.6 Hz, 1.7 Hz, 1H), 3.61 (d, J=11.6 Hz, 1H), 3.76 (d, J=9.8 Hz, 1H), 3.91 (d, J=11.9 Hz, 1H), 5.50 (m, 1H), 5.84 (m, 1H).

m/z=655.43 (M+H).

Example 24

(1S,4aR,6aS,7R,8R,10aR,10bR,12aR,14R,15R)-15-[(3-amino-3-methylpentyl)oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

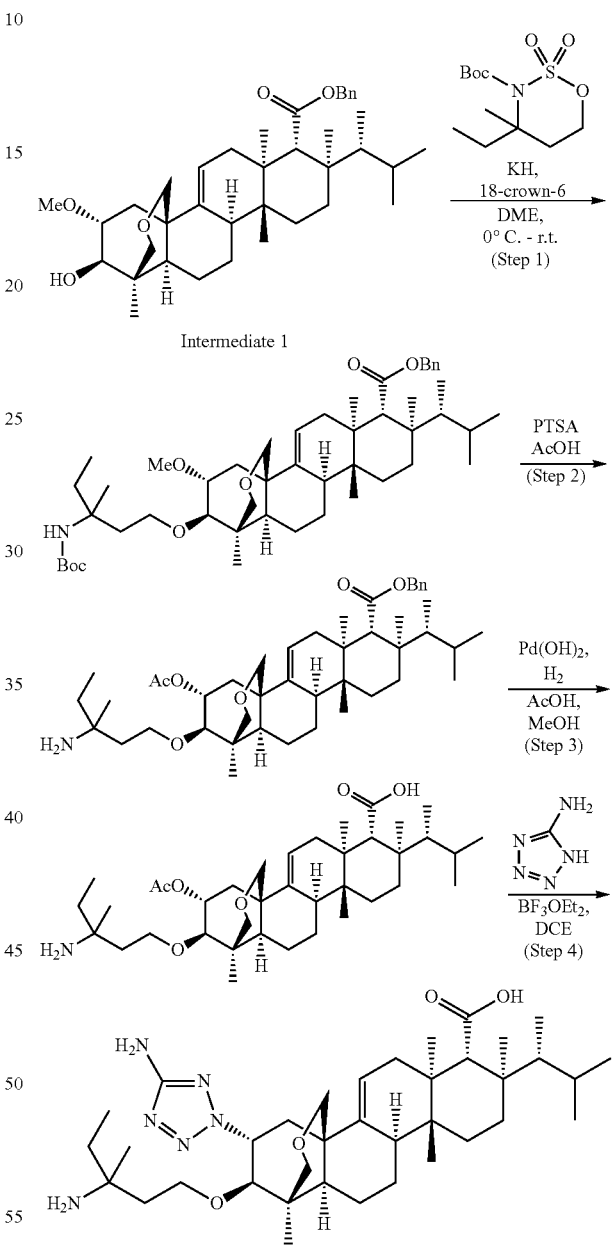

Step 1:

Intermediate 1 (0.4 g), 18-crown-6 (0.6 g), and 1,1-dimethylethyl 4-ethyl-4-methyldihydro-1,2,3-oxathiazine-3(4H)-carboxylate 2,2-dioxide (0.6 g) were dissolved in toluene and concentrated then placed under high vacuum for 1 hour. The resulting mixture was dissolved in dimethoxyethane (5 mL) placed under nitrogen atmosphere and cooled to 0° C. Potassium hydride (30% dispersion in mineral oil, 0.2 g) was added and the reaction evacuated and charged with nitrogen (repeat three times). After an additional hour the reaction mixture was treated with aqueous KH$_2$PO$_4$ (1 N)

carefully, and the mixture was extracted with dichloromethane (2×20 mL). The combined organic phase was dried over MgSO₄, filtered then concentrated. The crude product was purified by flash chromatography (20% ethyl acetate/hexane) to yield the product (0.6 g) as white foam.

Step 2:

To a stirred solution of the product from Step 1 (0.108 g) in acetic acid (1.5 mL) was added p-TsOH—H₂O (0.058 g) and the reaction mixture was heated at 90° C. (internal temperature) for 1.5 h. The reaction mixture was then allowed to cool to room temperature and the residue was dissolved in dichloromethane and washed with a saturated NaHCO₃ solution carefully. The aqueous phase was re-extracted with dichloromethane (2×20 mL). The combined organic solutions were dried over anhydrous Na₂SO₄. After filtration and evaporation of the solvent, the desired product was isolated as a pale yellow solid (0.081 g) and used directly in the next step.

Step 3:

To a stirred solution of the crude product from Step 2 (0.100 g) in methanol (1 mL) was added acetic acid (0.05 mL) and Pd(OH)₂ (0.100 g). The reaction mixture was stirred under hydrogen for 3 h, and filtered through a pad of Celite then concentrated to give the desired amino acid (0.08 g), which was used directly in the next step.

Step 4:

Following an analogous procedure to that described in Example 4, the product from Step 3 was reacted with 5-aminotetrazole and BF₃O(CH₂CH₃)₂ in 1,2-dichloroethane at 50° C. to provide the title compound (1S,4aR,6aS,7R,8R,10aR,10bR,12aR,14R,15R)-15-[(3-amino-3-methylpentyl)oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid.

¹H NMR CD₃OD δ (PPM) 5.77 and 5.26(m, 1H, H14); 5.50 (m, 1H, H5); 3.72-3.76 (m); 3.89 (d, 1H); 3.59-3.66 (m); 3.46-3.56 (m); 2.99 (m); 2.88 (m); 2.84 (s, 1H, H7); 2.47 (m, 1H); 2.40-2.47 (m, 1H, H13); 2.18 (m, 1H); 2.12-2.17 (m); 2.05-2.19 (m); 1.70-2.00 (m); 1.48-1.67 (m); 1.40-1.44 (m); 1.22-1.34 (m); 1.21 (s, 3H, Me); 1.13-1.19 (m); 0.89 (d, 3H, Me); 0.86 (d, 3H, Me); 0.85 (s, 3H, Me); 0.77 (d, 3H, Me) and 0.76 (s, 3H, Me).

LC/MS m/z (positive ion scan) M+1=655.64.

Example 25

(1S,4aR,6aS,7R,8R,10aR,10bR,12aR,14R,15R)-15-[2-(1-aminocyclopentyl)ethoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

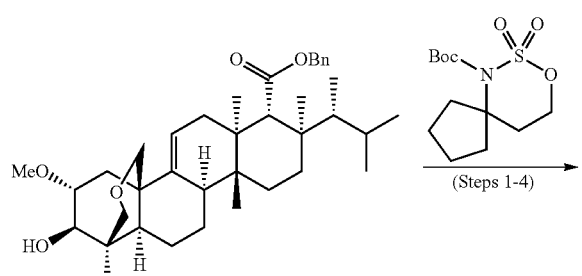

Intermediate 1

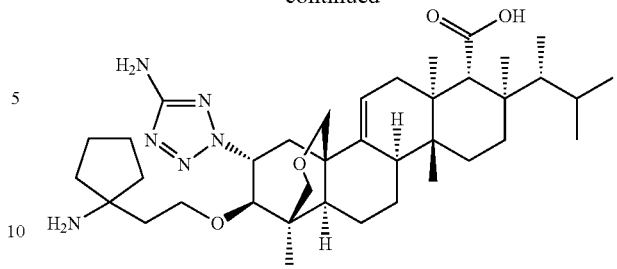

Following procedures analogous to those described in Example 24, but using 1,1-dimethylethyl 8-oxa-7-thia-6-azaspiro[4.5]decane-6-carboxylate 7,7-dioxide in Step 1, the title compound (1S,4aR,6aS,7R,8R,10aR,10bR,12aR,14R,15R)-15-[2-(1-aminocyclopentyl)ethoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid was prepared.

¹H NMR CD₃OD δ (PPM) 5.77 (m, 1H, H14); 5.51 (m, 1H, H5); 3.75 (d, 1H); 3.61 (d, 1H); 3.52-3.57 (m); 3.51 (d, 1H); 3.49 (d, 1H); 2.89 (m, 1H); 2.84 (s, 1H, H7); 2.46 (dd, 1H, H13); 2.19 (m, 1H); 2.10-2.16 (m); 1.92-1.97 (m); 1.89 (m); 1.48-1.84 (m); 1.40-1.44 (m); 1.23-1.34 (m); 1.21 (s, 3H, Me); 1.17 (s, 3H, Me); 0.90 (d, 3H, Me); 0.85 (d, 3H, Me); 0.84 (s, 3H, Me); 0.77 (d, 3H, Me) and 0.76 (s, 3H, Me).

LC/MS m/z (positive ion scan) M+1=667.60.

Example 26

(1S,4aR,6aS,7R,8R,10aR,10bR,12aR,14R,15R)-15-[(4-aminotetrahydro-2H-pyran-4-yl)methoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

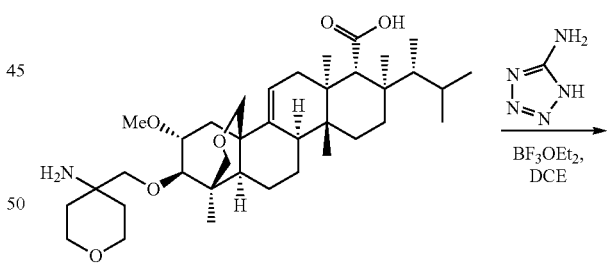

Intermediate 27

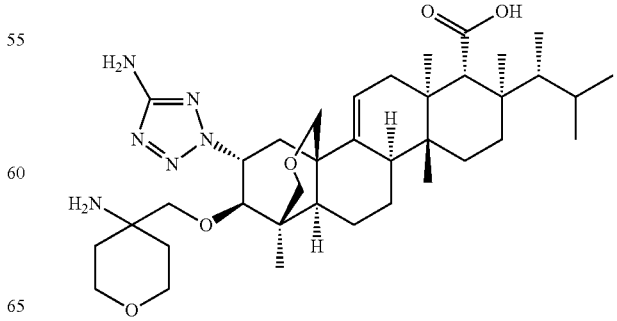

Intermediate 27 (80 mg, 0.13 mmol) and 5-aminotetrazole (55.2 mg, 0.65 mmol) were combined then diluted with dichloroethane (1.3 mL) then treated with $BF_3OEt_2$ (0.165 mL, 1.3 mmol) and this mixture was heated to 55° C. under nitrogen. After 1 hour the reaction was cooled to room temperature and filtered through a sintered glass funnel. The filtrate was concentrated and dissolved in methanol then purified by preparative LCMS (30×100 mm Waters Sunfire column, 5 µm, Electrospray positive detection, 0-100% MeCN/water with 0.05% TFA over 12 minutes, using Masslynx software). The product fractions were combined and partially concentrated by rotovap then frozen and lyophilized to give the title compound (41 mg) as a white amorphous solid.

$^1$H NMR ($CD_3OD$, 500 MHz, ppm) δ 0.78 (s, 3H), 0.79 (d, 3H, partially obscured), 0.87 (d, J=6.9 Hz, 3H), 0.90 (s, 3H), 0.91 (d, J=6.9 Hz, 3H), 1.17 (s, 3H), 1.22 (s, 3H), 1.24-1.38 (m), 1.42-1.76 (m), 1.80-2.02 (m), 2.16 (m, 1H), 2.20 (m, 1H), 2.46 (dd, J=13.5 Hz, 6.4 Hz, 1H), 2.86 (s, 1H), 3.10 (m, 1H), 3.20 (d, J=10.3 Hz, 1H), 3.35 (m, 1H), 3.40 (m, 1H), 3.75 (m, 1H), 3.50 (d, J=12.2 Hz, 1H), 3.55 (dd, J=11.9 Hz, 1.9 Hz, 1H), 3.61 (s, 1H), 3.85 (d, J=9.9 Hz, 1H), 3.93 (d, J=11.9 Hz, 1H), 5.51 (m, 1H), 5.86 (m, 1H).

m/z=669.74 (M+H).

Example 27

(1S,4aR,6aS,7R,8R,10aR,10bR,12aR,14R,15R)-14-(5-amino-2H-tetrazol-2-yl)-8-[(1R)-1,2-dimethylpropyl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

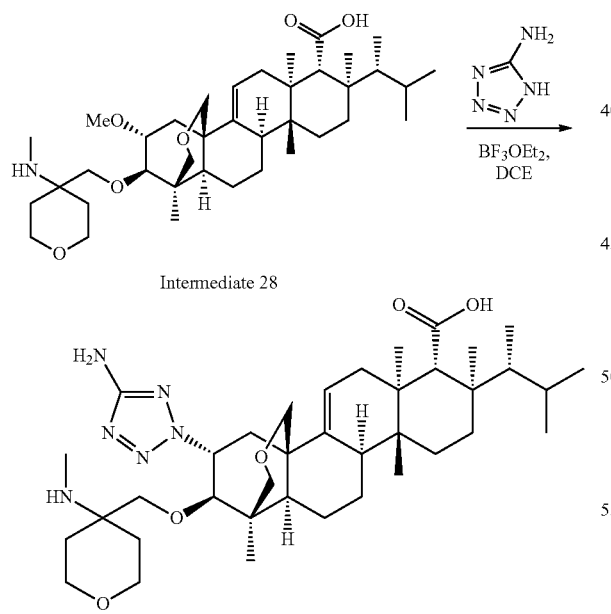

Intermediate 28 (80 mg, 0.13 mmol) and 5-aminotetrazole (54 mg, 0.64 mmol) were combined then diluted with dichloroethane (1.3 mL) then treated with $BF_3OEt_2$ (0.16 mL, 1.3 mmol) and this mixture was heated to 55° C. under nitrogen. After 1 hour, the reaction was cooled to room temperature and filtered through a sintered glass funnel. The filtrate was concentrated and dissolved in methanol then purified by preparative LCMS (30×100 mm Waters Sunfire column, 5 µm, Electrospray positive detection, 0-100% MeCN/water with 0.05% TFA over 12 minutes, using Masslynx software). The product fractions were combined and partially concentrated by rotovap then frozen and lyophilized to give the title compound (57 mg) as a white amorphous solid.

$^1$H NMR ($CD_3OD$, 500 MHz, ppm) δ 0.78 (s, 3H), 0.79 (d, 3H, partially obscured), 0.87 (d, J=6.6 Hz, 3H), 0.91 (s, 3H), 0.92 (d, J=5.9 Hz, 3H), 1.17 (s, 3H), 1.23 (s, 3H), 1.24-1.38 (m), 1.42-1.76 (m), 1.82-2.00 (m), 2.17 (m, 1H), 2.20 (m, 1H), 2.45 (m, 1H, partially obscured), 2.48 (s, 3H), 2.86 (s, 1H), 3.13 (m, 1H), 3.23 (d, J=10.9 Hz, 1H), 3.38 (m, 1H), 3.32 (d, J=12.1 Hz, 1H), 3.55 (m, 1H), 3.62 (d, J=11.6 Hz, 1H), 3.70 (m, 1H), 3.82 (m, 1H), 3.83 (d, J=11.2 Hz, 1H), 3.88 (d, J=11.1 Hz, 1H), 3.94 (d, J=10.1 Hz, 1H), 5.51 (m, 1H), 5.88 (m, 1H).

m/z=683.81 (M+H).

Example 28

(1S,4aR,6aS,7R,8R,10aR,10bR,12aR,14R,15R)-14-(5-amino-2H-tetrazol-2-yl)-8-[(1R)-1,2-dimethylpropyl]-15-[[4-(ethylamino)tetrahydro-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

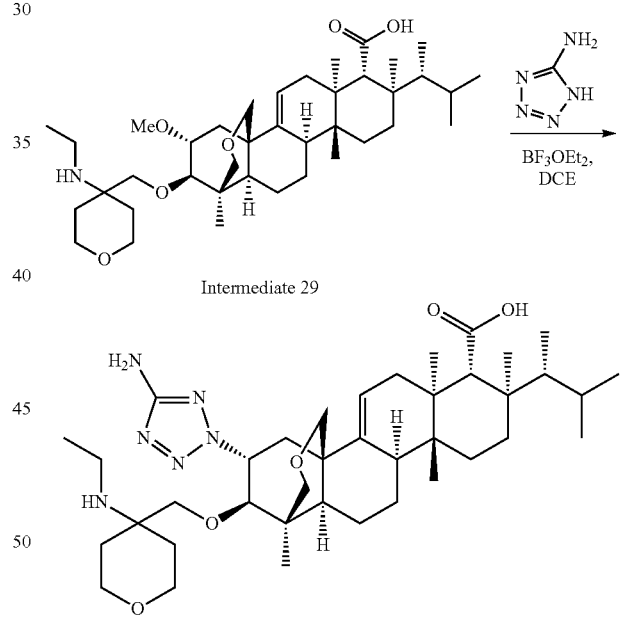

Intermediate 29 (80 mg, 0.12 mmol) and 5-aminotetrazole (53 mg, 0.62 mmol) were combined then diluted with dichloroethane (1.3 mL) then treated with $BF_3OEt_2$ (0.16 mL, 1.3 mmol) and this mixture was heated to 55° C. under nitrogen. After 1 hour the reaction was cooled to room temperature and filtered through a sintered glass funnel. The filtrate was concentrated and dissolved in methanol then purified by preparative LCMS (30×100 mm Waters Sunfire column, 5 µm, Electrospray positive detection, 0-100% MeCN/water with 0.05% TFA over 12 minutes, using Masslynx software). The product fractions were combined and partially concentrated by rotovap then frozen and lyophilized to give the title compound (58 mg) as a white amorphous solid.

¹H NMR (CD₃OD, 500 MHz, ppm) δ 0.78 (s, 3H), 0.79 (d, 3H, partially obscured), 0.87 (d, J=6.8 Hz, 3H), 0.91 (s, 3H), 0.92 (d, J=7.1 Hz, 3H), 1.17 (s, 3H), 1.23 (s, 3H), 1.24-1.38 (m), 1.42-1.76 (m), 1.82-2.00 (m), 2.17 (m, 1H), 2.20 (m, 1H), 2.46 (dd, J=13.5 Hz, 6.4 Hz, 1H), 2.66 (m, 1H), 2.86 (s, 1H), 2.88 (m, 1H), 3.11(m, 1H), 3.25 (d, J=10.9 Hz, 1H), 3.36 (m, 1H), 3.53 (d, J=12.5 Hz, 1H), 3.56 (m, 1H), 3.63 (d, J=11.7 Hz, 1H), 3.73 (m, 1H), 3.82-3.92(m, 3H), 3.96 (d, J=10.1 Hz, 1H), 5.51 (m, 1H), 5.88 (m, 1H).

m/z=697.83 (M+H).

Example 29

(1S,4aR,6aS,7R,8R,10aR,10bR,12aR,14R,15R)-14-(5-amino-2H-tetrazol-2-yl)-15-[[4-(dimethylamino)tetrahydro-2H-pyran-4-yl]methoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

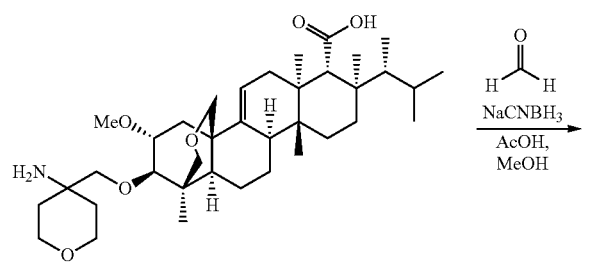

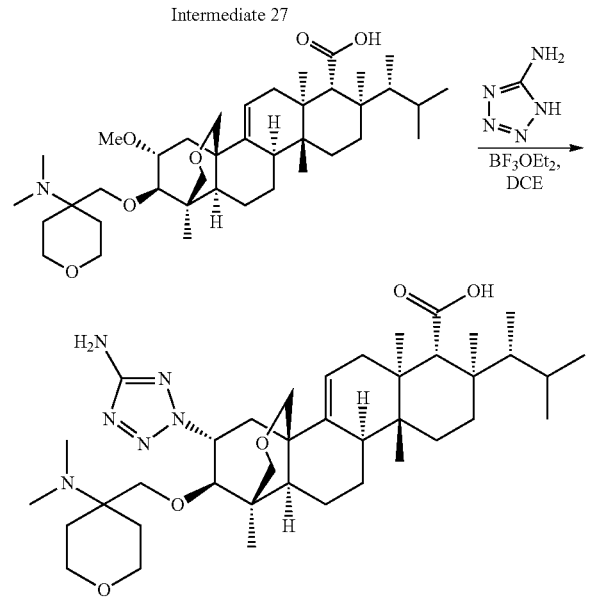

A solution of Intermediate 27 (80 mg, 0.13 mmol) in MeOH (1.3 mL) was treated with acetic acid (0.015 mL, 0.26 mmol), formaldehyde (37% aq., 0.39 mL, 0.52 mmol) and sodium cyanoborohydride (33 mg, 0.52 mmol) at room temperature under nitrogen. After 18 hour the reaction was concentrated in vacuo to give about 85 mg of crude intermediate.

The intermediate product (85 mg, 0.13 mmol) in dichloroethane (1.3 mL) was treated with 5-aminotetrazole (56 mg, 0.66 mmol) then BF₃OEt₂ (0.17 mL, 1.3 mmol) and this mixture was heated to 55° C. under nitrogen. After 1 hour the reaction was cooled to room temperature and filtered through a sintered glass funnel. The filtrate was concentrated and dissolved in methanol then purified by preparative LCMS (30×100 mm Waters Sunfire column, 5 μm, Electrospray positive detection, 0-100% MeCN/water with 0.05% TFA over 12 minutes, using Masslynx software). The product fractions were combined and partially concentrated by rotovap then frozen and lyophilized to give the title compound (58 mg) as a white amorphous solid.

¹H NMR (CD₃OD, 500 MHz, ppm) δ 0.78 (s, 3H), 0.79 (d, 3H, partially obscured), 0.87 (d, J=6.6 Hz, 3H), 0.91 (s, 3H), 0.92 (d, J=5.2 Hz, 3H), 1.17 (s, 3H), 1.22 (s, 3H), 1.24-1.38 (m), 1.42-2.02 (m), 2.08 (m, 1H), 2.15 (m, 1H), 2.20 (m, 1H), 2.47 (dd, J=13.5 Hz, 6.6 Hz, 1H), 2.74 (s, 3H), 2.82 (s, 3H), 2.86 (s, 1H), 3.15(m, 1H), 3.25 (d, J=12.1 Hz, 1H), 3.39 (m, 1H), 3.50-3.58(m, 2H), 3.63 (d, J=11.7 Hz, 1H), 3.76-3.83 (m, 2H), 3.88-3.94 (m, 2H), 3.97 (d, J=12.2 Hz, 1H), 5.51 (m, 1H), 5.87 (m, 1H).

m/z=697.74 (M+H).

Example 30

(1S,4aR,6aS,7R,8R,10aR,10bR,12aR,14R,15R)-15-[(4-aminotetrahydro-2H-thiopyran-4-yl)methoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

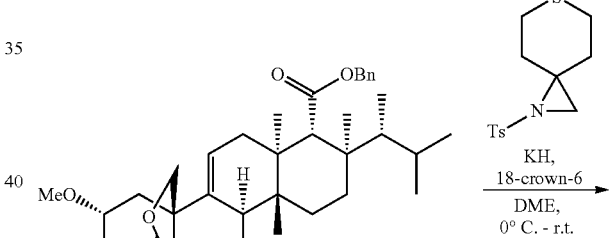

Intermediate 1

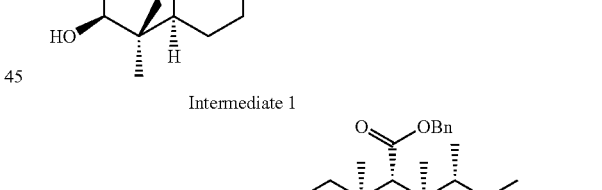

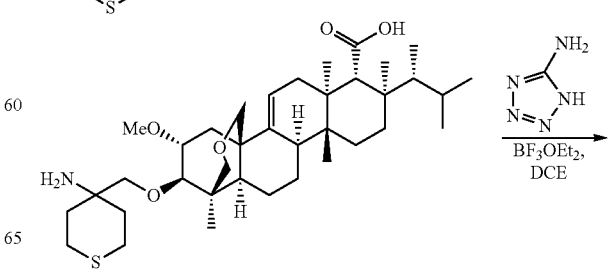

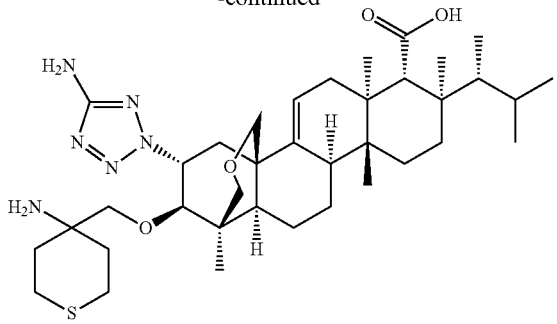

Employing procedures analogous to those described previously for the synthesis of Intermediates 26 and 27 and Example 26, the title compound (1S,4aR,6aS,7R,8R,10aR,10bR,12aR,14R,15R)-15-[(4-aminotetrahydro-2H-thiopyran-4-yl)methoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid was prepared.

$^1$H NMR (CD$_3$OD, 500 MHz, ppm) δ 0.78 (s, 3H), 0.79 (d, 3H, partially obscured), 0.87 (d, J=6.6 Hz, 3H), 0.90 (s, 3H), 0.91 (d, J=6.7 Hz, 3H), 1.17 (s, 3H), 1.22 (s, 3H), 1.24-1.38 (m), 1.41-1.73(m), 1.78-2.02 (m), 2.15 (m, 1H), 2.20 (m, 1H), 2.30 (m, 1H), 2.46 (dd, J=13.7 Hz, 6.6 Hz, 1H), 2.58 (m, 1H), 2.86 (s, 1H), 3.05(d, J=10.3 Hz, 1H), 3.50 (d, J=12.1 Hz, 1H), 3.53 (d, J=10.0 Hz, 1H), 3.55 (dd, J=11.4 Hz, 1.8 Hz, 1H), 3.62 (d, J=11.7 Hz, 1H), 3.83 (d, J=10.1 Hz, 1H), 3.91 (d, J=11.9 Hz, 1H), 5.51 (m, 1H), 5.86 (m, 1H).

m/z=685.71 (M +H).

Example 31

(1S,4aR,6aS,7R,8R,10aR,10bR,12aR,14R,15R)-15-[(1-aminocyclohexyl)methoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

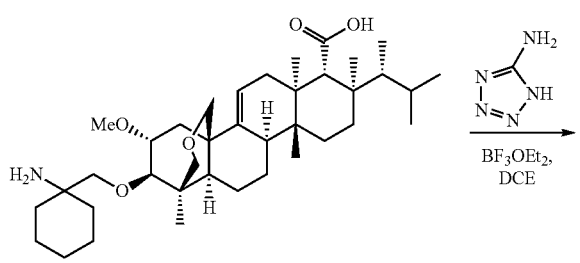

Intermediate 30

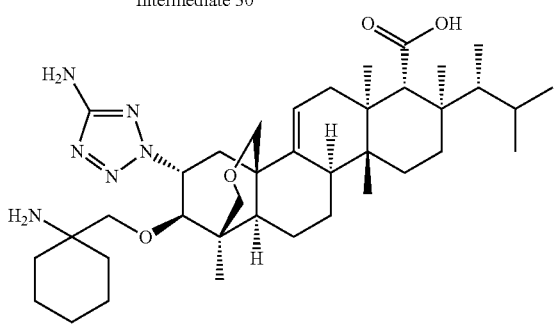

To a solution of Intermediate 30 (143 mg, 0.233 mmol) in DCE (2 mL) under a nitrogen atmosphere was added 5-aminotetrazole (99 mg, 1.16 mmol). Boron trifluoride etherate solution (0.3 mL, 2.33 mmol) was added and the mixture was heated to 50° C. for 2 hours. The volatiles were evaporated and the residue was dissolved in 50%MeOH/CH$_3$CN (2 mL). The mixture was filtered and purified by reverse phase HPLC using 30-100% CH$_3$CN/H$_2$O as gradient. The combined product fractions were freeze dried to afford the title compound as a white solid (67mg).

MS (ESI) m/z=667 (M+H).

Example 32

(1S,4aR,6aS,7R,8R,10aR,10bR,12aR,14R,15R)-14-(5-amino-2H-tetrazol-2-yl)-8-[(1R)-1,2-dimethylpropyl]-15-[[1-(methylamino)cyclohexyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

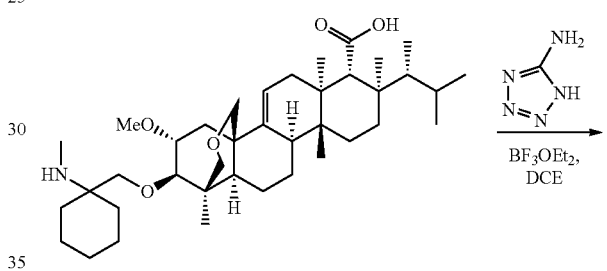

Intermediate 31

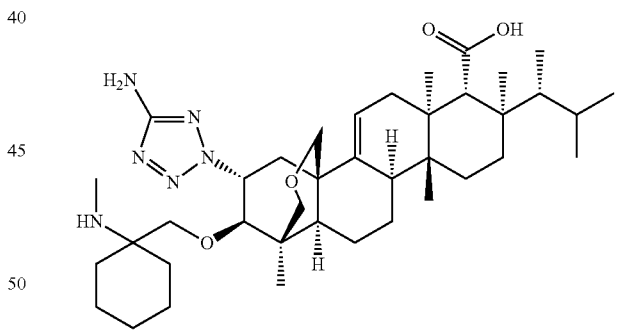

To a solution of Intermediate 31 (100 mg, 0.159 mmol) in DCE (2 mL) under a nitrogen atmosphere was added 5-aminotetrazole (68 mg, 0.796 mmol). Boron trifluoride etherate solution (0.2 mL, 1.59 mmol) was added and the mixture was heated to 50° C. for 2 hours. The volatiles were evaporated and the residue was dissolved in 50%MeOH/CH$_3$CN (2 mL). The mixture was filtered and purified by reverse phase HPLC using 30-100% CH$_3$CN/H$_2$O as gradient. The combined product fractions were freeze dried to afford the title compound as a white solid (46 mg).

MS (ESI) m/z=681 (M+H).

Example 33

(1S,4aR,6aS,7R,8R,10aR,10bR,12aR,14R,15R)-15-[(1-aminocyclopentyl)methoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

Example 34

(1S,4aR,6aS,7R,8R,10aR,10bR,12aR,14R,15R)-14-(5-amino-2H-tetrazol-2-yl)-8-[(1R)-1,2-dimethylpropyl]-15-[[1-(methylamino)cyclopentyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

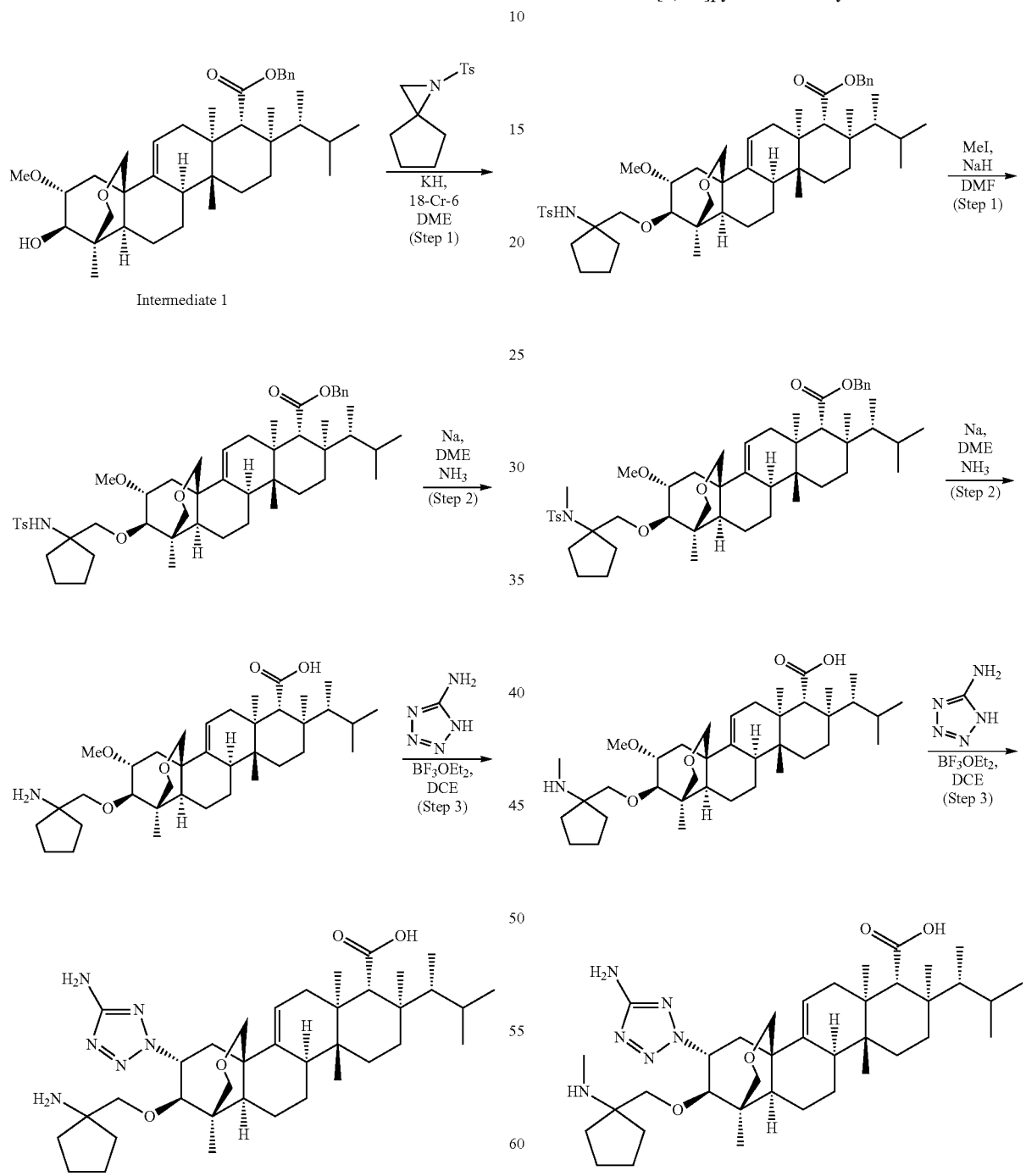

Following procedures analogous to those described for Intermediate 30 and Example 31, the title compound was prepared and isolated as a white solid.

MS (ESI) m/z=653 (M+H).

Following procedures analogous to those described for Intermediate 31 and Example 32, the title compound was prepared and isolated as a white solid.

MS (ESI) m/z=667 (M+H).

Example 35

(1S,4aR,6aS,7R,8R,10aR,10bR,12aR,14R,15R)-14-(5-amino-2H-tetrazol-2-yl)-8-[(1R)-1,2-dimethylpropyl]-15-[2-(4-methyl-1-piperazinyl)ethoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

Step 1:

A mixture of the product of Step 2 in the synthesis of Intermediate 2, benzyl (1S,4aR,6aS,7R,8R,10aR,10bR,12aR,14R,15R)-8-[(1R)-1,2-dimethylpropyl]-15-(2-oxoethoxy)-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate (100 mg, 0.158 mmol), acetic acid (18 µL, 0.315 mmol), N-methylpiperazine (35 µL, 0.315 mmol) and lastly 1 M in THF sodium

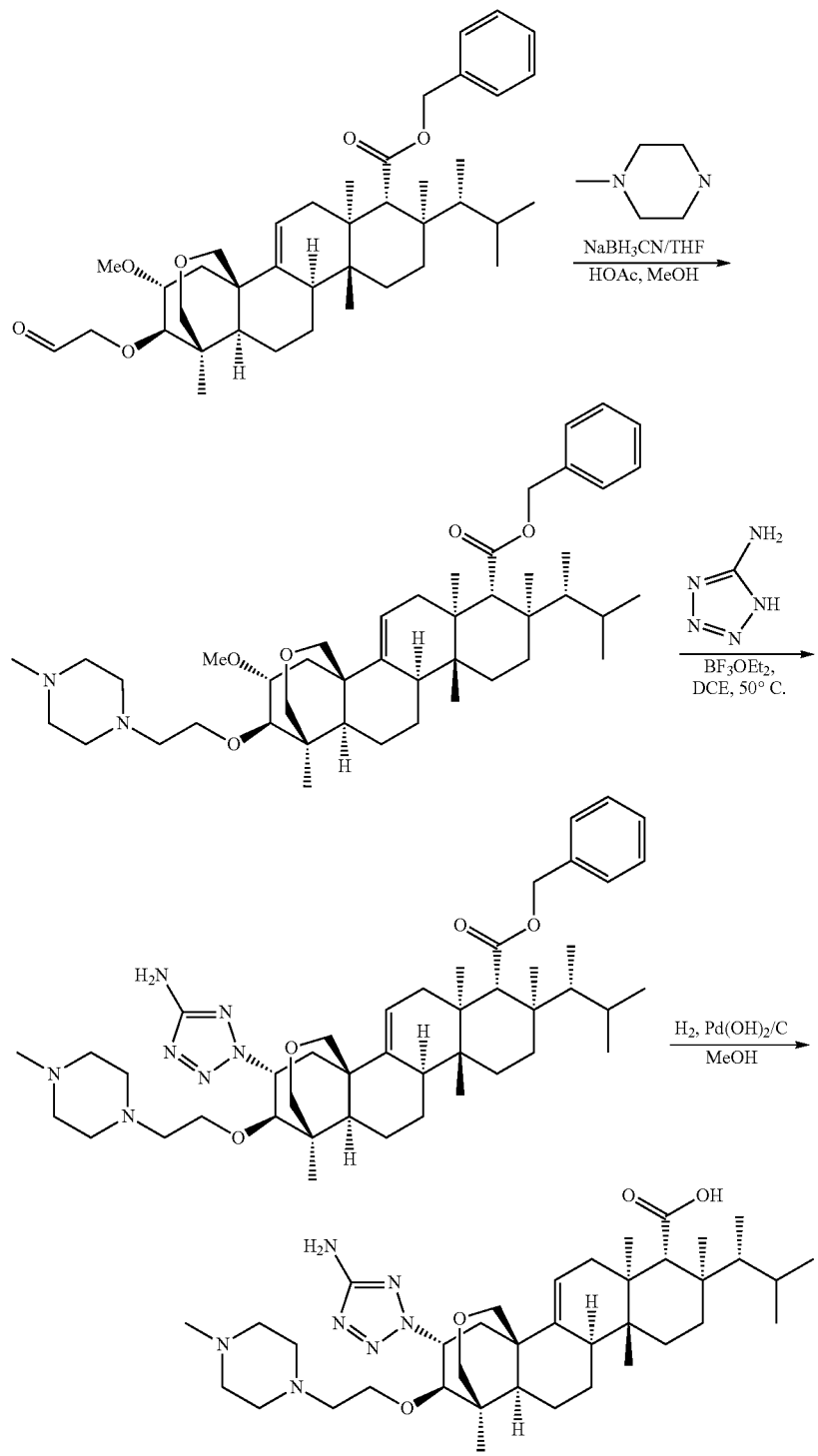

cyanoborohydride (0.63 μL, 0.63 mmol) in methanol (1.5 mL) was stirred at room temperature for 3 hours. The mixture was purified by reverse phase HPLC using a 19×150 mm Sunfire Preparative C18 OBD column. Fractions containing the product were evaporated and freeze-dried from a mixture of ethanol and benzene to give a solid (46.1 mg).

LC/MS m/z (positive ion scan) M+1=720.08.

Step 2:

A mixture of the product from Step 1 (25 mg, 0.035 mmol), 5-aminotetrazole (30 mg, 0.35 mmol) and boron trifluoride etherate (75 μL, 0.58 mmol) was heated in a 50° C. oil bath for 4 hours. The solution was evaporated to a solid.

LC/MS m/z (positive ion scan) M+1=773.12.

Step 3:

The above solid was dissolved in methanol (2 mL), 20% Pd(OH)$_2$/C (22.8 mg) was added and the suspension was placed under a balloon of hydrogen. The mixture was stirred at room temperature for 18 hours. The suspension was filtered, evaporated and purified by reverse phase HPLC using a 19×150 mm Swifire Preparative C18 OBD column. Fractions containing the product were evaporated and freeze-dried from a mixture of ethanol and benzene to give the title compound as a solid (12.4 mg).

$^1$H NMR CD$_3$OD δ (PPM) 5.75 (m, 1H, H14); 5.49 (dd, 1H, H5); 3.77 (d, 1H); 3.58 (d, 1H); 3.50-3.53 (m); 3.45 (d, 1H); 2.93 (m); 2.84 (s, 1H, H7), 2.81 (s, 3H, NMe); 2.61 (m); 2.45 (m); 2.43 (dd, 1H, H13), 2.18 (m); 2.10-2.14 (m); 1.75-2.03 (m); 1.46-1.65 (m); 1.40-1.42 (m); 1.22-1.34 (m); 1.21 (s, 3H, Me); 1.16 (s, 3H, Me); 0.90 (d, 3H, Me); 0.86 (d, 3H, Me); 0.85 (s, 3H, Me); 0.77 (d, 3H, Me) and 0.76 (s, 3H, Me).

LC/MS m/z (positive ion scan) M+1=683.05.

Example 36

(1S,4aR,6aS,7R,8R,10aR,10bR,12aR,14R,15R)-14-(5-amino-2H-tetrazol-2-yl)-15-[2-[[3-(dimethylamino)propyl]amino]ethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

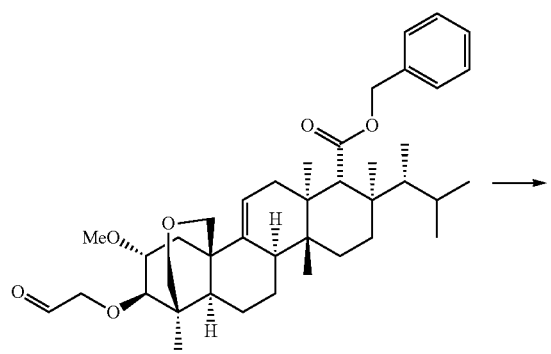

-continued

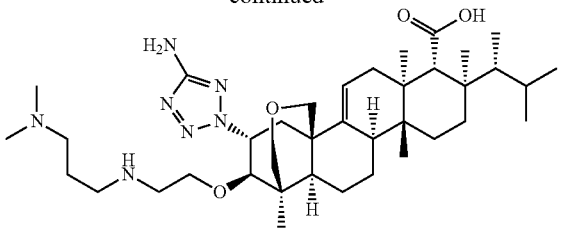

By procedures analogous to those described in Example 35, but using N,N-dimethylpropane-1,3-diamine in Step 1, the title compound was prepared.

$^1$H NMR CD$_3$OD δ (PPM) 5.83 (m, 1H, H14); 5.50 (dd, 1H, H5); 3.85 (d, 1H); 3.70 (m); 3.65 (d, 1H); 3.60 (d, 1H); 3.54 (dd, 1H); 3.48 (d, 1H); 3.23 (m); 3.13-3.18 (m); 2.79-3.01 (m); 2.94 (s, NMe2); 2.84 (s, 1H, H7), 2.81 (s, 3H, NMe); 2.45 (dd, 1H, H13), 2.18 (m); 2.04-2.14 (m); 1.78-1.96 (m); 1.46-1.65 (m); 1.40-1.42 (m); 1.23-1.34 (m); 1.21 (s, 3H, Me); 1.16 (s, 3H, Me); 0.90 (d, 3H, Me); 0.86 (s, 3H, Me); 0.85 (d, 3H, Me); 0.77 (d, 3H, Me) and 0.76 (s, 3H, Me).

LC/MS m/z (positive ion scan) M+1=684.43

Example 37

(1S,4aR,6aS,7R,8R,10aR,10bR,12aR,14R,15R)-15-(2-amino-2,3-dimethylbutoxy)-8-[(1R)-1,2-dimethylpropyl]-14-[5-(methylamino)-2H-tetrazol-2-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

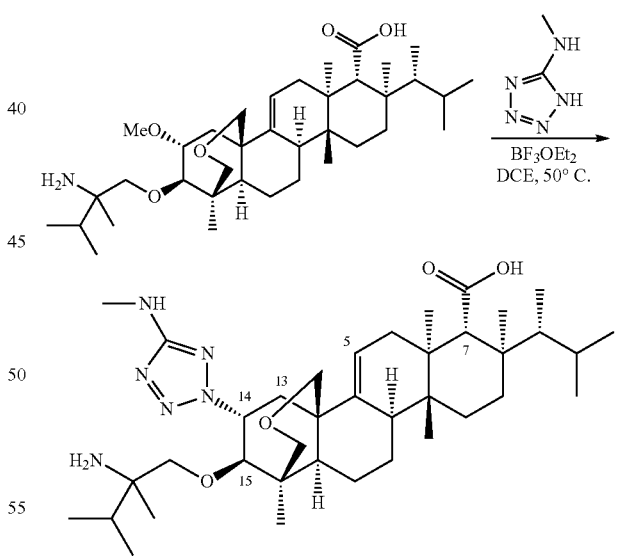

Employing a procedure analogous that described in the preceding Examples, but using N-methyl-1H-tetrazol-5-amine, the title compound was prepared from (1S,4aR,6aS,7R,8R,10aR,10bR,12aR,14R,15R)-15-(2-amino-2,3-dimethylbutoxy)-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (prepared as described for Intermediate 6, but as a ~1:1 mixture of diastereomers).

¹H NMR CD₃OD δ (PPM) 5.82-5.90 (m, 1H, H14); 5.48-5.51 (m, 1H, H5); 3.92 and 3.94 (d, 1H); 3.81 and 3.83 (d, 1H); 3.59-3.62 (m, 1H); 3.52 and 3.54 (dd, 1H); 3.48 and 3.50 (d, 1H); 3.39 (d, 1H); 2.92 (d, 1H); 2.89 (s, 3H, tetrazole Me); 2.84 (s, 1H, H7), 2.74 (d, 1H); 2.44 and 2.46 (dd, 1H, H13); 2.10-2.21 (m); 1.80-1.98 (m); 1.48-1.65 (m); 1.42 (m); 1.23-1.34 (m); 1.21 (s, 3H, Me); 1.15 and 1.03 (s, 3H, Me); 0.88 (m, 3H, Me); 0.86 (m, 3H, Me); 0.82 (d, 3H, Me); 0.77 (d, 3H, Me); 0.76 (s, 3H, Me) and 0.61 (d, 3H, Me).

LC/MS m/z (positive ion scan) M+1=670.08.

Example 38

(1S,4aR,6aS,7R,8R,10aR,10bR,12aR,14R,15R)-14-[5-(acetylamino)-1H-tetrazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 38A) and (1S,4aR,6aS,7R,8R,10aR,10bR,12aR,14R,15R)-14-[5-(acetylamino)-2H-tetrazol-2-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 38B)

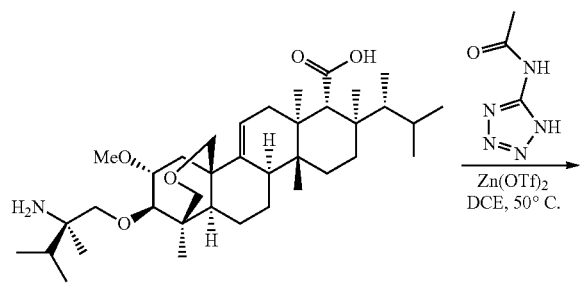

Intermediate 6

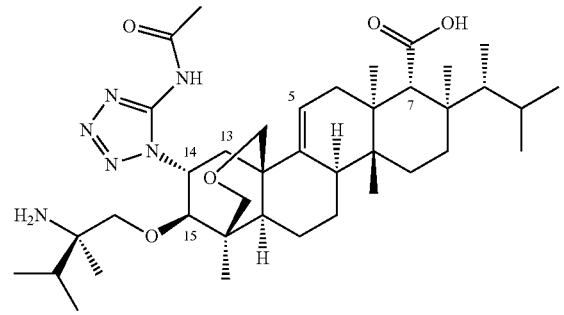

EXAMPLE 38A

+

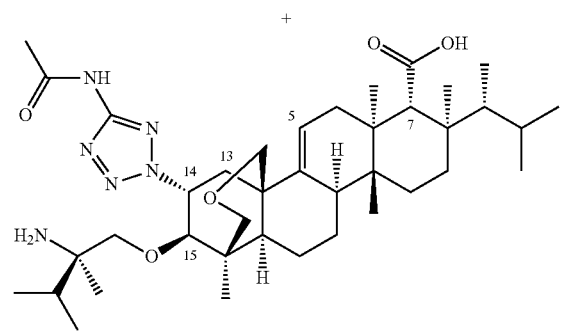

EXAMPLE 38B

A mixture of Intermediate 6 (25 mg, 0.042 mmol), N-(1H-tetrazol-5-yl)acetamide (17 mg, 0.134 mmol) and zinc trifluoromethanesulphonate (73 mg, 0.201 mmol) in dichloroethane (0.8 mL) was heated in a 50° C. oil bath for 24 hours. The suspension was evaporated, the residue was dissolved in methanol (0.5 mL) and separated by reverse phase HPLC using a 19×150 mm Sunfire Preparative C18 OBD column. The fractions containing the faster eluting regioisomer were combined, evaporated and freeze-dried from benzene to give Example 38A as a solid. The fractions containing the slower eluting regioisomer were combined, evaporated and freeze-dried from benzene to give Example 38B as a solid.

Example 38A

¹H NMR CD₃OD δ (PPM) 5.51 (br dd, 1H, H14); 5.49 (dd, 1H, H5); 4.02 (d, 1H); 3.88 (d, 1H); 3.52-3.59 (m); 3.50 (d, 1H); 3.48 (d, 1H); 2.84 (s, 1H, H7), 2.81 (br d, 1H); 2.61 (dd, 1H, H13), 2.30 (br s, 3H, NAc); 2.18 (m, 1H); 2.12 (m, 1H); 1.80-1.97 (m); 1.48-1.64 (m); 1.40-1.44 (m); 1.22-1.34 (m); 1.21 (s, 3H, Me); 1.15 (s, 3H, Me); 0.82-0.90 (br m); 0.77 (d, 3H, Me) and 0.76 (s, 3H, Me).

LC/MS m/z (positive ion scan) M+1=697.4.

Example 38B

¹H NMR CD₃OD δ (PPM) 5.98 (m, 1H, H14); 5.52 (dd, 1H, H5); 3.92 (d, 1H); 3.77 (d, 1H); 3.63 (d, 1H); 3.56 (d, 1H); 3.54 (dd, 1H), 3.49 (d, 1H); 2.84 (s, 1H, H7), 2.71 (d, 1H); 2.57 (dd, 1H, H13), 2.20 (s, 3H, NMe); 2.12-2.20 (m); 1.82-1.99 (m); 1.48-1.65 (m, 3H); 1.42 (m, 1H); 1.22-1.34 (m); 1.20 (s, 3H, Me); 1.16 (s, 3H, Me); 0.89 (d, 3H, Me); 0.88 (s, 3H, Me); 0.85 (d, 3H, Me); 0.77 (d, 3H, Me) and 0.76 (s, 3H, Me).

LC/MS m/z (positive ion scan) M+1=697.4.

Example 39

(1S,4aR,6aS,7R,8R,10aR,10bR,12aR,14R,15R)-14-[5-(acetylamino)-1H-tetrazol-1-yl]-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 39A) and (1S,4aR,6aS,7R,8R,10aR,10bR,12aR,14R,15R)-14-[5-(acetylamino)-2H-tetrazol-2-yl]-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 39B)

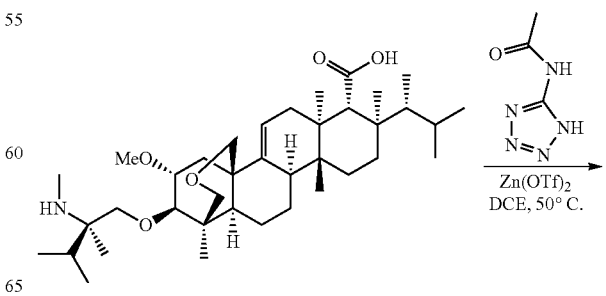

Intermediate 8

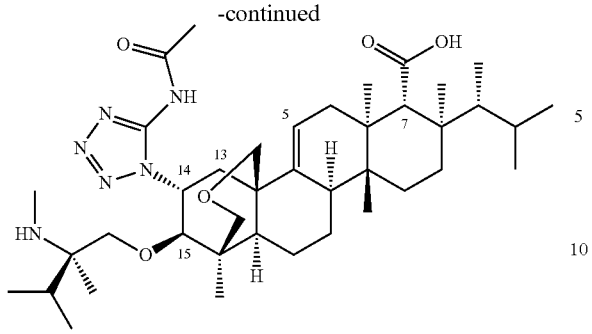

EXAMPLE 39A

+

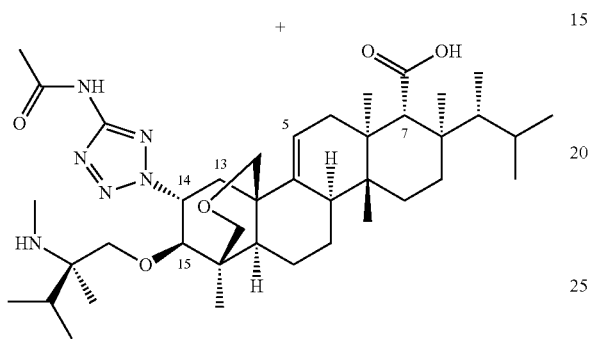

EXAMPLE 39B

By a procedure analogous to that described in Example 38, but starting with Intermediate 8, the title compounds were prepared.

Example 39A

Selected $^1$H NMR CD$_3$OD δ (PPM) (rotamers are likely causing the doubling of many NMR signals) 6.05 and 5.87 (dd, 1H, H14); 5.52 (brdd, 1H, H5); 3.86-3.95 (m); 3.50-3.69 (m); 2.97 and 2.94 (d, 1H); 2.86 (brs, 1H, H7), 2.55 and 2.46 (dd, 1H, H13); 2.45 and 2.44 (s, 3H, Me).
LC/MS m/z (positive ion scan) M+1=711.69.

Example 39B

Selected NMR CD$_3$OD δ (PPM) 5.54 (brm, 1H, H14); 5.49 (dd, 1H, H5); 4.18 (d, 1H); 3.83 (d, 1H); 3.50-3.68 (m); 3.21 (d, 1H); 2.86 (s, 1H, H7), 2.55 (dd, 1H, H13); 2.30 (s, Me) and 2.26 (s, 3H, Me).
LC/MS m/z (positive ion scan) M+1=711.69.

Example 40

(1S,4aR,6aS,7R,8R,10aR,10bR,12aR,14R,15R)-14-[5-(acetylamino)-2H-tetrazol-2-yl]-15-(2-aminoethoxy)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

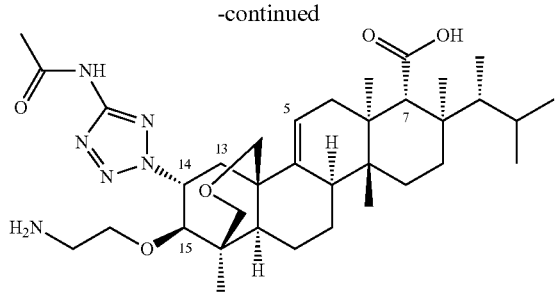

By a procedure analogous to that described in Example 38, but starting with Intermediate 2, the title compound was prepared.

$^1$H NMR CD$_3$OD δ (PPM) (rotamers are likely causing the doubling of many NMR signals) 5.97 and 5.50 (m, 1H, H14); 5.52 and 5.47 (dd, 1H, H5); 3.86-3.94 (m); 3.82 (d, 1H); 3.69 (d, 1H); 3.50-3.64 (m); 3.53 (dd, 1H); 3.48 (d, 1H); 2.80-2.98 (m); 2.84 and 2.83 (s, 1H, H7), 2.70-2.78 (m); 2.54 (dd, 1H, H13); 2.42-2.48 (m); 2.10-2.24 (m); 1.80-1.96 (m); 1.48-1.64 (m); 1.42 (m); 1.23-1.34 (m); 1.21 (s, 3H, Me); 1.17 and 1.15 (s, 3H, Me); 0.89 (d, 3H, Me); 0.86 (s, 3H, Me); 0.85 (d, 3H, Me); 0.77 and 0.76 (d, 3H, Me) and 0.76 (s, 3H, Me).

LC/MS m/z (positive ion scan) M+1=642.01.

Example 41

(1S,4aR,6aS,7R,8R,10aR,10bR,12aR,14R,15R)-15-(2-aminoethoxy)-8-[(1R)-1,2-dimethylpropyl]-14-(5-methyl-1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 41A) and (1S,4aR,6aS,7R,8R,10aR,10bR,12aR,14R,15R)-15-(2-aminoethoxy)-8-[(1R)-1,2-dimethylpropyl]-14-(5-methyl-2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 41B)

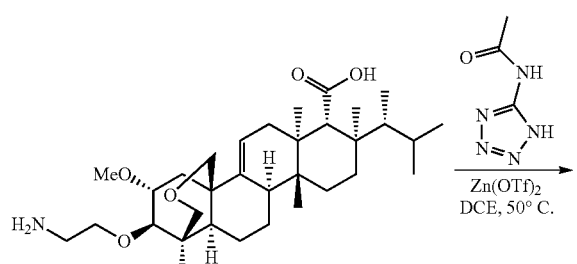

Intermediate 2

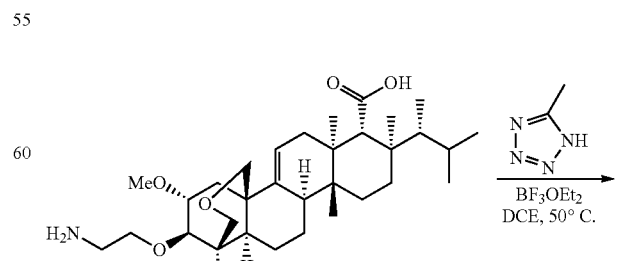

Intermediate 2

135

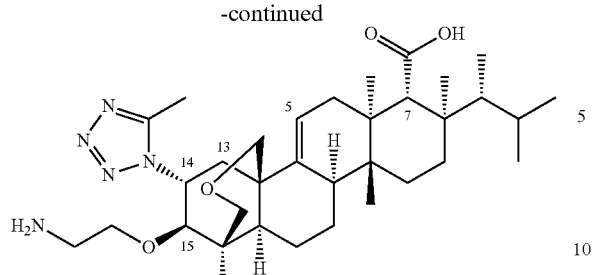

EXAMPLE 41A

+

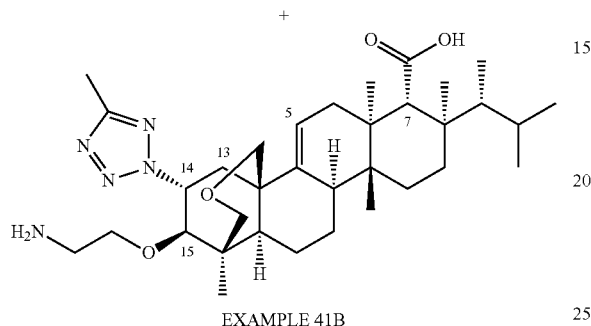

EXAMPLE 41B

A mixture of Intermediate 2 (35 mg, 0.055 mmol), 5-methyltetrazole (32 mg, 0.38 mmol) and boron trifluoride etherate (100 μL, 0.775 mmol) in dichloroethane (0.7 mL) was heated in a 50° C. oil bath for 18 hours. The solvent was removed under vacuum and the residue was separated by reverse phase HPLC using a 19×150 mm Sunfire Preparative C18 OBD column. Fractions containing the slower eluting isomer were combined, evaporated and freeze-dried from benzene to give Example 41B as a solid (9.6 mg). The faster eluting isomer (Example 41A) was not completely separated and was isolated as a 1:1 mixture with the slower eluting isomer (Example 41B). Assignment of the regiochemistry of the two isomers was based on an $^1$H NMR NOE between the methyl group of the tetrazole and the H14 proton of the enfumafungin core which was observed for Example 41A but not for Example 41B.

Example 41A

Selected NMR CD$_3$OD δ (PPM) 5.57 (m, 1H, H14); 5.51 (dd, 1H, H5); 3.88 (d, 1H); 3.79 (d, 1H); 3.64 (d, 1H); 3.70-3.90 (m); 3.51 (d, 1H), 3.49 (d, 1H); 2.84 (s, 1H, H7), 2.61 (s, 3H, tetrazole Me).

LC/MS m/z (positive ion scan) M+1=598.50.

Example 41B $^1$H NMR CD$_3$OD δ (PPM) 6.01 (m, 1H, H14); 5.49 (dd, 1H, H5); 3.90 (d, 1H); 3.72 (d, 1H); 3.62 (d, 1H); 3.6-3.8 (m); 3.53 (dd, 1H), 3.48 (d, 1H); 2.88 (m); 2.84 (s, 1H, H7), 2.51 (s, 3H, tetrazole Me); 2.74 (m); 2.67 (m), 2.50 (dd, 1H, H13); 2.18 (m, 1H); 2.15 (m, 1H); 2.05 (ddd, 1H); 1.92 (m, 2H); 1.80-1.88 (m); 1.62 (ddd, 1H); 1.60-1.66 (m, 3H); 1.40-1.44 (m); 1.22-1.28 (m); 1.21 (s, 3H, Me); 1.16 (s, 3H, Me); 0.89 (d, 3H, Me); 0.86 (s, 3H, Me); 0.85 (d, 3H, Me); 0.77 (d, 3H, Me) and 0.76 (s, 3H, Me).

LC/MS m/z (positive ion scan) M+1=598.50.

136

Example 42

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-methyl-1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 42A) and (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-methyl-2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 42B)

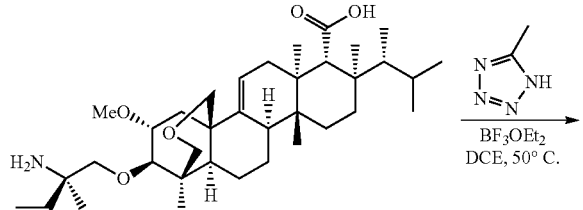

Intermediate 6

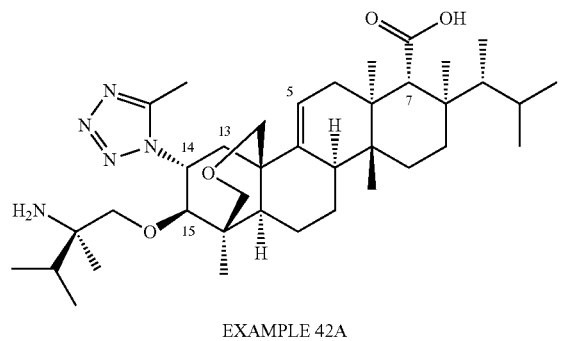

EXAMPLE 42A

+

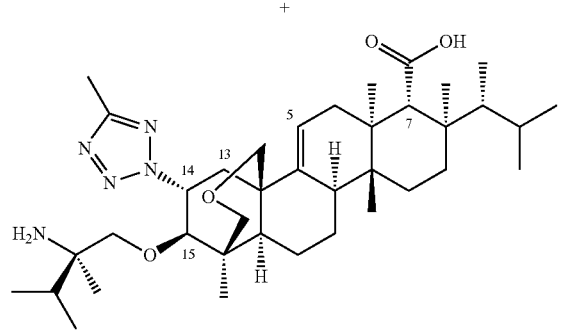

EXAMPLE 42B

In a manner analogous to that described in Example 41, the title compounds (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-methyl-1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 42A) and (1S,4aR,6aS,7R, 8R,10aR,10bR,12aR,14R,15R)-15-[[(2R)-2-amino-2,3-dimethylbutyl]oxy]-8-[(1R)-1,2-dimethylpropyl]-14-(5-methyl-2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 42B) were prepared starting with Intermediate 6.

Example 42A $^1$H NMR (CD$_3$OD, 600 MHz, ppm) δ 0.75 (s, 3H, Me), 0.76 (s, 3H, Me), 0.76 (d, 3H, Me), 0.80 (d, 3H, Me), 0.82 (d, 3H, Me), 0.85 (d, 3H, Me), 0.89 (d, 3H, Me), 0.91 (s, 3H, Me), 1.14 (s, 3H, Me), 1.20 (s, 3H, Me), 1.22-1.36 (m), 1.40-1.65 (m), 1.72-1.79 (m), 1.79-1.98 (m), 2.12-2.22 (m), 2.49 (dd, 1H, H13), 2.61 (s, 3H, Me), 2.80 (d, 1H), 2.84 (s, 1H, H7) 3.53 (d, 1H), 3.56 (d, 1H), 3.56 (d, 1H), 3.65 (d, 1H), 3.93 (d, 1H), 4.04 (d, 1H), 5.52 (dd, 1H, H5), 5.57-5.63 (m, 1H, H14).

Mass Spectrum: (ESI) m/z=654.50 (M+H).

Example 42B $^1$H NMR (CD$_3$OD, 600 MHz, ppm) δ 0.76 (s, 3H, Me), 0.77 (d, 3H, Me), 0.80 (d, 3H, Me), 0.82 (s, 3H, Me), 0.84 (d, 3H, Me), 0.85 (d, 3H, Me), 0.89 (s, 3H, Me), 0.90 (d, 3H, Me), 1.15 (s, 3H, Me), 1.20 (s, 3H, Me), 1.22-1.36 (m), 1.40-1.45 (m), 1.48-1.57 (m), 1.59-1.65 (m), 1.75-1.99 (m), 2.12-2.21 (m), 2.50 (s, 3H, Me), 2.51 (dd, 1H, H13), 2.60 (d, 1H), 2.84 (s, 1H, H7), 3.49 (d, 1H), 3.50 (d, 1H), 3.55 (dd, 1H), 3.63 (d, 1H), 3.87 (d, 1H), 3.95 (d, 1H), 4.49 (dd, 1H, H5), 6.04-6.09 (m, 1H, H14).

Mass Spectrum: (ESI) m/z=654.50 (M+H).

Example 43

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(hydroxymethyl)-1H-tetrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 43A) and (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(hydroxymethyl)-2H-tetrazol-2-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 43B)

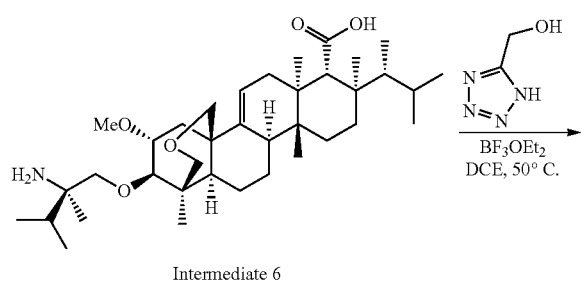

Intermediate 6

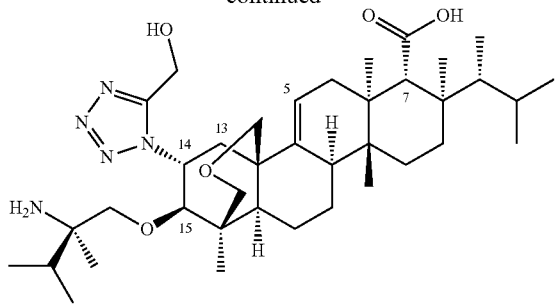

EXAMPLE 43A

+

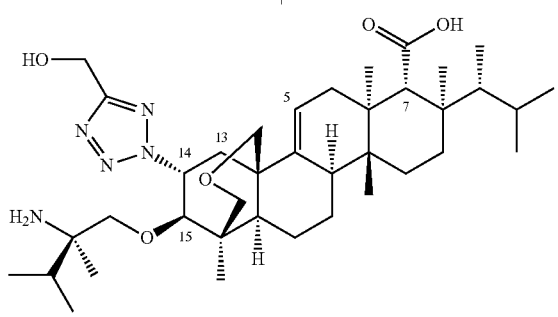

EXAMPLE 43B 1H-tetrazole-5-ylmethanol (21.5 mg, 0.215 mmol) and BF$_3$O(CH$_2$CH$_3$)$_2$ (54 µl, 0.426 mmol) were added to a stirred solution of Intermediate 6 (25.7 mg, 0.043 mmol) in 1,2-dichloroethane (0.6 ml). The reaction mixture was a yellow solution that was heated to 50° C. After 1.5 hours, LCMS and $^1$H NMR showed complete conversion of Intermediate 6 to a mixture of the two tetrazole regioisomers at C14. The reaction mixture was cooled to room temperature, the solvent was evaporated under reduced pressure, and the residue was placed under high vacuum. The residue was dissolved in methanol and separated using a single HPLC run on a 19×150 mm Sunfire Prep C18 OBD 10 µcolumn by eluting with acetonitrile/water+0.1% TFA. The HPLC fractions of the faster eluting regioisomer were combined, the solvent was evaporated under reduced pressure, and the residue was lyophilized from ethanol and benzene to give EXAMPLE 43A as a white solid (6.3 mg). The HPLC fractions containing the slower eluting regioisomer were combined, the solvent was evaporated under reduced pressure, and the residue was lyophilized from ethanol and benzene to give a 60:40 mixture of EXAMPLE 43A and EXAMPLE 43B as a white solid (11.6 mg). The assignment of the regiochemistry of the two isomers was based on an NOE observed from H14 to the CH$_2$OH of the tetrazole in EXAMPLE 43A.

Example 43A $^1$H NMR (CD$_3$OD, 600 MHz, ppm) δ 0.76 (s, 3H, Me), 0.76 (d, 3H, Me), 0.81 (d, 3H, Me), 0.82 (s, 3H, Me), 0.85 (d, 3H, Me), 0.85 (d, 3H, Me), 0.89 (d, 3H, Me), 0.90 (s, 3H, Me), 1.14 (s, 3H, Me), 1.20 (s, 3H; Me), 1.22-1.36 (m), 1.40-1.44 (m), 1.48-1.56 (m), 1.59-1.65 (m), 1.79-1.96 (m), 1.99-2.04 (m), 2.12-2.21 (m), 2.54 (dd, 1H, H13), 2.58 (d, 1H), 2.84 (s, 1H, H7), 3.50 (d, 1H), 3.50 (d, 1H), 3.55 (dd, 1H), 3.63 (d, 1H), 3.86 (d, 1H), 3.95 (d, 1H), 4.80 (s, 2H), 5.49 (dd, 1H, H5), 6.09-6.14 (m, 1H, H14)

Mass Spectrum: (ESI) m/z=670.34 (M+H).

Example 43B

Selected Characteristic NMR Resonances:
¹H NMR (CD₃OD, 600 MHz, ppm) δ 2.82 (d, 1H), 2.84 (s, 1H, H7), 3.93 (d, 1H), 4.07 (d, 1H), 4.93 (abq, 2H), 5.46 (dd, 1H, H5), 5.86-5.91 (m, 1H, H14).
Mass Spectrum: (ESI) m/z=670.32 (M+H).

Example 44

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-oxopropyl)-2H-tetrazol-2-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

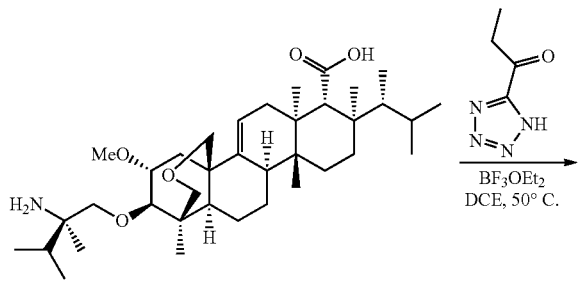

Intermediate 6

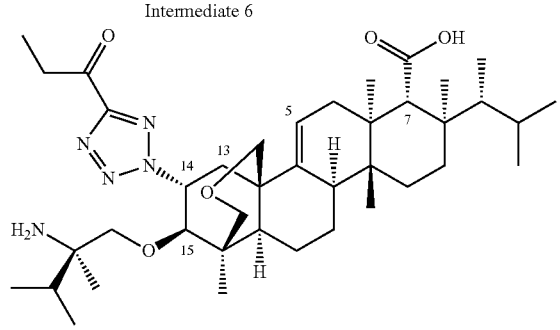

1-(1H-tetrazole-5-yl)propan-1-one (28.0 mg, 0.222 mmol) and BF₃O(CH₂CH₃)₂ (52 μl, 0.410 mmol) were added to a stirred solution of Intermediate 6 (24.7 mg, 0.041 mmol) in 1,2-dichloroethane (0.41 ml). The reaction mixture was a yellow solution that was heated to 50° C. After 1.75 hours, LCMS and ¹H NMR showed complete consumption of Intermediate 6. The reaction mixture was cooled to room temperature, the solvent was evaporated under reduced pressure, and the residue was placed under high vacuum. The residue was dissolved in methanol and purified using a single HPLC run on a 19×150 mm Sunfire Prep C18 OBD 10 μm column by eluting with acetonitrile/water+0.1% TFA. The product HPLC fractions were combined, the solvent was evaporated under reduced pressure, and the residue was lyophilized from ethanol and benzene to give the title compound as a white solid (22.8 mg).

¹H NMR (CD₃OD, 500 MHz, ppm) δ 0.79 (s, 3H, Me), 0.79 (d, 3H, Me), 0.80 (s, 3H, Me), 0.80 (d, 3H, Me), 0.85 (d, 3H, Me), 0.88 (d, 3H, Me), 0.92 (d, 3H, Me), 0.94 (s, 3H, Me), 1.17 (s, 3H, Me), 1.22 (s, 3H, Me), 1.23 (t, 3H), 1.22-1.39 (m), 1.42-1.47 (m), 1.49-1.68 (m), 1.77-2.06 (m), 2.14-2.24 (m), 2.62 (dd, 1H, H13), 2.68 (d, 1H), 2.86 (s, 1H, H7), 3.19 (q, 2H), 3.54 (d, 1H), 3.58 (d, 1H), 3.58 (d, 1H), 3.67 (d, 1H), 3.97 (d, 1H), 3.99 (d, 1H), 5.53 (dd, 1H, H5), 6.21-6.28 (m, 1H, H14).

Mass Spectrum: (ESI) m/z=696.30 (M+H).

Example 45

(1S,4aR,6aS,7R,8R,10aR,10bR,12aR,14R,15R)-14-(5-amino-2H-tetrazol-2-yl)-8-[(1R)-1,2-dimethylpropyl]-15-(2-pyrrolidinylmethoxy)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

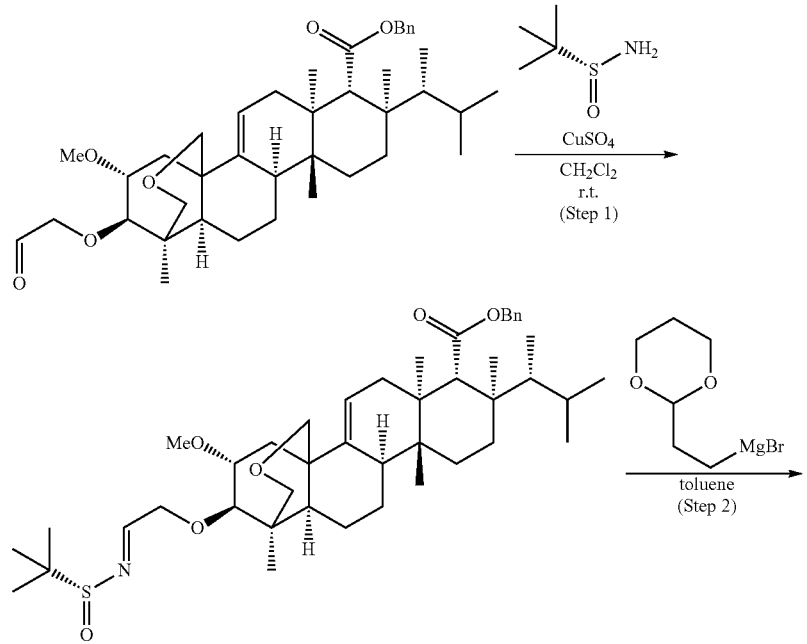

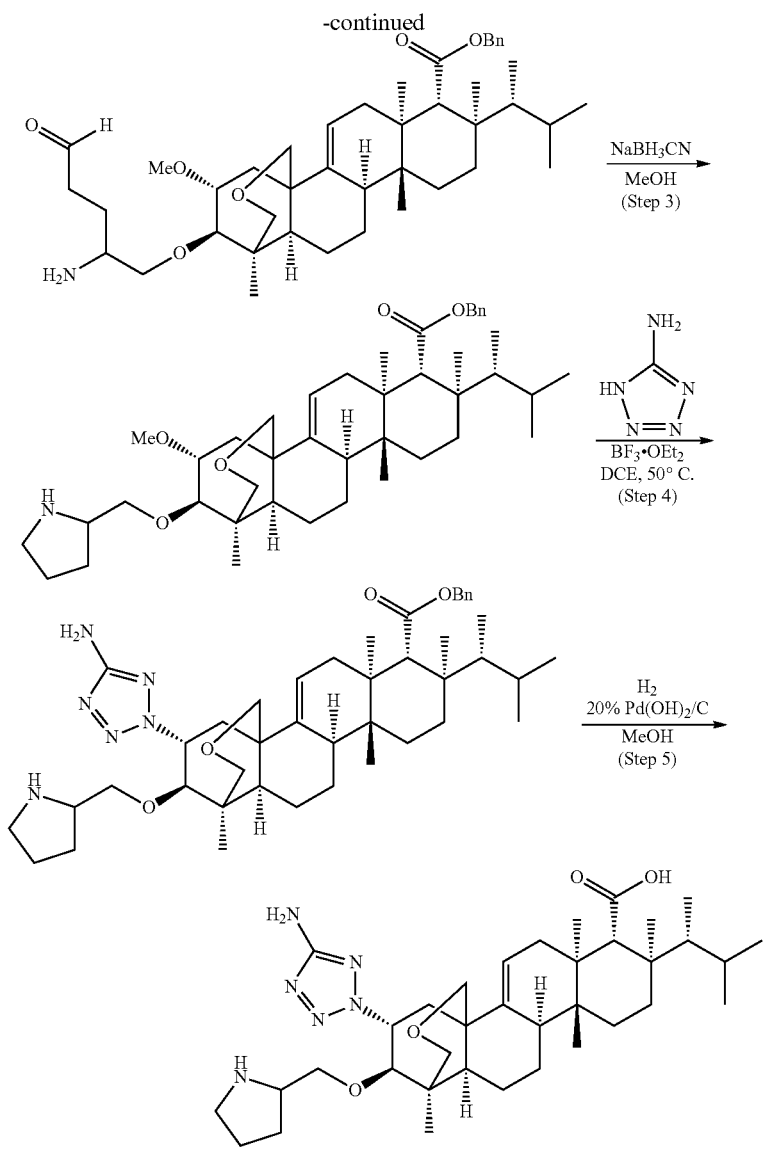

Step 1:

To a stirred solution of the product of Step 2 in the synthesis of Intermediate 2, benzyl(1S,4aR,6aS,7R,8R,10aR,10bR,12aR,14R,15R)-8-[(1R)-1,2-dimethylpropyl]-15-(2-oxoethoxy)-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate (1.00 g, 1.58 mmol) in dichloromethane (15.75 mL) at room temperature was added (R)-(+)-tert-butanesulfinylamide (239 mg, 1.97 mmol) and copper(II) sulfate (880 mg, 5.51 mmol). After 16 hours the reaction was filtered, diluted with dichloromethane (15 mL), and washed with saturated aqueous sodium bicarbonate solution (30 mL), dried over magnesium sulfate, and evaporated under vacuum to give a solid which was flash chromatographed (silica gel, 10-65% ethyl acetate:hexane) to give the product as a white solid (636 mg, 55%).

Selected $^1$H NMR (CD$_3$OD, 600 MHz, ppm) 8.08 (t, 1H, NCH), 5.45 (m, 1H, H-5), 5.08 (d, 1H, CO$_2$CH$_a$H$_b$), 5.00 (d, 1H, CO$_2$CH$_a$H$_b$), 4.20 (m, 1H, H-14), 3.38 (s, 3H, 14-OMe), 2.96 (d, 1H, H-15), 2.90 (s, 1H, H-7).

Step 2:

To a stirred solution of sulfinylimine product from Step 1 (500 mg, 0.677 mmol) in toluene (3.4 mL) at −78° C. was added a 0.5M solution of 2-[2-(1,3-dioxanyl)ethylmagnesium bromide (2.1 mL, 1.05 mmol) in tetrahydrofuran. After 45 minutes additional 0.5M solution of 2-[2-(1,3-dioxanyl)ethylmagnesium bromide (1.0 mL, 0.5 mmol) in tetrahydrofuran added. After 102 minutes the reaction was placed in an ice bath. At 132 minutes the reaction was quenched with a saturated aqueous ammonium chloride solution. The reaction was diluted with EtOAc (25 mL) and washed with water (25 mL), brine (25 mL), dried over MgSO$_4$, filtered, and evaporated to a solid. The solid was dissolved at room temperature in tetrahydrofuran (10 mL) and treated with 2N HCl (10 mL). After stirring 16 hours the reaction was diluted with EtOAc (50 mL), washed with 0.5N NaOH, brine (25 mL), dried over MgSO$_4$, filtered, and evaporated to a solid (522 mg, 111%).

LC/MS m/z (positive ion scan) M+1=692.5.

Step 3:

A room temperature solution of the aldehyde product from Step 2 (472 mg, 0.68 mmol) in methanol (6.8 mL) was treated with acetic acid (78 µL, 1.36 mmol) and stirred. After 1 hour a 1M solution of sodium cyanoborohydride (1.36 mL, 1.36 mmol) in tetrahydrofuran was added. After 18 hours the reaction was treated with 2N HCl (700 µL), stirred for 30 minutes, filtered, and reverse phase HPLC chromatographed (C-18, acetonitrile: 0.1% trifluoroacetic acid in water) to give the product as a solid (110 mg, 20%).

LC/MS m/z (positive ion scan) M+1=676.38.

Step 4:

A room temperature solution of pyrrolidine derivative from Step 3 (110 mg, 0.14 mmol) in 1,2-dichloroethane (2.79 mL) treated with 5-aminotetrazole (59 mg, 0.70 mmol) and borontrifluoride etherate (176 µL, 0.18 mmol) and heated under nitrogen at 50° C. After 1 hour the reaction was cooled to room temperature, mixed with methanol (2 mL), and concentrated under vacuum, and lyophilized from benzene. The crude product was chromatographed by reverse phase HPLC (C-18, acetonitrile: 0.1% trifluoroacetic acid in water) to give a white solid (65.2 mg).

LC/MS m/z (positive ion scan) M+1=729.54.

Selected $^1$H NMR (CD$_3$OD, 600 MHz, ppm) 7.3-7.4 (m, 5, ArH), 5.80 (m, 1H, H-14), 5.43 (m, 1H, H-5), 5.05 (d, J=12.2 Hz, 1H, CO$_2$CH$_a$H$_b$), 4.99 (d, J=12.2 Hz, 1H, CO$_2$CH$_a$H$_b$), 3.63 (d, J=9.7 Hz, 1H, H-15), 2.90 (s, 1H, H7), 2.44 (dd, J=6.6, 13.6 Hz, 1H, H-13).

Step 5:

A solution of pyrrolidine benzyl ester product from Step 4 (25 mg, 0.030 mmol) in methanol (1.5 mL) was treated with trifluoroacetic acid (11 µL, 0.143 mmol) and 20% Palladium hydroxide on carbon (13 mg) and hydrogenated under balloon hydrogen at room temperature. After 17 hours the reaction was nitrogen purged and the reaction mixture filtered. The filtrate was concentrated and the product lyophilized from benzene to give the title compound as a white solid (24 mg).

Selected $^1$H NMR (CD$_3$OD, 600 MHz, ppm) 5.81 (m, 1H, H-14), 5.51 (m, 1H, H-5), 3.2-3.3 (m, 1H), 2.85 (s, 1H, H-7), 2.47 (dd, J=6.5, 13.5 Hz, 1H, H-13), 1.22 (s, 3H), 1.17 (s, 3H), 0.90 (d, J=6.9 Hz, 3H), 0.87 (s, 3H), 0.86 (d, J=6.8 Hz, 3H), 0.78 (d, J=6.3 Hz, 3H), 0.78 (s, 3H).

LC/MS m/z (positive ion scan) M+1=639.36.

Example 46

(1S,4aR,6aS,7R,8R,10aR,10bR,12aR,14R,15R)-14-(5-amino-2H-tetrazol-2-yl)-8-[(1R)-1,2-dimethylpropyl]-15-[(1-methyl-2-pyrrolidinyl)methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

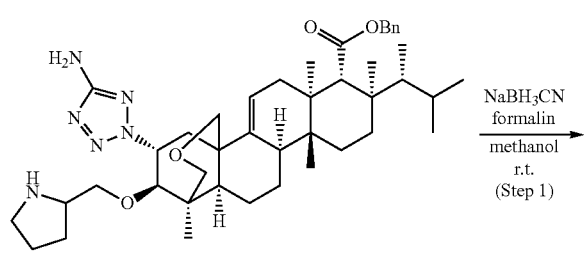

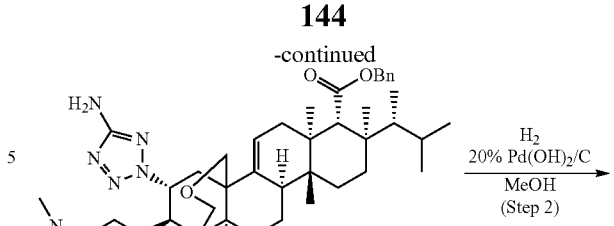

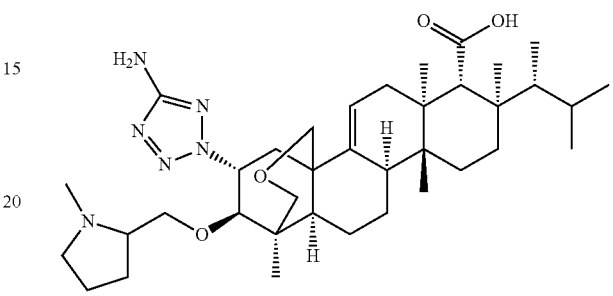

Step 1:

A solution of the product of Step 4 in Example 45, benzyl (1S,4aR,6aS,7R,8R,10aR,10bR,12aR, 1 4R,15R)-14-(5-amino-2H-tetrazol-2-yl)-8-[(1R)-1,2-dimethylpropyl]-15-(2-pyrrolidinylmethoxy)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate (25 mg, 0.030 mmol) in methanol (900 µL) was treated with formalin (13 µL, 0.18 mmol) and acetic acid (3.4 µL, 0.059 mmol) and stirred at room temperature. After 30 minutes the solution was treated with a 1N solution of sodium cyanoborohydride in tetrahydrofuran (59 µL, 0.059 mmol). After 18 hours the reaction was treated with 2N HCl (0.1 mL), and after several minutes chromatographed by reverse phase HPLC (C-18, acetonitrile: 0.1% trifluoroacetic acid in water) to give a white solid (10 mg).

LC/MS m/z (positive ion scan) M+1=743.58.

Selected $^1$H NMR (CD$_3$OD, 600 MHz, ppm) 7.3-7.4 (m, 5, ArH), 5.84 (m, 1H, H-14), 5.44 (m, 1H, H-5), 5.05 (d, J=12.2 Hz, 1H, CO$_2$CH$_a$H$_b$), 4.99 (d, J=12.2 Hz, 1H, CO$_2$CH$_a$H$_b$), 2.90(s, 1H, H-7), 2.76 (s, 3H, NMe), 2.45 (dd, J=6.6, 13.7 Hz, 1H, H-13).

Step 2:

A solution of the product from Step 1 (10 mg, 0.012 mmol) in methanol (1.00 mL) was treated with trifluoroacetic acid (4.5 µL, 0.058 mmol) and 20% Palladium hydroxide on carbon (5 mg) and hydrogenated under a balloon of hydrogen at room temperature. After 18 hours the reaction was filtered, concentrated, and chromatographed by reverse phase HPLC (C-18, acetonitrile: 0.1% trifluoroacetic acid in water) to give the title compound as a white solid (8.3 mg).

Selected $^1$H NMR (CD$_3$OD, 600 MHz, ppm) 5.85 (m, 1H, H-14), 5.52 (m, 1H, H-5), 2.85 (s, 1H, H-7), 2.76 (s, 3H, NMe), 2.48 (dd, J=6.6, 13.6 Hz, 1H, H-13).

LC/MS m/z (positive ion scan) M+1=653.51.

Example 47
(1S,4aR,6aS,7R,8R,10aR,10bR,12aR,14R,15R)-14-(5-amino-2H-tetrazol-2-yl)-8-[(1R)-1,2-dimethylpropyl]-15-(3-pyrrolidinyloxy)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid
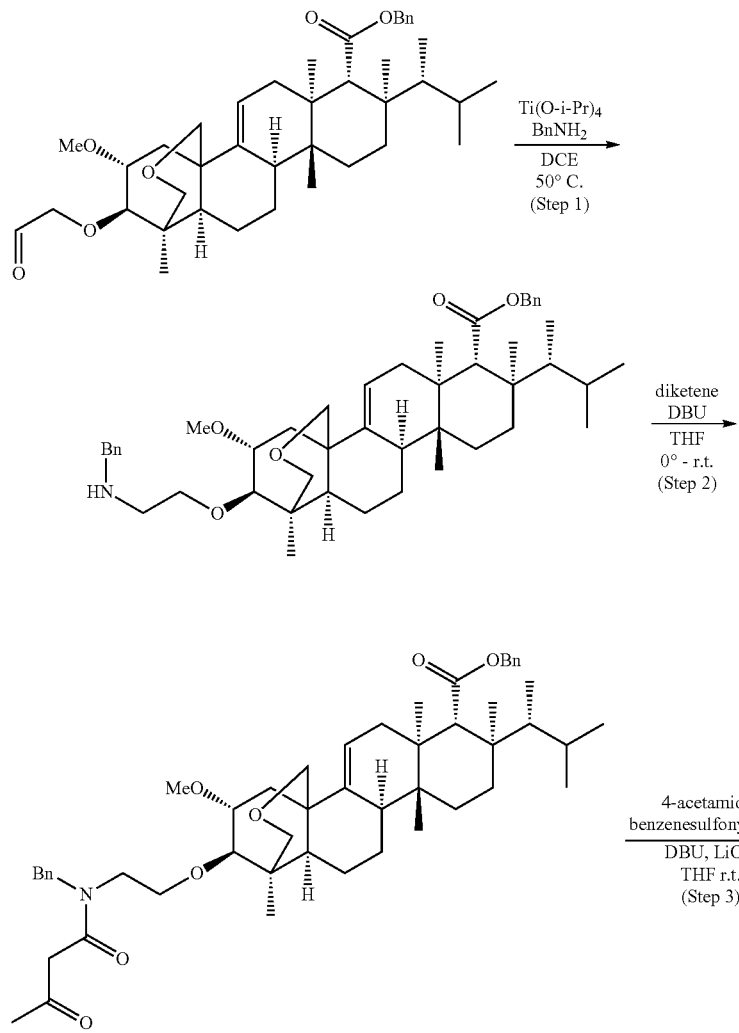
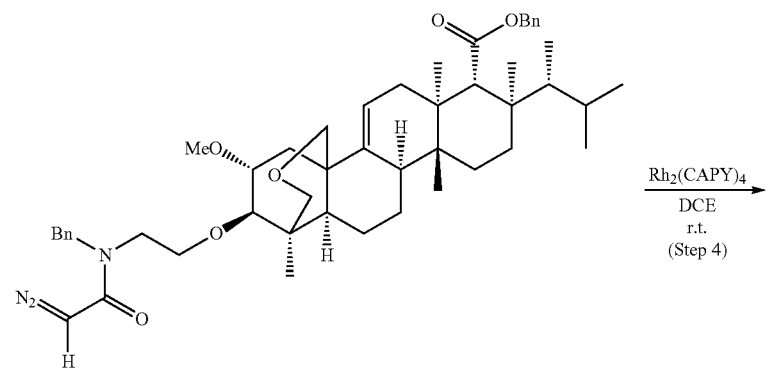

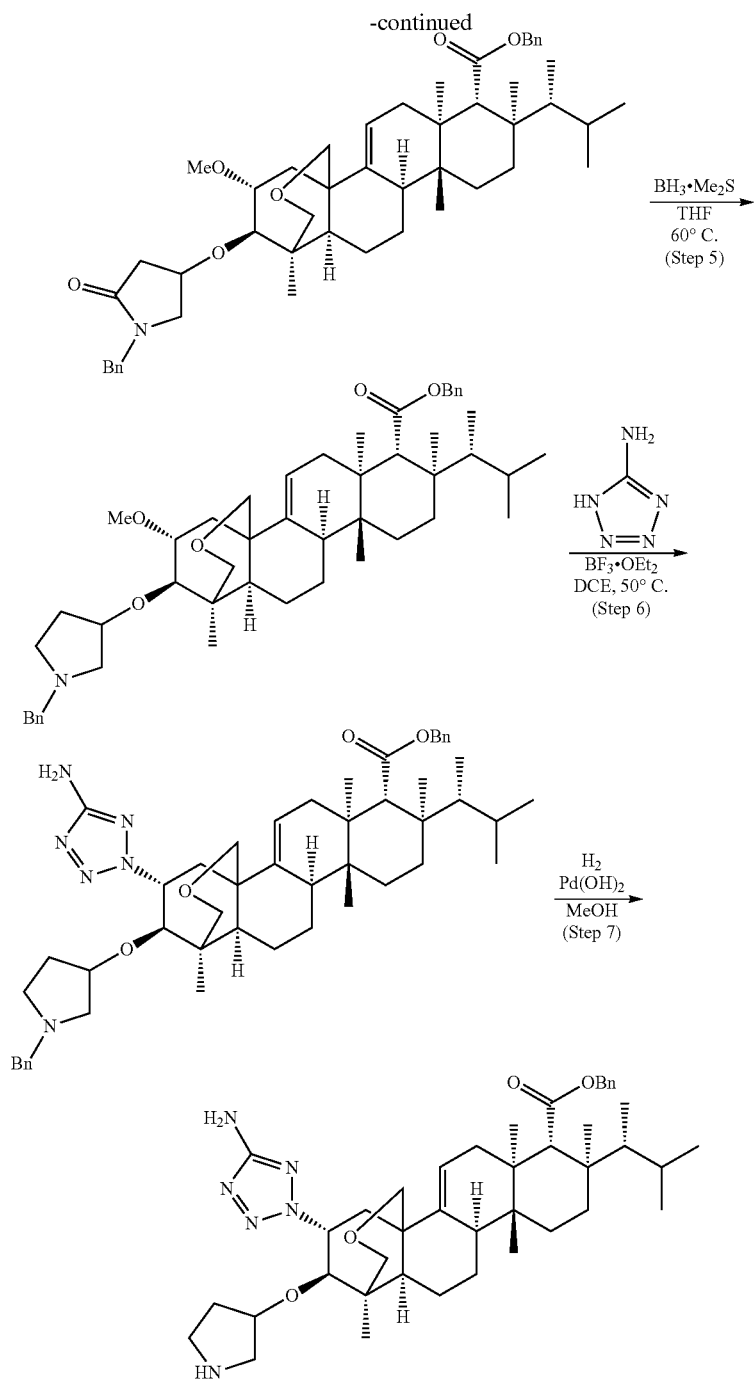

Step 1:

To a stirred solution of the product of Step 2 in the synthesis of Intermediate 2, benzyl(1S,4aR,6aS,7R,8R,10aR,10bR,12aR,14R,15R)-8-[(1R)-1,2-dimethylpropyl]-15-(2-oxoethoxy)-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate (500 mg, 0.788 mmol) in 1,2-dichloroethane (1.5 mL) was added at room temperature benzylamine (95 μL, 0.866 mmol) and titanium isopropoxide (288 μL, 0.984 mmol). The reaction was heated at 50° C. After 30 minutes the reaction was removed from heating to cool to room temperature and partitioned between ethyl acetate (40 mL) and saturated aqueous sodium bicarbonate (40 mL). The mixture was filtered, the organic phase recovered and washed with brine (25 mL), dried over magnesium sulfate, filtered, and evaporated under vacuum to give the benzylamine product as a solid (487.7 mg).

LC/MS m/z (positive ion scan) M+1=726.49.

Step 2:

To a stirred solution of benzylamine derivative from Step 1 (486 mg, 0.669 mmol) in tetrahydrofuran (6.7 mL) under nitrogen cooled at 0° C. was added diketene (65 μL, 0.843 mmol) followed by 1,8-diazobicyclo[5.4.0]undec-7-ene (101 μL, 0.669 mmol). After 15 minutes the reaction was stirred at room temperature. After 25 minutes at room temperature the reation was diluted with ethyl acetate (25 mL) and washed with 0.2 N HCl (25 mL), brine (25 mL), dried over magnesium sulfate, filtered, and evaporated to a solid which was flash chromatographed (silica gel, 10-65% ethyl acetate:hexane) to give the acetylated product as a solid (281.6 mg).

LC/MS m/z (positive ion scan) M+1=810.55.

Step 3:

To a stirred solution of the acetylated product from Step 2 (280 mg, 0.346 mmol) in tetrahydrofuran (4.6 mL) at room temperature was added 4-acetamidobenzenesulfonyl azide (95 mg, 0.397 mmol) and 1,8-diazobicyclo[5.4.0]undec-7-ene (65 µL, 0.432 mmol). After stirring 18 hours the reaction diluted with ethyl acetate (30 mL) and washed 0.1 N HCl in brine (30 mL), brine (30 mL), dried over magnesium sulfate, filtered, filtered and evaporated to a solid which was flash chromatographed (silica gel, 10-65% ethyl acetate:hexane) to give the diazo derivative as white solid (217.7 mg).

IR (thin film) 2105 cm$^{-1}$ (diazo absorption).

Step 4:

A stirred solution of thecdiazo derivative from Step 3 (50 mg, 0.063 mmol) in 1,2-dichloroethane (4.0 mL) at room temperature was treated with Doyle catalyst, $Rh_2(CAPY)_4$, (2 mg, 3.2 µmol). After 17 hours the reaction was concentrated under vacuum and flash chromatographed (silica gel, 10-65% ethyl acetate:hexane) to give the pyrrolidinone derivative (a mixture of diastereomers) as white solid (22.8 mg).

Selected $^1$H NMR (CDCl$_3$, 600 MHz, ppm) δ 2.38-2.44 (m, 1H, 13-H), 2.86 (br s, 1H, 7-H), 4.04-4.13 (m, 1H, 14-H), 4.4-4.51 (AB q, 2H, NCH$_2$Ar), 4.97 (d, J=12.4 Hz, 1H, CO$_2$CH$_A$H$_B$), 5.10 (d, J=12.4 Hz, 1H, CO$_2$CH$_A$H$_B$), 5.38 (m, 1H, H-5), 7.2-7.4 (m, 10H, ArH).

Step 5:

To a stirred solution of pyrrolidinone derivative from Step 4 (22 mg, 0.029 mmol) in tetrahydrofuran (1.0 mL) at room temperature was added a 2N solution of borane-methyl sulfide complex in tetrahydrofuran (144 µL, 0.288 mmol). The solution was heated at 60° C. After 24 hours the reaction was cooled to room temperature and evaporated to a residue.

LC/MS m/z (positive ion scan) M+1=752.35.

Step 6:

To a stirred solution of the pyrrolidine product from Step 5 (25.1 mg, 0.029 mmol) in 1,2-dichloroethane (580 µL) at room temperature was added 5-amino-1H-tetrazole (12 mg, 0.141 mmol) and boron trifluoride etherate (37 µL, 0.292 mmol). The solution was heated at 50° C. After 2 days the reaction allowed to cool to room temperature and the chromatographed by reverse phase HPLC (C-18, acetonitrile: 0.1% trifluoroacetic acid in water) to give a white solid (4.4 mg).

LC/MS m/z (positive ion scan) M+1=805.36.

Selected $^1$H NMR (CD$_3$OD, 600 MHz, ppm) δ 2.89.(br s, 1H,H-7), 4.98-5.05 (ABq, 2H, CO$_2$CH$_2$Ph), 5.42 (m, 1H, H-5), 5.72-5.81 (m, 2H, pyrrolidine), 7.3-7.5 (m, 10H, 2 Ar).

Step 7:

To a solution of the amino tetrazole derivative from Step 6 (4.4 mg, 4.79 µmol) in methanol (750 µL) at room temperature was added 20% palladium on carbon (4 mg) and the reaction hydrogenated under balloon pressure of hydrogen. After 22 hours the reaction nitrogen flushed and the mixture filtered, the solvent evaporated, and the product lyophilized from benzene to give the title compound as a white solid (3.1 mg).

$^1$H NMR (CD$_3$OD, 600 MHz, ppm) δ 0.71-0.80 (m), 0.82-0.91 (m), 1.12-2.2 (m), 2.35-2.45 (m, including H-13), 2.8-2.9 (m), 3.2-3.6 (m), 3.7-3.9 (m), 5.5 (m, H-5), 5.7-5.9 (m, including H-14).

LC/MS m/z (positive ion scan) M+1=625.22.

Example 48

(1S,4aR,6aS,7R,8R,10aR,10bR,12aR,14R,15R)-15-(2-amino-1,3-dimethylbutoxy)-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

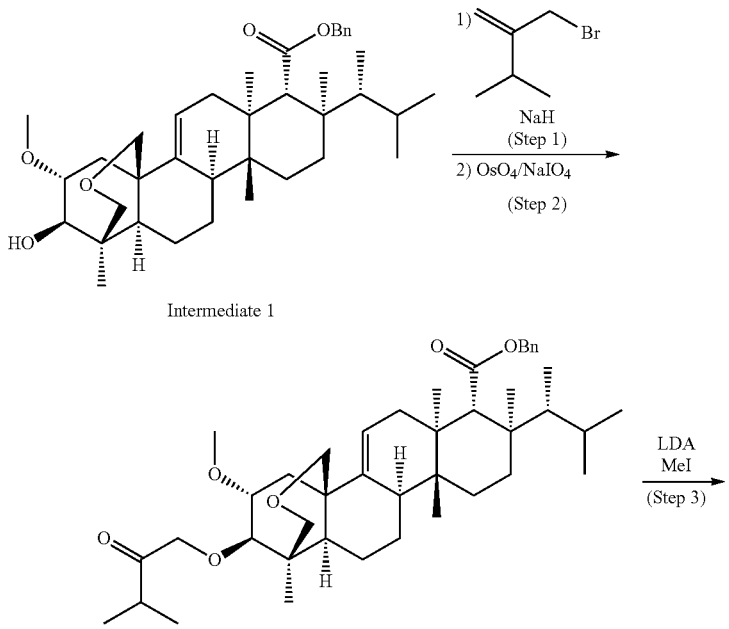

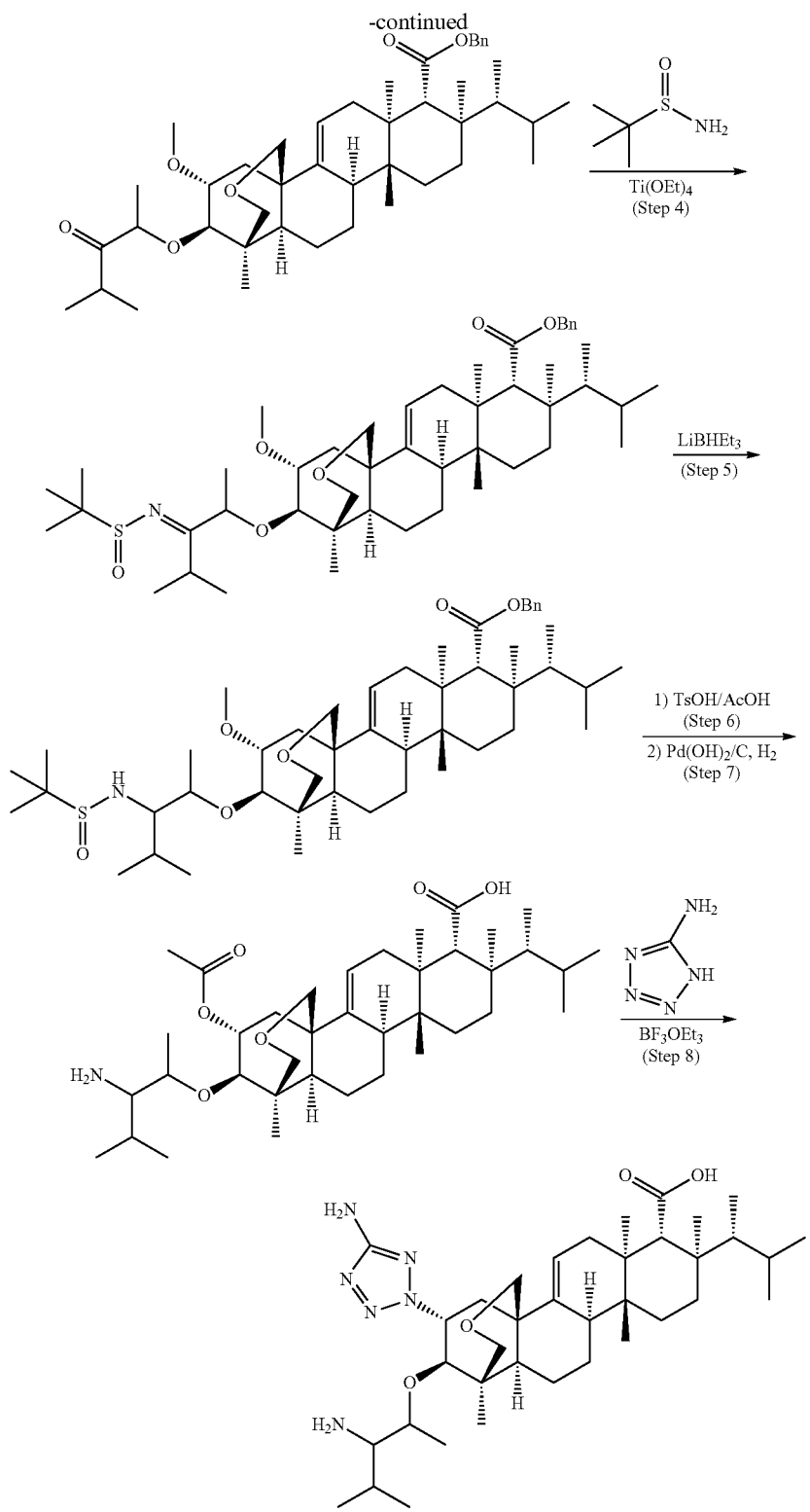

Step 1:

To a suspension of 60% NaH (2.02 g, 50.6 mmol) in DME (100 mL) under a nitrogen atmosphere was added 15-crown-5 (7.34 g, 33.7 mmol) and Intermediate 1 (10.0 g, 16.87 mmol). The mixture was stirred for 30 minutes and 2-(bromomethyl)-3-methylbut-1-ene (5.50 g, 33.7 mmol) was added. The mixture was heated to 70° C. for 3 hours and stirred at room temperature for 16 hours. The mixture was partitioned between EtOAc and 1 N HCl. The organic layer was washed with water (2×), brine and dried over NaSO$_4$. The solvent was evaporated and the residue was chromatographed on silica gel with an ISCO Combiflash using 20% EtOAc/hexanes as eluent. The solvent was evaporated to afford a yellow solid (8.0 g).

$^1$H NMR (CDCl$_3$, 500 MHz, ppm) δ 0.72 (m, 6H), 0.80 (m, 6H), 0.82 (m, 3H), 1.10 (m, 6H), 1.20 (s, 3H), 1.23 (s, 3H), 1.20-1.60 (m, 8H), 1.75 (m, 4H), 1.90 (m, 1H), 2.05 (m, 1H), 2.15 (m, 1H), 2.38 (m, 1H), 2.42 (m, 1H), 2.90 (m, 2H), 3.25 (d, 1H), 3.30-3.42 (m, 2H), 3.43 (s, 3H), 3.80 (d, 1H), 4.00 (d, 1H), 4.22 (m, 1H), 4.40 (d, 1H), 4.85 (s, 1H), 5.00 (d, 1H), 5.05 (s, 1H), 5.15 (d, 1H), 5.42 (m, 1H), 7.30-7.40 (m, 5H).

Step 2:

To a solution of the olefin product from Step 1 (8.0 g, 11.85 mmol) in dioxane (100 mL) was added water (10 mL) and NaIO$_4$ (12.7 g, 59.3 mmol) followed by 2,6-lutidine (2.54 g, 23.7 mmol) and a 2.5% solution of OsO$_4$ in t-butanol (14.8 mL, 1.19 mmol). The mixture was vigorously stirred for 16 hours and then partitioned between EtOAc and 1 N HCl. The organic layer was washed with brine, dried over NaSO$_4$ and concentrated.

The residue was chromatographed on silica gel with an ISCO Combiflash using 30% EtOAc/hexanes as eluent to give the product as a beige foam (6.19g).

$^1$H NMR (CDCl$_3$, 500 MHz, ppm) δ 0.67 (m, 6H), 0.80 (m,9H), 1.15 (m, 9H), 1.25 (m, 6H), 1.38-1.60 (m, 5H), 1.70-1.80 (m, 4H), 1.90 (m, 1H), 2.05 (m, 1H), 2.15 (m, 1H), 2.45 (m, 1H), 2.90 (m,3H), 3.30 (d, 1H), 3.40 (s, 3H), 3.42 (m, 2H), 3.80 (d, 1H), 4.28 (d, 2H), 4.56 (d, 1H), 5.00 (d, 1H), 5.15 (d, 1H), 5.22 (m, 1H), 7.30-7.40 (m, 5H).

Step 3:

To a fresh solution of lithium diisopropylamide (1.58 mmol) in THF (10 mL) cooled to −70° C. under a nitrogen atmosphere was added a solution of the ketone product from Step 2 (1.07 g, 1.58 mmol) in THF (2 mL). The mixture was stirred for 15 minutes and iodomethane (0.22 g, 1.58 mmol) was added. The cooling bath was removed and the mixture was stirred for 1 hour. The reaction was quenched with 1 N HCl and extracted with EtOAc. The organic layer was dried over NaSO$_4$ and concentrated. The residue was chromatographed on silica gel with an ISCO Combiflash using 10% EtOAc/hexanes as eluent to provide the product (400 mg).

$^1$H NMR (CDCl$_3$, 500 MHz, ppm, selected resonances) δ 1.38 (d, 3H), 3.30 (s, 1H), 3.40, (s, 3H), 5.00 (d, 1H), 5.33 (d, 1H), 5.42 (m, 1H), 7.30-7.40 (m, (5H).

Step 4:

To a solution of the product from Step 3 (400 mg, 0.579 mmol) in toluene (2 mL) under a nitrogen atmosphere was added 2-methylpropane-2-sulfinamide (351 mg, 2.89 mmol). Titanium ethoxide (660 mg, 2.89 mmol) was added and the mixture was heated to 70° C. for 16 hours. The mixture was partitioned between EtOAc and water. The resulting emulsion was filtered through a plug of Celite and the layers were separated. The organic layer was dried over NaSO$_4$ and concentrated. The residue was chromatographed on silica gel with an ISCO Combiflash using 10-50% EtOAc/hexanes as gradient to give the product (150 mg).

$^1$H NMR (CDCl$_3$, 500 MHz, ppm, selected resonances) δ 1.20 (s, 9H), 1.22 (d, 3H), 2.84 (s, 1H), 3.40 (s, 3H), 7.30-7.40 (m, h), 8.15 (m, 1H).

Step 5:

To a solution of imine product from Step 4 (140 mg, 0.176 mmol) in THF (3 mL) under a nitrogen atmosphere cooled to −70° C. was added lithium triethylborohydride (1 M in THF, 0.88 mL, 0.88 mmol). The cooling bath was removed and the mixture was stirred at room temperature for 4 hours. The mixture was partitioned between EtOAc and 1 N HCl and the organic layer was dried over NaSO$_4$ and concentrated. The residue was chromatographed on silica gel with an ISCO Combiflash using 30-50% EtOAc/hexanes as gradient to provide the product (97 mg).

MS (ESI) m/z=797 (M+H).

Step 6:

To a solution of the product from Step 5 (97 mg, 0.122 mmol) in acetic acid (2 mL) was added p-toluenesulfonic acid (70 mg, 0.365 mmol). The mixture was heated to 70° C. for 90 minutes and the solvent was evaporated. The mixture was partitioned between EtOAc and 1 N HCl and the organic layer was dried over NaSO$_4$ and concentrated. The residue was chromatographed on silica gel using 5% MeOH/NH$_3$/CH$_2$Cl$_2$ as eluent. The solvent was evaporated to give a white foam (36 mg).

MS (ESI) m/z=721 (M+H).

Step 7:

To a solution of the product from Step 6 (36 mg, 0.050 mmol) in MeOH (2 mL) was added 20% palladium hydroxide on carbon (35 mg). The mixture was stirred under 1 atm of H$_2$ for 1 hour and the catalyst was filtered. The solvent was evaporated to give a white solid (30 mg).

MS (ESI) m/z=630 (M+H).

Step 8:

To a solution of the product from Step 7 (28 mg, 0.044 mmol) in DCE (2 mL) under a nitrogen atmosphere was added 5-aminotetrazole (19 mg, 0.222 mmol). Boron trifluoride etherate solution (0.06 mL, 0.442 mmol) was added and the mixture was heated to 50° C. for 2 hours. The volatiles were evaporated and the residue was dissolved in 50% MeOH/CH$_3$CN (2 mL). The mixture was filtered and purified by reverse phase HPLC using 30-100% CH$_3$CN/H$_2$O as gradient. The combined product fractions were freeze dried to afford the title compound as a white solid (12 mg).

MS (ESI) m/z=655 (M+H).

Example 49

(1S,4aR,6aS,7R,8R,10aR,10bR,12aR,14R,15R)-14-(5-amino-2H-tetrazol-2-yl)-15-[2-(dimethylamino)-1,3-dimethylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

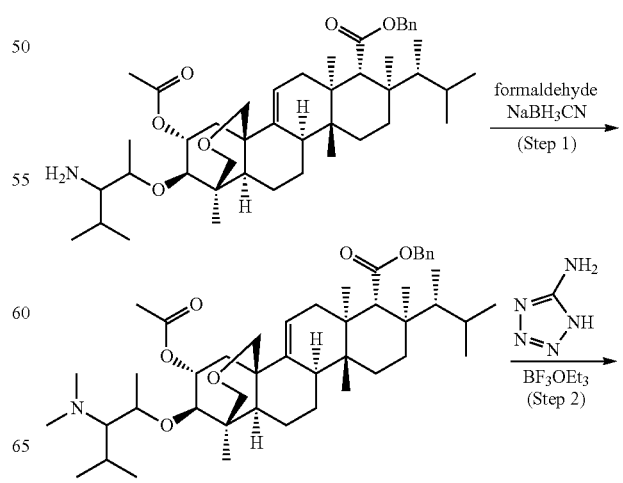

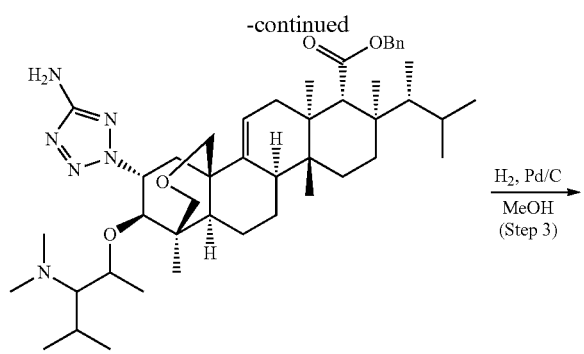

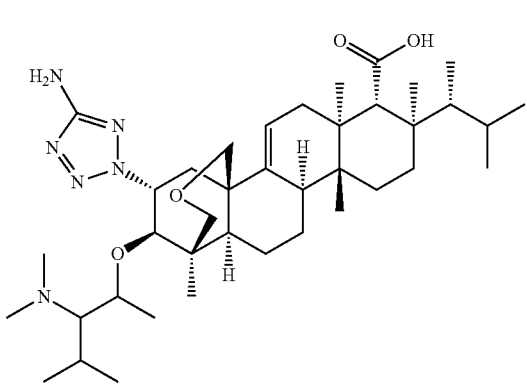

Step 1:

To a solution of the product from Step 6 in Example 48 (40 mg, 0.056 mmol), in MeOH (2 mL) was added AcOH (0.006 mL, 0.111 mmol) and formalin solution (0.056 mL, 0.278 mmol). Sodium cyanoborohydride (14 mg, 0.222 mmol) was added and the mixture was stirred at room temperature for 16 hours. The solvent was evaporated and the residue was partitioned between EtOAc and saturated ammonium chloride solution. The organic layer was dried over NaSO$_4$ and concentrated to yield the product (40 mg).

MS (ESI) m/z=749 (M+H).

Step 2:

To a solution of the product from Step 1 (40 mg, 0.053 mmol) in DCE (1 mL) under a nitrogen atmosphere was added 5-aminotetrazole (22 mg, 0.267 mmol). Boron trifluoride etherate solution (0.07 mL, 0.535 mmol) was added and the mixture was heated to 60° C. for 3 hours. The volatiles were evaporated and the residue was dissolved in 50% MeOH/water (2 mL). The mixture was filtered and purified by reverse phase HPLC using 50-100% CH$_3$CN/H$_2$O as gradient. The combined product fractions were freeze dried to afford the product as a white solid (19 mg).

MS (ESI) m/z=774 (M+H).

Step 3:

To a solution of the product from Step 2 (19 mg, 0.025 mmol) in MeOH (2 mL) was added palladium on carbon (10 mg). The mixture was stirred under 1 atm of H$_2$ for 90 minutes and the catalyst was filtered. The solvent was evaporated and the residue was purified by reverse phase HPLC using 40-60% CH$_3$CN/H$_2$O as gradient. The combined product fractions were freeze dried to afford the title compound as a white solid (5 mg).

MS (ESI) m/z=683 (M+H).

Example 50

(1S,4aR,6aS,7R,8R,10aR,10bR,12aR,14R,15R)-14-(5-amino-2H-tetrazol-2-yl)-15-[2,3-dihydroxy-2-(hydroxymethyl)propoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

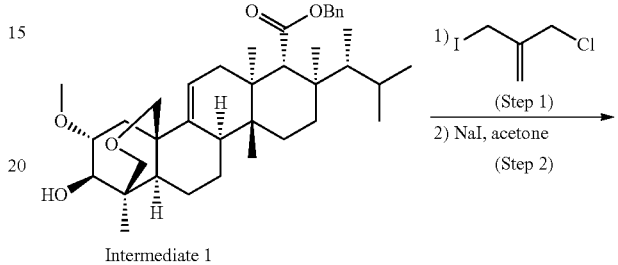

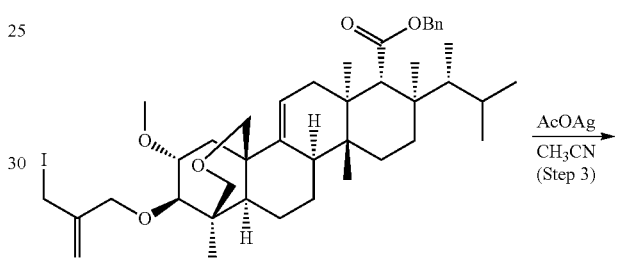

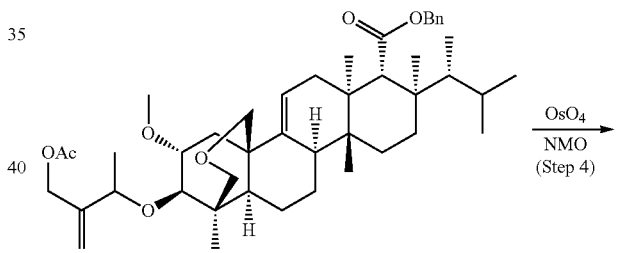

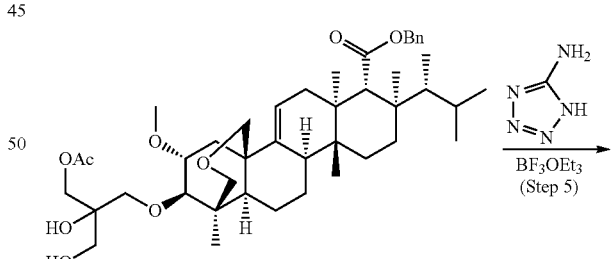

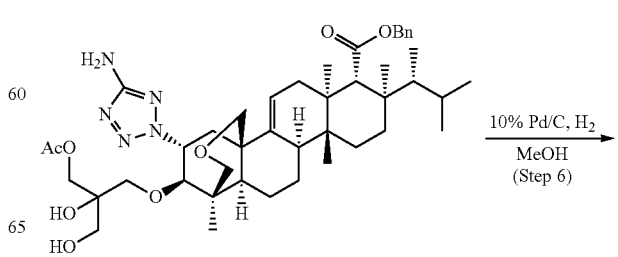

-continued

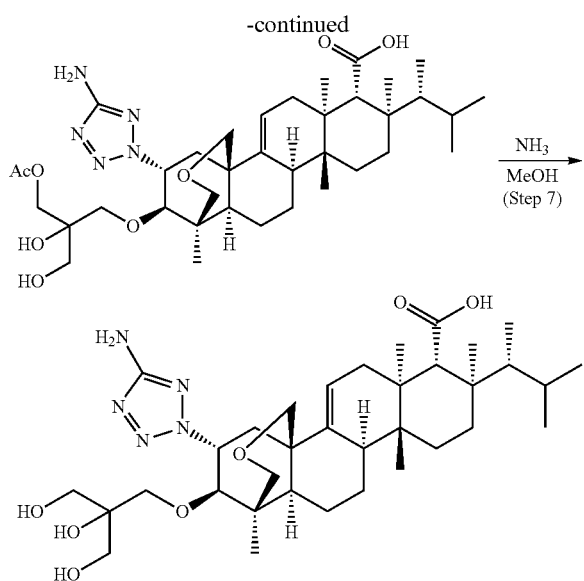

Step 1:

To a solution of Intermediate 1 (1.00 g, 1.69 mmol) in DME (5 mL) under a nitrogen atmosphere was added 18-crown-6 (0.45 g, 1.69 mmol) and 3-chloro-2-(iodomethyl)prop-1-ene (1.46 g, 6.75 mmol). A 30% suspension of KH (0.90 g, 6.75 mmol) was added and the mixture was stirred at room temperature for 72 hours. The mixture was partitioned between EtOAc and 1 N HCl. The organic layer was dried over NaSO₄ and concentrated. The residue was chromatographed on silica gel using 15% EtOAc/hexanes as eluent to give a clear oil (1.15 g).

Step 2:

The compound from Step 1 was dissolved in acetone (20 mL) and NaI (0.51 g, 3.37 mmol) was added. The mixture was heated to reflux for 3 hours and the solvent was evaporated. The residue was dissolved in CH₂Cl₂, dried over Na₂SO₄ and filtered through a plug of Celite. The solvent was evaporated to give an amber oil which was used without further purification.

Step 3:

The product compound from Step 2 (1.30 g, 1.69 mmol) was dissolved in CH₃CN (15 mL) and silver acetate (2.82 g, 16.87 mmol) was added. The mixture was heated to reflux for 2 hours and filtered through a plug of Celite. The solvent was evaporated and the residue was partitioned between EtOAc and water. The organic layer was dried over NaSO₄ and concentrated. The residue was chromatographed on silica gel using 15% EtOAc/hexanes as eluent to give a clear oil (657 mg).

MS (ESI) m/z=727 (M+Na).

Step 4:

To a solution of the product compound from Step 3 (378 mg, 0.536 mmol) in THF (3 mL) was added N-methylmorpholine N-oxide (314 mg, 2.68 mmol) and a solution of 2.5% osmium tetroxide in t-BuOH (6.73 mL, 0.054 mmol). The mixture was stirred at room temperature for 16 hours and the volatiles were evaporated. The residue was chromatographed on silica gel using 5% MeOH/ CH₂Cl₂ to give a white solid (300 mg).

MS (ESI) m/z=761 (M+Na).

Step 5:

To a solution of the product compound from Step 4 (233 mg, 0.315 mmol) in DCE (3 mL) under a nitrogen atmosphere was added 5-aminotetrazole (134 mg, 0.267 mmol). Boron trifluoride etherate solution (0.4 mL), 3.15 mmol) was added and the mixture was heated to 50° C. for 4 hours. The volatiles were evaporated and the residue was dissolved in CH₃CN (2 mL). The mixture was filtered and purified by reverse phase HPLC using 50-100% CH₃CN/H₂O as gradient. The combined product fractions were freeze dried to afford a white solid (62 mg).

MS (ESI) m/z=793 (M+H).

Step 6:

To a solution of the product compound from Step 5 (62 mg, 0.068 mmol) in MeOH (2 mL) was added 10% Pd/C catalyst (20 mg) and the mixture was stirred under 1 atm of H₂ for 2 hours. The catalyst was filtered and the solvent was evaporated to give a white solid (48 mg).

MS (ESI) m/z=702 (M+H).

Step 7:

A solution of the product compound from Step 6 (48 mg, 0.059 mmol) in 2 M methanolic ammonia was stirred at room temperature for 16 hours. The volatiles were evaporated to give the title compound (not a salt) as a white solid (40 mg).

MS (ESI) m/z=660 (M+H).

Example 51

(1S,4aR,6aS,7R,8R,10aR,10bR,12aR,14R,15R)-15-[[(2S)-2-amino-2,3-dimethylbutyl]oxy]-14-(5-amino-2H-tetrazol-2-yl)-8-[(1 R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxamide

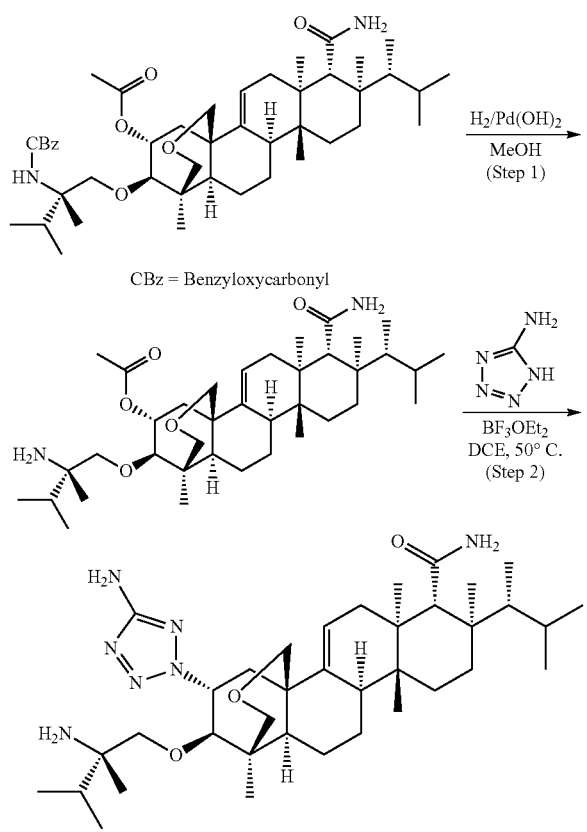

CBz = Benzyloxycarbonyl

Step 1:

To a solution of (1S,2R,3R,4aR,6aS,7R,8R,10aR,10bR,12aR)-3-acetoxy-2-[[(2S)-2-[(benzyloxy)carbonyl]amino-2,3-dimethylbutyl]oxy]-8-[(1 R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxamide [the product compound of Example 148, Step 6, in WO2007127012, incorporated by reference herein in its entirety] (236 mg, 0.31 mmol) in MeOH/CH$_2$Cl$_2$ (8 ml, 1/1) was added Pd(OH)$_2$ (20% weight %, 160 mg). The mixture was purged with hydrogen then stirred under H$_2$ (1 atm, balloon) for 1 h. The reaction mixture was filtered through a pad of Celite, and the filter cake was washed with MeOH. The filtrate was concentrated under reduced pressure to afford the product (190 mg, 97% yield) as a white solid.

Step 2:

To a solution of the product compound from Step 1 (62.9 mg, 0.1 mmol) in 1,2-dichloroethane (1 mL), boron trifluoride etherate (126 μL, 1 mmol) was added, followed by 5-aminotetrazole (42.5 mg, 0.5 mmol). The reaction mixture was heated at 50° C. for 5 h, was diluted with MeOH, and was concentrated under reduced pressure. The residue was purified by RP HPLC to give the title compound (as an acetate salt, 30 mg, 46%) as a white solid.

$^1$H NMR (400 MHz, METHANOL-d$_4$) δ 0.66 (d, J=6.83 Hz, 3 H) 0.76 (d, J=7.22 Hz, 3 H) 0.78 (s, 3 H) 0.84 (d, J=7.22 Hz, 3 H) 0.86 (d, J=6.83 Hz, 3 H) 0.88 (s, 3 H) 0.92 (d, J=6.83 Hz, 3 H) 0.94 (s, 3 H) 1.19 (s, 3 H) 1.23 (s, 3 H) 1.27-1.35 (m, 3 H) 1.41 (d, J=14.25 Hz, 2 H) 1.51 (br s, 2 H) 1.53 (br s, 1 H) 1.62 (d, J=9.37 Hz, 2 H) 1.71 (d, J=6.83 Hz, 3 H) 1.83 (dd, J=9.57, 5.86 Hz, 2 H) 2.14 (d, J=1.76 Hz, 1 H) 2.18-2.24 (m, 1 H) 2.42 (dd, J=13.37, 6.54 Hz, 1 H) 2.67 (s, 1 H) 2.75 (d, J=9.37 Hz, 1 H) 3.44-3.50 (m, 1 H) 3.51 (d, J=1.95 Hz, 1 H) 3.58-3.62 (m, 1 H) 3.72 (d, J=9.76 Hz, 1 H) 3.88 (d, J=11.91 Hz, 1 H) 5.49 (d, J=5.86 Hz, 1 H) 5.80 (ddd, J=12.25, 9.91, 6.54 Hz, 1 H); MS:654, MH+.

Examples 52-62

The following compounds were prepared using methods analogous to those described in the preceding examples:

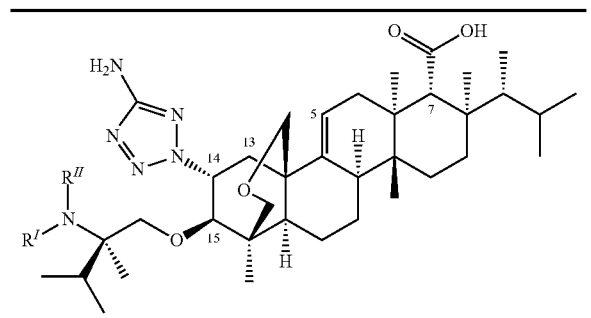

| | | |
|---|---|---|
| 52 | R$^I$ = Me<br>R$^{II}$ = H | (1S,4aR,6aS,7R,8R,10aR,10bR,12aR,14R,15R)-14-(5-amino-2H-tetrazol-2-yl)-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 5.86 (m, 1H, H14); 5.49 (dd, 1H, H5); 3.89 (d, 1H); 3.86 (d, 1H); 3.61 (d, 1H); 3.59 (d, 1H); 3.53 (dd, 1H); 3.49 (d, 1H); 2.84 (s, 1H, H7); 2.81 (d, 1H); 2.46 (dd, 1H, H13); 2.44 (s, 3H, NMe); 2.04-2.21 (m, 3H); 1.79-1.96 (m, 6H); 1.46-1.65 (m, 3H); 1.42 (m, 1H); 1.22-1.32 (m, 3H); 1.20 (s, 3H, Me); 1.15 (s, 3H, Me); 0.90 (s, 3H, Me); 0.89 (s, 3H, Me); 0.89 (s, 3H, Me); 0.86 (d, 3H, Me); 0.85 (d, 3H, Me); 0.85 (s, 3H, Me); 0.77 (d, 3H, Me) and 0.76 (s, 3H, Me).

LC/MS m/z (positive ion scan) M + 1 = 669.62.

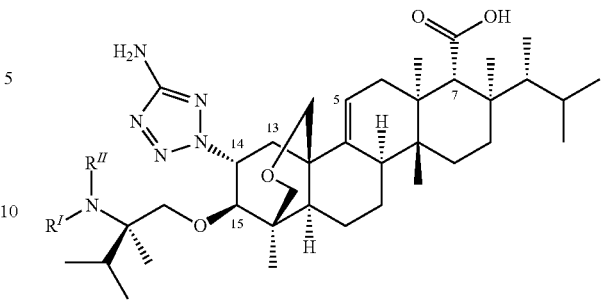

| | | |
|---|---|---|
| 53 | R$^I$ = Et<br>R$^{II}$ = H | (1S,4aR,6aS,7R,8R,10aR,10bR,12aR,14R,15R)-14-(5-amino-2H-tetrazol-2-yl)-15-[[(2R)-2-(ethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 5.85 (m, 1H, H14); 5.49 (m, 1H, H5); 3.91 (d, 1H); 3.89 (d, 1H); 3.61 (d, 1H); 3.54 (d, 1H); 3.53 (d, 1H); 3.51 (d, 1H); 2.99 (d, 1H); 2.84 (m); 2.84 (s, 1H, H7); 2.47 (m, 1H); 2.45 (dd, 1H, H13); 2.18 (m, 1H); 2.10-2.14 (m); 1.96-1.81 (m); 1.79 (m); 1.48-1.65 (m); 1.40-1.44 (m); 1.23-1.34 (m); 1.27 (t, 3H, Me); 1.20 (s, 3H, Me); 1.17 (s, 3H, Me); 1.14 (s, 3H, Me); 0.89 (d, 3H, Me); 0.89 (s, 3H, Me); 0.88 (d, 3H, Me); 0.85 (d, 3H, Me); 0.77 (d, 3H, Me); 0.76 (s, 3H, Me) and 0.74 (d, 3H, Me).

LC/MS m/z (positive ion scan) M + 1 = 683.67.

| | | |
|---|---|---|
| 54 | R$^I$ = Et<br>R$^{II}$ = Me | (1S,4aR,6aS,7R,8R,10aR,10bR,12aR,14R,15R)-14-(5-amino-2H-tetrazol-2-yl)-15-[[(2R)-2-(ethylmethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD/K$_2$CO$_3$ δ (PPM) (The TFA salt of this compound exhibited doubling of some HNMR signals, possibly due to a pseudo chiral ammonium group. Neutralization with potassium carbonate resolved this $^1$H NMR effect) 5.72 (m, 1H, H14); 5.46 (m, 1H, H5); 3.79 (d, 1H); 3.61 (d, 1H); 3.57 (d, 1H); 3.50 (dd, 1H); 3.44 (d, 1H); 3.32 (d, 1H); 2.80 (d, 1H); 2.69 (s, 1H, H7), 2.41 (m, 1H); 2.37 (dd, 1H, H13); 2.31 (m, 1H); 2.06-2.11 (m); 1.98-2.02 (m); 1.72-1.94 (m); 1.54-1.64 (m); 1.40-1.50 (m); 1.26-1.34 (m); 1.24 (s, 3H, Me); 1.19 (s, 3H, Me); 0.94 (t, 3H, Me); 0.89 (d, 3H, Me); 0.87 (s, 3H, Me); 0.82 (d, 3H, Me); 0.75 (d, 3H, Me); 0.75 (s, 3H, Me); 0.70 (d, 3H, Me) and 0.60 (s, 3H, Me).

LC/MS m/z (positive ion scan) M + 1 = 697.63.

| | | |
|---|---|---|
| 55 | R$^I$ = n-Pr<br>R$^{II}$ = H | (1S,4aR,6aS,7R,8R,10aR,10bR,12aR,14R,15R)-14-(5-amino-2H-tetrazol-2-yl)-15-[[(2R)-2,3-dimethyl-2-(propylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.82 (d, 3H, Me), 0.85 (d, 3H, Me), 0.86 (s, 3H, Me), 0.88 (s, 3H, Me), 0.90 (d, 3H, Me), 0.91 (d, 3H, Me), 1.13 (t, 3H), 1.14 (s, 3H, Me), 1.20 (s, 3H, Me), 1.22-1.35 (m), 1.40-1.44 (m), 1.47-1.71 (m), 1.79-1.96 (m), 2.06-2.22 (m), 2.46 (dd, 1H, H13), 2.74 (t, 2H), 2.82 (d, 1H), 2.84 (s, 1H, H7), 3.50 (d, 1H), 3.54 (dd, 1H), 3.62 (d, 1H), 3.62 (d, 1H), 3.87 (d, 1H), 3.88 (d, 1H), 5.49 (dd, 1H, H5), 5.84-5.89 (m, 1H, H14).

Mass Spectrum: (ESI) m/z = 697.65 (M + H).

| | | |
|---|---|---|
| 56 | R$^I$ = n-Pr<br>R$^{II}$ = Me | (1S,4aR,6aS,7R,8R,10aR,10bR,12aR,14R,15R)-14-(5-amino-2H-tetrazol-2-yl)-15-[[(2R)-2,3-dimethyl-2-(methylpropylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid. |

$^1$H NMR (CD$_3$OD, 600 MHz, ppm; The TFA salt of this compound produced a pseudo chiral amine which exhibited doubling of some $^1$H NMR signals. Neutralization with potassium carbonate resolved this $^1$H NMR effect.) δ 0.59 (s, 3H, Me), 0.68 (d, 3H, Me), 0.75 (d, 3H, Me), 0.75 (s, 3H, Me), 0.75 (d, 3H, Me), 0.82 (t, 3H), 0.82 (d, 3H, Me), 0.88 (s, 3H, Me), 0.89 (d, 3H, Me), 1.14-1.19 (m, 3H, Me), 1.19 (s, 3H, Me), 1.24 (s, 3H, Me), 1.23-1.51 (m), 1.54-1.65 (m), 1.71-1.91 (m), 1.97-2.03 (m), 2.07-2.12 (m), -continued

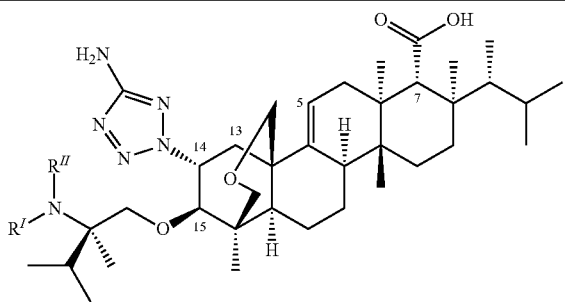

2.17 (s, 3H, Me) 2.26-2.47 (m), 2.69 (s, 1H, H7), 2.78 (d, 1H), 3.35 (d, 1H), 3.44 (d, 1H), 3.50 (dd, 1H), 3.57 (d, 1H), 3.61 (d, 1H), 3.81 (d, 1H), 5.46 (dd, 1H, H5), 5.69-5.75 (m, 1H, H14).
Mass Spectrum: (ESI) m/z = 711.66 (M + H).

| 57 | $R^I$ = i-Pr<br>$R^{II}$ = H | (1S,4aR,6aS,7R,8R,10aR,10bR,12aR,14R, 15R)-14-(5-amino-2H-tetrazol-2-yl)-15-[[(2R)-2,3-dimethyl-2-[(1-methylethyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.83 (d, 3H, Me), 0.84 (s, 3H, Me), 0.85 (d, 3H, Me), 0.90 (d, 3H, Me), 0.91 (s, 3H, Me), 0.93 (d, 3H, Me), 1.14 (s, 3H, Me), 1.20 (s, 3H, Me), 1.22-1.44 (m), 1.32 (d, 3H, Me), 1.33 (d, 3H, Me), 1.47-1.65 (m), 1.79-1.96 (m), 2.10-2.21 (m), 2.46 (dd, 1H, H13), 2.84 (s, 1H, H7), 2.96 (d, 1H), 3.40-3.46 (m, 1H), 3.51 (d, 1H), 3.54 (dd, 1H), 3.62 (d, 1H), 3.70 (d, 1H), 3.88 (d, 1H), 3.93 (d, 1H), 5.49 (dd, 1H, H5), 5.85-5.91 (m, 1H, H14).
Mass Spectrum: (ESI) m/z = 697.42 (M + H).

| 58 | $R^I$ = n-Bu<br>$R^{II}$ = H | (1S,4aR,6aS,7R,8R,10aR,10bR,12aR,14R, 15R)-14-(5-amino-2H-tetrazol-2-yl)-15-[[(2R)-2-(butylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.82 (d, 3H, Me), 0.85 (d, 3H, Me), 0.85 (s, 3H, Me), 0.88 (s, 3H, Me), 0.90 (d, 3H, Me), 0.91 (d, 3H, Me), 0.99 (t, 3H), 1.14 (s, 3H, Me), 1.20 (s, 3H, Me), 1.22-1.35 (m), 1.37-1.68 (m), 1.79-1.96 (m), 2.46 (dd, 1H, H133), 2.78 (d, 1H), 2.80 (t, 2H), 2.84 (s, 1H, H7), 3.50 (d, 1H), 3.56 (dd, 1H), 3.61 (d, 1H), 3.62 (d, 1H), 3.86 (d, 1H), 3.88 (d, 1H), 5.50 (dd, 1H, H5), 5.84-5.89 (m, 1H, H14).
Mass Spectrum: (ESI) m/z = 711.52 (M + H).

| 59 | $R^I$ = i-Bu<br>$R^{II}$ = H | (1S,4aR,6aS,7R,8R,10aR,10bR,12aR,14R, 15R)-14-(5-amino-2H-tetrazol-2-yl)-15-[[(2R)-2,3-dimethyl-2-[(2-methylpropyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.81 (d, 3H, Me), 0.85 (s, 3H, Me), 0.85 (d, 3H, Me), 0.89 (s, 3H, Me), 0.90 (d, 3H, Me), 0.91 (d, 3H, Me), 1.05 (d, 3H, Me), 1.08 (d, 3H, Me), 1.14 (s, 3H, Me), 1.20 (s, 3H, Me), 1.22-1.36 (m), 1.39-1.44 (m), 1.47-1.65 (m), 1.79-1.96 (m), 2.05-2.21 (m), 2.46 (dd, 1H, H13), 2.65-2.75 (dq, 2H), 2.83 (d, 1H), 2.84 (s, 1H, H7), 3.50 (d, 1H), 3.53 (dd, 1H), 3.62 (d, 1H), 3.64 (d, 1H), 3.87 (d, 1H), 3.87 (d, 1H), 5.50 (dd, 1H, H5), 5.86-5.91 (m, 1H, H14).
Mass Spectrum: (ESI) m/z = 711.33 (M + H).

| 60 | $R^I$ = i-Pentyl<br>$R^{II}$ = H | (1S,4aR,6aS,7R,8R,10aR,10bR,12aR,14R, 15R)-14-(5-amino-2H-tetrazol-2-yl)-15-[[(2R)-2,3-dimethyl-2-[(3-methylbutyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.81 (d, 3H, Me), 0.84 (s, 3H, Me), 0.85 (d, 3H, Me), 0.88 (s, 3H, Me), 0.90 (d, 3H, Me), 0.91 (d, 3H, Me), 0.96 (d, 3H, Me), 0.99 (d, 3H, Me), 1.15 (s, 3H, Me), 1.20 (s, 3H, Me), 1.22-1.35 (m), 1.39-1.44 (m), 1.47-1.65 (m), 1.67-1.74 (m), 1.79-1.96 (m), 2.04-2.22 (m), 2.46 (dd, 1H, H13), 2.79 (d, 1H), 2.83 (s, 1H, H7), 2.85 (t, 2H), 3.50 (d, 1H), 3.54 (dd, 1H), 3.62 (d, 1H), 3.62 (d, 1H), 3.86 (d, 1H), 3.88 (d, 1H) 5.50 (dd, 1H, H5), 5.84-5.89 (m, 1H, H14).
Mass Spectrum: (ESI) m/z = 725.55 (M + H).

-continued

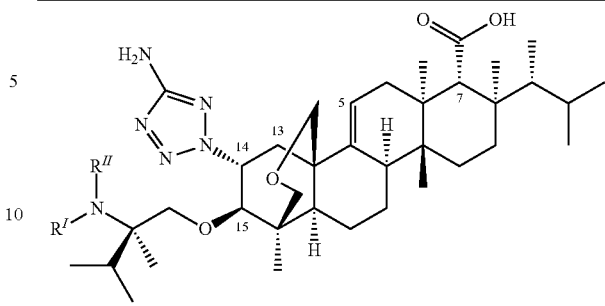

| 61 | $R^I$ = Benzyl<br>$R^{II}$ = H | (1S,4aR,6aS,7R,8R,10aR,10bR,12aR,14R, 15R)-14-(5-amino-2H-tetrazol-2-yl)-15-[[(2R)-2,3-dimethyl-2-[(phenylmethyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (s, 3H, Me), 0.77 (d, 3H, Me), 0.85 (d, 3H, Me), 0.87 (d, 3H, Me), 0.90 (d, 3H, Me), 0.90 (s, 3H, Me), 0.95 (s, 3H, Me), 0.96 (d, 3H, Me), 1.15 (s, 3H, Me), 1.20 (s, 3H, Me), 1.22-1.37 (m), 1.40-1.45 (m), 1.48-1.66 (m), 1.81-1.98 (m), 2.11-2.22 (m), 2.24-2.30 (m), 2.49 (dd, 1H, H13), 2.84 (s, 1H, H7), 2.93 (d, 1H), 3.54 (d, 1H), 3.56 (dd, 1H), 3.65 (d, 1H), 3.74 (d, 1H), 3.91 (d, 1H), 3.94 (d, 1H), 4.06 (abq, 2H), 5.51 (dd, 1H, H5), 5.91-5.97 (m, 1H, H14), 7.43-7.51 (m, 5H).
Mass Spectrum: (ESI) m/z = 745.67 (M + H).

| 62 | $R^I$ = 2-methoxyethyl<br>$R^{II}$ = H | (1S,4aR,6aS,7R,8R,10aR,10bR,12aR,14R, 15R)-14-(5-amino-2H-tetrazol-2-yl)-15-[[(2R)-2-[(2-methoxyethyl)amino]-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 5.87 (m, 1H, H14); 5.49 (dd, 1H, H5); 3.92 (d, 1H); 3.88 (d, 1H); 3.66 (d, 1H); 3.56-3.64 (m); 3.54 (dd, 1H); 3.48 (d, 1H); 3.41 (m); 3.40 (s, 3H, OMe); 3.05 (m); 2.89 (d, 1H); 2.84 (s, 1H, H7); 2.46 (dd, 1H, H13), 2.18 (m, 1H); 2.10-2.14 (m); 2.04 (m, 1H); 1.79-1.96 (m); 1.46-1.65 (m); 1.42 (m); 1.22-1.34 (m); 1.20 (s, 3H, Me); 1.14 (s, 3H, Me); 0.91 (s, 3H, Me); 0.89 (s, 3H, Me); 0.85 (d, 3H, Me); 0.84 (s, 3H, Me); 0.80 (d, 3H, Me); 0.77 (d, 3H, Me) and 0.76 (s, 3H, Me).
LC/MS m/z (positive ion scan) M + 1 = 713.55.

Examples 63-74

The following compounds were prepared using methods analogous to those described in the preceding examples:

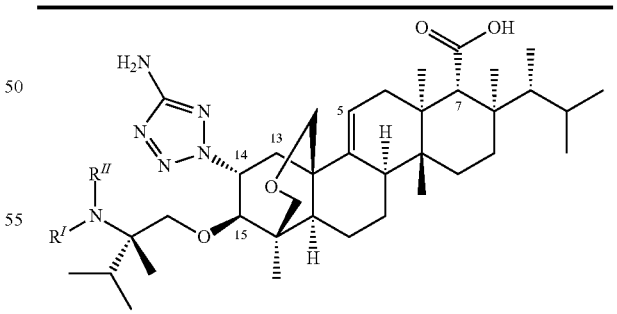

| 63 | $R^I$ = H<br>$R^{II}$ = H | (1S,4aR,6aS,7R,8R,10aR,10bR,12aR, 14R,15R)-14-(5-amino-2H-tetrazol-2-yl)-15-[[(2S)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.66 (d, 3H, Me), 0.78 (s, 3H, Me), 0.79 (d, 3H, Me), 0.88 (d, 3H, Me), 0.89 (d, 3H, Me), 0.91 (s, 3H, Me), 0.92

-continued (d, 3H, Me), 1.06 (s, 3H, Me), 1.17 (s, 3H, Me), 1.23 (s, 3H, Me), 1.24-1.37 (m), 1.14-1.47 (m), 1.49-1.68 (m), 1.79-1.99 (m), 2.12-2.24 (m), 2.45 (dd, 1H, H13), 2.86 (s, 1H, H7), 2.92 (d, 1H), 3.40 (d, 1H), 3.50 (d, 1H), 3.55 (dd, 1H), 3.63 (d, 1H), 3.80 (d, 1H), 3.94 (d, H1), 5.51 (dd, 1H, H5), 5.82-5.89 (m, 1H, H14).
Mass Spectrum: (ESI) m/z = 655.60 (M + H).

| 64 | $R^I$ = Me<br>$R^{II}$ = H | (1S,4aR,6aS,7R,8R,10aR,10bR,12aR,14R,15R)-14-(5-amino-2H-tetrazol-2-yl)-15-[[(2S)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 5.85 (m, 1H, H14); 5.49 (m, 1H, H5); 3.89 (d, 1H); 3.86 (d, 1H); 3.61 (d, 1H); 3.53 (dd, 1H); 3.50 (d, 2H); 2.94 (d, 1H); 2.84 (s, 1H, H7), 2.44 (dd, 1H, H13); 2.18 (m, 1H); 2.10-2.14 (m); 1.80-1.96 (m); 1.77 (m); 1.48-1.64 (m); 1.40-1.44 (m); 1.22-1.34 (m); 1.20 (s, 3H, Me); 1.15 (s, 3H, Me); 1.13 (s, 3H, Me); 0.89 (d, 3H, Me); 0.89 (s, 3H, Me); 0.87 (d, 3H, Me); 0.85 (d, 3H, Me); 0.77 (d, 3H, Me); 0.76 (s, 3H, Me) and 0.73 (d, 3H, Me).
LC/MS m/z (positive ion scan) M + 1 = 669.62.

| 65 | $R^I$ = Me<br>$R^{II}$ = Me | (1S,4aR,6aS,7R,8R,10aR,10bR,12aR,14R,15R)-14-(5-amino-2H-tetrazol-2-yl)-15-[[(2S)-2-(dimethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.78 (s, 3H, Me), 0.79 (d, 3H, Me), 0.83 (d, 3H, Me), 0.97 (d, 3H, Me), 0.92 (d, 3H, Me), 0.92 (s, 3H, Me), 0.93 (d, 3H, Me), 1.17 (s, 3H, Me), 1.23 (s, 3H, Me), 1.25 (s, 3H, Me), 1.22-1.38 (m), 1.42-1.47 (m), 1.49-1.68 (m), 1.81-2.01 (m), 2.01-2.25 (m), 2.47 (dd, 1H, H13), 2.80 (s, 3H, Me), 2.83 (s, 3H, Me), 2.86 (s, 1H, H7), 3.08 (d, 1H), 3.54 (d, 1H), 3.55 (dd, 1H), 3.61 (d, 1H), 3.64 (d, 1H), 3.84 (d, 1H), 3.86 (d, 1H), 5.51 (dd, 1H, H5), 5.82-5.89 (m, 1H, H14).
Mass Spectrum: (ESI) m/z = 683.65 (M + H).

| 66 | $R^I$ = Et<br>$R^{II}$ = H | (1S,4aR,6aS,7R,8R,10aR,10bR,12aR,14R,15R)-14-(5-amino-2H-tetrazol-2-yl)-15-[[(2S)-2-(ethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 5.85 (m, 1H, H14); 5.49 (m, 1H, H5); 3.91 (d, 1H); 3.89 (d, 1H); 3.61 (d, 1H); 3.54 (d, 1H); 3.53 (d, 1H); 3.50 (d, 1H); 3.00 (d, 1H); 2.85 (m, 1H); 2.84 (s, 1H, H7), 2.47 (m, 1H); 2.45 (dd, 1H, H13); 2.18 (m, 1H); 2.10-2.14 (m); 1.96-1.81 (m); 1.79 (m); 1.48-1.64 (m); 1.40-1.44 (m); 1.22-1.34 (m); 1.26 (t, 3H, Me); 1.20 (s, 3H, Me); 1.17 (s, 3H, Me); 1.14 (s, 3H, Me); 0.89 (d, 3H, Me); 0.89 (s, 3H, Me); 0.88 (d, 3H, Me); 0.85 (d, 3H, Me); 0.77 (d, 3H, Me); 0.76 (s, 3H, Me) and 0.74 (d, 3H, Me).
LC/MS m/z (positive ion scan) M + 1 = 683.67.

| 67 | $R^I$ = Et<br>$R^{II}$ = Me | (1S,4aR,6aS,7R,8R,10aR,10bR,12aR,14R,15R)-14-(5-amino-2H-tetrazol-2-yl)-15-[[(2S)-2-(ethylmethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD/K$_2$CO$_3$ δ (PPM) (The TFA salt of this compound exhibited doubling of some HNMR signals, possibly due to a pseudo chiral ammonium group. Neutralization with potassium carbonate resolved this HNMR effect) 5.71 (m, 1H, H14); 5.45 (m, 1H, H5); 3.82 (d, 1H); 3.65 (d, 1H); 3.56 (d, 1H); 3.50 (dd, 1H); 3.44 (d, 1H); 2.94 (d, 1H); 2.69 (s, 1H, H7), 2.46 (m, 1H); 2.36 (dd, 1H, H13); 2.28-2.34 (m); 2.06-2.11 (m); 1.98-2.03 (m); 1.72-1.91 (m); 1.54-1.64 (m); 1.40-1.50 (m); 1.34 (m); 1.24 (s, 3H, Me); 1.19 (s, 3H, Me); 0.92 (t, 3H, Me); 0.89 (d, 3H, Me); 0.88 (s, 3H, Me); 0.82 (d, 3H, Me); 0.77 (d, 3H, Me); 0.77 (s, 3H, Me); 0.75 (d, 3H, Me); 0.75 (s, 3H, Me) and 0.62 (d, 3H, Me).
LC/MS m/z (positive ion scan) M + 1 = 697.63.

| 68 | $R^I$ = n-Pr<br>$R^{II}$ = H | (1S,4aR,6aS,7R,8R,10aR,10bR,12aR,14R,15R)-14-(5-amino-2H-tetrazol-2-yl)-15-[[(2S)-2,3-dimethyl-2-(propylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.73 (d, 3H, Me), 0.76 (s, 3H, Me), 0.77 (d, 3H, Me), 0.85 (d, 3H, Me), 0.89 (d, 3H, Me), 0.90 (s, 3H, Me), 0.90 (d, 3H, Me), 1.04 (t, 3H), 1.14 (s, 3H, Me), 1.18 (s, 3H, Me), 1.20 (s, 3H, Me), 1.22-1.36 (m), 2.39-1.44 (m), 1.47-1.72 (m), 1.77-1.96 (m), 2.10-2.22 (m), 2.45 (dd, 1H, H13), 2.56 (dt, 1H), 2.70 (dt, 1H), 2.84 (s, 1H, H7), 2.98 (d, 1H), 3.50 (d, 1H), 3.52 (d, 1H), 3.53 (dd, 1H), 3.61 (d, 1H), 3.89 (d, 1H), 3.92 (d, 1H), 5.49 (dd, 1H, H5), 5.81-5.86 (m, 1H, H14).
Mass Spectrum: (ESI) m/z = 697.59 (M + H).

| 69 | $R^I$ = n-Pr<br>$R^{II}$ = Me | (1S,4aR,6aS,7R,8R,10aR,10bR,12aR,14R,15R)-14-(5-amino-2H-tetrazol-2-yl)-15-[[(2S)-2,3-dimethyl-2-(methylpropylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm; The TFA salt of this compound produced a pseudo chiral amine which exhibited doubling of some $^1$H NMR signals. Neutralization with potassium carbonate resolved this $^1$H NMR effect.) δ 0.62 (d, 3H, Me), 0.75 (s, 3H, Me), 0.75 (d, 3H, Me), 0.77 (d, 3H, Me), 0.78 (s, 3H, Me), 0.81 (t, 3H), 0.82 (d, 3H, Me), 0.88 (s, 3H, Me), 0.89 (d, 3H, Me), 1.14-1.19 (m), 1.19 (s, 3H), 1.24 (s), 1.23-1.51 (m), 1.54-1.65 (m), 1.72-1.91 (m), 1.97-2.03 (m), 2.06-2.13 (m), 2.11 (s, 3H, Me) 2.24-2.39 (m), 2.69 (s, 1H, H7), 2.95 (d, 1H), 3.31 (d, 1H, under MeOH peak), 3.44 (d, 1H), 3.50 (dd, 1H), 3.57 (d, 1H), 3.66 (d, 1H), 3.83 (d, 1H), 5.45 (dd, 1H, H5), 5.68-5.74 (m, 1H, H14).
Mass Spectrum: (ESI) m/z = 711.69 (M + H).

| 70 | $R^I$ = Et<br>$R^{II}$ = Et | (1S,4aR,6aS,7R,8R,10aR,10bR,12aR,14R,15R)-14-(5-amino-2H-tetrazol-2-yl)-15-[[(2S)-2-(diethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 5.86 (m, 1H, H14); 5.49 (m, 1H, H5); 3.90-3.92 (m); 3.60-3.64 (m); 3.50-3.56 (m); 2.99 (d, 1H); 2.86 (m); 2.84 (s, 1H, H7), 2.46 (m); 2.18 (m, 1H); 2.10-2.14 (m); 1.80-1.96 (m); 1.78 (m); 1.48-1.65 (m); 1.40-1.44 (m); 1.22-1.34 (m); 1.20 (s, 3H, Me); 1.16 (s, 3H, Me); 1.15 (s, 3H Me); 0.89 (d, 3H, Me); 0.89 (s, 3H, Me); 0.87 (d, 3H, Me); 0.85 (d, 3H, Me); 0.77 (d, 3H, Me); 0.76 (s, 3H, Me) and 0.72 (d, 3H, Me).
LC/MS m/z (positive ion scan) M + 1 = 711.69.

| 71 | $R^I$ = n-Bu<br>$R^{II}$ = H | (1S,4aR,6aS,7R,8R,10aR,10bR,12aR,14R,15R)-14-(5-amino-2H-tetrazol-2-yl)-15-[[(2S)-2-(butylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.72 (d, 3H, Me), 0.76 (s, 3H, Me), 0.77 (d, 3H, Me), 0.85 (d, 3H, Me), 0.89 (d, 3H, Me), 0.90 (s, 3H, Me), 0.90 (d, 3H, Me), 1.00 (t, 3H), 1.14 (s, 3H, Me), 1.17 (s, 3H, Me), 1.20 (s, 3H, Me), 1.22-1.35 (m), 1.37-1.68 (m), 1.78-1.96 (m), 2.09-2.22 (m), 2.45 (dd, 1H, H13), 2.53 (dt, 1H), 2.76 (dt, 1H), 2.84 (s, 1H, H7), 2.97 (d, 1H), 3.50 (d, 1H), 3.52 (d, 1H), 3.54 (dd, 1H), 3.62 (d, 1H), 3.89 (d, 1H), 3.92 (d, 1H), 5.49 (dd, 1H, H5), 5.81-5.86 (m, 1H, H14).
Mass Spectrum: (ESI) m/z = 711.61 (M + H).

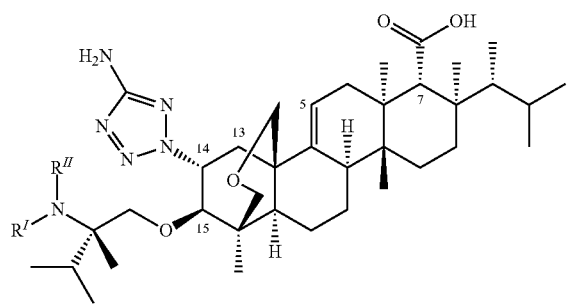

| | | |
|---|---|---|
| 72 | $R^I$ = i-Bu<br>$R^{II}$ = H | (1S,4aR,6aS,7R,8R,10aR,10bR,12aR,14R,15R)-14-(5-amino-2H-tetrazol-2-yl)-15-[[(2S)-2,3-dimethyl-2-[(2-methylpropyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.74 (d, 3H, Me), 0.76 (s, 3H, Me), 0.77 (d, 3H, Me), 0.85 (d, 3H, Me), 0.90 (d, 3H, Me), 0.90 (d, 3H, Me), 0.90 (s, 3H, Me), 1.06 (d, 3H, Me), 1.10 (d, 3H, Me), 1.14 (s, 3H, Me), 1.20 (s, 3H, Me), 1.23 (s, 3H, Me), 1.22-1.36 (m), 1.39-1.44 (m), 1.47-1.65 (m), 1.78-1.96 (m), 2.10-2.22 (m), 2.44 (dq, 2H), 2.63 (dd, 1H, H13), 2.84 (s, 1H, H7), 2.90 (d, 1H), 3.51 (d, 1H), 3.51 (d, 1H), 3.53 (dd, 1H), 3.62 (d, 1H), 3.88 (d, 1H), 3.95 (d, 1H), 5.49 (dd, 1H, H5), 5.81-5.86 (m, 1H, H14). Mass Spectrum: (ESI) m/z = 711.33 (M + H).

| | | |
|---|---|---|
| 73 | $R^I$ = i-Pentyl<br>$R^{II}$ = H | (1S,4aR,6aS,7R,8R,10aR,10bR,12aR,14R,15R)-14-(5-amino-2H-tetrazol-2-yl)-15-[[(2S)-2,3-dimethyl-2-[(3-methylbutyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.70 (d, 3H, Me), 0.76 (s, 3H, Me), 0.77 (d, 3H, Me), 0.85 (d, 3H, Me), 0.88 (d, 3H, Me), 0.90 (d, 3H, Me), 0.90 (s, 3H, Me), 0.97 (d, 3H, Me), 1.00 (d, 3H, Me), 1.14 (s, 3H, Me), 1.14 (s, 3H, Me), 1.20 (s, 3H, Me), 1.22-1.36 (m), 1.40-1.65 (m), 1.69-1.76 (m), 1.77-1.96 (m), 2.09-2.22 (m), 2.44 (dd, 1H, H13), 2.68 (dt, 1H), 2.82 (dt, 1H), 2.83 (s, 1H, H7), 2.96 (d, 1H), 3.50 (d, 1H), 3.53 (d, 1H), 3.53 (dd, 1H), 3.62 (d, 1H), 3.88 (d, 1H), 3.91 (d, 1H), 5.49 (dd, 1H, H5), 5.81-5.86 (m, 1H, H14). Mass Spectrum: (ESI) m/z = 725.68 (M + H).

| | | |
|---|---|---|
| 74 | $R^I$ = Benzyl<br>$R^{II}$ = H | (1S,4aR,6aS,7R,8R,10aR,10bR,12aR,14R,15R)-14-(5-amino-2H-tetrazol-2-yl)-15-[[(2S)-2,3-dimethyl-2-[(phenylmethyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.79 (d, 3H, Me), 0.80 (s, 3H, Me), 0.81 (d, 3H, Me), 0.88 (d, 3H, Me), 0.92 (d, 3H, Me), 0.95 (s, 3H, Me), 0.99 (d, 3H, Me), 1.18 (s, 3H, Me), 1.23 (s, 3H, Me), 1.26 (s, 3H, Me), 1.25-1.39 (m), 1.42-1.48 (m), 1.50-1.69 (m), 1.82-2.07 (m), 2.14-2.25 (m), 2.54 (dd, 1H, H13), 2.87 (s, 1H, H7), 3.02 (d, 1H), 3.54 (d, 1H), 3.59 (dd, 1H), 3.61 (d, 1H), 3.69 (d, 1H), 3.84 (d, 1H), 3.94 (d, 1H), 4.00 (d, 1H), 4.03 (d, 1H), 5.54 (dd, 1H, H5), 5.96-6.03 (m, 1H, H14), 7.45-7.52 (m), 7.53-7.57 (m). Mass Spectrum: (ESI) m/z = 745.67 (M + H).

Examples 75-89

The following compounds were prepared using methods analogous to those described in the preceding examples:

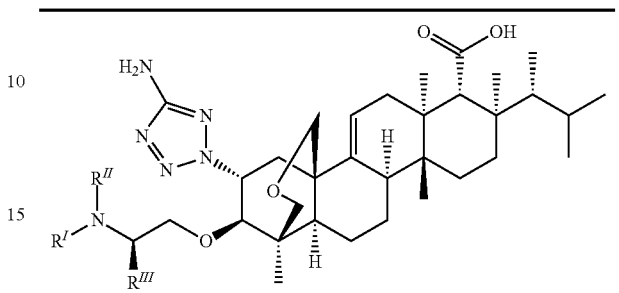

| | | |
|---|---|---|
| 75 | $R^I$ = H<br>$R^{II}$ = H<br>$R^{III}$ = n-Pr | (1S,4aR,6aS,7R,8R,10aR,10bR,12aR,14R,15R)-14-(5-amino-2H-tetrazol-2-yl)-15-[[(2R)-2-aminopentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 0.90 (t, 3H), 2.85 (s, 1H), 5.55 (m, 1H), 5.82 (m, 1H).
Mass spectrum: (ESI) m/z = 639.3 (M − H).

| | | |
|---|---|---|
| 76 | $R^I$ = Me<br>$R^{II}$ = H<br>$R^{III}$ = n-Pr | (1S,4aR,6aS,7R,8R,10aR,10bR,12aR,14R,15R)-14-(5-amino-2H-tetrazol-2-yl)-15-[[(2R)-2-(methylamino)pentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 0.92 (t, 3H), 2.57 (s, 3H), 2.85 (s, 1H), 5.52 (m, 1H), 5.83 (m, 1H).
Mass spectrum: (ESI) m/z = 653.3 (M − H).

| | | |
|---|---|---|
| 77 | $R^I$ = Me<br>$R^{II}$ = Me<br>$R^{III}$ = n-Pr | (1S,4aR,6aS,7R,8R,10aR,10bR,12aR,14R,15R)-14-(5-amino-2H-tetrazol-2-yl)-15-[[(2R)-2-(dimethylamino)pentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 0.92 (t, 3H), 2.66 (s, 3H), 2.78 (s, 3H), 2.83 (s, 1H), 5.50 (m, 1H), 5.83 (m, 1H).
Mass spectrum: (ESI) m/z = 669.3 (M + H).

| | | |
|---|---|---|
| 78 | $R^I$ = H<br>$R^{II}$ = H<br>$R^{III}$ = i-Pr | (1S,4aR,6aS,7R,8R,10aR,10bR,12aR,14R,15R)-14-(5-amino-2H-tetrazol-2-yl)-15-[[(2R)-2-amino-3-methylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 0.83 (d, 3H), 0.90 (d, 3H), 2.83 (s, 1H), 5.50 (m, 1H), 5.80 (m, 1H).
Mass spectrum: (ESI) m/z = 641.5 (M + H).

| | | |
|---|---|---|
| 79 | $R^I$ = Me<br>$R^{II}$ = H<br>$R^{III}$ = i-Pr | (1S,4aR,6aS,7R,8R,10aR,10bR,12aR,14R,15R)-14-(5-amino-2H-tetrazol-2-yl)-15-[[(2R)-3-methyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 0.83 (d, 3H), 0.92 (d, 3H), 2.60 (s, 3H), 2.84 (s, 1H), 5.51 (m, 1H), 5.84 (m, 1H).
Mass spectrum: (ESI) m/z = 655.5 (M + H).

| | | |
|---|---|---|
| 80 | $R^I$ = Me<br>$R^{II}$ = Me<br>$R^{III}$ = i-Pr | (1S,4aR,6aS,7R,8R,10aR,10bR,12aR,14R,15R)-14-(5-amino-2H-tetrazol-2-yl)-15-[[(2R)-2-(dimethylamino)-3-methylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 0.84 (d, 3H), 0.99 (d, 3H), 2.81 (s, 3H), 2.84 (s, 3H), 2.85 (s, 1H), 5.52 (m, 1H), 5.83 (m, 1H).
Mass spectrum: (ESI) m/z = 669.5 (M + H).

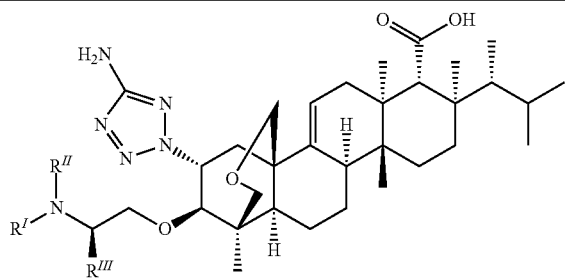

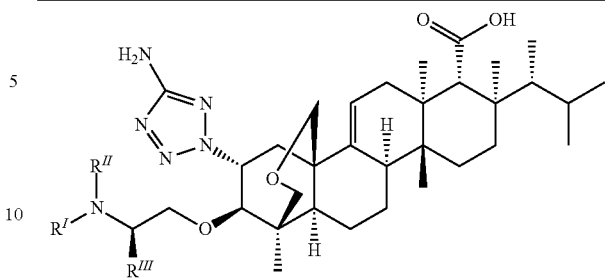

| | | |
|---|---|---|
| 81 | $R^I$ = H<br>$R^{II}$ = H<br>$R^{III}$ = c-Pr | (1S,4aR,6aS,7R,8R,10aR,10bR,12aR,14R,15R)-14-(5-amino-2H-tetrazol-2-yl)-15-[(2R)-2-amino-2-cyclopropylethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 0.20 (m, 1H), 0.35 (m, 1H), 0.58 (m, 1H), 0.62 (m, 1H), 2.83 (s, 1H), 5.50 (m, 1H), 5.80 (m, 1H).
Mass spectrum: (ESI) m/z = 639.2 (M + H).

| | | |
|---|---|---|
| 82 | $R^I$ = Me<br>$R^{II}$ = H<br>$R^{III}$ = c-Pr | (1S,4aR,6aS,7R,8R,10aR,10bR,12aR,14R,15R)-14-(5-amino-2H-tetrazol-2-yl)-15-[(2R)-2-cyclopropyl-2-(methylamino)ethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 0.23 (m, 1H), 0.43 (m, 1H), 0.62 (m, 1H), 2.60 (s, 3H), 2.83 (s, 1H), 5.52 (m, 1H), 5.83 (m, 1H).
Mass spectrum: (ESI) m/z = 653.3 (M + H).

| | | |
|---|---|---|
| 83 | $R^I$ = Me<br>$R^{II}$ = Me<br>$R^{III}$ = c-Pr | (1S,4aR,6aS,7R,8R,10aR,10bR,12aR,14R,15R)-14-(5-amino-2H-tetrazol-2-yl)-15-[(2R)-2-cyclopropyl-2-(dimethylamino)ethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 0.22 (m, 1H), 0.52 (m, 1H), 0.63 (m, 1H), 2.82 (s, 3H), 2.84 (s, 3H), 2.85 (s, 1H), 5.52 (m, 1H), 5.83 (m, 1H).
Mass spectrum: (ESI) m/z = 667.2 (M + H).

| | | |
|---|---|---|
| 84 | $R^I$ = Me<br>$R^{II}$ = H<br>$R^{III}$ = t-Bu | (1S,4aR,6aS,7R,8R,10aR,10bR,12aR,14R,15R)-14-(5-amino-2H-tetrazol-2-yl)-15-[[(2R)-3,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H), 0.86 (d, 3H), 0.90 (d, 3H), 0.91 (s, 3H), 0.93 (s, 9H), 1.16 (s, 3H), 1.22 (s, 3H), 1.23-1.67 (m), 1.79-2.05 (m), 2.14 (m, 1H), 2.19 (m, 1H), 2.34 (dd, 1H), 2.47 (dd, 1H), 2.72 (s, 1H), 2.85 (s, 1H), 3.19 (dd, 1H), 3.52 (d, 1H), 3.54 (dd, 1H), 3.62 (d, 1H), 3.74 (d, 1H), 3.78 (d, 1H), 3.84 (dd, 1H), 5.51 (m, 1H), 5.82 (m, 1H).
Mass spectrum: (ESI) m/z = 669.53 (M + H).

| | | |
|---|---|---|
| 85 | $R^I$ = Me<br>$R^{II}$ = Me<br>$R^{III}$ = t-Bu | (1S,4aR,6aS,7R,8R,10aR,10bR,12aR,14R,15R)-14-(5-amino-2H-tetrazol-2-yl)-15-[[(2R)-2-(dimethylamino)-3,3-dimethylbutyl]oxy]-8-[(1R)-1,2-dimethylpropyl]-1,6,6a,7,8,9,10,10a,10b,11,12,12a-dodecahydro-1,6a,8,10 a-tetramethyl-4H-1,4a-propano-2H-phenanthro[1,2-c]pyran-7-carboxylic acid |

$^1$H NMR (CD$_3$OD, 500 MHz, ppm) δ 0.77 (d, 3H), 0.77 (s, 3H), 0.86 (d, 3H), 0.91 (d, 3H), 0.91 (s, 3H), 0.94 (s, 9H), 1.17 (s, 3H), 1.22 (s, 3H), 1.24-1.68 (m), 1.82-2.08 (m), 2.12-2.23 (m, 2H), 2.45 (m, 1H), 2.49 (dd, 1H), 2.85 (s, 1H), 2.95 (s, 3H), 2.98 (s, 3H), 3.23 (m, 1H), 3.55 (m, 2H), 3.63 (d, 1H), 3.75 (m, 2H), 4.16 (dd, 1H), 5.52 (m, 1H), 5.82 (m, 1H).
Mass spectrum: (ESI) m/z = 683.58 (M + H).

| | | |
|---|---|---|
| 86 | $R^I$ = Et<br>$R^{II}$ = H<br>$R^{III}$ = t-Bu | (1S,4aR,6aS,7R,8R,10aR,10bR,12aR,14R,15R)-14-(5-amino-2H-tetrazol-2-yl)-15-[[(2R)-2-(ethylamino)-3,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H), 0.86 (d, 3H), 0.91 (d, 3H), 0.92 (s, 3H), 0.93 (s, 9H), 1.16 (s, 3H), 1.21 (s, 3H), 1.2-1.67 (m), 1.32 (t, 3H), 1.8-2.06 (m), 2.12-2.24 (m, 2H), 2.46 (m, 2H), 2.85 (s, 1H), 3.16-3.26 (m, 3H), 3.54 (m, 2H), 3.62 (d, 1H), 3.74 (m, 2H), 3.84 (dd, 1H), 5.51 (m, 1H), 5.80 (m, 1H).
Mass spectrum: (ESI) m/z = 683.58 (M + H).

| | | |
|---|---|---|
| 87 | $R^I$ = n-Pr<br>$R^{II}$ = H<br>$R^{III}$ = t-Bu | (1S,4aR,6aS,7R,8R,10aR,10bR,12aR,14R,15R)-14-(5-amino-2H-tetrazol-2-yl)-15-[[(2R)-3,3-dimethyl-2-(propylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (s, 3H), 0.86 (d, 3H), 0.91 (d, 3H), 0.92 (s, 3H), 0.93 (s, 9H), 1.03 (t, 3H), 1.16 (s, 3H), 1.22 (s, 3H), 1.23-1.68 (m), 1.72-2.05 (m), 2.11-2.20 (m, 2H), 2.47 (m, 2H), 2.85 (s, 1H), 3.00 (m, 1h), 3.08 (m, 1H), 3.17 (m, 1H), 3.54 (m, 2H), 3.62 (d, 1H), 3.74 (m, 2H), 3.86 (dd, 1H), 5.51 (m, 1H), 5.80 (m, 1H).
Mass spectrum: (ESI) m/z = 697.54 (M + H).

| | | |
|---|---|---|
| 88 | $R^I$ = H<br>$R^{II}$ = H<br>$R^{III}$ = Ph | (1S,4aR,6aS,7R,8R,10aR,10bR,12aR,14R,15R)-14-(5-amino-2H-tetrazol-2-yl)-15-[(2R)-2-amino-2-phenylethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 2.83 (s, 1H), 5.53 (m, 1H), 5.84 (m, 1H), 7.24-7.50 (m, 5H).
Mass spectrum: (ESI) m/z = 675.3 (M + H).

| | | |
|---|---|---|
| 89 | $R^I$ = Me<br>$R^{II}$ = Me<br>$R^{III}$ = Ph | (1S,4aR,6aS,7R,8R,10aR,10bR,12aR,14R,15R)-14-(5-amino-2H-tetrazol-2-yl)-15-[(2R)-2-(dimethylamino)-2-phenylethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 2.63 (s, 3H), 2.72 (s, 3H), 2.83 (s, 1H), 5.52 (m, 1H), 5.93 (m, 1H), 7.20-7.30 (m, 5H).
Mass spectrum: (ESI) m/z = 703.3 (M + H).

Examples 90-104

The following compounds were prepared using methods analogous to those described in the preceding examples:

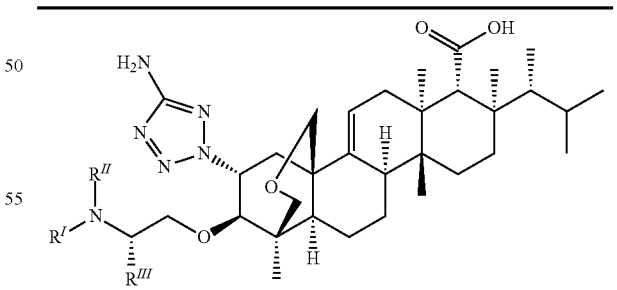

| | | |
|---|---|---|
| 90 | $R^I$ = H<br>$R^{II}$ = H<br>$R^{III}$ = n-Pr | (1S,4aR,6aS,7R,8R,10aR,10bR,12aR,14R,15R)-14-(5-amino-2H-tetrazol-2-yl)-15-[[(2S)-2-amino-pentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 0.88 (t, 3H), 2.83 (s, 1H), 5.50 (m, 1H), 5.82 (m, 1H).
Mass spectrum: (ESI) m/z = 641.3 (M + H).

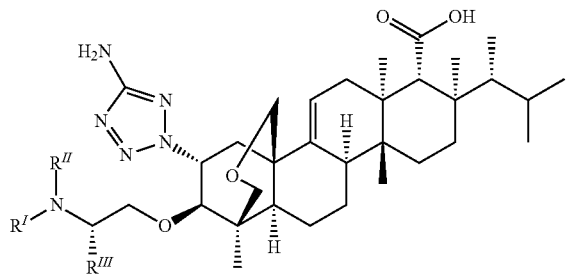
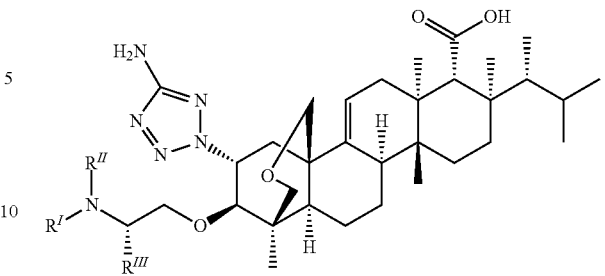

| 91 | $R^I$ = Me<br>$R^{II}$ = H<br>$R^{III}$ = n-Pr | (1S,4aR,6aS,7R,8R,10aR,10bR,12aR,14R,15R)-14-(5-amino-2H-tetrazol-2-yl)-15-[[(2S)-2-(methyl-amino)pentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm; selected resonaces) δ 0.88 (t, 3H), 2.60 (s, 3H), 2.82 (s, 1H), 5.50 (m, 1H), 5.82 (m, 1H).
Mass spectrum: (ESI) m/z = 655.3 (M + H).

| 92 | $R^I$ = Me<br>$R^{II}$ = Me<br>$R^{III}$ = n-Pr | (1S,4aR,6aS,7R,8R,10aR,10bR,12aR,14R,15R)-14-(5-amino-2H-tetrazol-2-yl)-15-[[(2S)-2-(dimethyl-amino)pentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm; selected resonaces) δ 0.88 (t, 3H), 2.63 (s, 3H), 2.80 (s, 3H), 2.84 (s, 1H), 5.52 (m, 1H), 5.84 (m, 1H).
Mass spectrum: (ESI) m/z = 669.2 (M + H).

| 93 | $R^I$ = H<br>$R^{II}$ = H<br>$R^{III}$ = i-Pr | (1S,4aR,6aS,7R,8R,10aR,10bR,12aR,14R,15R)-14-(5-amino-2H-tetrazol-2-yl)-15-[[(2S)-2-amino-3-methylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm; selected resonaces) δ 0.89 (d, 3H), 0.91 (d, 3H), 2.82 (s, 1H), 5.50 (m, 1H), 5.81 (m, 1H).
Mass spectrum: (ESI) m/z = 641.5 (M + H).

| 94 | $R^I$ = Me<br>$R^{II}$ = Me<br>$R^{III}$ = i-Pr | (1S,4aR,6aS,7R,8R,10aR,10bR,12aR,14R,15R)-14-(5-amino-2H-tetrazol-2-yl)-15-[[(2S)-2-(dimethyl-amino)-3-methylbutyl]oxy]-8-[(1R)-1,2-dimethyl-propyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm; selected resonaces) δ 0.89 (d, 3H), 0.91 (d, 3H), 2.78 (s, 3H), 2.82 (s, 3H), 2.84 (s, 1H), 5.52 (m, 1H), 5.84 (m, 1H).
Mass spectrum: (ESI) m/z = 669.5 (M + H).

| 95 | $R^I$ = H<br>$R^{II}$ = H<br>$R^{III}$ = t-Bu | (1S,4aR,6aS,7R,8R,10aR,10bR,12aR,14R,15R)-14-(5-amino-2H-tetrazol-2-yl)-15-[[(2S)-2-amino-3,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.77 (s, 3H), 0.78 (d, 3H), 0.86 (d, 3H), 0.86 (s, 3H), 0.90 (s, 9H), 0.91 (d, 3H), 1.16 (s, 3H), 1.21 (s, 3H), 1.24-1.66 (m), 1.8-2.24 (m), 2.47 (dd, 1H), 2.26 (m, 1H), 2.85 (m), 3.01 (m), 3.47 (d, 1H), 3.49 (m, 1H), 3.54 (dd, 1H), 3.62 (d, 1H), 3.70 (d, 1H), 3.88 (d, 1H), 5.51 (m, 1H), 5.85 (m, 1H).
m/z = 655.47 (M + H).

| 96 | $R^I$ = Me<br>$R^{II}$ = H<br>$R^{III}$ = t-Bu | (1S,4aR,6aS,7R,8R,10aR,10bR,12aR,14R,15R)-14-(5-amino-2H-tetrazol-2-yl)-15-[[(2S)-3,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.77 (s, 3H), 0.78 (d, 3H), 0.86 (d, 3H), 0.88 (s, 3H), 0.90 (d, 3H), 0.94 (s, 9H), 1.16 (s, 3H), 1.22 (s, 3H), 1.23-1.37 (m), 1.4-1.67 (m), 1.78-2.26 (m), 2.10-2.24 (m, 2H), 2.46 (dd, 1H), 2.73 (s, 3H), 2.85 (m), 2.90-2.96 (m, 2H), 3.49 (d, 1H), 3.54 (dd, 1H), 3.59-3.67 (m, 2H), 3.74 (d, 1H), 3.81 (d, 1H), 5.50 (m, 1H), 5.82 (m, 1H).
Mass spectrum: (ESI) m/z = 669.53 (M + H).

| 97 | $R^I$ = Et<br>$R^{II}$ = H<br>$R^{III}$ = t-Bu | (1S,4aR,6aS,7R,8R,10aR,10bR,12aR,14R,15R)-14-(5-amino-2H-tetrazol-2-yl)-15-[[(2S)-2-(ethylamino)-3,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.77 (s, 3H), 0.78 (d, 3H), 0.86 (d, 3H), 0.88 (s, 3H), 0.91 (d, 3H), 0.96 (s, 9H), 1.17 (s, 3H), 1.24-1.66 (m), 1.78-1.98 (m), 2.02-2.23 (m), 2.48 (dd, 1H), 2.85 (s, 1H), 2.86 (m, 1H), 3.02 (m, 1H), 3.04-3.2 (m, 2H), 3.50 (d, 1H), 3.53 (dd, 1H), 3.62 (d, 1H), 3.7 (m, 2H), 3.78 (d, 1H), 5.51 (m, 1H), 5.81 (m, 1H).
Mass spectrum: (ESI) m/z = 683.53 (M + H).

| 98 | $R^I$ = n-Pr<br>$R^{II}$ = H<br>$R^{III}$ = t-Bu | (1S,4aR,6aS,7R,8R,10aR,10bR,12aR,14R,15R)-14-(5-amino-2H-tetrazol-2-yl)-15-[[(2S)-3,3-dimethyl-2-(propylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.77 (s, 3H), 0.78 (d, 3H), 0.86 (d, 3H), 0.87 (s, 3H), 0.91 (d, 3H), 0.96 (s, 9H), 1.05 (t, 3H), 1.17 (s, 3H), 1.22 (s, 3H), 1.24-1.38 (m), 1.4-1.98 (m), 2.04-2.23 (m, 3H), 2.49 (dd, 1H), 2.84 (m, H), 2.85 (s, 1H), 3.0-3.08 (m, 3H), 3.50 (d, 1H), 3.54 (dd, 1H), 3.62 (d, 1H), 3.68 (d, 1H), 3.69 (d, 1H), 3.78 (d, 1H), 5.52 (m, 1H), 5.81 (m, 1H).
Mass spectrum: (ESI) m/z = 697.58 (M + H).

| 99 | $R^I$ = H<br>$R^{II}$ = H<br>$R^{III}$ = (S)-2-Bu | (1S,4aR,6aS,7R,8R,10aR,10bR,12aR,14R,15R)-14-(5-amino-2H-tetrazol-2-yl)-15-[[(2S,3S)-2-amino-3-methylpentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm; selected resonaces) δ 0.78 (m, 9H), 0.84 (m, 6H), 0.91 (m, 6H), 1.09 (s, 3H), 1.12 (s, 3H), 2.83 (s, 1H), 5.51 (m, 1H), 5.82 (m, 1H).
Mass spectrum: (ESI) m/z = 655.3 (M + H).

| 100 | $R^I$ = Me<br>$R^{II}$ = H<br>$R^{III}$ = (S)-2-Bu | (1S,4aR,6aS,7R,8R,10aR,10bR,12aR,14R,15R)-14-(5-amino-2H-tetrazol-2-yl)-15-[[(2S,3S)-3-methyl-2-(methylamino)pentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm; selected resonaces) δ 0.78 (m, 9H), 0.84 (m, 6H), 0.91 (m, 6H), 1.09 (s, 3H), 1.12 (s, 3H), 2.63 (s, 3H), 2.83 (s, 1H), 5.51 (m, 1H), 5.82 (m, 1H).
Mass spectrum: (ESI) m/z = 669.3 (M + H).

| 101 | $R^I$ = Me<br>$R^{II}$ = Me<br>$R^{III}$ = (S)-2-Bu | (1S,4aR,6aS,7R,8R,10aR,10bR,12aR,14R,15R)-14-(5-amino-2H-tetrazol-2-yl)-15-[[(2S,3S)-2-(dimethylamino)-3-methylpentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm; selected resonaces) δ 0.80 (m, 9H), 0.84 (m, 6H), 0.86 (m, 3H), 0.88 (m, 3H), 1.20 (s, 3H), 1.22 (s, 3H), 2.80 (s, 6H), 2.83 (s, 1H), 5.52 (m, 1H), 5.83 (m, 1H).
Mass spectrum: (ESI) m/z = 683.3 (M + H).

| 102 | $R^I$ = H<br>$R^{II}$ = H<br>$R^{III}$ = Ph | (1S,4aR,6aS,7R,8R,10aR,10bR,12aR,14R,15R)-14-(5-amino-2H-tetrazol-2-yl)-15-[(2S)-2-amino-2-phenylethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm; selected resonaces) δ 2.83 (s, 1H), 5.50 (m, 1H), 5.82 (m, 1H), 7.28 (m, 2H), 7.41 (m, 3H).
Mass spectrum: (ESI) m/z = 675.3 (M + H).

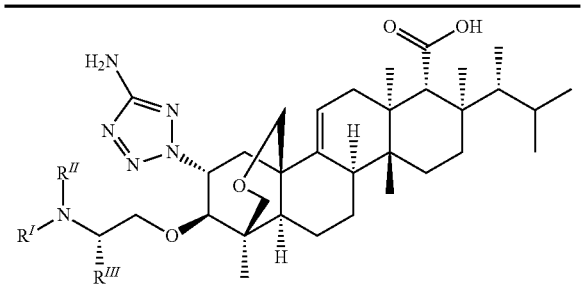

| 103 | $R^I$ = Me<br>$R^{II}$ = Me<br>$R^{III}$ = Ph | (1S,4aR,6aS,7R,8R,10aR,10bR,12aR,14R,15R)-14-(5-amino-2H-tetrazol-2-yl)-15-[(2S)-2-(dimethyl-amino)-2-phenylethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonaces) δ 2.55 (s, 3H), 2.78 (s, 3H), 2.83 (s, 1H), 5.52 (m, 1H), 5.92 (m, 1H).
Mass spectrum: (ESI) m/z = 703.4 (M + H).

Examples 104-106

The following compounds were prepared using methods analogous to those described in the preceding examples:

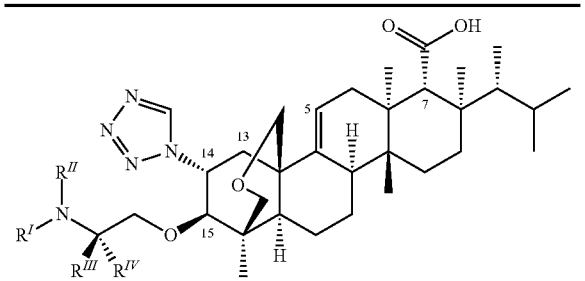

| 104 | $R^I$ = H<br>$R^{II}$ = H<br>$R^{III}$ = H<br>$R^{IV}$ = H | (1S,4aR,6aS,7R,8R,10aR,10bR,12aR,14R,15R)-15-(2-aminoethoxy)-8-[(1R)-1,2-dimethylpropyl]-14-(1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 9.28 (s, 1H, tetrazole); 5.83 (m, 1H, H14); 5.51 (dd, 1H, H5); 3.88 (d, 1H); 3.69 (d, 1H); 3.62 (d, 1H); 3.56-3.60 (m); 3.49 (d, 1H); 2.86-2.91 (m); 2.84 (s, 1H, H7); 2.76 (m); 2.68 (m); 2.55 (dd, 1H, H13); 2.18 (m, 1H); 2.16 (m, 1H); 2.09 (m, 1H); 1.82-1.96 (m); 1.48-1.65 (m); 1.43 (m); 1.23-1.28 (m); 1.21 (s, 3H, Me); 1.18 (s, 3H, Me); 0.90 (d, 3H, Me); 0.86 (s, 3H, Me); 0.85 (d, 3H, Me); 0.77 (d, 3H, Me) and 0.77 (s, 3H, Me).
Mass spectrum: (positive ion scan) m/z = 584.93 (M + H).

| 105 | $R^I$ = Me<br>$R^{II}$ = Me<br>$R^{III}$ = Me<br>$R^{IV}$ = i-Pr | (1S,4aR,6aS,7R,8R,10aR,10bR,12aR,14R,15R)-15-[[(2S)-2-(dimethylamino)-2,3-dimethylbutyl]oxy]-8-[(1R)-1,2-dimethylpropyl]-14-(1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.71 (d, 3H, Me), 0.77 (s, 3H, Me), 0.77 (d, 3H, Me), 0.85 (d, 3H, Me), 0.86 (d, 3H, Me), 0.89 (d, 3H, Me), 0.93 (s, 3H, Me), 1.15 (s, 3H, Me), 1.18 (s, 3H, Me), 1.20 (s, 3H, Me), 1.22-1.37 (m), 1.40-1.45 (m), 1.48-1.67 (m), 1.82-1.96 (m), 2.14-2.23 (m), 2.54 (dd, 1H, H13), 2.74 (s, 3H, Me), 2.76 (s, 3H, Me), 2.84 (s, 1H, H7), 3.03 (d, 1H), 3.55 (d, 1H), 3.55 (d, 1H), 3.63 (d, 1H), 3.67 (d, 1H), 3.83 (d, 1H), 3.96 (d, 1H), 5.49 (dd, 1H, H5), 5.89-5.96 (m, 1H, H14), 9.44 (s, 1H, tetrazole).
Mass Spectrum: (ESI) m/z = 668.71 (M + H).

| 106 | $R^I$ = Et<br>$R^{II}$ = H<br>$R^{III}$ = Me | (1S,4aR,6aS,7R,8R,10aR,10bR,12aR,14R,15R)-8-[(1R)-1,2-dimethylpropyl]-15-[[(2S)-2-(ethylamino)-2,3-dimethylbutyl]oxy]-14-(1H-tetrazol-1-yl)- |

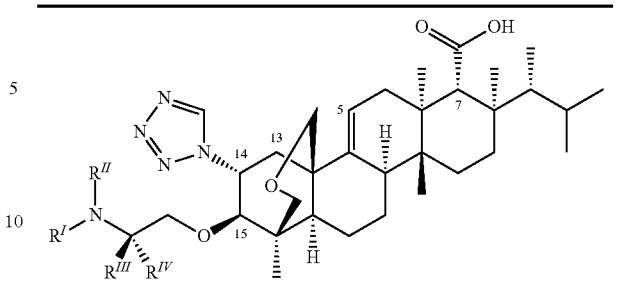

| | $R^{IV}$ = i-Pr | 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

1H NMR CD$_3$OD δ (PPM) 9.39 (s, 1H, tetrazole), 5.93 (m, 1H, H14); 5.49 (m, 1H, H5); 3.98 (d, 1H); 3.90 (d, 1H); 3.63 (d, 1H); 3.60 (d, 1H); 3.56 (dd, 1H); 3.54 (d, 2H); 2.96 (d, 1H); 2.84 (s, 1H, H7); 2.84 (m, 1H); 2.54 (dd, 1H, H13); 2.35 (m, 1H); 2.18 (m, 1H); 2.12-2.14 (m); 1.82-1.96 (m); 1.73 (m); 1.48-1.66 (m); 1.40-1.44 (m); 1.24-1.36 (m); 1.22 (t, 3H); 1.20 (s, 3H, Me); 1.15 (s, 3H, Me); 1.13 (s, 3H, Me); 0.92 (s, 3H, Me); 0.89 (d, 3H, Me); 0.86 (d, 3H, Me); 0.85 (d, 3H, Me); 0.77 (d, 3H, Me); 0.76 (s, 3H, Me) and 0.64 (d, 3H, Me).
LC/MS m/z (positive ion scan) M + 1 = 668.65.

Examples 107-109

The following compounds were prepared using methods analogous to those described in the preceding examples:

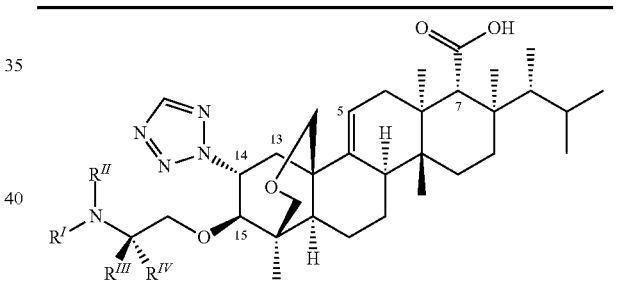

| 107 | $R^I$ = H<br>$R^{II}$ = H<br>$R^{III}$ = H<br>$R^{IV}$ = H | (1S,4aR,6aS,7R,8R,10aR,10bR,12aR,14R,15R)-15-(2-aminoethoxy)-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 8.76 (s, 1H, tetrazole); 6.14 (m, 1H, H14); 5.50 (dd, 1H, H5); 3.91 (d, 1H); 3.76 (d, 1H); 3.63 (d, 1H); 3.52-3.57 (m); 3.49 (d, 1H); 2.84-2.88 (m); 2.84 (s, 1H, H7); 2.62-2.70 (m); 2.53 (dd, 1H, H13); 2.18 (m, 1H); 2.16 (m, 1H); 2.09 (m, 1H); 1.82-1.96 (m); 1.48-1.65 (m); 1.43 (m); 1.30-1.36 (m); 1.23-1.27 (m); 1.21 (s, 3H, Me); 1.16 (s, 3H, Me); 0.89 (d, 3H, Me); 0.87 (s, 3H, Me); 0.85 (d, 3H, Me); 0.77 (d, 3H, Me) and 0.77 (s, 3H, Me).
Mass spectrum: (positive ion scan) m/z = 584.93 (M + H).

| 108 | $R^I$ = Me<br>$R^{II}$ = Me<br>$R^{III}$ = Me<br>$R^{IV}$ = i-Pr | (1S,4aR,6aS,7R,8R,10aR,10bR,12aR,14R,15R)-15-[[(2S)-2-(dimethylamino)-2,3-dimethylbutyl]oxy]-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.72 (d, 3H, Me), 0.77 (s, 3H, Me), 0.77 (d, 3H, Me), 0.85 (d, 3H, Me), 0.86 (d, 3H, Me), 0.89 (d, 3H, Me), 0.93 (s, 3H, Me), 1.14 (s, 3H, Me), 1.20 (s, 3H, Me), 1.20 (s, 3H, Me), 1.22-1.36 (m), 1.40-1.45 (m), 1.48-1.67 (m), 1.82-2.01 (m), 2.11-2.21 (m), 2.52 (dd, 1H, H13), 2.73 (s, 3H, Me), 2.77 (s, 3H, Me), 2.84 (s, 1H, H7), 2.84 (d, 1H), 3.55 (d, 3H), 3.65 (d, 1H), 3.86 (d, 1H), 3.98 (d, 1H), 5.49 (dd, 1H, H5), 6.14-6.20 (m, 1H, H14), 8.82 (s, 1H, tetrazole).
Mass Spectrum: (ESI) m/z = 668.72 (M + H).

173

-continued

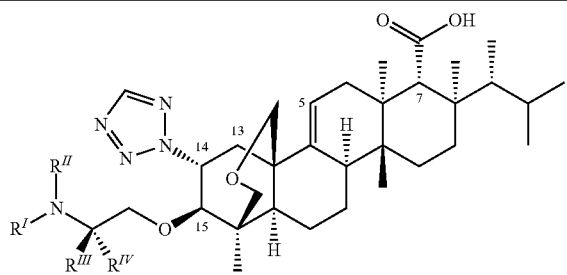

| 109 | $R^I$ = Et<br>$R^{II}$ = H<br>$R^{III}$ = Me<br>$R^{IV}$ = i-Pr | (1S,4aR,6aS,7R,8R,10aR,10bR,12aR,14R,15R)-8-[(1R)-1,2-dimethylpropyl]-15-[[(2S)-2-(ethylamino)-2,3-dimethylbutyl]oxy]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 8.81 (s, 1H, tetrazole), 6.19 (m, 1H, H14); 5.48 (m, 1H, H5); 4.20 (d, 1H); 3.95 (d, 1H); 3.63 (d, 1H); 3.65 (d, 1H); 3.56 (dd, 1H); 3.54 (d, 2H); 3.51 (d, 1H); 2.84 (s, 1H, H7); 2.78 (m); 2.52 (dd, 1H, H13); 2.27 (m, 1H); 2.18 (m, 1H); 2.12-2.14 (m); 1.82-1.97 (m); 1.72 (m); 1.48-1.66 (m); 1.40-1.44 (m); 1.24-1.36 (m); 1.25 (t, 3H); 1.20 (s, 3H, Me); 1.15 (s, 3H, Me); 1.14 (s, 3H, Me); 0.91 (s, 3H, Me); 0.89 (d, 3H, Me); 0.86 (d, 3H, Me); 0.85 (d, 3H, Me); 0.77 (d, 3H, Me); 0.76 (s, 3H, Me) and 0.66 (d, 3H, Me).
LC/MS m/z (positive ion scan) M + 1 = 668.65.

Examples 110-115

The following compounds were prepared using methods analogous to those described in the preceding examples:

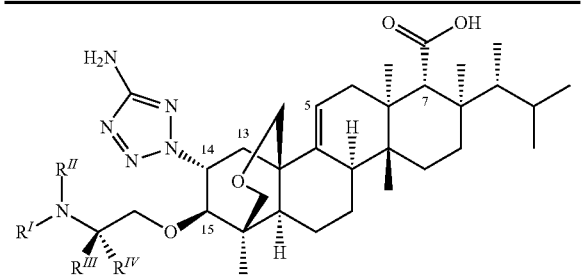

| 110 | $R^I$ = Me<br>$R^{II}$ = Me<br>$R^{III}$ = Et<br>$R^{IV}$ = Et | (1S,4aR,6aS,7R,8R,10aR,10bR,12aR,14R,15R)-14-(5-amino-2H-tetrazol-2-yl)-15-[2-(dimethylamino)-2-ethylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H), 0.83 (t, 3H), 0.86 (d, 3H), 0.90 (d, 3H), 0.90 (s, 3H), 0.91 (t, 3H), 1.16 (s, 3H), 1.21 (s, 3H), 1.24-1.66 (m), 1.78-2.0 (m), 2.13 (m, 1H), 2.19 (m, 1H), 2.47 (m, 1H), 2.72 (s, 3H), 2.81 (s, 3H), 2.84 (s, 1H), 2.92 (d, 1H), 3.53 (d, 1H), 3.54 (dd, 1H), 3.58 (d, 1H), 3.62 (d, 1H), 3.8 (m, 2H), 5.50 (m, 1H), 5.85 (m, 1H).
Mass spectrum: (ESI) m/z = 683.53 (M + H).

| 111 | $R^I$ = n-Pr<br>$R^{II}$ = H<br>$R^{III}$ = Et<br>$R^{IV}$ = Et | (1S,4aR,6aS,7R,8R,10aR,10bR,12aR,14R,15R)-14-(5-amino-2H-tetrazol-2-yl)-8-[(1R)-1,2-dimethylpropyl]-15-[2-ethyl-2-(propylamino)butoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.75 (t, 3H), 0.76 (s, 3H), 0.77 (d, 3H), 0.86 (t, 3H), 0.86 (d, 3H), 0.89 (s, 3H), 0.90 (d, 3H), 1.04 (t, 3H), 1.15 (s, 3H), 1.21 (s, 3H), 1.23-1.72 (m), 1.78-1.97 (m), 2.13 (m, 1H), 2.19 (m, 1H), 2.45 (m, 1H), 2.58 (m, 1H), 2.71 (m, 1H), 2.84 (s, 1H), 2.85 (d, 1H), 3.49-3.57 (m, 3H), 3.62 (d, 1H), 3.84-3.92 (m, 2H), 5.49 (m, 1H), 5.84 (m, 1H).
Mass spectrum: (ESI) m/z = 697.68 (M + H)

174

-continued

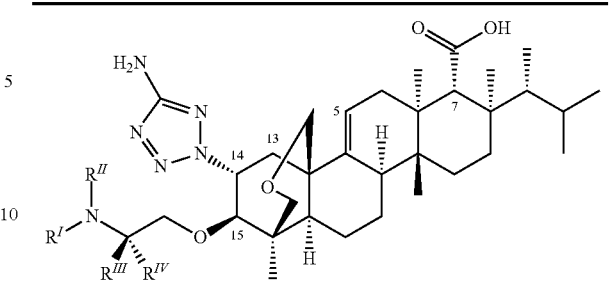

| 112 | $R^I$ = Me<br>$R^{II}$ = H<br>$R^{III}$ = Me<br>$R^{IV}$ = t-Bu | (1S,4aR,6aS,7R,8R,10aR,10bR,12aR,14R,15R)-14-(5-amino-2H-tetrazol-2-yl)-8-[(1R)-1,2-dimethylpropyl]-15-[[(2S)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H), 0.86 (d, 3H), 0.88-0.96 (m, 15H), 1.16 (s, 3H), 1.21 (s, 3H), 1.14-1.67 (m), 1.78-2.0 (m), 2.1-2.22 (m, 2H), 2.47 (dd, 1H), 2.61 (s, 3H), 2.85 (s, 1H), 2.89 (d, 1H), 3.43 (d, 1H), 3.53 (m, 2H), 3.63 (d, 1H), 3.83 (m, 2H), 5.50 (m, 1H), 5.85 (m, 1H).
Mass spectrum: (ESI) m/z = 683.49 (M + H).

| 113 | $R^I$ = H<br>$R^{II}$ = H<br>$R^{III}$ = H<br>$R^{IV}$ = H | (1S,4aR,6aS,7R,8R,10aR,10bR,12aR,14R,15R)-14-(5-amino-2H-tetrazol-2-yl)-15-[2-(dimethylamino)ethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 5.80 (m, 1H, H14); 5.50 (dd, 1H, H5); 3.87 (d, 1H); 3.64 (d, 1H); 3.60 (d, 1H); 3.55-3.59 (m); 3.53 (dd, 1H); 3.46 (d, 1H); 2.84-2.94 (m); 2.84 (s, 1H, H7); 2.73 (m); 2.45 (dd, 1H, H13); 2.18 (m, 1H); 2.13 (m, 1H); 2.02 (m, 1H); 1.76-1.96 (m); 1.48-1.65 (m); 1.42 (m); 1.23-1.34 (m); 1.21 (s, 3H, Me); 1.16 (s, 3H, Me); 0.89 (d, 3H, Me); 0.85 (s, 3H, Me); 0.85 (d, 3H, Me); 0.77 (d, 3H, Me) and 0.76 (s, 3H, Me).
Mass spectrum: (positive ion scan) m/z = 600.01 (M + H).

| 114 | $R^I$ = Me<br>$R^{II}$ = Me<br>$R^{III}$ = H<br>$R^{IV}$ = H | (1S,4aR,6aS,7R,8R,10aR,10bR,12aR,14R,15R)-14-(5-amino-2H-tetrazol-2-yl)-15-[2-(dimethylamino)ethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR CD$_3$OD δ (PPM) 5.82 (m, 1H, H14); 5.50 (dd, 1H, H5); 3.84 (d, 1H); 3.66 (d, 1H); 3.63 (m); 3.60 (d, 1H); 3.53 (dd, 1H); 3.48 (d, 1H); 3.20-3.26 (m); 2.99 (m); 2.84-2.88 (m); 2.84 (s, 1H, H7); 2.73 (s, NMe2); 2.46 (dd, 1H, H13); 2.18 (m, 1H); 2.14 (m, 1H); 2.05 (m, 1H); 1.78-1.96 (m); 1.48-1.65 (m); 1.42 (m); 1.23-1.34 (m); 1.21 (s, 3H, Me); 1.16 (s, 3H, Me); 0.89 (d, 3H, Me); 0.86 (s, 3H, Me); 0.85 (d, 3H, Me); 0.77 (d, 3H, Me) and 0.76 (s, 3H, Me).
Mass spectrum: (positive ion scan) m/z = 627.39 (M + H).

| 115 | $R^I$ = H<br>$R^{II}$ = H<br>$R^{III}$ = i-Bu<br>$R^{IV}$ = Me | (1S,4aR,6aS,7R,8R,10aR,10bR,12aR,14R,15R)-15-[[(2R)-2-amino-2,4-dimethylpentyl]oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (400 MHz, CD$_3$OD) δ 0.75-0.81 (m, 6 H) 0.85-0.91 (m, 9 H) 0.91-0.94 (m, 3 H) 1.05 (s, 3 H) 1.10-1.72 (m, 14 H) 1.74-2.04 (m, 6 H) 2.07-2.28 (m, 2 H) 2.48 (dd, J = 13.50, 6.61 Hz, 1 H) 2.73 (d, J = 9.71 Hz, 1 H) 2.86 (s, 1 H) 3.48 (d, J = 5.95 Hz, 1 H) 3.49-3.52 (m, 1 H) 3.52-3.58 (m, 1 H) 3.59-3.67 (m, 1 H) 3.78 (d, J = 10.15 Hz, 1 H) 3.94 (d, J = 11.86 Hz, 1 H) 5.52 (d, J = 5.86 Hz, 1 H) 5.86 (ddd, J = 12.25, 10.20, 6.59 Hz, 1 H). LC/MS 669 (M + H$^{1+}$).
Mass spectrum: (ESI) m/z = 669 (M + H).

Examples 116-129

The following compounds were prepared using methods analogous to those described in the preceding examples:

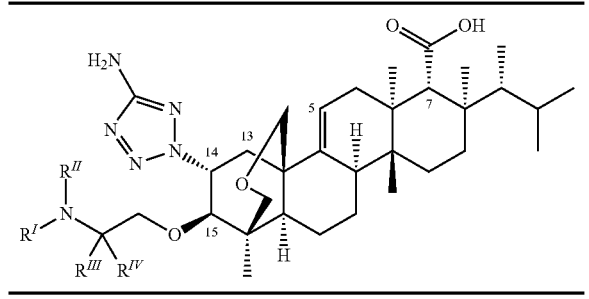

116 $R^I$ = H
$R^{II}$ = H
$R^{III}$ = n-Pentyl
$R^{IV}$ = Me (1S,4aR,6aS,7R,8R,10aR,10bR,12aR,14R,15R)-15-[(2-amino-2-methylheptyl)oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (acetate salt)

1H NMR (400 MHz, METHANOL-d$_4$) δ 0.75-0.79 (m, 6 H) 0.85 (s, 1 H) 0.86 (br. s., 3 H) 0.87 (d, J = 2.73 Hz, 3 H) 0.89 (s, 3 H) 0.91 (d, J = 1.76 Hz, 3 H) 0.99 (s, 1 H) 1.12 (s, 1 H) 1.14-1.17 (m, 3 H) 1.16 (d, J = 1.76 Hz, 3 H) 1.21 (s, 3 H) 1.23-1.37 (m, 9 H) 1.42 (d, J = 13.47 Hz, 1 H) 1.46-1.55 (m, 1 H) 1.59 (d, J = 0.78 Hz, 2 H) 1.82 (br. s., 4 H) 1.97 (br. s., 2 H) 2.13 (d, J = 11.91 Hz, 1 H) 2.44 (dd, J = 11.52, 6.64 Hz, 1 H) 2.65 (d, J = 9.57 Hz, 0 H) 2.76 (d, J = 9.57 Hz, 0 H) 2.83 (s, 1 H) 3.35-3.44 (m, 1 H) 3.45-3.48 (m, 1 H) 3.52 (d, J = 18.94 Hz, 1 H) 3.59-3.64 (m, 1 H) 3.77 (d, J = 10.54 Hz, 1 H) 3.90 (d, J = 11.71 Hz, 1 H) 5.50 (br. s., 1 H) 5.83 (br. s., 1 H).
Mass spectrum: (ESI) m/z = 683 (M + H).

117 $R^I$ = Me
$R^{II}$ = Me
$R^{III}$ = n-Pentyl
$R^{IV}$ = Me (1S,4aR,6aS,7R,8R,10aR,10bR,12aR,14R,15R)-14-(5-amino-2H-tetrazol-2-yl)-15-[[2-(dimethylamino)-2-methylheptyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (acetate salt)

1H NMR (400 MHz, METHANOL-d$_4$) δ 0.74-0.78 (m, 6 H) 0.85 (d, J = 6.64 Hz, 3 H) 0.89 (d, J = 2.15 Hz, 6 H) 0.92 (s, 3 H) 0.95 (d, J = 1.16 (s, 3 H) 1.21 (s, 3 H) 1.24-1.26 (m, 4 H) 1.27-1.37 (m, 9 H) 1.43 (br. s., 2 H) 1.52 (d, J = 16.40 Hz, 3 H) 1.60 (d, J = 8.79 Hz, 3 H) 1.82 (br. s., 3 H) 1.92 (br. s., 2 H) 1.97 (br. s., 0 H) 2.12 (d, J = 11.91 Hz, 1 H) 2.20 (d, J = 6.44 Hz, 1 H) 2.45 (dd, J = 13.76, 6.74 Hz, 1 H) 2.55 (s, 3 H) 2.61 (s, 3 H) 2.82 (s, 1 H) 2.87 (d, J = 10.93 Hz, 0 H) 2.94 (d, J = 10.74 Hz, 0 H) 3.12 (d, J = 1.76 Hz, 0 H) 3.46-3.52 (m, 1 H) 3.55 (d, J = 1.56 Hz, 1 H) 3.58-3.64 (m, 1 H) 3.82 (d, J = 9.57 Hz, 0 H) 3.84-3.90 (m, 1 H) 5.49 (d, J = 5.86 Hz, 1 H) 5.74-5.92 (m, 1 H).
Mass spectrum: (ESI) m/z = 711 (M + H).

118 $R^I$ = Et
$R^{II}$ = Et
$R^{III}$ = n-Pentyl
$R^{IV}$ = Me (1S,4aR,6aS,7R,8R,10aR,10bR,12aR,14R,15R)-14-(5-amino-2H-tetrazol-2-yl)-15-[[2-(diethylamino)-2-methylheptyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (free base)

1H NMR (400 MHz, METHANOL-d$_4$) δ 0.73-0.78 (m, 6 H) 0.85 (d, J = 6.64 Hz, 3 H) 0.87-0.89 (m, 6 H) 0.89-0.91 (m, 3 H) 0.98-1.05 (m, 4 H) 1.04 (s, 1 H) 1.14 (s, 3 H) 1.20 (s, 3 H) 1.22-1.37 (m, 11 H) 1.37-1.54 (m, 5 H) 1.54-1.71 (m, 5 H) 1.77-1.98 (m, 6 H) 2.15 (br. s., 1 H) 2.16-2.23 (m, 5 H) 2.44 (dt, J = 13.67, 6.69 Hz, 1 H) 2.56 (dd, J = 11.42, 7.13 Hz, 1 H) 2.65-2.75 (m, 2 H) 2.80 (d, J = 10.54 Hz, 1 H) 2.84 (s, 1 H) 3.42-3.56 (m, 3 H) 3.58-3.67 (m, 1 H) 3.84 (d, J = 9.76 Hz, 1 H) 3.86-3.91 (m, 1 H) 5.48 (ddd, J = 3.71, 1.76, 1.56 Hz, 1 H) 5.82 (ddd, J = 12.15, 10.01, 6.54 Hz, 1 H).
Mass spectrum: (ESI) m/z = 739 (M + H).

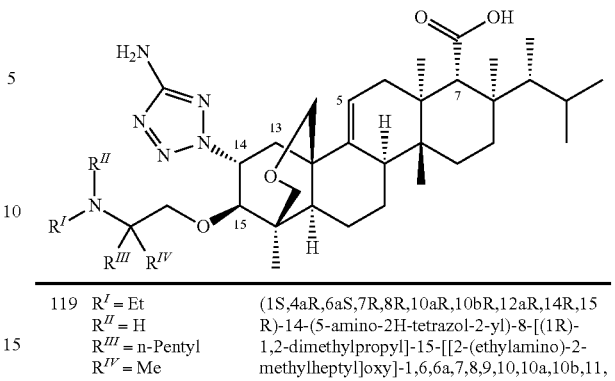

119 $R^I$ = Et
$R^{II}$ = H
$R^{III}$ = n-Pentyl
$R^{IV}$ = Me (1S,4aR,6aS,7R,8R,10aR,10bR,12aR,14R,15R)-14-(5-amino-2H-tetrazol-2-yl)-8-[(1R)-1,2-dimethylpropyl]-15-[[2-(ethylamino)-2-methylheptyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (acetate salt)

1H NMR (400 MHz, METHANOL-d$_4$) δ 0.73-0.78 (m, 6 H) 0.85 (d, J = 6.64 Hz, 3 H) 0.89 (d, J = 1.95 Hz, 6 H) 0.90-0.92 (m, 3 H) 0.99 (s, 1 H) 1.15 (s, 3 H) 1.21 (s, 3 H) 1.23-1.42 (m, 15 H) 1.45-1.73 (m, 3 H) 1.86 (br. s., 3 H) 1.93 (s, 5 H) 2.08-2.17 (m, 1 H) 2.20 (d, J = 6.64 Hz, 1 H) 2.46 (d, J = 13.47 Hz, 1 H) 2.55 (dd, J = 11.91, 7.03 Hz, 1 H) 2.73-2.86 (m, 2 H) 2.92 (d, J = 10.35 Hz, 1 H) 3.44-3.57 (m, 3 H) 3.58-3.67 (m, 1 H) 3.80-3.94 (m, 2 H) 5.49 (d, J = 5.47 Hz, 1 H) 5.75-5.90 (m, 1 H).
Mass spectrum: (ESI) m/z = 711 (M + H).

120 $R^I$ = n-Pr
$R^{II}$ = H
$R^{III}$ = n-Pentyl
$R^{IV}$ = Me (1S,4aR,6aS,7R,8R,10aR,10bR,12aR,14R,15R)-14-(5-amino-2H-tetrazol-2-yl)-8-[(1R)-1,2-dimethylpropyl]-15-[[2-methyl-2-(propylamino)heptyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (acetate salt)

1H NMR (400 MHz, METHANOL-d$_4$) δ 0.74-0.78 (m, 6 H) 0.85 (d, J = 6.64 Hz, 3 H) 0.88 (d, J = 5.86 Hz, 3 H) 0.90 (d, J = 1.76 Hz, 3 H) 0.99 (s, 3 H) 1.03 (t, J = 7.32 Hz, 3 H) 1.15 (s, 3 H) 1.21 (s, 3 H) 1.25-1.38 (m, 10 H) 1.52 (d, J = 14.06 Hz, 4 H) 1.57-1.68 (m, 5 H) 1.85 (d, J = 4.88 Hz, 4 H) 1.90 (s, 5 H) 2.12 (d, J = 15.23 Hz, 1 H) 2.21 (d, J = 6.44 Hz, 1 H) 2.44 (t, J = 13.96 Hz, 1 H) 2.54 (d, J = 12.10 Hz, 1 H) 2.63-2.74 (m, 1 H) 2.79 (d, J = 10.54 Hz, 1 H) 2.82 (s, 1 H) 3.41-3.58 (m, 3 H) 3.64 (d, J = 11.91 Hz, 0 H) 3.79-3.93 (m, 1 H) 5.48 (s, 1 H) 5.82 (dd, J = 12.10, 6.44 Hz, 1 H).
Mass spectrum: (ESI) m/z = 725 (M + H).

121 $R^I$ = Me
$R^{II}$ = Me
$R^{III}$ = i-Pr
$R^{IV}$ = Et (1S,4aR,6aS,7R,8R,10aR,10bR,12aR,14R,15R)-14-(5-amino-2H-tetrazol-2-yl)-15-[2-(dimethylamino)-2-ethyl-3-methylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid Mass spectrum: (ESI) m/z = 698 (M + H).

122 $R^I$ = H
$R^{II}$ = H
$R^{III}$ = CH$_2$CH$_2$OH
$R^{IV}$ = Me (1S,4aR,6aS,7R,8R,10aR,10bR,12aR,14R,15R)-15-(2-amino-4-hydroxy-2-methylbutoxy)-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid Mass spectrum: (ESI) m/z = 657.57 (M + H).

123 $R^I$ = H
$R^{II}$ = H
$R^{III}$ = CH$_2$CH$_2$OMe
$R^{IV}$ = Me (1S,4aR,6aS,7R,8R,10aR,10bR,12aR,14R,15R)-15-(2-amino-4-methoxy-2-methylbutoxy)-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid Mass spectrum: (ESI) m/z = 671.59 (M + H).

124 $R^I$ = Me
$R^{II}$ = H
$R^{III}$ = CH$_2$CH$_2$OMe
$R^{IV}$ = Me (1S,4aR,6aS,7R,8R,10aR,10bR,12aR,14R,15R)-14-(5-amino-2H-tetrazol-2-yl)-8-[(1R)-1,2-dimethylpropyl]-15-[4-methoxy-2-methyl-2-(methylamino)butoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid Mass spectrum: (ESI) m/z = 685.72 (M + H).

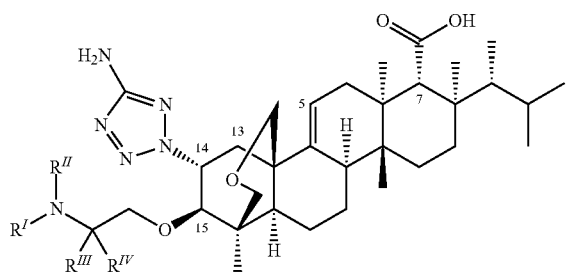

| 125 | $R^I$ = Me<br>$R^{II}$ = Me<br>$R^{III}$ = CH$_2$CH$_2$OMe<br>$R^{IV}$ = Me | (1S,4aR,6aS,7R,8R,10aR,10bR,12aR,14R,15R)-14-(5-amino-2H-tetrazol-2-yl)-15-[2-(dimethylamino)-4-methoxy-2-methylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|
| | Mass spectrum: (ESI) m/z = 699.54 (M + H). | |
| 126 | $R^I$ = Et<br>$R^{II}$ = H<br>$R^{III}$ = CH$_2$CH$_2$OMe<br>$R^{IV}$ = Me | (1S,4aR,6aS,7R,8R,10aR,10bR,12aR,14R,15R)-14-(5-amino-2H-tetrazol-2-yl)-8-[(1R)-1,2-dimethylpropyl]-15-[2-(ethylamino)-4-methoxy-2-methylbutoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
| | Mass spectrum: (ESI) m/z = 699.73 (M + H). | |
| 127 | $R^I$ = Et<br>$R^{II}$ = Me<br>$R^{III}$ = CH$_2$CH$_2$OMe<br>$R^{IV}$ = Me | (1S,4aR,6aS,7R,8R,10aR,10bR,12aR,14R,15R)-14-(5-amino-2H-tetrazol-2-yl)-8-[(1R)-1,2-dimethylpropyl]-15-[2-(ethylmethylamino)-4-methoxy-2-methylbutoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
| | Mass spectrum: (ESI) m/z = 713.42 (M + H). | |
| 128 | $R^I$ = Et<br>$R^{II}$ = Et<br>$R^{III}$ = CH$_2$CH$_2$OMe<br>$R^{IV}$ = Me | (1S,4aR,6aS,7R,8R,10aR,10bR,12aR,14R,15R)-14-(5-amino-2H-tetrazol-2-yl)-15-[2-(diethylamino)-4-methoxy-2-methylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
| | Mass spectrum: (ESI) m/z = 727.79 (M + H). | |
| 129 | $R^I$ = Me<br>$R^{II}$ = H<br>$R^{III}$ = CH$_2$CH$_2$F<br>$R^{IV}$ = Me | (1S,4aR,6aS,7R,8R,10aR,10bR,12aR,14R,15R)-14-(5-amino-2H-tetrazol-2-yl)-8-[(1R)-1,2-dimethylpropyl]-15-[4-fluoro-2-methyl-2-(methylamino)butoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
| | Mass spectrum: (ESI) m/z = 673.73 (M + H). | |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound of Formula (I):

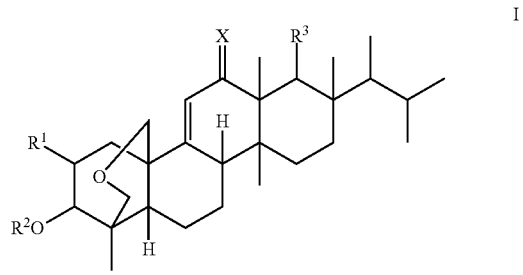

or a pharmaceutically acceptable salt thereof, wherein:
$R^1$ is a group of the following structure:

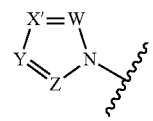

wherein W, X', Y, and Z are independently selected from N and CR$^e$ provided that only one of W, X', Y and Z is CR$^e$;
R$^e$ is independently selected from the group consisting of:
a) H;
b) Halogen;
c) NR$^f$R$^g$;
d) NHC(O)R$^o$;
e) NHC(O)NR$^f$R$^g$;
f) NHC(O)OR$^o$;
g) NO$_2$
h) OR$^o$;
i) SR$^o$;
j) SO$_2$R$^o$;
k) SO$_2$N(R$^o$)$_2$;
l) CN;
m) C(O)R$^o$;
n) C(O)OR$^o$;
o) C(O)NR$^f$R$^g$;
p) C(=NR$^o$)N(R$^o$)$_2$;
q) C$_1$-C$_6$-alkyl optionally substituted with 1 to 3 substituents independently selected from phenyl, pyridyl, OR$^o$, N(R$^o$)$_2$, CO$_2$R$^o$, C(O)N(R$^o$)$_2$ or halogen;
r) C$_2$-C$_6$-alkenyl optionally substituted with 1 to 3 substituents independently selected from phenyl, OR$^o$, N(R$^o$)$_2$, CO$_2$R$^o$, C(O)N(R$^o$)$_2$ or halogen;
s) C$_3$-C$_6$-cycloalkyl, optionally substituted with oxo, OR$^o$, N(R$^o$)$_2$, CO$_2$R$^o$ or C(O)N(R$^o$)$_2$;
t) heterocyclyl, wherein the heterocyclyl is a 4- to 6-membered saturated or unsaturated non-aromatic ring having 1, 2 or 3 heteroatoms selected from N, O or S, attached through a carbon or nitrogen on the ring, and optionally substituted on a ring carbon with 1 to 2 substituents independently selected from N(R$^o$)$_2$, imino, oxo, OR$^o$, CO$_2$R$^o$, C(O)N(R$^o$)$_2$ and C$_1$-C$_6$-alkyl unsubstituted or substituted with 1 to 3 substituents independently selected from N(R$^o$)$_2$, OR$^o$, CO$_2$R$^o$, C(O)N(R$^o$)$_2$ and halogen; the heterocyclyl may also be optionally substituted on a ring nitrogen atom that is not the point of attachment with C(O)R$^o$, CO$_2$R$^o$, C(O)N(R$^o$)$_2$, SO$_2$R$^o$ or C$_1$-C$_6$ alkyl unsubstituted or substituted with 1 to 3 substituents independently selected from N(R$^o$)$_2$, OR$^o$, $CO_2R^o$, $C(O)N(R^o)_2$ and halogen; the heterocyclyl may also be optionally substituted on a sulfur atom with 1 or 2 oxo groups;

u) aryl, wherein aryl is phenyl or naphthyl and aryl is unsubstituted or substituted with 1 or 2 substituents independently selected from halogen, $N(R^o)_2$, $OR^o$, $CO_2R^o$, CN, $C(O)N(R^o)_2$, $C(=NR^o)N(R^o)_2$, heterocyclyl as defined above, phenyl, pyridyl, and $C_1$-$C_6$-alkyl wherein said alkyl is optionally substituted with 1 to 3 substituents independently selected from $NR^o_2$, $OR^o$, or halogen;

v) heteroaryl, wherein heteroaryl is a 5- or 6-membered monocyclic aromatic ring or 9- or 10-membered bicyclic aromatic ring having 1, 2 or 3 heteroatoms selected from N, O or S, attached through a ring carbon or nitrogen, and optionally substituted on a ring carbon that is not the point of attachment, with 1 or 2 substituents independently selected from halogen, $CF_3$, $NR^fR^g$, $NHC(O)R^o$, $OR^o$, $CO_2R^o$, $CON(R^o)_2$, $C(=NR^o)N(R^o)_2$, CN, heterocyclyl as defined above, phenyl, pyridyl, and $C_1$-$C_6$ alkyl unsubstituted or substituted with 1 or 2 substituents independently selected from $N(R^o)_2$ and $OR^o$; the heteroaryl may also be optionally substituted on a ring nitrogen atom that is not the point of attachment with O or $C_1$-$C_6$ alkyl;

$R^f$ is H, $C_1$-$C_6$-alkyl, $C_3$-$C_6$-cycloalkyl or phenyl;

$R^g$ is H or $C_1$-$C_6$-alkyl optionally substituted with 1 to 3 substituents independently selected from phenyl, $OR^o$, $N(R^o)_2$ or halogen;

$R^f$ and $R^g$ are optionally taken together with the attached nitrogen atom to form a 3-to 7-membered ring having 0-1 additional heteroatoms independently selected from N, O and S wherein said ring may be optionally substituted on a ring nitrogen atom that is not the point of attachment with $C(O)R^o$, $CO_2R^o$, $C(O)N(R^o)_2$, $SO_2R^o$, or $C_1$-$C_6$ alkyl unsubstituted or substituted with 1 or 2 substituents independently selected from $N(R^o)_2$, $OR^o$, $CO_2R^o$, $C(O)N(R^o)_2$ or halogen; said ring may also be optionally substituted on a sulfur atom with 1 or 2 oxo groups;

$R^2$ is a group of the following structure:

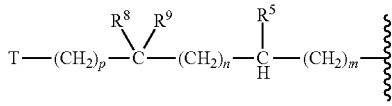

m is 0 or 1;
n is 0 or 1;
p is 0 or 1;
T is $NR^6R^7$ or $OR^{10}$;

$R^5$ is H or $C_1$-$C_6$-alkyl, unsubstituted or substituted with 1 or 2 substituents independently selected from $N(R^o)_2$ and $OR^o$;

$R^6$ is H, $C_1$-$C_6$-alkyl or $C_3$-$C_6$cycloalkyl;

$R^7$ is
a) H;
b) $C_1$-$C_6$-alkyl, unsubstituted or substituted with 1 or 2 substituents independently selected from $N(R^o)_2$, $OR^o$, $CO_2R^o$, $OC(O)R^o$, $NHC(O)R^o$, $C(O)N(R^o)_2$, phenyl, heteroaryl, and heterocyclyl, wherein heteroaryl and heterocyclyl are as defined above in the definition of $R^e$;
c) $C_3$-$C_6$-cycloalkyl;
d) $C(O)R^o$;
e) $C(O)OC_1$-$C_6$-alkyl;
f) $C(O)NHR^o$;
g) $C(=NH)R^o$;
h) $C(=NR^o)NHR^o$;

$R^6$ and $R^7$ are optionally taken together with the attached nitrogen atom to form a 4-to 7-membered saturated, unsaturated or aromatic ring having 0 or 1 additional heteroatoms independently selected from N, O and S, wherein said ring is optionally substituted on a ring carbon with 1 to 2 substituents independently selected from halogen, $CF_3$, $N(R^o)_2$, $OR^o$, $CO_2R^o$, $C(O)N(R^o)_2$, and $C_1$-$C_6$ alkyl unsubstituted or substituted with 1 or 2 substituents independently selected from $OR^o$ and $N(R^o)_2$; said ring may also be optionally substituted on a ring nitrogen atom that is not the point of attachment with $C(O)R^o$, $CO_2R^o$, $C(O)N(R^o)_2$, $SO_2R^o$ or $C_1$-$C_6$ alkyl unsubstituted or substituted with 1 to 3 substituents independently selected from $N(R^o)_2$, $OR^o$, $CO_2R^o$, $C(O)N(R^o)_2$ and halogen; said ring may also be optionally substituted on a sulfur atom with 1 or 2 oxo groups;

$R^6$ and $R^8$ are optionally taken together to form, with the intervening atoms, a 4- to 7-membered saturated ring having 0 or 1 additional heteroatoms independently selected from N, O and S wherein said ring is optionally substituted as defined above for $R^6$ and $R^7$ when joined together to form a ring;

$R^6$ and $R^5$ are optionally taken together to form, with the intervening atoms, a 4- to 7-membered saturated ring having 0 or 1 additional heteroatoms independently selected from N, O and S wherein said ring is optionally substituted as defined above for $R^6$ and $R^7$ when joined together to form a ring;

$R^8$ is selected from the group consisting of
a) hydrogen,
b) $C_1$-$C_6$-alkyl, unsubstituted or substituted with F, $OR^o$, $N(R^o)_2$, or $SO_2R^o$,
c) $C_3$-$C_6$-cycloalkyl,
d) $C_4$-$C_7$-cycloalkyl-alkyl,
e) aryl, wherein aryl is phenyl or naphthyl and said aryl is unsubstituted or substituted with 1 to 3 substituents selected from $C_1$-$C_6$-alkyl, halogen, $OCF_3$, $CF_3$, $N(R^o)_2$ and $OR^o$, and
f) heteroaryl, wherein heteroaryl is as defined above in the definition of $R^e$;

$R^9$ is H, or $C_1$-$C_6$-alkyl, unsubstituted or substituted with $OR^o$ or $SO_2R^o$;

$R^8$ and $R^9$ are optionally taken together to form a 3- to 7-membered saturated ring having 0 or 1 additional heteroatoms independently selected from N, O, and S, wherein said ring is optionally substituted as defined above for $R^6$ and $R^7$ when joined to form a ring;

$R^{10}$ is selected from the group consisting of
a) H,
b) $C_1$-$C_6$-alkyl, unsubstituted or substituted with 1 or 2 substituents selected from $N(R^o)_2$, $OR^o$, $CO_2R^o$, $OC(O)R^o$, $NHC(O)R^o$, $C(O)N(R^o)_2$, phenyl, heteroaryl, and heterocyclyl, wherein heteroaryl and heterocyclyl are as defined above in the definition of $R^e$,
c) $C_3$-$C_6$-cycloalkyl,
d) $C(O)R^o$,
e) $C(O)NHR^o$, $R^3$ is $C(O)R^{14}$;
$R^{14}$ is OH, $OR^{15}$ or $N(R^o)_2$;
$R^{15}$ is $C_1$-$C_6$-alkyl, unsubstituted or substituted with 1 or 2 substituents independently selected from phenyl and $OC(O)R^o$, wherein said phenyl is optionally substituted with 1 to 3 $OR^o$ groups;

X is O or H, H;

each $R^0$ is independently H, $C_1$-$C_6$ alkyl, $C_3$-$C_6$ cycloalkyl or benzyl.

2. The compound of claim 1, wherein $R^3$ is C(O)OH.

3. The compound of claim 2, wherein the compound is of Formula Ia, or a pharmaceutically acceptable salt thereof:

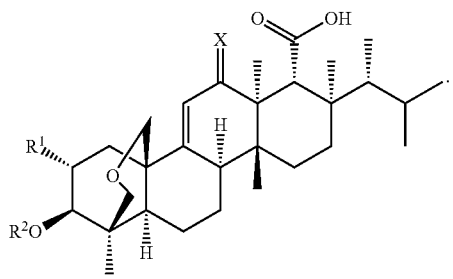

Ia

4. The compound of claim 1, wherein X is H, H.
5. The compound of claim 1, wherein X is O.
6. The compound of claim 1, wherein T is $OR^{10}$.
7. The compound of claim 1, wherein T is $NR^6R^7$.
8. The compound of claim 7, wherein $R^2$ is

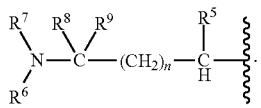

9. The compound of claim 7, wherein $R^2$ is

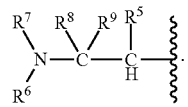

10. The compound of claim 9, wherein $R^2$ is

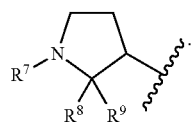

11. The compound of claim 7, wherein $R^2$ is

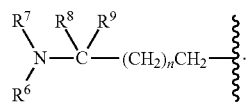

12. The compound of claim 7, wherein $R^2$ is

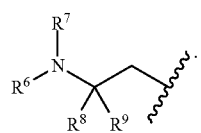

13. The compound of claim 12, wherein $R^2$ is

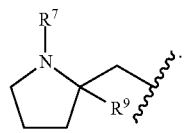

14. The compound of claim 7, wherein $R^2$ is

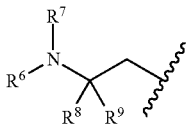

and wherein
$R^6$ is H or $C_1$-$C_3$-alkyl;
$R^7$ is H or methyl;
$R^8$ is $C_1$-$C_5$-alkyl, $C_3$-$C_5$ cycloalkyl or $C_4$-$C_6$ cycloalkyl-alkyl;
$R^9$ is H or $C_1$-$C_3$-alkyl;
or $R^8$ and $R^9$ are optionally taken together to form a 5- to 6-membered saturated ring having 0-1 heteroatom selected from O or S.

15. The compound of claim 7, wherein $R^2$ is

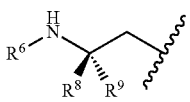

wherein
$R^6$ is H, methyl, ethyl or n-propyl;
$R^8$ is ethyl, i-propyl, t-butyl or 1-methylcyclopropyl;
$R^9$ is methyl or ethyl;
or $R^8$ and $R^9$ are optionally taken together to form a 6-membered saturated ring containing 0 or 1 oxygen atoms.

16. The compound of claim 1, wherein $R^2$ is selected from the group consisting of:

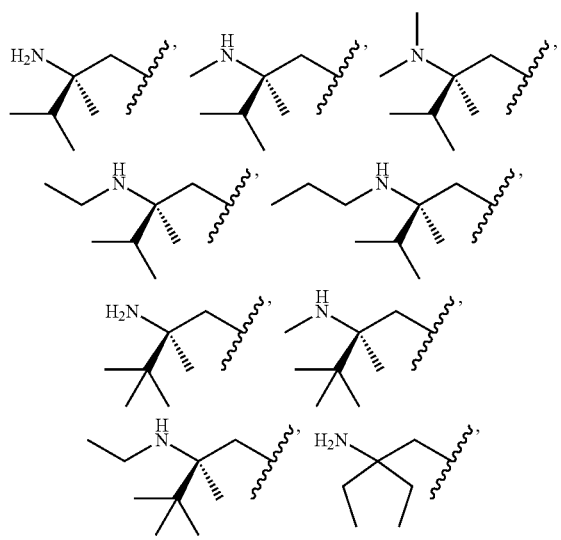

-continued

17. The compound of claim 1, wherein $R^1$ is

18. The compound of claim 1, wherein $R^1$ is

19. The compound of claim 18, wherein $R^e$ is independently selected from the group consisting of:
   a) H;
   b) $NR^fR^g$;
   c) $NHC(O)R^o$;
   d) $NHC(O)NR^fR^g$;
   e) $NHC(O)OR^o$;
   f) $OR^o$;
   g) $C(O)R^o$;
   h) $C(O)OR^o$;
   i) $C(O)NR^fR^g$;
   j) $C_1$-$C_6$-alkyl optionally substituted with phenyl, pyridyl, $OR^o$, $N(R^o)_2$, $CO_2R^o$, $C(O)N(R^o)_2$, or halogen; and
   k) $C_3$-$C_6$-cycloalkyl, optionally substituted with oxo, $OR^o$, $N(R^o)_2$, $CO_2R^o$ or $C(O)N(R^o)_2$.

20. The compound of claim 18, wherein $R^e$ is hydrogen or $NR^fR^g$.

21. The compound according to claim 18, wherein $R^1$ is

22. The compound according to claim 1 having formula (II):

or a pharmaceutically acceptable salt thereof, wherein:
   X is O or H, H;
   $R^e$ is hydrogen or $NR^fR^g$;
   $R^f$ and $R^g$ are each independently hydrogen or methyl;
   $R^6$ and $R^7$ are each independently hydrogen or $C_1$-$C_4$ alkyl;
   $R^8$ is $C_1$-$C_4$ alkyl, $C_3$-$C_4$ cycloalkyl or $C_4$-$C_5$ cycloalkyl-alkyl;
   $R^9$ is methyl or ethyl;
   or $R^8$ and $R^9$ are optionally taken together to form a 5- to 6-membered saturated ring having 0-1 heteroatom selected from O or S.

23. The compound according to claim 22, wherein X is H, H.

24. The compound according to claim 22, wherein $R^e$ is $NH_2$ or hydrogen.

25. The compound according to claim 24, wherein $R^e$ is $NH_2$.

26. The compound according to claim 22, wherein $R^8$ is $C_1$-$C_4$ alkyl and $R^9$ is methyl.

27. The compound according to claim 22, wherein $R^8$ is isopropyl or t-butyl, and $R^9$ is methyl.

28. The compound according to claim 22, wherein $R^6$ and $R^7$ are independently hydrogen or methyl.

29. The compound according to claim 22, wherein $R^6$ is hydrogen, methyl, ethyl or n-propyl, and $R^7$ is hydrogen.

30. The compound according to claim 1, wherein the compound is selected from the group consisting of:
   (1S,4aR,6aS,7R,8R,10aR,10bR,12aR,14R,15R)-15-(2-amino-2-methylpropoxy)-8-[(1R)-1,2-dimethylpropyl]-14-(1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;
   (1S,4aR,6aS,7R,8R,10aR,10bR,12aR,14R,15R)-15-(2-amino-2-methylpropoxy)-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;
   (1S,4aR,6aS,7R,8R,10aR,10bR,12aR,14R,15R)-15-(2-amino-2,3-dimethylbutoxy)-8-[(1R)-1,2-dimethylpropyl]-14-(1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;
   (1S,4aR,6aS,7R,8R,10aR,10bR,12aR,14R,15R)-15-(2-amino-2,3-dimethylbutoxy)-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-
[[(2R)-2-(dimethylamino)-2,3-dimethylbutyl]oxy]-8-
[(1R)-1,2-dimethylpropyl]-14-(1H-tetrazol-1-yl)-1,6,
6a,7,8,9,10,10a,10b,11,12,12a-dodecahydro-1,6a,8,
10a-tetramethyl-4H-1,4a-propano-2H-phenanthro[1,2-
c]pyran-7-carboxylic acid;

(1S,4aR,6aS,7R,8R,10aR,10bR,12aR,14R,15R)-15-
[[(2R)-2-(dimethylamino)-2,3-dimethylbutyl]oxy]-8-
[(1R)-1,2-dimethylpropyl]-14-(2H-tetrazol-2-yl)-1,6,
6a,7,8,9,10,10a,10b,11,12,12a-dodecahydro-1,6a,8,
10a-tetramethyl-4H-1,4a-propano-2H-phenanthro[1,2-
c]pyran-7-carboxylic acid;

(1S,4aR,6aS,7R,8R,10aR,10bR,12aR,14R,15R)-15-[2-
(dimethylamino)-2,3-dimethylbutoxy]-8-[(1R)-1,2-
dimethylpropyl]-14-(1H-tetrazol-1-yl)-1,6,6a,7,8,9,10,
10a,10b,11,12,12a-dodecahydro-1,6a,8,10a-
tetramethyl-6-oxo-4H-1,4a-propano-2H-phenanthro[1,
2-c]pyran-7-carboxylic acid;

(1S,4aR,6aS,7R,8R,10aR,10bR,12aR,14R,15R)-15-[2-
(dimethylamino)-2,3-dimethylbutoxy]-8-[(1R)-1,2-
dimethylpropyl]-14-(2H-tetrazol-2-yl)-1,6,6a,7,8,9,10,
10a,10b,11,12,12a-dodecahydro-1,6a,8,10a-
tetramethyl-6-oxo-4H-1,4a-propano-2H-phenanthro[1,
2-c]pyran-7-carboxylic acid;

(1S,4aR,6aS,7R,8R,10aR,10bR,12aR,14R,1 5 R)-15-(2-
amino-2,3-dimethylbutoxy)-8-[(1R)-1,2-dimethylpro-
pyl]-14-(2H-tetrazol-2-yl)-1,6,6a,7,8,9,10,10a,10b,11,
12,12a-dodecahydro-1,6a,8,10a-tetramethyl-6-oxo-
4H-1,4a-propano-2H-phenanthro[1,2-c]pyran-7-
carboxylic acid;

(1S,4aR,6aS,7R,8R,10aR,10bR,12aR,14R,15R)-15-(2-
amino-2-methylpropoxy)-14-(5-amino-2H-tetrazol-2-
yl)-8-[(1R)-1,2-dimethylpropyl]-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid;

(1S,4aR,6aS,7R,8R,10aR,10bR,12aR,14R,15R)-15-
[[(2R)-2-amino-2,3-dimethylbutyl]oxy]-14-(5-amino-
2H-tetrazol-2-yl)-8-[(1R)-1,2-dimethylpropyl]-1,6,6a,
7,8,9,10,10a,10b,11,12,12a-dodecahydro-1,6a,8,10a-
tetramethyl-4H-1,4a-propano-2H-phenanthro[1,2-c]
pyran-7-carboxylic acid;

(1S,4aR,6aS,7R,8R,10aR,10bR,12aR,14R,15R)-14-(5-
amino-2H-tetrazol-2-yl)-15-[[(2R)-2-(dimethy-
lamino)-2,3-dimethylbutyl]oxy]-8-[(1R)-1,2-dimethyl-
propyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-14-(5-amino-
1H-tetrazol-1-yl)-8-[(1R)-1,2-dimethylpropyl]-1,6,6a,
7,8,9,10,10a,10b,11,12,12a-dodecahydro-1,6a,8,10a-
tetramethyl-4H-1,4a-propano-2H-phenanthro[1,2-c]
pyran-7-carboxylic acid;

(1S,4aR,6aS,7R,8R,10aR,10bR,12aR,14R,15R)-14-(5-
amino-2H-tetrazol-2-yl)-15-[[(2R)-2,3-dimethyl-2-(1-
piperidinyl)butyl]oxy]-8-[(1R)-1,2-dimethylpropyl]-1,
6,6a,7,8,9,10,10a,10b,11,12,12a-dodecahydro-1,6a,8,
10a-tetramethyl-4H-1,4a-propano-2H-phenanthro[1,2-
c]pyran-7-carboxylic acid;

(1S,4aR,6aS,7R,8R,10aR,10bR,12aR,14R,15R)-14-(5-
amino-2H-tetrazol-2-yl)-15-[[(2S)-2,3-dimethyl-2-(1-
piperidinyl)butyl]oxy]-8-[(1R)-1,2-dimethylpropyl]-1,
6,6a,7,8,9,10,10a,10b,11,12,12a-dodecahydro-1,6a,8,
10a-tetramethyl-4H-1,4a-propano-2H-phenanthro[1,2-
c]pyran-7-carboxylic acid;

(1S,4aR,6aS,7R,8R,10aR,10bR,12aR,14R,15R)-14-(5-
amino-2H-tetrazol-2-yl)-8-[(1R)-1,2-dimethylpropyl]-
15-[[(2R)-2-[(2-hydroxyethylamino]-2,3-dimethylbu-
tyl]oxy]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-(5-
amino-2H-tetrazol-2-yl)-8-[(1R)-1,2-dimethylpropyl]-
15-[[(2R)-2-[(3-hydroxypropyl)amino]-2,3-dimethyl-
butyl]oxy]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-[(2-amino-2-oxoethyl)amino]-2,3-dimethyl-
butyl]oxy]-14-(5-amino-2H-tetrazol-2-yl)-8-[(1R)-1,2-
dimethylpropyl]-1,6,6a,7,8,9,10,10a,10b,11,12,12a-
dodecahydro-1,6a,8,10a-tetramethyl-4H-1,4a-
propano-2H-phenanthro [1,2-c]pyran-7-carboxylic
acid;

(1S,4aR,6aS,7R,8R,10aR,10bR,12aR,14R,15R)-14-(5-
amino-2H-tetrazol-2-yl)-15-[[(2S)-2-(dimethylamino)-
2,3-dimethylbutyl]oxy]-8-[(1R)-1,2-dimethylpropyl]-
1,6,6a,7,8,9,10,10a,10b,11,12,12a-dodecahydro-1,6a,
8,10a-tetramethyl-6-oxo-4H-1,4a-propano-2H-
phenanthro[1,2-c]pyran-7-carboxylic acid;

(1S,4aR,6aS,7R,8R,10aR,10bR,12aR,14R,15R)-14-(5-
amino-2H-tetrazol-2-yl)-15-[[(2R)-2-(dimethy-
lamino)-2,3-dimethylbutyl]oxy]-8-[(1R)-1,2-dimethyl-
propyl]-1,6,6a,7,8,9,10,10a,10b,11,12,12a-
dodecahydro-1,6a,8,10a-tetramethyl-6-oxo-4H-1,4a-
propano-2H-phenanthro[1,2-c]pyran-7-carboxylic
acid;

(1S,4aR,6aS,7R,8R,10aR,10bR,12aR,14R,15R)-15-(2-
amino-2,3-dimethylbutoxy)-14-(5-amino-2H-tetrazol-
2-yl)-8-[(1R)-1,2-dimethylpropyl]-1,6,6a,7,8,9,10,10a,
10b,11,12,12a-dodecahydro-1,6a,8,10a-tetramethyl-6-
oxo-4H-1,4a-propano-2H-phenanthro[1,2-c]pyran-7-
carboxylic acid;

(1S,4aR,6aS,7R,8R,10aR,10bR,12aR,14R,15R)-14-(5-
amino-2H-tetrazol-2-yl)-15-[[(2R)-2-amino-2,3,3-tri-
methylbutyl]oxy]-8-[(1R)-1,2-dimethylpropyl]-1,6,6a,
7,8,9,10,10a,10b,11,12,12a-dodecahydro-1,6a,8,10a-
tetramethyl-4H-1,4a-propano-2H-phenanthro[1,2-c]
pyran-7-carboxylic acid;

(1S,4aR,6aS,7R,8R,10aR,10bR,12aR,14R,15R)-14-(5-
amino-2H-tetrazol-2-yl)-15-[[(2S)-2-amino-2,3,3-tri-
methylbutyl]oxy]-8-[(1R)-1,2-dimethylpropyl]-1,6,6a,
7,8,9,10,10a,10b,11,12,12a-dodecahydro-1,6a,8,10a-
tetramethyl-4H-1,4a-propano-2H-phenanthro[1,2-c]
pyran-7-carboxylic acid;

(1S,4aR,6aS,7R,8R,10aR,10bR,12aR,14R,15R)-14-(5-
amino-2H-tetrazol-2-yl)-8-[(1R)-1,2-dimethylpropyl]-
15-[[(2R)-2,3,3-trimethyl-2-(methylamino)butyl]oxy]-
1,6,6a,7,8,9,10,10a,10b,11,12,12a-dodecahydro-1,6a,
8,10a-tetramethyl-4H-1,4a-propano-2H-phenanthro[1,
2-c]pyran-7-carboxylic acid;

(1S,4aR,6aS,7R,8R,10aR,10bR,12aR,14R,15R)-14-(5-
amino-2H-tetrazol-2-yl)-8-[(1R)-1,2-dimethylpropyl]-
15-[[(2R)-2-(ethylamino)-2,3,3-trimethylbutyl]oxy]-1,
6,6a,7,8,9,10,10a,10b,11,12,12a-dodecahydro-1,6a,8,
10a-tetramethyl-4H-1,4a-propano-2H-phenanthro[1,2-
c]pyran-7-carboxylic acid;

(1S,4aR,6aS,7R,8R,10aR,10bR,12aR,14R,15R)-14-(5-amino-2H-tetrazol-2-yl)-15-[[(2S)-2-(dimethylamino)-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-3,3-dimethylbutyl]oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-2-ethylbotoxy)-14-(5-amino-2H-tetrazol-2-yl)-8-[(1R) -1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(3-amino-3-methylphentyl)oxy]-14-(5-amino-2H-tetrazol-2-yl)-8-[(1R) -1,2-dimethylpropyl]-1,6,6a,7,8,9,10,10a,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[2-(1-aminocyclopentyl)ethoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R) -15-[(4-aminotetrahydro-2H-pyran-4-yl)methoxy]-14-(5-amino-2H-tetrazol-2-yl)-8-[(1R) -1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[[4-(ethylamino)tetrahydro-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[4-(dimethylamino)tetrahydro-2H-pyran-4-yl]methoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-thiopyran--yl)methoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(1-aminocyclohexyl)methoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[[1-(methylamino)cyclohexyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(1-aminocyclopentyl)methoxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[[1-(methylamino)cyclopentyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[2-(4-methyl-1-piperazinyl)ethoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[2-[[3-(dimethylamino)propyl]amino]ethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-2,3-dimethylbutoxy)-8-[(1R)-1,2-dimethylpropyl]-14-[5-(methylamino)-2H-tetrazol-2-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(acetylamino)-1H-tetrazol-1-yl]-15-[[(2R)-2-amino-2,3-dimethylbutyl]oxy]-8-[(1R) -1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(acetylamino)-2H-tetrazol-2-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(acetylamino)-1H-tetrazol-1-yl]-15-[[(2R)-2,3-dimethyl-2-(methylamino)butyl]oxy]-8-[(1R) -1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(acetylamino)-2H-tetrazol-2-yl]-15-[[(2R)-2,3-dimethyl-2-(methylamino)butyl]oxy]-8-[(1R) -1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(acetylamino)-2H-tetrazol-2-yl]-15-(2-aminoethoxy)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-aminoethoxy)-8-[(1R)-1,2-dimethylpropyl]-14-(5-methyl-1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-aminoethoxy)-8-[(1R)-1,2-dimethylpropyl]-14-(5-methyl-2H-tetrazol-2-yl)-1,6,6a,7,8,9,10,10a,10b,11,12,12a-dodecahydro-1,6a,8,10a-tetramethyl-4H-1,4a-propano-2H-phenanthro [1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-methyl-1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-methyl-2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(hydroxymethyl)-1H-tetrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(hydroxymethyl)-2H-tetrazol-2-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-oxopropyl)-2H-tetrazol-2-yl]-1,6,6a,7,8,9,10,10a,10,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-(2-pyrrolidinylmethoxy)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[(1-methyl-2-pyrrolidinyl)methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-3-yl)-8-[(1R)-1,2-dimethylpropyl]-15-(3-pyrrolidinyloxy)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-1,3-dimethylbotoxy)-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[2-(dimethylamino)-1,3-dimethylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[2,3-dihydroxy-2-(hydroxymethyppropoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2S)-2-amino-2,3-dimethylbutyl]oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxamide;

(1S,4aR,6aS,7R,8R,10aR,10bR,12aR,14R,15R)-14-(5-amino-2H-tetrazol-2-yl)-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-(ethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-(ethylmethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2,3-dimethyl-2-(propylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2,3-dimethyl-2-(methylpropylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2,3-dimethyl-2-[(1-methylethyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-(butylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2,3-dimethyl-2-[(2-methylpropyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2,3-dimethyl-2-[(3-methylbutyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2,3-dimethyl-2-[(phenylmethyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-[(2-methoxyethyl)amino]-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-(dimethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-(ethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-(ethylmethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2,3-dimethyl-2-(propylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2,3-dimethyl-2-(methylpropylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-(diethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15[[(2S)-2-(butylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2,3-dimethyl-2-[(2-methylpropyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2,3-dimethyl-2-[(3-methylbutyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2,3-dimethyl-2-[(phenylmethyl)amino]butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-aminopentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-(methylamino)pentyl]oxy]-8-[(1R)-1,2-dimethylpropyl]-1,6,6a,7,8,9,10,10a,10b,11,12,12a,-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-(dimethylamino)pentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-amino-3-methylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-3-methyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-(dimethylamino)-3-methylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[(2R)-2-amino-2-cyclopropylethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[(2R)-2-cyclopropyl-2-(methylamino)ethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[(2R)-2-cyclopropyl-2-(dimethylamino)ethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-3,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-(dimethylamino)-3,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-(ethylamino)-3,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-3,3-dimethyl-2-(propylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[(2R)-2-amino-2-phenylethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[(2R)-2-(dimethylamino)-2-phenylethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-aminopentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-(methylamino)pentyl]oxy]-8-[(1R)-1,2-dimethylpropyl]-1,6,6a,7,8,9,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-(dimethylamino)pentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15[[(2S)-2-amino-3-methylbutyl]oxy]-8-[(1R)-1,2-dimethylpropyl]-1,6,6a,7,8,9,10,10a,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-(dimethylamino)-3-methylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-amino-3,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15[[(2S)-3,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-2-(ethylamino)-3,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S)-3,3-dimethyl-2-(propylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S,3S)-2-amino-3-methylpentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S,3S)-3-methyl-2-(methylamino)pentyl]oxy]-8-[(1R)-1,2-dimethylpropyl]-1,6,6a,7,8,9, 10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2S,3S)-2-(dimethylamino)-3-methylpentyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[(2S)-2-amino-2-phenylethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[(2S)-2-(dimethylamino)-2-phenylethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-aminoethoxy)-8-[(1R)-1,2-dimethylpropyl]-14-(1H-tetrazol-1-yl)-1,6,6a,7,8,9,10,10a,10b,11,12,12a-dodecahydro-1,6a,8,10a-tetramethyl-4H-1,4a-propano-2H-phenanthro [1,2-c]pyran-7-carboxylic acid;

(1S,4aR,6aS,7R,8R,10aR,10bR,12aR,14R,15R)-15-[[(2S)-2-dimethylamino)-2,3-dimethylbutyl]oxy]-8-[(1R)-1,2-dimethylpropyl]-14-(1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2S)-2-(ethylamino)-2,3-dimethylbutyl]oxy]-14-(1H-tetrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-aminoethoxy)-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2S)-2-(dimethylamino)-2,3-dimethylbutyl]oxy]-8-[(1R)-1,2-dimethylpropyl]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2S)-2-(ethylamino)-2,3-dimethylbutyl]oxy]-14-(2H-tetrazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[2-(dimethylamino)-2-ethylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[2-ethyl-2-(propylamino)butoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[[(2S)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[2-(dimethylamino)ethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[2-(dimethylamino)ethoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,4-dimethylpentyl]oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(2-amino-2-methylheptyl)oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[2-(dimethylamino)-2-methylheptyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[2-(diethylamino)-2-methylheptyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[[2-(ethylamino)-2-methylheptyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[[2-methyl-2-(propylamino)heptyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[2-(dimethylamino)-2-ethyl-3-methylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-4-hydroxy-2-methylbutoxy)-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-4-methoxy-2-methylbutoxy)-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[4-methoxy-2-methyl-2-(methylamino)butoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[2-(dimethylamino)-4-methoxy-2-methylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[2-(ethylamino)-4-methoxy-2-methylbutoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[2-(ethylmethylamino)-4-methoxy-2-methylbutoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[2-(diethylamino)-4-methoxy-2-methylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[4-fluoro-2-methyl-2-(methylamino)butoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid; and pharmaceutically acceptable salts thereof.

31. The compound according to claim 1, wherein the compound is selected from the group consisting of:

(1S,4aR,6aS,7R,8R,10aR,10bR,12aR,14R,15R)-15-[[(2R)-2-amino-2,3-dimethylbutyl]oxy]-14-(5-amino-2H-tetrazol-2-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (1S,4aR,6aS,7R,8R,10aR,10bR,12aR,14R,15R)-14-(5-amino-2H-tetrazol-2-yl)-15-[[(2R)-2-(dimethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[[tetrahydro-4-(methylamino)-2H-pyran-4-yl]methoxy]-1,6,6a,7,8,9,10,10a,10,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-8-[(1R)-1,2-dimethylpropyl]-15-[[1-(methylamino)cyclohexyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2-(ethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[[(2R)-2,3-dimethyl-2-(propylamino)butyl]oxy]-8-[(1R)-1,2-dimethylpropyl]-1,6,6a,7,8,9,10,10a,10,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-2H-tetrazol-2-yl)-15-[2-(dimethylamino)-2-ethylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid; and (1S,4aR,6aS,7R,8R,10aR,10bR,12aR,14R,15R)-14-(5-amino-2H-tetrazol-2-yl)-15-[2-(dimethylamino)-4-methoxy-2-methylbutoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid; and pharmaceutically acceptable salts thereof.

32. A composition comprising the compound of claim 1 or a pharmaceutically acceptable salt therof, and a pharmaceutically acceptable carrier, adjuvant or vehicle.

33. The composition according to claim 32, further comprising a second therapeutic agent.

34. A method of treating a fungal infection in a patient in need thereof, comprising administering to said patient an effective amount of the compound of claim 1 or a pharmaceutically acceptable salt thereof.

35. The method according to claim 34, wherein said fungal infection is caused by *Cryptococcus* spp., *Candida* spp. or *Aspergillus* spp. fungi.

* * * * *

UNITED STATES PATENT AND TRADEMARK OFFICE
CERTIFICATE OF CORRECTION

PATENT NO.        : 8,722,727 B2                                                                  Page 1 of 1
APPLICATION NO.   : 13/058227
DATED             : May 13, 2014
INVENTOR(S)       : Greenlee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this
Twenty-ninth Day of September, 2015

Michelle K. Lee
*Director of the United States Patent and Trademark Office*